(12) United States Patent
Jolidon et al.

(10) Patent No.: US 7,319,099 B2
(45) Date of Patent: Jan. 15, 2008

(54) BENZOYL-PIPERAZINE DERIVATIVES

(75) Inventors: Synese Jolidon, Blauen (CH); Robert Narquizian, St. Louis (FR); Matthias Heinrich Nettekoven, Grenzach-Wyhlen (DE); Roger David Norcross, Rheinfelden (CH); Emmanuel Pinard, Linsdorf (FR); Henri Stadler, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 500 days.

(21) Appl. No.: 10/911,359

(22) Filed: Aug. 4, 2004

(65) Prior Publication Data

US 2005/0209241 A1 Sep. 22, 2005

(30) Foreign Application Priority Data

Aug. 11, 2003 (EP) ................... 03017614

(51) Int. Cl.
*C07D 251/48* (2006.01)
*C07D 241/20* (2006.01)
*C07D 239/42* (2006.01)
*C07D 237/20* (2006.01)
*A61K 31/496* (2006.01)
*A61K 31/501* (2006.01)
*A61K 31/53* (2006.01)
*A61K 31/495* (2006.01)
*C07D 295/192* (2006.01)

(52) U.S. Cl. ............ 514/245; 514/252.02; 514/252.11; 514/252.14; 514/253.01; 514/255.03; 544/209; 544/212; 544/238; 544/295; 544/357; 544/360; 544/391

(58) Field of Classification Search .................... None
See application file for complete search history.

(56) References Cited

U.S. PATENT DOCUMENTS 5,081,112 A 1/1992 Tsutsumi et al.
6,916,804 B2 * 7/2005 Castelhano et al. .... 514/217.06

FOREIGN PATENT DOCUMENTS

EP 0 171 636 2/1985
WO WO 02/22612 3/2002

OTHER PUBLICATIONS

Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 28) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. Neurobiol. vol. 67, pp. 173-202 (2002).
Carlsson M. L., J. Neural Trans. vol. 105, pp. 525-535 (1998).
Chem. Abstract XP-002299148, Chemcats No. 2004:3653471 (2004).
Caulfield W. L. et al., Journal of Med. Chem. vol. 44(17) pp. 2679-2682, 2001.
Chem. Abstract XP-002299149, Chemcats No. 2004:2179871 (2004).

* cited by examiner

*Primary Examiner*—Emily Bernhardt
(74) *Attorney, Agent, or Firm*—George W. Johnston; Patricia S. Rocha-Tramaloni; Kimberly J. Prior

(57) ABSTRACT

The invention relates to compounds of formula

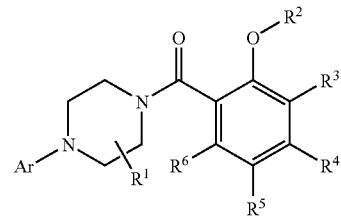

wherein the substituents are described herein. The compounds may be used in the treatment of illnesses based on the glycine uptake inhibitor, such as psychoses, pain, neurodegenerative disfunction in memory and learning, schizophrenia, dementia and other diseases in which cognitive processes are impaired, such as attention deficit disorders or Alzheimer's disease.

15 Claims, No Drawings

BENZOYL-PIPERAZINE DERIVATIVES

FIELD OF THE INVENTION

The present invention relates to the treatment of CNS disorders such as schizophrenia and Alzheimer's disease. More particularly, the invention relates to inhibition of GlyT-1.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach poorly address negative and cognitive symptoms which are the best predictors of functional outcome (Sharma T., *Br. J. Psychiatry*, 174(suppl. 28): 44-51, 1999).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., *Biol. Psychiatry*, 45: 668-679, 1999). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., *Cell*, 98: 427-236, 1999).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Wiley, N Y; Bliss T V and Collingridge G L, *Nature*, 361: 31-39, 1993). Transgenic mice over expressing the NMDA NR2B subunit exhibit enhanced synaptic plasticity and superior ability in learning and memory (Tang J P et al., *Nature*, 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, *Trends in Pharm. Sci.*, 23(8): 367-373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., *Mol. Mem. Biol.*, 18:13-20, 2001). Thus, one strategy to enhance NMDA receptor activity is to elevate the glycine concentration in the local microenvironment of synaptic NMDA receptors by inhibition of GlyT-1 transporter (Bergereon R. et al., *Proc. Natl. Acad. Sci. USA*, 95: 15730-15734, 1998; Chen L. et al., *J. Neurophysiol.*, 89(2): 691-703, 2003).

Glycine transporters inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans,*. 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563-572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I per se, and pharmaceutically acceptable salts thereof. The invention also provides compositions containing a compound of formula I or a pharmaceutically acceptable salt thereof. The invention further provides treatments for diseases related to activation of NMDA receptors via Glyt-1 inhibition, which comprises administering a therapeutically effective amount of a compound of the invention. For example, the invention provides for control or prevention of illnesses such as psychoses, disfunction in memory and learning, schizophrenia, dementia and other diseases in which cognitive processes are impaired, such as attention deficit disorders or Alzheimer's disease. The invention further provides processes for manufacturing compounds of the invention and compositions containing them. In one aspect, the present invention relates to compounds of the general formula I

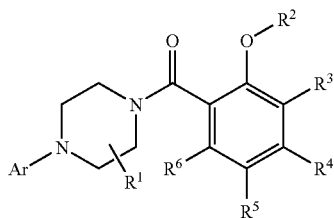

wherein

Ar is unsubstituted or substituted aryl or 6-membered heteroaryl containing one, two or three nitrogen atoms, and wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkyl substituted by hydroxy, $(CH_2)_n$—$(C_1-C_6)$-alkoxy, $(C_1-C_6)$-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by $(C_1-C_6)$-alkyl;

$R^1$ is hydrogen or $(C_1-C_6)$-alkyl;

$R^2$ is hydrogen, $(C_1-C_6)$-alkyl, $(C_2-C_6)$-alkenyl, $(C_1-C_6)$-alkyl substituted by halogen, $(C_1-C_6)$-alkyl substituted by hydroxy, $(CH_2)_n$—$(C_3-C_7)$-cycloalkyl optionally substituted by $(C_1-C_6)$-alkoxy or by halogen, $CH(CH_3)$—$(C_3-C_7)$-cycloalkyl, $(CH_2)_{n+1}$—$C(O)$—$R^9$, $(CH_2)_{n+1}$—CN, bicyclo[2.2.1]heptyl, $(CH_2)_{n+1}$—O—$(C_1-C_6)$-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy;

$R^3$, $R^4$ and $R^6$ are each independently hydrogen, hydroxy, halogen, $(C_1-C_6)$-alkyl, $(C_1-C_6)$-alkoxy or O—$(C_3-C_6)$-cycloalkyl;

$R^5$ is $NO_2$, CN, $C(O)R^9$ or $SO_2R^{10}$;

$R^7$ and $R^8$ are each independently hydrogen or $(C_1-C_6)$-alkyl;

$R^9$ is hydrogen, $(C_1-C_6)$-alkyl, $(C_1-C_6)$-alkoxy or $NR^7R^8$;

$R^{10}$ is $(C_1-C_6)$-alkyl optionally substituted by halogen, $(CH_2)_n$—$(C_3-C_6)$-cycloalkyl, $(CH_2)_n$—$(C_3-C_6)$-alkoxy, $(CH_2)_n$-heterocycloalkyl or $NR^7R^8$;

n is 0, 1, or 2;

or a pharmaceutically acceptable acid addition salt thereof, with the proviso that 1-[5-(aminosulfonyl)-2-methoxybenzoyl]-4-(3-chlorophenyl)-piperazine, 1-[5-(aminosulfonyl)-2-methoxybenzoyl]-4-(4-fluorophenyl)-piperazine, 1-[5-(aminosulfonyl)-2-methoxybenzoyl]-4-[3-(trifluoromethyl)phenyl]-piperazine, 4-(3-amino-4-nitrophenyl)-1-[4-(dimethylamino)-2-methoxy-5-nitrobenzoyl]-2-methyl-piperazine, 1-[4-(dimethylamino)-2-methoxy-5-nitrobenzoyl]-2-methyl-4-(4-nitrophenyl)-piperazine, 4-[4-(dimethylamino)-2-methoxy-5-nitrobenzoyl]-2-methyl-1-(4-nitrophenyl)-piperazine, 1-(2-chloro-4-nitrophenyl)-4-[4-(dimethylamino)-2-methoxy-5-nitrobenzoyl]-piperazine, 1-[4-(dimethylamino)-2-methoxy-5-nitrobenzoyl]-4-(2,4-dinitrophenyl)-2-methyl-piperazine, 1-(4-chloro-2-nitrophenyl)-4-[4-(dimethylamino)-2-methoxy-5-nitrobenzoyl]-piperazine and 4-[4-(dimethylamino)-2-methoxy-5-nitrobenzoyl]-1-(2,4-dinitrophenyl)-2-methyl-piperazine are excluded.

The compounds 1-[5-(aminosulfonyl)-2-methoxybenzoyl]-4-(3-chlorophenyl)-piperazine, 1-[5-(aminosulfonyl)-2-methoxybenzoyl]-4-(4-fluorophenyl)-piperazine and 1-[5-(aminosulfonyl)-2-methoxybenzoyl]-4-[3-(trifluoromethyl)phenyl]-piperazine are specifically described in EP 0171636, possessing inhibiting activity towards carbonic anhydrase which plays a determining role in many physiological and pathological processes.

The other excluded compounds are commercially available products.

The present invention relates to compounds of general formula I, to pharmaceutical composition containing them and their use in the treatment of neurological and neuropsychiatric disorders. It has surprisingly been found that the compounds of general formula I are good inhibitors of the glycine transporter 1 (GlyT-1), and that they have a good selectivity to glycine transporter 2 (GlyT-2) inhibitors.

DETAILED DESCRIPTION OF THE INVENTION

The preferred indications using the compounds of the present invention are schizophrenia, cognitive impairment and Alzheimer's disease.

Furthermore, the invention includes all racemic mixtures, all their corresponding enantiomers and/or optical isomers.

As used herein, the term "alkyl" denotes a saturated straight- or branched-chain group containing from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

The term "alkoxy" denotes a group wherein the alkyl residues is as defined above, and which is attached via an oxygen atom.

The term "cycloalkyl" denotes a saturated carbocyclic group containing 3-7 carbon atoms.

The term "alkenyl" denotes an unsaturated straight- or branched alkyl chain containing from 2 to 6 carbon atoms and having one or more double bonds, for example methylene, ethylene, propylene, isopropylene, and the like.

The term "halogen" denotes chlorine, iodine, fluorine and bromine.

The term "aryl" denotes a monovalent cyclic aromatic hydrocarbon radical consisting of one or more fused rings in which at least one ring is aromatic in nature, for example phenyl, benzyl, naphthyl, biphenyl or indanyl.

The term "6-membered heteroaryl containing one, two or three nitrogen atoms" denotes a monovalent aromatic carbocyclic radical, for example pyridyl, pyrazinyl, pyrimidinyl, pyridazinyl or 1,3,5-triazinyl.

The term "heterocycloalkyl" denotes a non aromatic hydrocarbon radical, for example oxetanyl, tetrahydrofuranyl, tetrahydropyranyl, azetidinyl, pyrrolidinyl, piperidinyl, piperazinyl, morpholinyl or thiomorpholinyl.

The term "5-membered aromatic heterocycle containing 1-4 heteroatoms, selected from N and O" denotes for example 1,2,4-oxadiazolyl, oxazolyl, 1,3,4-oxadiazolyl or tetrazolyl.

The term "5 or 6-membered heteroaryl containing one, two or three heteroatoms, selected from the group consisting of oxygen, sulphur or nitrogen" denotes a monovalent aromatic carbocyclic radical, for example pyridyl, pyrazinyl, pyrimidinyl, pyridazinyl, triazinyl, thiazolyl, thienyl, furyl, pyrrolyl, imidazolyl, pyrazolyl, isothiazolyl or isoxazolyl.

The term "alkyl, substituted by halogen" denotes for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$.

The term "alkyl, substituted by hydroxy" denotes for example the following groups: $CH(OH)CH_3$, $CH_2CH(OH)CH_3$, $CH_2CH(CH_3)CH_2OH$, $(CH_2)_2OH$, $(CH_2)_3OH$ or $CH_2C[(CH_3)]_2$—$CH_2OH$.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Pharmaceutically acceptable," such as pharmaceutically acceptable carrier, excipient, etc., means pharmacologically acceptable and substantially non-toxic to the subject to which the particular compound is administered.

The term "therapeutically effective amount" denotes an amount that is effective to prevent, alleviate or ameliorate symptoms of disease or prolong the survival of the subject being treated.

In one embodiment, the invention provides compounds of the general formula

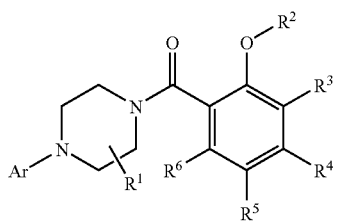

I-1 wherein

Ar is substituted aryl or unsubstituted or substituted 6-membered heteroaryl containing one, two or three nitrogen atoms, and wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ is $(C_1-C_6)$-alkyl, $(C_1-C_6)$-alkyl substituted by halogen, $(C_3-C_6)$-cycloalkyl, heterocycloalkyl, $(C_1-C_6)$-alkyl-$(C_3-C_6)$-cycloalkyl, $(C_1-C_6)$-alkyl-heterocycloalkyl, $(C_1-C_6)$-alkyl-C(O)—$R^9$, $(C_1-C_6)$-alkyl-CN, $(C_2-C_6)$-alkyl-O—$R^{13}$, $(C_2-C_6)$-alkyl-$NR^7R^8$, aryl, 6-membered heteroaryl containing one, two or three nitrogen atoms, $(C_1-C_6)$-alkyl-aryl, or $(C_1-C_6)$-alkyl-5 or -6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy;

$R^3$, $R^4$ and $R^6$ are each independently hydrogen, hydroxy, halogen, CN, $(C_1-C_6)$-alkyl, $(C_1-C_6)$-alkoxy or $NR^7R^8$;

$R^5$ is $NO_2$, CN, $C(O)R^9$, $SO_2R^{10}$ or $NR^{11}R^{12}$;

$R^7$ and $R^8$ are each independently hydrogen or $(C_1-C_6)$-alkyl;

$R^9$ is hydroxy, $(C_1-C_6)$-alkyl, $(C_3-C_6)$-cycloalkyl, $(C_1-C_6)$-alkoxy or $NR^7R^8$;

$R^{10}$ is $(C_1-C_6)$-alkyl, $(C_3-C_6)$-cycloalkyl or $NR^7R^8$;

$R^{11}$ and $R^{12}$ are each independently hydrogen, C(O)—$(C_1-C_6)$-alkyl, or $SO_2$—$(C_1-C_6)$-alkyl, or form together with the N-atom to which they are attached a 5-membered heteroaryl group, optionally substituted by halogen, $(C_1-C_6)$-alkyl, $(C_1-C_6)$-alkyl substituted by halogen or $(C_3-C_6)$-cycloalkyl;

$R^{13}$ is hydroxy, $(C_1-C_6)$-alkyl or $(C_3-C_6)$-cycloalkyl;

or a pharmaceutically acceptable acid addition salt thereof, with the proviso that 1-[5-(aminosulfonyl)-2-methoxybenzoyl]-4-(3-chlorophenyl)-piperazine, 1-[5-(aminosulfonyl)-2-methoxybenzoyl]-4-(4-fluorophenyl)-piperazine, 1-[5-(aminosulfonyl)-2-methoxybenzoyl]-4-[3-(trifluoromethyl)phenyl]-piperazine, 4-(3-amino-4-nitrophenyl)-1-[4-(dimethylamino)-2-methoxy-5-nitrobenzoyl]-2-methyl-piperazine, 1-[4-(dimethylamino)-2-methoxy-5-nitrobenzoyl]-2-methyl-4-(4-nitrophenyl)-piperazine, 4-[4-(dimethylamino)-2-methoxy-5-nitrobenzoyl]-2-methyl-1-(4-nitrophenyl)-piperazine, 1-(2-chloro-4-nitrophenyl)-4-[4-(dimethylamino)-2-methoxy-5-nitrobenzoyl]-piperazine, 1-[4-(dimethylamino)-2-methoxy-5-nitrobenzoyl]-4-(2,4-dinitrophenyl)-2-methyl-piperazine, 1-(4-chloro-2-nitrophenyl)-4-[4-(dimethylamino)-2-methoxy-5-nitrobenzoyl]-piperazine and 4-[4-(dimethylamino)-2-methoxy-5-nitrobenzoyl]-1-(2,4-dinitrophenyl)-2-methyl-piperazine are excluded.

In another embodiment, the present invention provides compounds of formula Ia

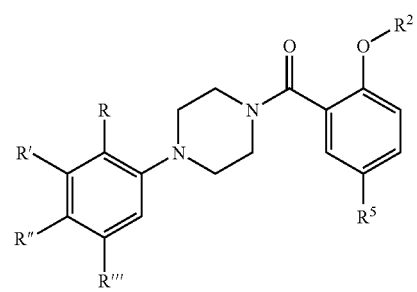

Ia wherein

R is hydrogen or halogen;

R' is hydrogen or halogen;

R" is CN, C(O)—$(C_1-C_6)$-alkyl, $(C_1-C_6)$-alkyl substituted by halogen or $S(O)_2$—$(C_1-C_6)$-alkyl;

R''' is hydrogen;
R⁵ is S(O)₂—(C₁-C₆)-alkyl, S(O)₂NH₂ or NO₂; and
R² is (C₁-C₆)-alkyl, (C₃-C₆)-cycloalkyl, (C₁-C₆)-alkyl-(C₃-C₆)-cycloalkyl, (C₁-C₆)-alkyl substituted by halogen, —(CH₂)₂O—(C₁-C₆)-alkyl, benzyl or aryl, optionally substituted by halogen;

or a pharmaceutically acceptable acid addition salt thereof, with the exception of 1-[5-(aminosulfonyl)-2-methoxybenzoyl]-4-(3-chlorophenyl)-piperazine and 1-[5-(aminosulfonyl)-2-methoxybenzoyl]-4-[3-(trifluoromethyl)phenyl]-piperazine.

A further embodiment of the invention provides those compounds of formula Ia, wherein
R is hydrogen or fluoro;
R' is hydrogen or fluoro;
R'' is CN, C(O)CH₃, CF₃ or S(O)₂—CH₃;
R''' is hydrogen;
R⁵ is S(O)₂—CH₃, S(O)₂NH₂ or NO₂; and
R² is (C₁-C₆)-alkyl, —CH₂-cyclopropyl, cyclopentyl, —CH₂—CF₃, —(CH₂)₂—O—CH₃, or is benzyl or phenyl substituted by fluoro.

Examples of such compounds are 2-Fluoro-4-[4-(2-isopropoxy-5-methanesulfonyl-benzoyl)-piperazin-1-yl]-benzonitrile,
[4-(3-fluoro-4-trifluoromethyl-phenyl)-piperazin-1-yl]-(2-isopropoxy-5-methanesulfonyl-phenyl)-methanone,
1-{3-fluoro-4-[4-(2-isobutoxy-5-methanesulfonyl-benzoyl)-piperazin-1-yl]-phenyl}-ethanone,
4-[4-(2-isobutoxy-5-methanesulfonyl-benzoyl)-piperazin-1-yl]-benzonitrile,
3-fluoro-4-[4-(2-isobutoxy-5-methanesulfonyl-benzoyl)-piperazin-1-yl]-benzonitrile,
2-fluoro-4-[4-(2-isobutoxy-5-methanesulfonyl-benzoyl)-piperazin-1-yl]-benzonitrile,
(2-isobutoxy-5-methanesulfonyl-phenyl)-[4-(4-trifluoromethyl-phenyl)-piperazin-1-yl]-methanone,
[4-(2-fluoro-4-trifluoromethyl-phenyl)-piperazin-1-yl]-(2-isobutoxy-5-methanesulfonyl-phenyl)-methanone and
[4-(3-fluoro-4-trifluoromethyl-phenyl)-piperazin-1-yl]-(2-isobutoxy-5-methanesulfonyl-phenyl)-methanone.

A further embodiment of the present invention provides compounds, wherein R⁵ is S(O)₂—CH₃ and R² is CH₂-cyclopropyl. An example of such compound is 4-[4-(2-cyclopropylmethoxy-5-methanesulfonyl-benzoyl)-piperazin-1-yl]-3-fluoro-benzonitrile.

Compounds of formula Ia are further those, wherein R⁵ is S(O)₂—CH₃ and R² is CH₂CF₃, for example the following compounds:
[4-(2-fluoro-4-trifluoromethyl-phenyl)-piperazin-1-yl]-[5-methanesulfonyl-2-(2,2,2-trifluoro-ethoxy)-phenyl]-methanone and
[4-(3-fluoro-4-trifluoromethyl-phenyl)-piperazin-1-yl]-[5-methanesulfonyl-2-(2,2,2-trifluoro-ethoxy)-phenyl]-methanone.

Compounds of formula Ia are further those, wherein R⁵ is S(O)₂—CH₃ and R² is cyclopentyl, for example the following compounds:
4-[4-(2-cyclopentyloxy-5-methanesulfonyl-benzoyl)-piperazin-1-yl]-3-fluoro-benzonitrile and
4-[4-(2-cyclopentyloxy-5-methanesulfonyl-benzoyl)-piperazin-1-yl]-2-fluoro-benzonitrile.

Preferred compounds of formula I of the present invention are those, wherein Ar is substituted phenyl, R² is (C₁-C₆)-alkyl and R⁵ is S(O)₂CH₃ or S(O)₂CH₂CH₃.

The following specific compounds relate to this group:
1-{3-fluoro-4-[4-(2-isopropoxy-5-methanesulfonyl-benzoyl)-piperazin-1-yl]-phenyl}-ethanone,
3-fluoro-4-[4-(2-isopropoxy-5-methanesulfonyl-benzoyl)-piperazin-1-yl]-benzonitrile,
2-Fluoro-4-[4-(2-isopropoxy-5-methanesulfonyl-benzoyl)-piperazin-1-yl]-benzonitrile,
[4-(2-fluoro-4-trifluoromethyl-phenyl)-piperazin-1-yl]-(2-isopropoxy-5-methanesulfonyl-phenyl)-methanone,
1-{3-fluoro-4-[4-(2-isobutoxy-5-methanesulfonyl-benzoyl)-piperazin-1-yl]-phenyl}-ethanone,
4-[4-(2-isobutoxy-5-methanesulfonyl-benzoyl)-piperazin-1-yl]-benzonitrile,
3-fluoro-4-[4-(2-isobutoxy-5-methanesulfonyl-benzoyl)-piperazin-1-yl]-benzonitrile,
2-fluoro-4-[4-(2-isobutoxy-5-methanesulfonyl-benzoyl)-piperazin-1-yl]-benzonitrile,
(2-isobutoxy-5-methanesulfonyl-phenyl)-[4-(4-trifluoromethyl-phenyl)-piperazin-1-yl]-methanone,
[4-(2-fluoro-4-trifluoromethyl-phenyl)-piperazin-1-yl]-(2-isobutoxy-5-methanesulfonyl-phenyl)-methanone,
[4-(3-fluoro-4-trifluoromethyl-phenyl)-piperazin-1-yl]-(2-isobutoxy-5-methanesulfonyl-phenyl)-methanone,
[4-(2-fluoro-4-methanesulfonyl-phenyl)-piperazin-1-yl]-(2-isobutoxy-5-methanesulfonyl-phenyl)-methanone,
[4-(2-fluoro-4-methanesulfonyl-phenyl)-piperazin-1-yl]-(2-isopropoxy-5-methanesulfonyl-phenyl)-methanone,
2,3-difluoro-4-[4-(2-isopropoxy-5-methanesulfonyl-benzoyl)-piperazin-1-yl]-benzonitrile,
2,3-difluoro-4-[4-(2-isobutoxy-5-methanesulfonyl-benzoyl)-piperazin-1-yl]-benzonitrile,
2,5-difluoro-4-[4-(2-isobutoxy-5-methanesulfonyl-benzoyl)-piperazin-1-yl]-benzonitrile,
2,6-difluoro-4-[4-(2-isobutoxy-5-methanesulfonyl-benzoyl)-piperazin-1-yl]-benzonitrile,
3,5-difluoro-4-[4-(2-isobutoxy-5-methanesulfonyl-benzoyl)-piperazin-1-yl]-benzonitrile,
4-[4-(2-tert-butoxy-5-methanesulfonyl-benzoyl)-piperazin-1-yl]-2,3-difluoro-benzonitrile,
5-chloro-2-[4-(2-isopropoxy-5-methanesulfonyl-benzoyl)-piperazin-1-yl]-benzonitrile,
4-[4-(2-tert-butoxy-5-methanesulfonyl-benzoyl)-piperazin-1-yl]-2,5-difluoro-benzonitrile,
4-[4-(2-tert-butoxy-5-methanesulfonyl-benzoyl)-piperazin-1-yl]-3-fluoro-benzonitrile,
(2-tert-butoxy-5-methanesulfonyl-phenyl)-[4-(2-fluoro-4-trifluoromethyl-phenyl)-piperazin-1-yl]-methanone,
(2-tert-butoxy-5-methanesulfonyl-phenyl)-[4-(2,5-difluoro-4-methanesulfonyl-phenyl)-piperazin-1-yl]-methanone,
1-(4-{4-[2-(2,2-dimethyl-propoxy)-5-methanesulfonyl-benzoyl]-piperazin-1-yl}-3-fluoro-phenyl)-ethanone,
4-{4-[2-(2,2-dimethyl-propoxy)-5-methanesulfonyl-benzoyl]-piperazin-1-yl}-benzonitrile,
4-{4-[2-(2,2-dimethyl-propoxy)-5-methanesulfonyl-benzoyl]-piperazin-1-yl}-3-fluoro-benzonitrile,
4-{4-[2-(2,2-dimethyl-propoxy)-5-methanesulfonyl-benzoyl]-piperazin-1-yl}-2-fluoro-benzonitrile,
[2-(2,2-dimethyl-propoxy)-5-methanesulfonyl-phenyl]-[4-(4-trifluoromethyl-phenyl)-piperazin-1-yl]-methanone,
[2-(2,2-dimethyl-propoxy)-5-methanesulfonyl-phenyl]-[4-(2-fluoro-4-trifluoromethyl-phenyl)-piperazin-1-yl]-methanone,
[2-(2,2-dimethyl-propoxy)-5-methanesulfonyl-phenyl]-[4-(3-fluoro-4-trifluoromethyl-phenyl)-piperazin-1-yl]-methanone,

[2-(2,2-dimethyl-propoxy)-5-methanesulfonyl-phenyl]-[4-(2-fluoro-4-ethanesulfonyl-phenyl)-piperazin-1-yl]-methanone,
rac-1-{4-[4-(2-sec-butoxy-5-methanesulfonyl-benzoyl)-piperazin-1-yl]-3-fluoro-phenyl}-ethanone,
rac-4-[4-(2-sec-butoxy-5-methanesulfonyl-benzoyl)-piperazin-1-yl]-3-fluoro-benzonitrile,
rac-4-[4-(2-sec-butoxy-5-methanesulfonyl-benzoyl)-piperazin-1-yl]-2-fluoro-benzonitrile,
rac-(2-sec-butoxy-5-methanesulfonyl-phenyl)-[4-(2-fluoro-4-trifluoromethyl-phenyl)-piperazin-1-yl]-methanone,
rac-(2-sec-butoxy-5-methanesulfonyl-phenyl)-[4-(3-fluoro-4-trifluoromethyl-phenyl)-piperazin-1-yl]-methanone,
(2-isopropoxy-5-methanesulfonyl-phenyl)-[4-(4-trifluoromethanesulfonyl-phenyl)-piperazin-1-yl]-methanone,
(2-isobutoxy-5-methanesulfonyl-phenyl)-[4-(4-trifluoromethanesulfonyl-phenyl)-piperazin-1-yl]-methanone,
2-[4-(2-isopropoxy-5-methanesulfonyl-benzoyl)-piperazin-1-yl]-5-trifluoromethyl-benzonitrile,
1-{2-fluoro-4-[4-(2-isopropoxy-5-methanesulfonyl-benzoyl)-piperazin-1-yl]-phenyl}-ethanone,
[4-(3-fluoro-4-methanesulfonyl-phenyl)-piperazin-1-yl]-(2-isobutoxy-5-methanesulfonyl-phenyl)-methanone,
1-{2-fluoro-4-[4-(2-isobutoxy-5-methanesulfonyl-benzoyl)-piperazin-1-yl]-phenyl}-ethanone,
2-[4-(2-isobutoxy-5-methanesulfonyl-benzoyl)-piperazin-1-yl]-5-trifluoromethyl-benzonitrile,
(5-ethanesulfonyl-2-isopropoxy-phenyl)-[4-(2-fluoro-4-trifluoromethyl-phenyl)-piperazin-1-yl]-methanone,
[4-(4-difluoromethyl-2-fluoro-phenyl)-piperazin-1-yl]-(2-isopropoxy-5-methanesulfonyl-phenyl)-methanone,
[4-(3-chloro-5-trifluoromethyl-pyridin-2-yl)-piperazin-1-yl]-(2-isopropoxy-5-methanesulfonyl-phenyl)-methanone,
3-fluoro-4-[4-(2-isopropoxy-5-methanesulfonyl-benzoyl)-piperazin-1-yl]-benzaldehyde,
[4-(4-ethanesulfonyl-2-fluoro-phenyl)-piperazin-1-yl]-(2-isobutoxy-5-methanesulfonyl-phenyl)-methanone,
rac-(2-sec-butoxy-5-methanesulfonyl-phenyl)-[4-(4-ethanesulfonyl-2-fluoro-phenyl)-piperazin-1-yl]-methanone,
[4-(4-cyclobutanesulfonyl-2-fluoro-phenyl)-piperazin-1-yl]-(2-isopropoxy-5-methanesulfonyl-phenyl)-methanone,
[4-(4-cyclopentanesulfonyl-2-fluoro-phenyl)-piperazin-1-yl]-(2-isopropoxy-5-methanesulfonyl-phenyl)-methanone,
[4-(4-cyclopropanesulfonyl-2-fluoro-phenyl)-piperazin-1-yl]-(2-isobutoxy-5-methanesulfonyl-phenyl)-methanone and
[4-(4-cyclopropanesulfonyl-2,5-difluoro-phenyl)-piperazin-1-yl]-(2-isopropoxy-5-methanesulfonyl-phenyl)-methanone.

A further preferred group of compounds of formula I are those, wherein Ar is substituted phenyl, $R^2$ is $(CH_2)_n$—$(C_3$-$C_7)$-cycloalkyl and $R^5$ is $S(O)_2CH_3$, for example the following compounds 1-{4-[4-(2-cyclopropylmethoxy-5-methanesulfonyl-benzoyl)-piperazin-1-yl]-3-fluoro-phenyl}-ethanone,
4-[4-(2-cyclopropylmethoxy-5-methanesulfonyl-benzoyl)-piperazin-1-yl]-benzonitrile,
4-[4-(2-cyclopropylmethoxy-5-methanesulfonyl-benzoyl)-piperazin-1-yl]-3-fluoro-benzonitrile,
4-[4-(2-cyclopropylmethoxy-5-methanesulfonyl-benzoyl)-piperazin-1-yl]-2-fluoro-benzonitrile,
(2-cyclopropylmethoxy-5-methanesulfonyl-phenyl)-[4-(4-trifluoromethyl-phenyl)-piperazin-1-yl]-methanone,
(2-cyclopropylmethoxy-5-methanesulfonyl-phenyl)-[4-(2-fluoro-4-trifluoromethyl-phenyl)-piperazin-1-yl]-methanone,
(2-cyclopropylmethoxy-5-methanesulfonyl-phenyl)-[4-(3-fluoro-4-trifluoromethyl-phenyl)-piperazin-1-yl]-methanone,
1-{4-[4-(2-cyclopentyloxy-5-methanesulfonyl-benzoyl)-piperazin-1-yl]-3-fluoro-phenyl}-ethanone,
4-[4-(2-cyclopentyloxy-5-methanesulfonyl-benzoyl)-piperazin-1-yl]-benzonitrile,
4-[4-(2-cyclopentyloxy-5-methanesulfonyl-benzoyl)-piperazin-1-yl]-3-fluoro-benzonitrile,
4-[4-(2-cyclopentyloxy-5-methanesulfonyl-benzoyl)-piperazin-1-yl]-2-fluoro-benzonitrile,
(2-cyclopentyloxy-5-methanesulfonyl-phenyl)-[4-(2-fluoro-4-trifluoromethyl-phenyl)-piperazin-1-yl]-methanone,
(2-cyclopentyloxy-5-methanesulfonyl-phenyl)-[4-(3-fluoro-4-trifluoromethyl-phenyl)-piperazin-1-yl]-methanone,
(2-cyclopentyloxy-5-methanesulfonyl-phenyl)-[4-(4-trifluoromethyl-phenyl)-piperazin-1-yl]-methanone,
Rac-[2-(1-cyclopropyl-ethoxy)-5-methanesulfonyl-phenyl]-[4-(4-trifluoromethyl-phenyl)-piperazin-1-yl]-methanone,
4-[4-(2-cyclopentyloxy-5-methanesulfonyl-benzoyl)-piperazin-1-yl]-2,3-difluoro-benzonitrile,
4-[4-(2-cyclopentyloxy-5-methanesulfonyl-benzoyl)-piperazin-1-yl]-2,5-difluoro-benzonitrile,
4-[4-(2-cyclobutylmethoxy-5-methanesulfonyl-benzoyl)-piperazin-1-yl]-benzonitrile,
4-[4-(2-cyclobutylmethoxy-5-methanesulfonyl-benzoyl)-piperazin-1-yl]-2-fluoro-benzonitrile,
4-[4-(2-cyclobutylmethoxy-5-methanesulfonyl-benzoyl)-piperazin-1-yl]-3-fluoro-benzonitrile,
(2-cyclobutylmethoxy-5-methanesulfonyl-phenyl)-[4-(4-trifluoromethyl-phenyl)-piperazin-1-yl]-methanone,
1-{4-[4-(2-cyclobutylmethoxy-5-methanesulfonyl-benzoyl)-piperazin-1-yl]-3-fluoro-phenyl}-ethanone,
2-[4-(2-cyclobutylmethoxy-5-methanesulfonyl-benzoyl)-piperazin-1-yl]-5-trifluoromethyl-benzonitrile,
4-[4-(2-cyclobutylmethoxy-5-methanesulfonyl-benzoyl)-piperazin-1-yl]-2,3-difluoro-benzonitrile,
4-[4-(2-cyclobutylmethoxy-5-methanesulfonyl-benzoyl)-piperazin-1-yl]-2,5-difluoro-benzonitrile,
4-[4-(2-cyclobutylmethoxy-5-methanesulfonyl-benzoyl)-piperazin-1-yl]-3,5-difluoro-benzonitrile,
4-[4-(2-cyclobutylmethoxy-5-methanesulfonyl-benzoyl)-piperazin-1-yl]-2,6-difluoro-benzonitrile,
4-[4-(2-cyclopropylmethoxy-5-methanesulfonyl-benzoyl)-piperazin-1-yl-3,5-difluoro-benzonitrile,
4-[4-(2-cyclopentyloxy-5-methanesulfonyl-benzoyl)-piperazin-1-yl]-3,5-difluoro-benzonitrile,
4-[4-(2-cyclopropylmethoxy-5-methanesulfonyl-benzoyl)-piperazin-1-yl]-2,6-difluoro-benzonitrile,
4-[4-(2-cyclopentyloxy-5-methanesulfonyl-benzoyl)-piperazin-1-yl]-2,6-difluoro-benzonitrile,
5-chloro-2-[4-(2-cyclopropylmethoxy-5-methanesulfonyl-benzoyl)-piperazin-1-yl]-benzonitrile,
4-[4-(2-cyclohexyloxy-5-methanesulfonyl-benzoyl)-piperazin-1-yl]-benzonitrile,
4-[4-(2-cyclohexyloxy-5-methanesulfonyl-benzoyl)-piperazin-1-yl]-3-fluoro-benzonitrile,
4-[4-(2-cyclohexyloxy-5methanesulfonyl-benzoyl)-piperazin-1-yl]-2-fluoro-benzonitrile,
(2-cyclohexyloxy-5-methanesulfonyl-phenyl)-[4-(4-trifluoromethyl-phenyl)-piperazin-1-yl]-methanone,
(2-cyclohexyloxy-5-methanesulfonyl-phenyl)-[4-(3-fluoro-4-trifluoromethyl-phenyl)-piperazin-1-yl]-methanone, (2-cyclohexyloxy-5-methanesulfonyl-phenyl)-[4-(2-fluoro-4-methanesulfonyl-phenyl)-piperazin-1-yl]-methanone,
1-{4-[4-(2-cyclobutoxy-5-methanesulfonyl-benzoyl)-piperazin-1-yl]-3-fluoro-phenyl}-ethanone,
4-[4-(2-cyclobutoxy-5-methanesulfonyl-benzoyl)-piperazin-1-yl]-3-fluoro-benzonitrile,
(2-cyclobutoxy-5-methanesulfonyl-phenyl)-[4-(3-fluoro-4-trifluoromethyl-phenyl)-piperazin-1-yl]-methanone,
(2-cyclopentyloxy-5-methanesulfonyl-phenyl)-[4-(4-trifluoromethanesulfonyl-phenyl)-piperazin-1-yl]-methanone,
1-{4-[4-(2-cyclopropylmethoxy-5-methanesulfonyl-benzoyl)-piperazin-1-yl]-2-fluoro-phenyl}-ethanone,
2-[4-(2-cyclopentyloxy-5-methanesulfonyl-benzoyl)-piperazin-1-yl]-5-trifluoromethyl-benzonitrile,
(2-cyclopropylmethoxy-5-methanesulfonyl-phenyl)-[4-(4-ethanesulfonyl-2-fluoro-phenyl)-piperazin-1-yl]-methanone,
(2-cyclopentyloxy-5-methanesulfonyl-phenyl)-[4-(4-ethanesulfonyl-2-fluoro-phenyl)-piperazin-1-yl]-methanone,
(2-cyclohexyloxy-5-methanesulfonyl-phenyl)-[4-(4-ethanesulfonyl-2-fluoro-phenyl)-piperazin-1-yl]-methanone,
(2-cyclopentyloxy-5-methanesulfonyl-phenyl)-[4-(4-cyclopropanesulfonyl-2-fluoro-phenyl)-piperazin-1-yl]-methanone,
(2-cyclohexyloxy-5-methanesulfonyl-phenyl)-[4-(4-cyclopropanesulfonyl-2-fluoro-phenyl)-piperazin-1-yl]-methanone,
(2-cyclobutoxy-5-methanesulfonyl-phenyl)-[4-(4-cyclopropanesulfonyl-2-fluoro-phenyl)-piperazin-1-yl]-methanone Preferred are further compounds, wherein Ar is substituted phenyl, $R^2$ is $(C_1-C_6)$-alkyl substituted by halogen and $R^5$ is $S(O)_2CH_3$. The following compounds relate to this group:

1-(3-fluoro-4-{4-[5-methanesulfonyl-2-(2,2,2-trifluoro-ethoxy)-benzoyl]-piperazin-1-yl}-phenyl)-ethanone,
3-fluoro-4-{4-[5-methanesulfonyl-2-(2,2,2-trifluoro-ethoxy)-benzoyl]-piperazin-1-yl}-benzonitrile,
[4-(2-fluoro-4-trifluoromethyl-phenyl)-piperazin-1-yl]-[5-methanesulfonyl-2-(2,2,2-tri-fluoro-ethoxy)-phenyl]-methanone,
[4-(3-fluoro-4-trifluoromethyl-phenyl)-piperazin-1-yl]-[5-methanesulfonyl-2-(2,2,2-tri-fluoro-ethoxy)-phenyl]-methanone,
[4-(2-fluoro-4-methanesulfonyl-phenyl)-piperazin-1-yl]-[5-methanesulfonyl-2-(2,2,2-trifluoro-ethoxy)-phenyl]-methanone,
3-fluoro-4-{4-[5-methanesulfonyl-2-(3,3,3-trifluoro-propoxy)-benzoyl]-piperazin-1-yl}-benzonitrile,
[4-(3-fluoro-4-trifluoromethyl-phenyl)-piperazin-1-yl]-[5-methanesulfonyl-2-(3,3,3-trifluoro-propoxy)-phenyl]-methanone,
[4-(2-fluoro-4-trifluoromethyl-phenyl)-piperazin-1-yl]-[5-methanesulfonyl-2-(3,3,3-trifluoro-propoxy)-phenyl]-methanone,
1-(3-fluoro-4-{4-[5-methanesulfonyl-2-(3,3,3-trifluoro-propoxy)-benzoyl]-piperazin -1-yl}-phenyl)-ethanone,
2,5-difluoro-4-[4-(5-methanesulfonyl-2-trifluoromethoxy-benzoyl)-piperazin-1-yl]-benzonitrile,
2,3-difluoro-4-{4-[2-(2-fluoro-1-fluoromethyl-ethoxy)-5-methanesulfonyl-benzoyl]-piperazin-1-yl}-benzonitrile,
2-fluoro-4-{4-[5-methanesulfonyl-2-(2,2,3,3,3-pentafluoro-propoxy)-benzoyl]-piperazin-1-yl}-benzonitrile,
[5-methanesulfonyl-2-(2,2,3,3,3-pentafluoro-propoxy)-phenyl]-[4-(4-trifluoromethyl-phenyl)-piperazin-1-yl]-methanone,
2,3-difluoro-4-{4-[5-methanesulfonyl-2-(2,2,3,3,3-pentafluoro-propoxy)-benzoyl]-piperazin-1-yl}-benzonitrile,
3,5-difluoro-4-{4-[5-methanesulfonyl-2-(2,2,3,3,3-pentafluoro-propoxy)-benzoyl]-piperazin-1-yl}-benzonitrile,
2-{4-[2-(2-fluoro-1-fluoromethyl-ethoxy)-5-methanesulfonyl-benzoyl]-piperazin-1-yl}-5-trifluoromethyl-benzonitrile,
rac-2,3-difluoro-4-{4-[5-methanesulfonyl-2-(2,2,2-trifluoro-1-methyl-ethoxy)-benzoyl]-piperazin-1-yl}-benzonitrile,
2-Fluoro-4-{4-[5-methanesulfonyl-2-(2,2,3,3-tetrafluoro-propoxy)-benzoyl]-piperazin-1-yl}-benzonitrile,
3-fluoro-4-{4-[5-methanesulfonyl-2-(2,2,3,3-tetrafluoro-propoxy)-benzoyl]-piperazin-1-yl}-benzonitrile,
[5-methanesulfonyl-2-(2,2,3,3-tetrafluoro-propoxy)-phenyl]-[4-(4-trifluoromethyl-phenyl)-piperazin-1-yl]-methanone,
[4-(2-fluoro-4-trifluoromethyl-phenyl)-piperazin-1-yl]-[5-methanesulfonyl-2-(2,2,3,3-tetrafluoro-propoxy)-phenyl]-methanone,
2,3-difluoro-4-{4-[5-methanesulfonyl-2-(2,2,3,3-tetrafluoro-propoxy)-benzoyl]-piperazin-1-yl}-benzonitrile,
3,5-Difluoro-4-{4-[5-methanesulfonyl-2-(2,2,3,3-tetrafluoro-propoxy)-benzoyl]-piperazin-1-yl}-benzonitrile,
[4-(3,4-dichloro-phenyl)-piperazin-1-yl]-[5-methanesulfonyl-2-(2,2,2-trifluoro-ethoxy)-phenyl]-methanone,
rac-5-chloro-2-{4-[5-methanesulfonyl-2-(2,2,2-trifluoro-1-methyl-ethoxy)-benzoyl]-piperazin-1-yl}-benzonitrile,
rac-3,5-difluoro-4-{4-[5-methanesulfonyl-2-(2,2,2-trifluoro-1-methyl-ethoxy)-benzoyl]-piperazin-1-yl}-benzonitrile,
rac-2,5-difluoro-4-{4-[5-methanesulfonyl-2-(2,2,2-trifluoro-1-methyl-ethoxy)-benzoyl]-piperazin-1-yl}-benzonitrile,
rac-2,6-difluoro-4-{4-[5-methanesulfonyl-2-(2,2,2-trifluoro-1-methyl-ethoxy)-benzoyl]-piperazin-1-yl}-benzonitrile,
rac-4-{4-[5-methanesulfonyl-2-(2,2,2-trifluoro-1-methyl-ethoxy)-benzoyl]-piperazin-1-yl}-benzonitrile,
rac-3-fluoro-4-{4-[5-methanesulfonyl-2-(2,2,2-trifluoro-1-methyl-ethoxy)-benzoyl]-piperazin-1-yl}-benzonitrile,
rac-2-fluoro-4-{4-[5-methanesulfonyl-2-(2,2,2-trifluoro-1-methyl-ethoxy)-benzoyl]-piperazin-1-yl}-benzonitrile,
rac-5-methanesulfonyl-2-(2,2,2-trifluoro-1-methyl-ethoxy)-phenyl]-[4-(4-trifluoromethyl-phenyl)-piperazin-1-yl]-methanone,
rac-[4-(2-fluoro-4-trifluoromethyl-phenyl)-piperazin-1-yl]-[5-methanesulfonyl-2-(2,2,2-trifluoro-1-methyl-ethoxy)-phenyl]-methanone,
rac-[4-(3-fluoro-4-trifluoromethyl-phenyl)-piperazin-1-yl]-[5-methanesulfonyl-2-(2,2,2-trifluoro-1-methyl-ethoxy)-phenyl]-methanone,
[4-(2-fluoro-4-trifluoromethyl-phenyl)-piperazin-1-yl]-[5-methanesulfonyl-2-((S or R)-2,2,2-trifluoro-1-methyl-ethoxy)-phenyl]-methanone,
[5-methanesulfonyl-2-((S or R)-2,2,2-trifluoro-1-methyl-ethoxy)-phenyl]-[4-(4-trifluoromethyl-phenyl)-piperazin-1-yl]-methanone and
[5-methanesulfonyl-2-((R or S)-2,2,2-trifluoro-1-methyl-ethoxy)-phenyl]-[4-(4-trifluoromethyl-phenyl)-piperazin-1-yl]-methanone.

Preferred compounds of formula I of the present invention are further those wherein Ar is substituted phenyl, $R^2$ is $(C_1-C_6)$-alkyl, $(C_1-C_6)$-alkyl substituted by halogen, $CH_2)_n$ —($C_3$-$C_7$)-cycloalkyl, bicycle[2.2.1]heptyl, ($CH_2$)$_n$—O—($C_1$-$C_6$)-alkyl or $CH_2$)$_n$-heterocycloalkyl, and $R^5$ is $NO_2$. Examples of such compounds include:

1-(3-fluoro-4-{4-[2-(2-methoxy-ethoxy)-5-nitro-benzoyl]-piperazin-1-yl}-phenyl)-ethanone,
(2-isopropoxy-5-nitro-phenyl)-[4-(4-trifluoromethyl-phenyl)-piperazin-1-yl]-methanone,
(2-cyclopropylmethoxy-5-nitro-phenyl)-[4-(4-trifluoromethyl-phenyl)-piperazin-1-yl]-methanone,
(2-cyclobutylmethoxy-5-nitro-phenyl)-[4-(4-trifluoromethyl-phenyl)-piperazin-1-yl]-methanone,
(2-butoxy-5-nitro-phenyl)-[4-(4-trifluoromethyl-phenyl)-piperazin-1-yl]-methanone,
[2-(2,2-dimethyl-propoxy)-5-nitro-phenyl]-[4-(4-trifluoromethyl-phenyl)-piperazin-1-yl]-methanone,
(2-isobutoxy-5-nitro-phenyl)-[4-(4-trifluoromethyl-phenyl)-piperazin-1-yl]-methanone,
(2-cyclopentyloxy-5-nitro-phenyl)-[4-(4-trifluoromethyl-phenyl)-piperazin-1-yl]-methanone,
(5-nitro-2-propoxy-phenyl)-[4-(4-trifluoromethyl-phenyl)-piperazin-1-yl]-methanone,
(2-cyclobutoxy-5-nitro-phenyl)-[4-(4-trifluoromethyl-phenyl)-piperazin-1-yl]-methanone,
Rac-(2-sec-butoxy-5-nitro-phenyl)-[4-(4-trifluoromethyl-phenyl)-piperazin-1-yl]-methanone,
[5-nitro-2-(2,2,3,3-tetrafluoro-propoxy)-phenyl]-[4-(4-trifluoromethyl-phenyl)-piperazin-1-yl]-methanone,
[5-nitro-2-(2,2,2-trifluoro-ethoxy)-phenyl]-[4-(4-trifluoromethyl-phenyl)-piperazin-1-yl]-methanone,
[2-(bicyclo[2.2.1]hept-2-yloxy)-5-nitro-phenyl]-[4-(4-trifluoromethyl-phenyl)-piperazin-1-yl]-methanone,
[2-(2-chloro-ethoxy)-5-nitro-phenyl]-[4-(4-trifluoromethyl-phenyl)-piperazin-1-yl]-methanone, and
[5-nitro-2-(2,2,3,3,3-pentafluoro-propoxy)-phenyl]-[4-(4-trifluoromethyl-phenyl)-piperazin-1-yl]-methanone.

Further preferred are compounds wherein Ar is substituted phenyl, $R^2$ is ($C_1$-$C_6$)-alkyl, ($C_1$-$C_6$)-alkyl substituted by halogen or ($CH_2$)$_n$—($C_3$-$C_7$)-cycloalkyl and $R^5$ is $S(O)_2$NHCH$_3$. Examples of such compounds include 3-[4-(4-Cyano-3-fluoro-phenyl)-piperazine-1-carbonyl]-N-methyl-4-trifluoromethoxy-benzenesulfonamide,
3-[4-(4-cyano-3-fluoro-phenyl)-piperazine-1-carbonyl]-4-isobutoxy-N-methyl-benzenesulfonamide,
3-[4-(4-cyano-3-fluoro-phenyl)-piperazine-1-carbonyl]-4-cyclopentyloxy-N-methyl-benzenesulfonamide,
3-[4-(4-cyano-3-fluoro-phenyl)-piperazine-1-carbonyl]-4-cyclobutoxy-N-methyl-benzenesulfonamide,
3-[4-(4-cyano-3-fluoro-phenyl)-piperazine-1-carbonyl]-4-cyclobutylmethoxy-N-methyl-benzenesulfonamide,
3-[4-(4-cyano-phenyl)-piperazine-1-carbonyl]-4-isobutoxy-N-methyl-benzenesulfonamide,
3-[4-(4-cyano-phenyl)-piperazine-1-carbonyl]-4-cyclopentyloxy-N-methyl-benzenesulfonamide,
3-[4-(4-cyano-phenyl)-piperazine-1-carbonyl]-4-cyclobutylmethoxy-N-methyl-benzenesulfonamide,
3-[4-(4-cyano-2-fluoro-phenyl)-piperazine-1-carbonyl]-4-isobutoxy-N-methyl-benzenesulfonamide,
3-[4-(4-cyano-2-fluoro-phenyl)-piperazine-1-carbonyl]-4-(2,2-dimethyl-propoxy)-N-methyl-benzenesulfonamide,
3-[4-(4-cyano-2-fluoro-phenyl)-piperazine-1-carbonyl]-4-isopropoxy-N-methyl-benzenesulfonamide,
3-[4-(4-cyano-2-fluoro-phenyl)-piperazine-1-carbonyl]-4-cyclopentyloxy-N-methyl-benzenesulfonamide,
3-[4-(4-cyano-2-fluoro-phenyl)-piperazine-1-carbonyl]-4-cyclobutoxy-N-methyl-benzenesulfonamide,
3-[4-(4-cyano-2-fluoro-phenyl)-piperazine-1-carbonyl]-4-cyclopropylmethoxy-N-methyl-benzenesulfonamide,
3-[4-(4-cyano-2-fluoro-phenyl)-piperazine-1-carbonyl]-4-cyclobutylmethoxy-N-methyl-benzenesulfonamide,
3-[4-(4-acetyl-2-fluoro-phenyl)-piperazine-1-carbonyl]-4-isobutoxy-N-methyl-benzenesulfonamide,
3-[4-(4-acetyl-2-fluoro-phenyl)-piperazine-1-carbonyl]-4-(2,2-dimethyl-propoxy)-N-methyl-benzenesulfonamide,
3-[4-(4-acetyl-2-fluoro-phenyl)-piperazine-1-carbonyl]-4-cyclopentyloxy-N-methyl-benzenesulfonamide,
3-[4-(4-acetyl-2-fluoro-phenyl)-piperazine-1-carbonyl]-4-cyclobutoxy-N-methyl-benzenesulfonamide,
3-[4-(4-acetyl-2-fluoro-phenyl)-piperazine-1-carbonyl]-4-cyclopropylmethoxy-N-methyl-benzenesulfonamide,
4-isobutoxy-N-methyl-3-[4-(4-trifluoromethyl-phenyl)-piperazine-1-carbonyl]-benzenesulfonamide,
4-(2,2-dimethyl-propoxy)-N-methyl-3-[4-(4-trifluoromethyl-phenyl)-piperazine-1-carbonyl]-benzenesulfonamide,
4-isopropoxy-N-methyl-3-[4-(4-trifluoromethyl-phenyl)-piperazine-1-carbonyl]-benzenesulfonamide,
4-cyclopentyloxy-N-methyl-3-[4-(4-trifluoromethyl-phenyl)-piperazine-1-carbonyl]-benzenesulfonamide,
4-cyclobutoxy-N-methyl-3-[4-(4-trifluoromethyl-phenyl)-piperazine-1-carbonyl]-benzenesulfonamide,
4-cyclopropylmethoxy-N-methyl-3-[4-(4-trifluoromethyl-phenyl)-piperazine-1-carbonyl]-benzenesulfonamide,
4-cyclobutylmethoxy-N-methyl-3-[4-(4-trifluoromethyl-phenyl)-piperazine-1-carbonyl]-benzenesulfonamide,
N-methyl-3-[4-(4-trifluoromethyl-phenyl)-piperazine-1-carbonyl]-4-(3,3,3-trifluoro-propoxy)-benzenesulfonamide,
3-[4-(4-cyano-2-fluoro-phenyl)-piperazine-1-carbonyl]-N-methyl-4-(2,2,2-trifluoro-ethoxy)-benzenesulfonamide,
N-methyl-4-(2,2,2-trifluoro-ethoxy)-3-[4-(4-trifluoromethyl-phenyl)-piperazine-1-carbonyl]-benzenesulfonamide,
rac-N-methyl-4-(2,2,2-trifluoro-1-methyl-ethoxy)-3-[4-(4-trifluoromethyl-phenyl)-piperazine-1-carbonyl]-benzenesulfonamide,
rac-3-[4-(4-cyano-2,5-difluoro-phenyl)-piperazine-1-carbonyl]-N-methyl-4-(2,2,2-trifluoro-1-methyl-ethoxy)-benzenesulfonamide, and
rac-3-[4-(4-cyano-2,3-difluoro-phenyl)-piperazine-1-carbonyl]-N-methyl-4-(2,2,2-trifluoro-1-methyl-ethoxy)-benzenesulfonamide.

A further preferred group of compounds of formula I are those wherein Ar is a substituted 6-membered heteroaryl group containing one, two or three nitrogen atoms, $R^2$ is ($C_1$-$C_6$)-alkyl or $CH_2$)$_n$—($C_3$-$C_7$)-cycloalkyl, and $R^5$ is $SO_2CH_3$. Examples of the compounds include:

[4-(3-chloro-5-trifluoromethyl-pyridin-2-yl)-piperazin-1-yl]-(2-cyclopropylmethoxy-5-methanesulfonyl-phenyl)-methanone,
6-[4-(2-cyclopentyloxy-5-methanesulfonyl-benzoyl)-piperazin-1-yl]-nicotinonitrile,
(2-cyclopentyloxy-5-methanesulfonyl-phenyl)-[4-(5-trifluoromethyl-pyridin-2-yl)-piperazin-1-yl]-methanone,
[4-(3-chloro-5-trifluoromethyl-pyridin-2-yl)-piperazin-1-yl]-(2-cyclopentyloxy-5-methanesulfonyl-phenyl)-methanone,
(2-cyclopentyloxy-5-methanesulfonyl-phenyl)-[4-(6-trifluoromethyl-pyridin-3-yl)-piperazin-1-yl]-methanone,
[4-(3-fluoro-5-trifluoromethyl-pyridin-2-yl)-piperazin-1-yl]-(2-isopropoxy-5-methanesulfonyl-phenyl)-methanone, and
(2-cyclopentyloxy-5-methanesulfonyl-phenyl)-[4-(3-fluoro-5-trifluoromethyl-pyridin-2-yl)-piperazin-1-yl]-methanone.

Further preferred are compounds of formula I, wherein Ar is a substituted 6-membered heteroaryl group containing one, two or three nitrogen atoms, $R^2$ is $(C_1-C_6)$-alkyl substituted by halogen and $R^5$ is $SO_2CH_3$. Examples of these compounds include:

rac-[4-(3-chloro-5-trifluoromethyl-pyridin-2-yl)-piperazin-1-yl]-[5-methanesulfonyl-2-(2,2,2-trifluoro-1-methyl-ethoxy)-phenyl]-methanone, rac-[5-methanesulfonyl-2-(2,2,2-trifluoro-1-methyl-ethoxy)-phenyl]-[4-(5-trifluoromethyl-pyridin-2-yl)-piperazin-1-yl]-methanone, rac-[4-(5-bromo-pyridin-2-yl)-piperazin-1-yl]-[5-methanesulfonyl-2-(2,2,2-trifluoro-1-methyl-ethoxy)-phenyl]-methanone, rac-[4-(3-fluoro-5-trifluoromethyl-pyridin-2-yl)-piperazin-1-yl]-[5-methanesulfonyl-2-(2,2,2-trifluoro-1-methyl-ethoxy)-phenyl]-methanone, rac-[5-methanesulfonyl-2-(2,2,2-trifluoro-1-methyl-ethoxy)-phenyl]-[4-(6-trifluoromethyl-pyridin-2-yl)-piperazin-1-yl]-methanone,

[5-methanesulfonyl-2-((S or R)-2,2,2-trifluoro-1-methyl-ethoxy)-phenyl]-[4-(5-trifluoromethyl-pyridin-2-yl)-piperazin-1-yl]-methanone,

[5-methanesulfonyl-2-((R or S)-2,2,2-trifluoro-1-methyl-ethoxy)-phenyl]-[4-(5-trifluoromethyl-pyridin-2-yl)-piperazin-1-yl]-methanone,

[4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone, and

[4-(3-fluoro-5-trifluoromethyl-pyridin-2-yl)-piperazin-1-yl]-[5-methanesulfonyl-2-(2,2,2-trifluoro-1,1-dimethyl-ethoxy)-phenyl]-methanone.

The present compounds of formula I and their pharmaceutically acceptable salts can be prepared by methods known in the art, for example, by processes described below. One such process comprises a) reacting a compound of formula

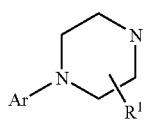

II with a compound of formula

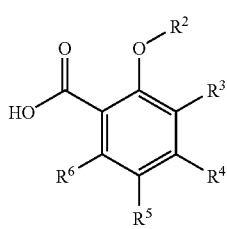

III in the presence of an activating agent, such as TBTU (2-(1H-benzotriazole-1-yl)-1,1,3,3-tetramethyluroniumtetrafluoroborate), to produce a compound of formula

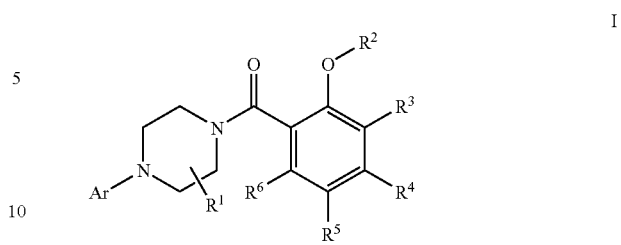

I wherein the substituents are as defined above, or b) reacting a compound of formula

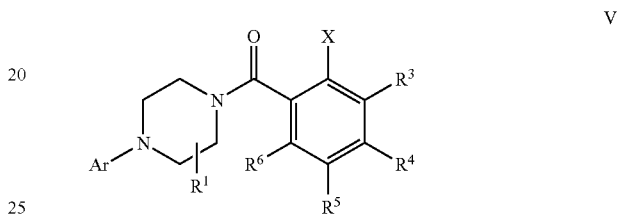

V with a compound of formula $R^2OH$ optionally in the presence of a catalyst, such as Cu(I)I, and a base, like potassium carbonate, cesium carbonate or sodium, to produce a compound of formula

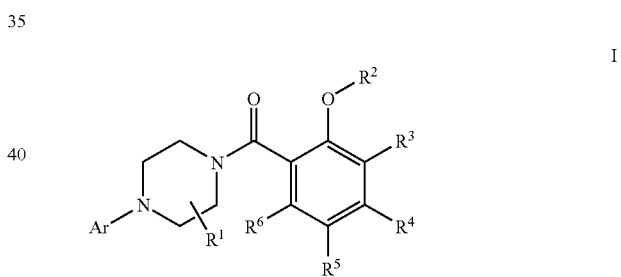

I wherein X is halogen and the other substituents are as defined above, or c) reacting a compound of formula

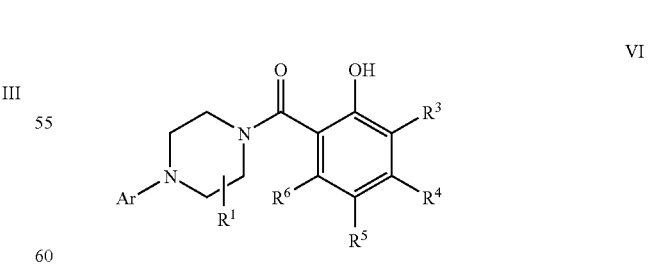

VI with a compound of formula $R^2X$ in the presence of a base and optionally in the presence of microwaves to produce a compound of formula

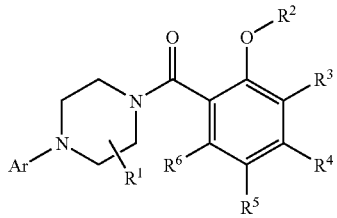

I wherein X is halogen, mesylate or triflate and the other substituents are as defined above, or d) reacting a compound of formula

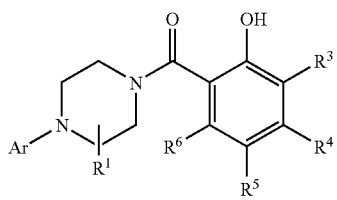

VI with a compound of formula

R²OH under Mitsunobu conditions in the presence of a phosphine to produce a compound of formula

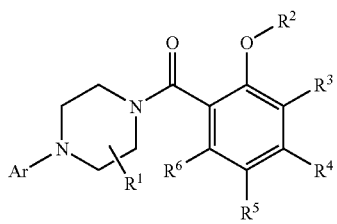

I wherein the substituents are as defined above, or e) reacting a compound of formula

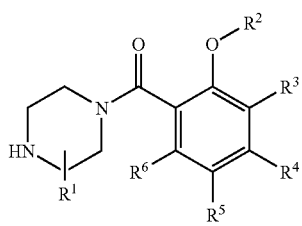

VIII with a compound of formula

ArX to produce a compound of formula

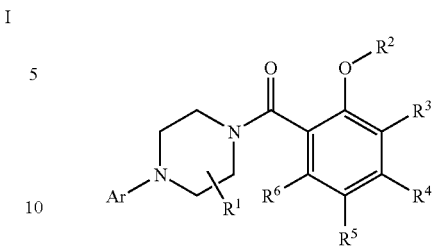

I wherein X is halogen and the other substituents are as defined above, or f) reacting a compound of formula

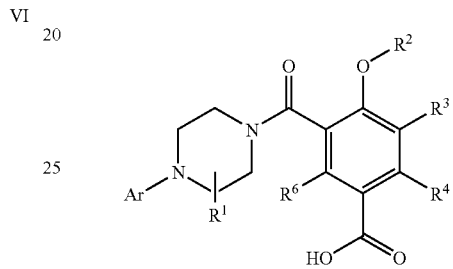

Ia with a corresponding amine or alcohol in the presence of an activating agent to produce a compound of formula

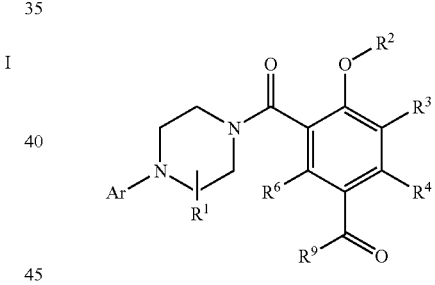

Ib wherein $R^9$ is $(C_1-C_6)$-alkyl, $(C_3-C_6)$-cycloalkyl, $(C_1-C_6)$-alkoxy or $NR^7R^8$; and the other substituents are as defined above, or g) reacting a compound of formula

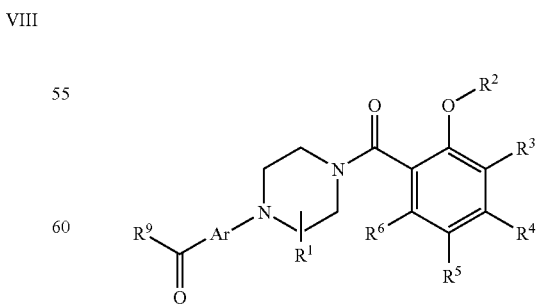

Ic with a compound of formula $RONH_2$ to produce a compound of formula

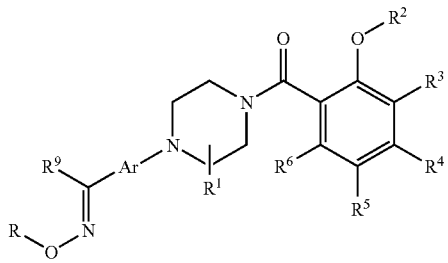

wherein R is H or alkyl and the other substituents are as defined above, or h) reacting a compound of formula

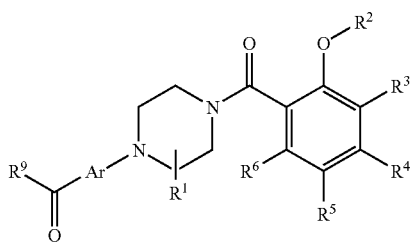

Ic with a reducing agent, like sodium borohydride (when R is H), or an alkylating agent, like alkyllithium (when R is alkyl), to produce a compound of formula

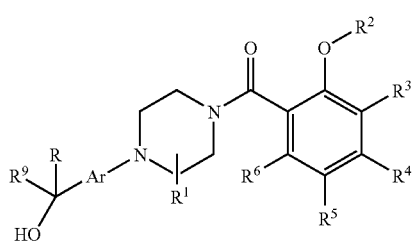

Ie wherein R is H or alkyl and the other substituents are as defined above, and if desired, converting the compounds obtained into pharmaceutically acceptable acid addition salts.

The compounds of formula I may be prepared in accordance with process variant a) to h) and with the following schemes 1 to 8. The starting materials are commercially available or maybe prepared in accordance with known methods.

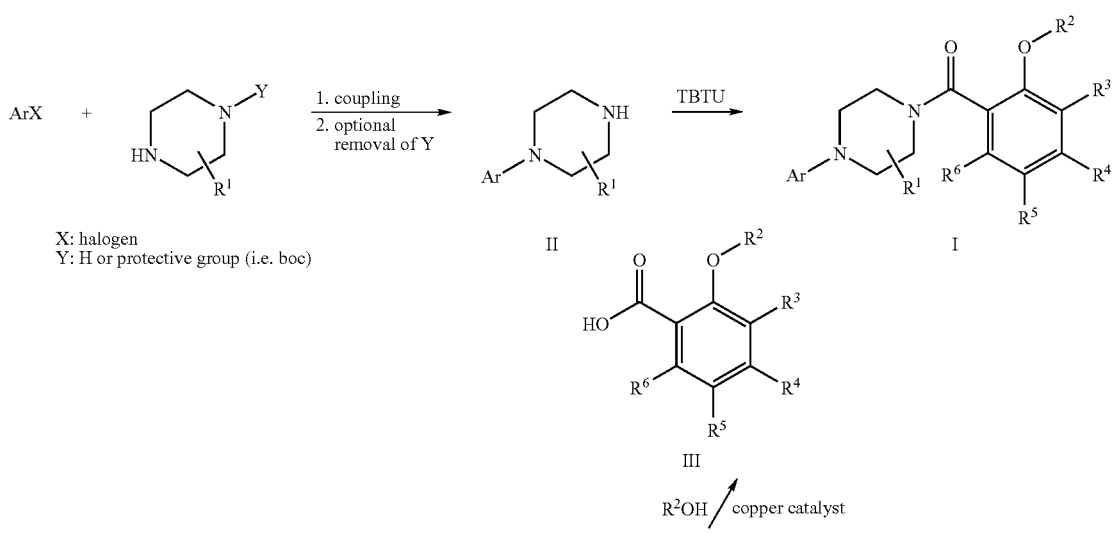

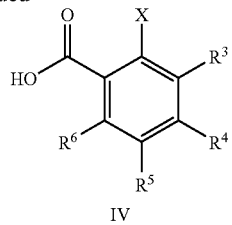

Compounds of general formula I can be prepared by reacting piperazine derivatives of formula II with a corresponding acid of formula III in the presence of an activating agent like TBTU (2-(1H-benzotriazole-1-yl)-1,1,3,3-tetramethyluroniumtetrafluoroborate). The acid of formula III can be prepared by reaction of an acid of formula IV with an alcohol of formula $R^2OH$, optionally in the presence of a copper salt like Cu(I)Br. Piperazine derivatives of formula II can be prepared by heating of the corresponding piperazine with ArX or by reacting of a N-protected piperazine with ArX in the presence of palladium catalyst followed by cleavage of the protective group. The protective group is typically tert-butoxycarbonyl (Boc).

an alcohol of formula $R^2OH$, optionally in the presence of a copper salt like Cu(I)I. Acylpiperazine derivatives of formula V can be prepared by reaction of an acid of formula IV with piperazine derivatives of formula II in the presence of an activating agent like TBTU (2-(1H-benzotriazole-1-yl)-1,1,3,3-tetramethyluroniumtetrafluoroborate).

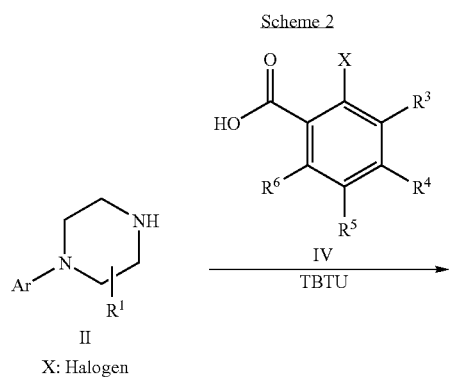

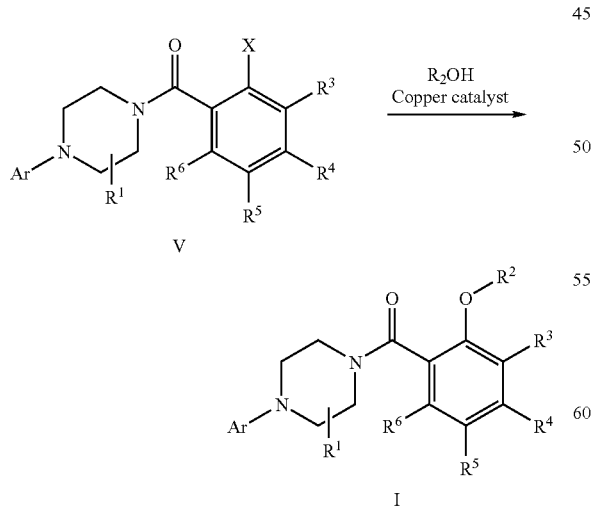

Alternatively, compounds of general formula I can be prepared by reaction of an acyl-piperazine of formula V and Compounds of general formula I can be prepared by reacting a compound of formula VI with an electrophile of formula $R^2X$ in the presence of base like potassium carbonate and optionally in the presence of microwaves, wherein X is halogen, mesylate or triflate.

Scheme 4

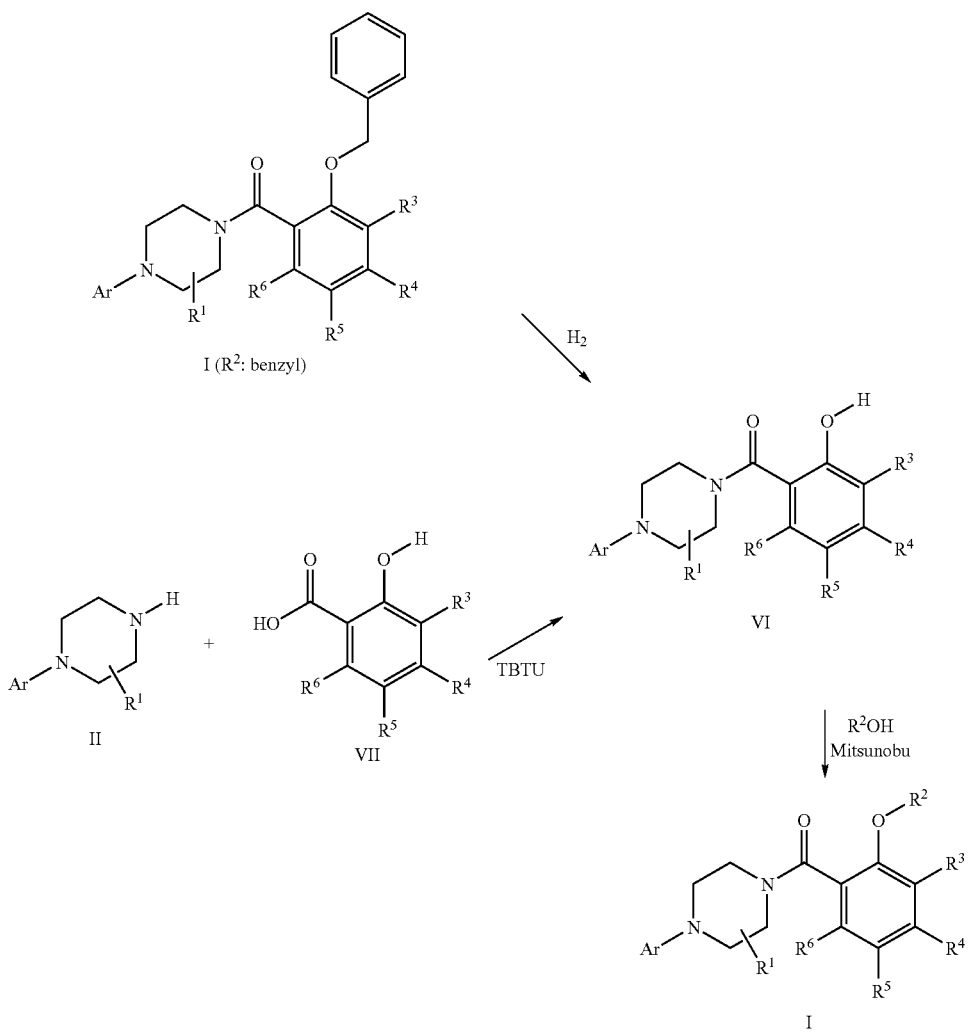

Compounds of general formula I can be prepared by reacting phenol of formula VI with an alcohol of formula R²OH under Mitsunobu conditions, in the presence of a phosphine, like triphenylphosphine or diphenyl-2-pyridylphosphine, and a dialkylazadicarboxylate, like diethylazadicarboxylate or di-tert-butyl azodicarboxylate.

The compound of formula VI can be prepared by deprotection (for example using hydrogen) of a phenol protected as a benzyl ether (I with R₂: benzyl).

Alternatively, a compound of formula VI can be prepared by reacting piperazine derivatives of formula II with an acid of formula VII in the presence of an activating agent like TBTU (2-(1H-benzotriazole-1-yl)-1,1,3,3-tetramethyluroniumtetrafluoroborate).

Scheme 5

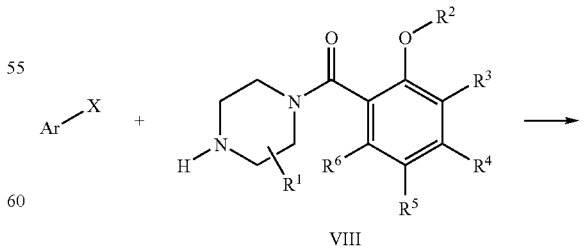

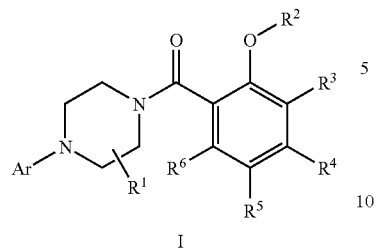

I

Compounds of general formula I can be prepared by reacting a piperazine of formula VIII with ArX.

Scheme 6

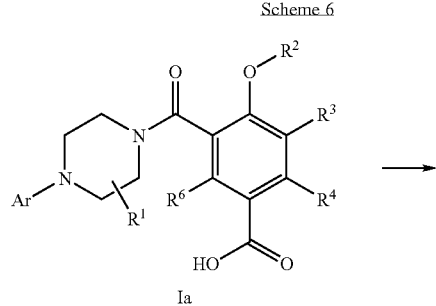

Ia

↓

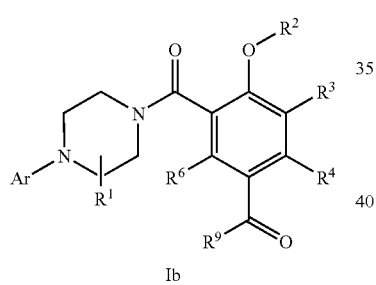

Ib wherein $R^9$ is $(C_1-C_6)$-alkoxy or $NR^7R^8$;

Compounds of general formula Ib wherein $R^9$ is as defined above can be prepared by reacting an acid of formula Ia with a corresponding amine or alcohol in the presence of an activating agent like carbonyldimidazole.

Scheme 7

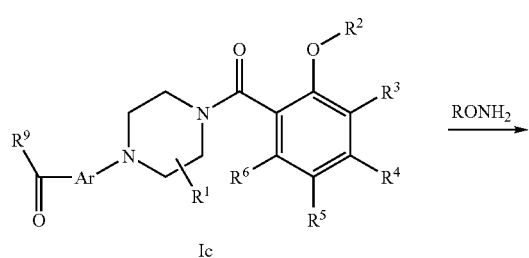

Ic

Compounds of general formula Id can be prepared in accordance with scheme 7 by reacting a compound of formula Ic bearing a carbonyl group, with a compound of formula $RONH_2$, wherein R is H or alkyl and $R^9$ is $(C_1-C_6)$-alkyl, $(C_3-C_6)$-cycloalkyl, $(C_1-C_6)$-alkoxy or $NR^7R^8$.

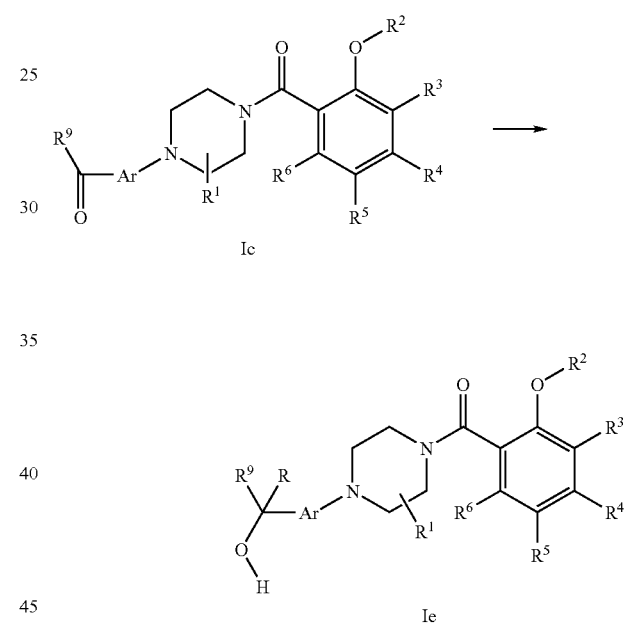

Compounds of general formula Ie wherein R is H or alkyl and $R^9$ is $(C_1-C_6)$-alkyl or $(C_3-C_6)$-cycloalkyl can be prepared by reacting a compound of formula Ic bearing a carbonyl group, with a reducing agent like sodium borohydride (when R is H) or an alkylating agent like alkyllithium (when R is alkyl).

Racemic mixtures of chiral compounds of formula I can be separated using chiral HPLC.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The following 660 examples illustrate the present invention without limiting it. All temperatures are given in degree Celsius.

The following abbreviations were used in the examples:
RT: room temperature;
n-Boc-piperazine: tert-Butyl 1-piperazinecarboxylate, oxone®: (potassium peroxymonosulfate) $2KHSO_5.KHSO_4.K_2SO_4$,
EtOAc: ethyl acetate;
THF: tetrahydrofuran;
TBTU: 2-(1H-benzotriazole-1-yl)-1,1,3,3-tetramethyluroniumtetrafluoroborate;
DIPEA: diisopropylethylamine,
DMF: N,N-dimetyhylformamide

EXAMPLE 1.1

Preparation of
1-(2-Fluoro-4-trifluoromethyl-phenyl)-piperazine (a) 4-(2-Fluoro-4-trifluoromethyl-phenyl)-piperazine-1-carboxylic acid tert-butyl ester A mixture of 20 mmol 1-bromo-2-fluoro-4-trifluoromethyl-benzene, 24.7 mmol n-Boc-piperazine, 0.1 mmol Tris(dibenzylideneacetone)dipalladium chloroform complex, 28.8 mmol sodium-t-butoxide and 0.4 mmol 2-(dicyclohexylphosphino)biphenyl in 50 ml toluene was heated for 16 h at 80° C. After cooling to RT the mixture was treated with 15 g Isolute HM-N and all volatiles were removed under vacuum. The residue was purified on silica eluting with a gradient of heptane/EtOAc to yield after evaporation the title compound.

(b) 1-(2-Fluoro-4-trifluoromethyl-phenyl)-piperazine

A mixture of 9 mmol 4-(2-fluoro-4-trifluoromethyl-phenyl)-piperazine-1-carboxylic acid tert-butyl ester in 20 ml dioxane was treated with 8.93 ml 4N HCl in dioxane for 2 h at 80° C. The mixture was concentrated and treated with 20 ml water, 20 ml 2M $Na_2CO_3$ and extracted with 50 ml EtOAc. The organic phase was washed with 30 ml saturated NaCl. AU aqueous phases were combined and extracted with 50 ml EtOAc. The combined organic phases were dried with $MgSO_4$ and evaporated to yield the title compound 1.1.

1-H-NMR (300 MHz, $CDCl_3$) δ=7.50 (d, J=13.3 Hz, 1H, H-3), 7.45 (d, J=8.8 Hz, 1H, H-5), 7.16 (dd, $J_1$=8.8 Hz, $J_2$=8.8 Hz, 1H, H-6), 3.5-3.2 (s, br, 1H, NH), 3.04 (m, 4H, piperazine), 2.87 (m, 4H, piperazine).

MS (m/e): 249.2 (MH+, 100%)

EXAMPLE 1.2

Preparation of
2-isopropoxy-5-methanesulfonyl-benzoic acid (a) 2-Chloro-5-methanesulfonyl-benzoic acid To 99 mmol 2-chloro-5-(methylthio) benzoic acid in 400 ml methanol at 0° C. 296 mmol oxone® was added, and the mixture was allowed to stir at RT for 3.5 h. The precipitate was filtered off, and the filtrate was concentrated under reduced pressure. The residue was extracted 3× with 400 ml ethyl acetate, and the combined organic phases washed 2× with 300 ml 1N HCl and with 300 ml saturated aqueous NaCl solution and dried with $MgSO_4$. Evaporation under reduced pressure yielded the title compound.

(b) 2-Isopropoxy-5-methanesulfonyl-benzoic acid

A mixture of 2.13 mmol 2-chloro-5-methanesulfonyl-benzoic acid, 0.64 mmol Cu(I)Br in 5 ml $NEt_3$ and 25 ml isopropanol was heated to 120° C. for 16 h in a sealed tube. The volatiles were removed under vacuum, and the residue was taken up in 70 ml 1N HCl. Extraction with ethyl acetate drying of the combined organic fractions and evaporation yielded a residue which was purified by reversed phase preparative HPLC eluting with an acetonitrile/water gradient. Evaporation of the product fractions yielded the title compound 1.2.

MS (m/e): 257.0 (MH−, 100%)

In analogy to Example 1.2(b) compounds 1.3 to 1.7 of the following table were prepared from 2-chloro-5-methanesulfonyl-benzoic acid and the appropriate alcohol:

|  | Compound Name | Alcohol | MS (m/e) |
| --- | --- | --- | --- |
| 1.3 | 2-isobutoxy-5-methanesulfonyl-benzoic acid | isobutanol | 271.1 (MH−, 100%) |
| 1.4 | 2-cyclopropylmethoxy-5-methanesulfonyl-benzoic acid | cyclopropyl-methanol | 269.1 (MH−, 100%) |
| 1.5 | 5-methanesulfonyl-2-(2,2,2-trifluoro-ethoxy)-benzoic acid | 2,2,2-trifluoro-ethanol | 297.0 (MH−, 100%) |
| 1.6 | 2-cyclopentyloxy-5-methanesulfonyl-benzoic acid | cyclopentanol | 282.9 (MH−, 100%) |
| 1.7 | 2-(4-fluoro-phenoxy)-5-methanesulfonyl-benzoic acid | 4-fluoro-phenol (in THF) | 309.1 (MH−, 100%) |

EXAMPLE 1.8

Preparation of 1-{3-fluoro-4-[4-(2-fluoro-5-nitro-benzoyl)-piperazin-1-yl]-phenyl}-ethanone A solution of 0.261 mmol 2-fluoro-5-nitro-benzoyl chloride [CAS: 7304-32-7; Feng and Burgess, Chem. Europ. J. EN, 5:3261-3272 (1999)] in 1 ml dioxane was treated with 0.522 mmol triethylamine and then with a solution of 0.261 mmol 1-(3-fluoro-4-piperazin-1-yl-phenyl)-ethanone (CAS: 189763-57-3; WO 97/14,690) in 1 ml dioxane. The mixture was stirred at RT for 30 min. The solvent was removed in vacuo. The crude oil was taken up in water. The aqueous layer was extracted 3 times with $CH_2Cl_2$. The combined extracts were dried over $Na_2SO_4$, filtered, and the solvent was removed in vacuo. The crude gum was purified on silica gel (eluent: heptane/ethylacetate 0%-20% (10 min) to provide the title compound 1.8.

MS (m/e): 390.2 (MH+, 100%)

EXAMPLE 1.9

Preparation of (2-iodo-5-methanesulfonyl-phenyl)-[4-(4-trifluoromethyl-phenyl)-piperazin-1-yl]-methanone (a) 2-Amino-5-methanesulfonyl-benzoic acid A mixture of 4.26 mmol 2-chloro-5-methanesulfonyl-benzoic acid, 0.39 mmol Copper powder and 10 ml ammonium hydroxide 25% was heated at 125-130° C. with stirring for 18 hours. Mixture was cooled to room temperature and filtered. The solid was washed with methanol. The filtrate was concentrated in vacuo. The residue was acidified with HCl 1N to pH=2. The obtained solid was washed with water and dried (HV, 50° C., 1 hour) to yield the title compound MS (m/e): 214.1 (M−H, 100%)

(b) 2-Iodo-5-methanesulfonyl-benzoic acid

To a suspension of 3.0 mmol 2-amino-5-methanesulfonyl-benzoic acid in a mixture of 1.7 ml sulfuric acid and 1.7 ml water was added dropwise a solution of 3.92 mmol sodium nitrite in 1.7 ml water at such rate that the temperature did not exceed 3° C. The mixture was stirred at 0° C. for 1 hour. A solution of 3.0 mmol KI in 1.7 ml water was added dropwise at 0° C. The brown suspension was allowed to warm to rt and stirred for 30 minutes. Excess iodine was destroyed by addition of a few drops of a sodium hydrogenosulfite solution. The solid was filtered, washed with water and dried (HV, 50° C., 1 hour) to yield the title compound. MS (m/e): 325.0 (M−H, 100%)

(c) (2-iodo-5-methanesulfonyl-phenyl)-[4-(4-trifluoromethyl-phenyl)-piperazin-1-yl]methanone To a solution of 9.2 mmol 2-iodo-5-methanesulfonyl-benzoic acid in 20 ml dimethylformamide 11.5 mmol TBTU, 46.0 mmol N-ethyldiisopropylamine and 11.0 mmol 1-(4-trifluoromethylphenyl)piperazine (ABCR F07741NB, [30459-17-7])were successively added. The reaction was then stirred at RT for two hours, concentrated in vacuo and purified by column chromatography (SiO$_2$, 50 g, CH$_2$Cl$_2$/MeOH/NH$_3$=100/0/0 to 95/4.5/0.5), to give the title compound 1.9. MS (m/e): 539.1 (M+H$^+$)

EXAMPLE 5

Preparation of [4-(2-fluoro-4-trifluoromethyl-phenyl)-piperazin-1-yl]-(2-isopropoxy-5-methanesulfonyl-phenyl)-methanone A mixture of 0.05 mmol 2-isopropoxy-5-methanesulfonyl-benzoic acid (Compound 1.2), 0.06 mmol 1-(2-fluoro-4-trifluoromethyl-phenyl)-piperazine, 0.055 mmol TBTU and 0.25 mmol DIPEA in 1 ml DMF was stirred at RT for 16 h. 0.5 ml MeOH/HCOOH 1/1 was added and the mixture was subjected to reversed phase preparative HPLC separation eluting with an acetonitrile/water gradient yielding the title compound. MS (m/e): 489.2 (MH$^+$, 100%)

In analogy to Example 5 compounds 1 to 4, 6 to 46 and 52-54 of the following table were prepared from the acid derivatives and piperazine derivatives:

| Expl. No. | Systematic Name | Starting materials | MW found (MH$^+$) |
|---|---|---|---|
| 1 | 1-{3-fluoro-4-[4-(2-isopropoxy-5-methanesulfonyl-benzoyl)-piperazin-1-yl]-phenyl}-ethanone | 1-(3-fluoro-4-piperazin-1-yl-phenyl)-ethanone and Compound 1.2 | 463.2 |
| 2 | 4-[4-(2-isopropoxy-5-methanesulfonyl-benzoyl)-piperazin-1-yl]-benzonitrile | 4-piperazin-1-yl-benzonitrile and Compound 1.2 | 428.2 |
| 3 | 3-fluoro-4-[4-(2-isopropoxy-5-methanesulfonyl-benzoyl)-piperazin-1-yl]-benzonitrile | 3-fluoro-4-piperazin-1-yl-benzonitrile and Compound 1.2 | 446.2 |
| 4 | 2-Fluoro-4-[4-(2-isopropoxy-5-methanesulfonyl-benzoyl)-piperazin-1-yl]-benzonitrile | 2-fluoro-4-piperazin-1-yl-benzonitrile and Compound 1.2 | 446.2 |
| 5 | [4-(2-fluoro-4-trifluoromethyl-phenyl)-piperazin-1-yl]-(2-isopropoxy-5-methanesulfonyl-phenyl)-methanone | 1-(2-fluoro-4-trifluoromethyl-phenyl)-piperazine and Compound 1.2 | 489.2 |
| 6 | [4-(3-fluoro-4-trifluoromethyl-phenyl)-piperazin-1-yl]-(2-isopropoxy-5-methanesulfonyl-phenyl)-methanone | 1-(3-fluoro-4-trifluoromethyl-phenyl)-piperazine and Compound 1.2 | 489.2 |
| 7 | 1-{3-fluoro-4-[4-(2-isobutoxy-5-methanesulfonyl-benzoyl)-piperazin-1-yl]-phenyl}-ethanone | 1-(3-fluoro-4-piperazin-1-yl-phenyl)-ethanone and Compound 1.3 | 477.2 |
| 8 | 4-[4-(2-isobutoxy-5-methanesulfonyl-benzoyl)-piperazin-1-yl]-benzonitrile | 4-piperazin-1-yl-benzonitrile and Compound 1.3 | 442.2 |
| 9 | 3-fluoro-4-[4-(2-isobutoxy-5-methanesulfonyl-benzoyl)-piperazin-1-yl]-benzonitrile | 3-fluoro-4-piperazin-1-yl-benzonitrile and Compound 1.3 | 460.3 |
| 10 | 2-fluoro-4-[4-(2-isobutoxy-5-methanesulfonyl-benzoyl)-piperazin-1-yl]-benzonitrile | 2-fluoro-4-piperazin-1-yl-benzonitrile and Compound 1.3 | 460.3 |
| 11 | (2-isobutoxy-5-methanesulfonyl-phenyl)-[4-(4-trifluoromethyl-phenyl)-piperazin-1-yl]-methanone | 1-(4-trifluoromethyl-phenyl)-piperazine and Compound 1.3 | 485.3 |
| 12 | [4-(2-fluoro-4-trifluoromethyl-phenyl)-piperazin-1-yl]-(2-isobutoxy-5-methanesulfonyl-phenyl)-methanone | 1-(2-fluoro-4-trifluoromethyl-phenyl)-piperazine and Compound 1.3 | 503.2 |
| 13 | [4-(3-fluoro-4-trifluoromethyl-phenyl)-piperazin-1-yl]-(2-isobutoxy-5-methanesulfonyl-phenyl)-methanone | 1-(3-fluoro-4-trifluoromethyl-phenyl)-piperazine and Compound 1.3 | 503.1 |
| 14 | [4-(2-fluoro-4-methanesulfonyl-phenyl)-piperazin-1-yl]-(2-isobutoxy- | 1-(2-fluoro-4-methanesulfonyl-phenyl)-piperazine and | 513.3 |

-continued

| Expl. No. | Systematic Name | Starting materials | MW found (MH⁺) |
|---|---|---|---|
|  | 5-methanesulfonyl-phenyl)-methanone | Compound 1.3 |  |
| 15 | 1-{4-[4-(2-cyclopropylmethoxy-5-methanesulfonyl-benzoyl)-piperazin-1-yl]-3-fluoro-phenyl}-ethanone | 1-(3-fluoro-4-piperazin-1-yl-phenyl)-ethanone and Compound 1.4 | 475.2 |
| 16 | 4-[4-(2-cyclopropylmethoxy-5-methanesulfonyl-benzoyl)-piperazin-1-yl]-benzonitrile | 4-piperazin-1-yl-benzonitrile and Compound 1.4 | 440.3 |
| 17 | 4-[4-(2-cyclopropylmethoxy-5-methanesulfonyl-benzoyl)-piperazin-1-yl]-3-fluoro-benzonitrile | 3-fluoro-4-piperazin-1-yl-benzonitrile and Compound 1.4 | 458.3 |
| 18 | 4-[4-(2-cyclopropylmethoxy-5-methanesulfonyl-benzoyl)-piperazin-1-yl]-2-fluoro-benzonitrile | 2-fluoro-4-piperazin-1-yl-benzonitrile and Compound 1.4 | 458.3 |
| 19 | (2-cyclopropylmethoxy-5-methanesulfonyl-phenyl)-[4-(4-trifluoromethyl-phenyl)-piperazin-1-yl]-methanone | 1-(4-trifluoromethyl-phenyl)-piperazine and Compound 1.4 | 483.2 |
| 20 | (2-cyclopropylmethoxy-5-methanesulfonyl-phenyl)-[4-(2-fluoro-4-trifluoromethyl-phenyl)-piperazin-1-yl]-methanone | 1-(2-fluoro-4-trifluoromethyl-phenyl)-piperazine and Compound 1.4 | 501.2 |
| 21 | (2-cyclopropylmethoxy-5-methanesulfonyl-phenyl)-[4-(3-fluoro-4-trifluoromethyl-phenyl)-piperazin-1-yl]-methanone | 1-(3-fluoro-4-trifluoromethyl-phenyl)-piperazine and Compound 1.4 | 501.2 |
| 22 | (2-cyclopropylmethoxy-5-methanesulfonyl-phenyl)-[4-(2-fluoro-4-methanesulfonyl-phenyl)-piperazin-1-yl]-methanone | 1-(2-fluoro-4-methanesulfonyl-phenyl)-piperazine and Compound 1.4 | 511.3 |
| 23 | 1-(3-fluoro-4-{4-[5-methanesulfonyl-2-(2,2,2-trifluoro-ethoxy)-benzoyl]-piperazin-1-yl}-phenyl)-ethanone | 1-(3-fluoro-4-piperazin-1-yl-phenyl)-ethanone and Compound 1.5 | 503.1 |
| 24 | 4-{4-[5-methanesulfonyl-2-(2,2,2-trifluoro-ethoxy)-benzoyl]-piperazin-1-yl}-benzonitrile | 4-piperazin-1-yl-benzonitrile and Compound 1.5 | 468.1 |
| 25 | 3-fluoro-4-{4-[5-methanesulfonyl-2-(2,2,2-trifluoro-ethoxy)-benzoyl]-piperazin-1-yl}-benzonitrile | 3-fluoro-4-piperazin-1-yl-benzonitrile and Compound 1.5 | 468.2 |
| 26 | 2-fluoro-4-{4-[5-methanesulfonyl-2-(2,2,2-trifluoro-ethoxy)-benzoyl]-piperazin-1-yl}-benzonitrile | 2-fluoro-4-piperazin-1-yl-benzonitrile and Compound 1.5 | 486.2 |
| 27 | [5-methanesulfonyl-2-(2,2,2-trifluoro-ethoxy)-phenyl]-[4-(4-trifluoromethyl-phenyl)-piperazin-1-yl]-methanone | 1-(4-trifluoromethyl-phenyl)-piperazine and Compound 1.5 | 511.2 |
| 28 | [4-(2-fluoro-4-trifluoromethyl-phenyl)-piperazin-1-yl]-[5-methanesulfonyl-2-(2,2,2-trifluoro-ethoxy)-phenyl]-methanone | 1-(2-fluoro-4-trifluoromethyl-phenyl)-piperazine and Compound 1.5 | 529.2 |
| 29 | [4-(3-fluoro-4-trifluoromethyl-phenyl)-piperazin-1-yl]-[5-methanesulfonyl-2-(2,2,2-trifluoro-ethoxy)-phenyl]-methanone | 1-(3-fluoro-4-trifluoromethyl-phenyl)-piperazine and Compound 1.5 | 529.2 |
| 30 | [4-(2-fluoro-4-methanesulfonyl-phenyl)-piperazin-1-yl]-[5-methanesulfonyl-2-(2,2,2-trifluoro-ethoxy)-phenyl]-methanone | 1-(2-fluoro-4-methanesulfonyl-phenyl)-piperazine and Compound 1.5 | 539.2 |
| 31 | 1-{4-[4-(2-cyclopentyloxy-5-methanesulfonyl-benzoyl)-piperazin-1-yl]-3-fluoro-phenyl}-ethanone | 1-(3-fluoro-4-piperazin-1-yl-phenyl)-ethanone and Compound 1.6 | 489.2 |
| 32 | 4-[4-(2-cyclopentyloxy-5-methanesulfonyl-benzoyl)-piperazin-1-yl]-benzonitrile | 4-piperazin-1-yl-benzonitrile and Compound 1.6 | 454.2 |
| 33 | 4-[4-(2-cyclopentyloxy-5-methanesulfonyl-benzoyl)-piperazin-1-yl]-3-fluoro-benzonitrile | 3-fluoro-4-piperazin-1-yl-benzonitrile and Compound 1.6 | 472.2 |
| 34 | 4-[4-(2-cyclopentyloxy-5-methanesulfonyl-benzoyl)-piperazin-1-yl]-2-fluoro-benzonitrile | 2-fluoro-4-piperazin-1-yl-benzonitrile and Compound 1.6 | 472.2 |
| 35 | (2-cyclopentyloxy-5-methanesulfonyl-phenyl)-[4-(2-fluoro-4-trifluoromethyl-phenyl)-piperazin-1-yl]-methanone | 1-(2-fluoro-4-trifluoromethyl-phenyl)-piperazine and Compound 1.6 | 515.2 |
| 36 | (2-cyclopentyloxy-5-methanesulfonyl-phenyl)-[4-(3-fluoro-4-trifluoromethyl-phenyl)-piperazin-1-yl]-methanone | 1-(3-fluoro-4-trifluoromethyl-phenyl)-piperazine and Compound 1.6 | 515.2 |

-continued

| Expl. No. | Systematic Name | Starting materials | MW found (MH+) |
|---|---|---|---|
| 37 | (2-cyclopentyloxy-5-methanesulfonyl-phenyl)-[4-(2-fluoro-4-methanesulfonyl-phenyl)-piperazin-1-yl]-methanone | 1-(2-fluoro-4-methanesulfonyl-phenyl)-piperazine and Compound 1.6 | 525.3 |
| 38 | 1-(3-fluoro-4-{4-[2-(4-fluoro-phenoxy)-5-methanesulfonyl-benzoyl]-piperazin-1-yl}-phenyl)-ethanone | 1-(3-fluoro-4-piperazin-1-yl-phenyl)-ethanone and Compound 1.7 | 515.2 |
| 39 | 4-{4-[2-(4-fluoro-phenoxy)-5-methanesulfonyl-benzoyl]-piperazin-1-yl}-benzonitrile | 4-piperazin-1-yl-benzonitrile and Compound 1.7 | 480.2 |
| 40 | 3-fluoro-4-{4-[2-(4-fluoro-phenoxy)-5-methanesulfonyl-benzoyl]-piperazin-1-yl}-benzonitrile | 3-fluoro-4-piperazin-1-yl-benzonitrile and Compound 1.7 | 498.2 |
| 41 | 2-fluoro-4-{4-[2-(4-fluoro-phenoxy)-5-methanesulfonyl-benzoyl]-piperazin-1-yl}-benzonitrile | 2-fluoro-4-piperazin-1-yl-benzonitrile and Compound 1.7 | 498.2 |
| 42 | [2-(4-fluoro-phenoxy)-5-methanesulfonyl-phenyl]-[4-(4-trifluoromethyl-phenyl)-piperazin-1-yl]-methanone | 1-(4-trifluoromethyl-phenyl)-piperazine and Compound 1.7 | 523.3 |
| 43 | [2-(4-fluoro-phenoxy)-5-methanesulfonyl-phenyl]-[4-(2-fluoro-4-trifluoromethyl-phenyl)-piperazin-1-yl]-methanone | 1-(2-fluoro-4-trifluoromethyl-phenyl)-piperazine and Compound 1.7 | 541.2 |
| 44 | [2-(4-fluoro-phenoxy)-5-methanesulfonyl-phenyl]-[4-(3-fluoro-4-trifluoromethyl-phenyl)-piperazin-1-yl]-methanone | 1-(3-fluoro-4-trifluoromethyl-phenyl)-piperazine and Compound 1.7 | 541.2 |
| 45 | [4-(2-fluoro-4-methanesulfonyl-phenyl)-piperazin-1-yl]-[2-(4-fluoro-phenoxy)-5-methanesulfonyl-phenyl]-methanone | 1-(2-fluoro-4-methanesulfonyl-phenyl)-piperazine and Compound 1.7 | 551.3 |
| 46 | [4-(2-fluoro-4-methanesulfonyl-phenyl)-piperazin-1-yl]-(2-isopropoxy-5-methanesulfonyl-phenyl)-methanone | 1-(2-fluoro-4-methanesulfonyl-phenyl)-piperazine and Compound 1.2 | 499.2 |
| 52 | 3-[4-(4-acetyl-2-fluoro-phenyl)-piperazine-1-carbonyl]-4-methoxy-benzenesulfonamide | 1-(3-Fluoro-4-piperazin-1-yl-phenyl)-ethanone and 2-methoxy-5-sulfamoyl-benzoic acid | 434.2 |
| 53 | 3-[4-(4-acetyl-2-fluoro-phenyl)-piperazine-1-carbonyl]-4-ethoxy-benzenesulfonamide | 1-(3-Fluoro-4-piperazin-1-yl-phenyl)-ethanone and 2-Ethoxy-5-sulfamoyl-benzoic acid | 448.2 |
| 54 | 1-(3-Fluoro-4-{4-[2-(2-methoxyethoxy)-5-nitro-benzoyl]-piperazin-1-yl}-phenyl)-ethanone | 1-(3-Fluoro-4-piperazin-1-yl-phenyl)-ethanone and 2-(2-Methoxyethoxy)-5-nitrobenzoic acid | 446.1 |

EXAMPLE 47

Preparation of 1-{3-fluoro-4-[4-(2-methoxy-5-nitro-benzoyl)-piperazin-1-yl]-phenyl}-ethanone To a solution of 0.257 mmol 1-{3-fluoro-4-[4-(2-fluoro-5-nitro-benzoyl)-piperazin-1-yl]-phenyl}-ethanone (Compound 1.8) in 1.5 ml dioxane 102 mg sodium methoxyde was added portionwise. The mixture was stirred at 100° C. for 4 h. The reaction mixture was diluted with 10 ml water, neutralized with 1N HCl and then extracted with ethylacetate (3×10 ml). Combined organic phases were concentrated in vacuo. The residue was chromatographed on silica gel:eluent:heptane/ethylacetate 0%-30% (10 min) to provide compound 47.

MS (m/e): 402.2 (M+H+, 100%).

EXAMPLE 48

Preparation of (2-benzyloxy-5-methanesulfonyl-phenyl)-[4-(4-trifluoromethyl-phenyl)-piperazin-1-yl]-methanone A mixture of 0.19 mmol (2-iodo-5-methanesulfonyl-phenyl)-[4-(4-trifluoromethyl-phenyl)-piperazin-1-yl]-methanone (Compound 1.9), 0.037 mmol CuI, 0.37 mmol $Cs_2CO_3$, 0.074 mmol 1,10-phenanthroline and 0.4 ml benzylic alcohol was heated at 110° C. for 16 hours. The mixture was cooled to RT, diluted with ethylacetate and filtered. The organic layer was washed twice with water, dried over $Na_2SO_4$, filtered and the solvent was removed in vacuo. The crude oil was purified on silica gel, eluent: heptane/ethylacetate 0%-50% (25 min) to provide compound 48.

MS (m/e): 519.2 (M+H+, 100%)

In analogy to Example 48 compounds 49 to 51 of the following table were prepared from (2-iodo-5-methanesulfonyl-phenyl)-[4-(4-trifluoromethyl-phenyl)-piperazin-1-yl]-methanone (Compound 1.9) and alcohols:

| Expl. No | Systematic Name | Starting materials | MW found (MH⁺) |
|---|---|---|---|
| 49 | (2-ethoxy-5-methanesulfonyl-phenyl)-[4-(4-trifluoromethyl-phenyl)-piperazin-1-yl]-methanone | Compound 1.9 and ethanol | 457.2 |
| 50 | (2-isopropoxy-5-methanesulfonyl-phenyl)-[4-(4-trifluoromethyl-phenyl)-piperazin-1-yl]-methanone | Compound 1.9 and isopropylalcohol | 471.2 |
| 51 | (2-cyclopentyloxy-5-methanesulfonyl-phenyl)-[4-(4-trifluoromethyl-phenyl)-piperazin-1-yl]-methanone | Compound 1.9 and cyclopentanol | 497.2 |

EXAMPLE 1.10

Preparation of
5-Methanesulfonyl-2-(2-methoxy-ethoxy)-benzoic acid (a) 2-Amino-5-methanesulfonyl-benzoic acid A mixture of 4.26 mmol 2-chloro-5-methanesulfonyl-benzoic acid (compound 1.2a), 0.39 mmol Copper powder and 10 ml ammonium hydroxide 25% was heated at 125-130° C. with stirring for 18 hours. The mixture was cooled to room temperature and filtered. The solid was washed with methanol. The filtrate was concentrated in vacuo. The residue was acidified with HCl 1N to pH=2. The obtained solid was washed with water and dried (HV, 50° C., 1 hour) to yield the title compound. MS (m/e): 214.1 (M−H, 100%)

(b) 2-Iodo-5-methanesulfonyl-benzoic acid

To a suspension of 3.0 mmol 2-amino-5-methanesulfonyl-benzoic acid in a mixture of 1.7 ml sulfuric acid and 1.7 ml water was added dropwise a solution of 3.92 mmol sodium nitrite in 1.7 ml water at such rate that the temperature did not exceed 3° C. The mixture was stirred at 0° C. for 1 hour. A solution of 3.0 mmol KI in 1.7 ml water was added dropwise at 0° C. The brown suspension was allowed to warm to rt and stirred for 30 minutes. Excess iodine was destroyed by addition of a few drops of a sodium hydrogenosulfite solution. The solid was filtered, washed with water and dried (HV, 50° C., 1 hour) to yield the title compound. MS (m/e): 325.0 (M−H, 100%)

(c) 5-Methanesulfonyl-2-(2-methoxy-ethoxy)-benzoic acid

To a solution of 1.6 mmol 2-iodo-5-methanesulfonyl-benzoic acid in 30 ml 2-methoxyethanol and 6 ml triethylamine were added 79 mg copper (I)bomide, and the reaction mixture heated to 120° C. for 4 h. The solvent was distilled off, and the residue dissolved in 90 ml 1N HCl. The aqueous phase was extracted twice with ethyl acetate, and the pooled organic extracts washed twice with water and once with brine. The organic layer was dried with $Na_2SO_4$, filtered and evaporated to yield the title compound 1.10. MS (m/e): 273.1 (MH⁻, 100%).

EXAMPLE 1.11

Preparation of
5-Cyano-2-(2-methoxy-ethoxy)-benzoic acid (a) 2-Bromo-5-cyano-benzoic acid To a suspension of 7.1 mmol copper (II) bromide in acetonitrile (30 ml) was added dropwise 8.63 mmol tert-butylnitrite at 0° C. within 2 minutes. 6.17 mmol 2-Amino-5-cyano-benzoic acid (CAS: 99767-45-0; WO9518097) was added portionwise within 10 minutes at 0° C. The mixture was stirred at 0° C. for 2 hours and then at room temperature overnight. Half of the solvent was removed in vacuo. The residue was taken in HCl 1N (15 ml) and ethyl acetate (30 ml). The organic layer was extracted with NaOH 1N (3×10 ml). The aqueous layer was acidified with HCl 2N. The resulting solid was filtered, washed with water and dried (high vacuum, 50° C.) to provide the title compound MS (m/e): 227.1 (M+H⁺, 100%)

(b) 5-Cyano-2-(2-methoxy-ethoxy)-benzoic acid

To a solution of 0.16 mmol 2-bromo-5-cyano-benzoic acid in 6 ml 2-methoxyethanol and 1.2 ml triethylamine were added 23 mg copper (I) bromide, and the reaction mixture heated to 120° C. for 4 h. The solvent was distilled off, and the residue dissolved in 20 ml 1N HCl. The aqueous phase was extracted twice with ethyl acetate, and the pooled organic extracts washed twice with water and once with brine. The organic layer was dried with $Na_2SO_4$, filtered and evaporated to yield the title compound 1.11. MS (m/e): 220.4 (MH⁻, 100%).

EXAMPLE 1.12

Preparation of
5-Cyano-2-(2,2,2-trifluoro-ethoxy)-benzoic acid

A mixture of 11.3 mmol sodium in 66 mmol 2,2,2-trifluoroethanol was heated to 100° C. until all sodium was dissolved (20 min.). Then a solution of 5.5 mmol 5-cyano-2-iodo-benzoic acid [CAS: 219841-92-6; WO9901455] in 2 ml N-methyl-2-pyrrolidone and 0.5 mmol copper (I) bromide were added, and the reaction mixture heated to 120° C. for 2 h. The reaction mixture was poured onto water, acidified to pH 2 with conc. HCl and extracted 3× with ethyl acetate. The pooled organic extracts were washed with brine, dried over $Na_2SO_4$ and evaporated. Flash chromatography on silica gel with heptane/ethyl acetate provided the title compound 1.12. MS (EI) (m/e): 245.1 (M⁺·, 94%), 146.0 ([M−CF₃CH₂O]⁺·, 100%).

In analogy to Example 1.12 compounds 1.13 to 1.16 of the following table were prepared from 5-cyano-2-iodo-benzoic acid and the appropriate alcohol:

|  | Compound Name | Alcohol | MS (m/e) |
|---|---|---|---|
| 1.13 | 5-Cyano-2-isopropoxy-benzoic acid | isopropanol | 204.1 (M − H⁻, 100%) |
| 1.14 | 5-Cyano-2-cyclopropylmethoxy-benzoic acid | cyclopropyl-methanol | 216.1 (M − H⁻, 100%) |
| 1.15 | 5-Cyano-2-isobutoxy-benzoic acid | isobutyl alcohol | 218.3 (M − H⁻, 100%) |
| 1.16 | 5-Cyano-2-cyclopentyloxy-benzoic acid | cyclopentanol | 230.1 (M − H⁻, 100%) |

In analogy to Example 5 compounds 55 to 61 of the following table were prepared from the acid derivatives and piperazine derivatives:

| Expl. No. | Systematic Name | Starting materials | MW found (MH⁺) |
|---|---|---|---|
| 55 | 1-(3-Fluoro-4-{4-[5-methanesulfonyl-2-(2-methoxyethoxy)-benzoyl]-piperazin-1-yl}-phenyl)-ethanone | 1-(3-Fluoro-4-piperazin-1-yl-phenyl)-ethanone (WO9714690) and 5-Methanesulfonyl-2-(2-methoxy-ethoxy)-benzoic acid (compound 1.10) | 479.5 |
| 56 | 4-(2-Methoxy-ethoxy)-3-[4-(4-trifluoromethyl-phenyl)-piperazine-1-carbonyl]-benzonitrile | 1-(4-Trifluoromethyl-phenyl)-piperazine and 5-cyano-2-(2-methoxy-ethoxy)-benzoic acid (compound 1.11) | 434.5 |
| 57 | 4-(2,2,2-Trifluoro-ethoxy)-3-[4-(4-trifluoromethyl-phenyl)-piperazine-1-carbonyl]-benzonitrile | 1-(4-trifluoromethylphenyl) piperazine and 5-Cyano-2-(2,2,2-trifluoro-ethoxy)-benzoic acid (compound 1.12) | 458.4 |
| 58 | 4-Isopropoxy-3-[4-(4-trifluoromethyl-phenyl)-piperazine-1-carbonyl]-benzonitrile | 1-(4-trifluoromethylphenyl) piperazine and 5-Cyano-2-isopropoxy-benzoic acid (compound 1.13) | 418.3 |
| 59 | 4-Cyclopropylmethoxy-3-[4-(4-trifluoromethyl-phenyl)-piperazine-1-carbonyl]-benzonitrile | 1-(4-trifluoromethylphenyl) piperazine and 5-Cyano-2-cyclopropylmethoxy-benzoic acid (compound 1.14) | 430.6 |
| 60 | 4-Isobutoxy-3-[4-(4-trifluoromethyl-phenyl)-piperazine-1-carbonyl]-benzonitrile | 1-(4-trifluoromethylphenyl) piperazine and 5-Cyano-2-isobutoxy-benzoic acid (compound 1.15) | 432.5 |
| 61 | 4-Cyclopentyloxy-3-[4-(4-trifluoromethyl-phenyl)-piperazine-1-carbonyl]-benzonitrile | 1-(4-trifluoromethylphenyl) piperazine and 5-Cyano-2-cyclopentyloxy-benzoic acid (compound 1.16) | 444.5 |

EXAMPLE 2.1

Preparation of (2-Hydroxy-5-nitro-phenyl)-[4-(4-trifluoromethyl-phenyl)-piperazin 1-yl]-methanone Compound 2.1 was prepared in analogy to Example 5 using 2-hydroxy-5-nitrobenzoic acid [96-97-9] and 1-(4-trifluoromethyl-phenyl)-piperazine. MS (m/e): 394.0 (M−H, 100%)

EXAMPLE 2.2

Preparation of (2-Hydroxy-5-methanesulfonyl-phenyl)-[4-(4-trifluoromethyl-phenyl)-piperazin-1-yl]-methanone Compound 2.2 was prepared in analogy to Example 5 using 2-hydroxy-5-(methylsulfonyl)benzoic acid [68029-77-6] and 1-(4-trifluoromethyl-phenyl)-piperazine. MS (m/e): 427.5 (M−H, 100%)

EXAMPLE 66

Preparation of (2-Butoxy-5-nitro-phenyl)-[4-(4-trifluoromethyl-phenyl)-piperazin-1-yl]-methanone A solution of (2-Hydroxy-5-nitro-phenyl)-[4-(4-trifluoromethyl-phenyl)-piperazin-1-yl]-methanone (50 mg), potassium carbonate (87 mg) and 1-bromobutane (0.15 mL) in dimethylacetamide (0.3 mL) was heated at 150° C. for 15 minutes in a microwave oven. The reaction mixture was then concentrated and purified by column chromatography ($SiO_2$) to give the title compound (55 mg).

In analogy to Example 66, compounds 62 to 97 of the following table were prepared from the acid derivatives and piperazine derivatives:

| Expl. No. | Systematic Name | Starting materials | MW found (MH+) |
|---|---|---|---|
| 62 | (2-Isopropoxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 2-bromopropane | 438.4 |
| 63 | (2-Cyclopropylmethoxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and cyclopropylmethylbromide | 450.5 |
| 64 | (2-Cyclobutylmethoxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and Cyclobutylmethylbromide | 464.5 |
| 65 | (2-Allyloxy-5-methanesulfonyl-phenyl)-[4-(4-trifluoromethyl-phenyl)-piperazin-1-yl]-methanone | (2-Hydroxy-5-methanesulfonyl-phenyl)-[4-(4-trifluoromethyl-phenyl)-piperazin-1-yl]-methanone (compound 2.2) and cyclopropylbromide | 469.5 |
| 66 | (2-Butoxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and bromobutane | 452.4 |
| 67 | Rac-[2-(2-Hydroxy-propoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and rac-1-Bromo-2-propanol | 454.6 |
| 68 | [2-(2,2-Dimethyl-propoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-Bromo-2,2-Dimethylpropane | 466.6 |
| 69 | [2-(3-Methyl-butoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-Bromo-3-methylbutane | 466.5 |
| 70 | (2-Isobutoxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-Bromo-3-methylpropane | 452.5 |
| 71 | (2-Cyclopentyloxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]- | 464.5 |

-continued

| Expl. No. | Systematic Name | Starting materials | MW found (MH+) |
|---|---|---|---|
| | piperazin-1-yl]-methanone | (compound 2.1) and Cyclopentyl bromide | |
| 72 | (5-Nitro-2-propoxy-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-Bromopropane | 438.5 |
| 73 | (2-Cycloheptyloxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and Bromocycloheptane | 492.5 |
| 74 | (2-Cyclobutoxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and Bromocyclobutane | 450.4 |
| 75 | [2-(2-Ethoxy-ethoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 2-Bromoethyl-ethylether | 468.5 |
| 76 | [2-((R)-3-Hydroxy-2-methyl-propoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and (R)-(−)-3-bromo-2-methyl-1-propanol | 468.4 |
| 77 | (2-Ethoxy-5-nitro-phenyl)-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 2-Bromo-1-ethoxy-1,1,2-trifluoro-ethane | 424.4 |
| 78 | Rac-(2-sec-Butoxy-5-nitro-phenyl)-[4-(4-trifluoromethyl-phenyl)-piperazin-1-yl]-methanone | Rac-(2-Hydroxy-5-nitro-phenyl)-[4-(4-trifluoromethyl-phenyl)-piperazin-1-yl]-methanone (compound 2.1) and 2-Bromobutane | 452.5 |
| 79 | [2-(2-Hydroxy-ethoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 2-Bromo-1-ethanol | 440.4 |
| 80 | [5-Nitro-2-(2,2,3,3-tetrafluoro-propoxy)-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-Iodo-2,2,3,3,-tetrafluoropropane | 510.5 |
| 81 | [5-Nitro-2-(4,4,4-trifluoro-butoxy)-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-Bromo-4,4,4,-trifluorobutane | 506.5 |
| 82 | [2-(2-Fluoro-ethoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-Bromo-2-fluoroethane | 442.5 |
| 83 | [2-(3-Hydroxy-2,2-dimethyl-propoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 3-Bromo-2,2-Dimethyl-2-propan-1-ol | 482.6 |
| 84 | [5-Nitro-2-(2,2,2-trifluoro-ethoxy)-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1,1,1-Trifluoro-2-iodo-ethane | 478.3 |
| 85 | [2-(1-Ethyl-propoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 3-Bromo-pentane | 466.5 |
| 86 | [5-Nitro-2-(oxetan-3-yloxy)-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and Toluene-4- | 452.4 |

-continued

| Expl. No. | Systematic Name | Starting materials | MW found (MH+) |
|---|---|---|---|
| 87 | [2-(3-Hydroxy-propoxy)-5-nitro-phenyl]-[4-(4-trifluoromethyl-phenyl)-piperazin-1-yl]-methanone | sulfonic acid oxetan-3-yl ester (CAS: 26272-83-3) (2-Hydroxy-5-nitro-phenyl)-[4-(4-trifluoromethyl-phenyl)-piperazin-1-yl]-methanone (compound 2.1) and Bromopropanole | 454.6 |
| 88 | [2-(Bicyclo[2.2.1]hept-2-yloxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and exo-2-Bromonorbornane | 490.5 |
| 89 | [2-(2-Methoxy-ethoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 2-bromoethylmethylether | 454.5 |
| 90 | [2-(3,3-Dimethyl-butoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-bromo-3,3-dimethylbutane | 480.8 |
| 91 | [2-(1-Ethoxy-cyclopropoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-Bromo-1-ethoxy-cyclopropane | 480.6 |
| 92 | [2-(2-Chloro-ethoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 2-Chloroethanol | 458.4 |
| 93 | {4-Nitro-2-[4-(4-trifluoromethyl-phenyl)-piperazine-1-carbonyl]-phenoxy}-acetonitrile | (2-Hydroxy-5-nitro-phenyl)-[4-(4-trifluoromethyl-phenyl)-piperazin-1-yl]-methanone (compound 2.1) and bromoacetonitrile | 435.4 |
| 94 | [5-Nitro-2-(3,3,3-trifluoro-propoxy)-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1,1,1-Trifluoro-1-Iodopropan | 492.4 |
| 95 | [5-Nitro-2-(tetrahydro-pyran-4-yloxy)-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 4-chloro-tetrahydropyrane | 480.4 |
| 96 | [2-(2,2-Difluoro-ethoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 1-bromo-2,2-difluoroethane | 460.5 |
| 97 | [2-(1,1,2,3,3,3-Hexafluoro-propoxy)-5-nitro-phenyl]-[4-(4-trifluoromethyl-phenyl)-piperazin-1-yl]-methanone | (2-Hydroxy-5-nitro-phenyl)-[4-(4-trifluoromethyl-phenyl)-piperazin-1-yl]-methanone (compound 2.1) and 3-Hexafluoropropane | 546.3 |

EXAMPLE 98

Preparation of (2-Difluoromethoxy-5-nitro-phenyl)-[4-(4-trifluoromethyl-phenyl)-piperazin-1-yl]-methanone In analogy to a procedure published in WO9749710, a solution of (2-Hydroxy-5-nitro-phenyl)-[4-(4-trifluoromethyl-phenyl)-piperazin-1-yl]-methanone (50 mg), potassium carbonate (1 eq), and ethyl chlorofluoroacetate (1 eq) in DMF (1 mL) was stirred at 65° C. for 16 hours. After such time the reaction mixture was concentrated in vacuo and purified by column chromatography (SiO$_2$) to yield the title compound (26 mg). MS (m/e): 446.0 (M+H+, 100%).

EXAMPLE 99

Preparation of 5-Nitro-2-(2,2,3,3-tetrafluoro-cyclobutylmethoxy)-phenyl-[4-(4-trifluoromethyl-phenyl)-piperazin-1-yl]-methanone Example 99 was prepared in analogy to Example 66 using 1-(chloromethyl)-2,2,3,3-tetrafluorocyclobutane [356-80-9]. MS (m/e): 536.3 (M+H+, 100%).

EXAMPLE 100

Preparation of [5-Nitro-2-(2,2,3,3,3-pentafluoro-propoxy)-phenyl]-[4-(4-trifluoromethyl-phenyl)-piperazin-1-yl]-methanone To a refluxing solution of 50 mg of (2-hydroxy-5-nitrophenyl)-[4-(4-trifluoromethyl-phenyl)-piperazin-1-yl]-methanone in acetone (2 mL) containing potassium carbonate (35 mg) was added 2,2,3,3,3-pentafluoropropyl trifluoromethanesulfonate (54 mg) over 10 min. The reaction mixture was refluxed for 20 hours before being concentrated in vacuo and purified by column chromatography ($SiO_2$, $CH_2Cl_2$/MeOH) to yield the title compound as a colorless solid (66 mg). MS (m/e): 569.0 (M+H$^+$, 100%).

EXAMPLE 101

Preparation of [2-(2-Fluoro-1-fluoromethyl-ethoxy)-5-nitro-phenyl]-[4-(4-trifluoromethyl-phenyl)-piperazin-1-yl]-methanone A solution of (2-hydroxy-5-nitro-phenyl)-[4-(4-trifluoromethyl-phenyl)-piperazin-1-yl]-methanone (50 mg), 1,3-difluoro-2-propanol [453-13-4] (27 mg), triphenylphosphine (76 mg) and diisopropylazodicarboxylate (48 mg) was refluxed overnight, concentrated in vacuo and purified by column chromatography ($SiO_2$) to yield the title compound as a colorless solid (68 mg). MS (m/e): 474.1 (M+H$^+$, 100%).

In analogy to Example 48, compounds 102 to 104 of the following table were prepared from (2-Iodo-5-methanesulfonyl-phenyl)-[4-(4-trifluoromethyl-phenyl)-piperazin-1-yl]-methanone (compound 1.9) and an alcohol:

EXAMPLE 105

Preparation of [5-Methanesulfonyl-2-(2,2,2-trifluoro-1,1-dimethyl-ethoxy)-phenyl]-[4-(5-trifluoromethyl-pyridin-2-yl)-piperazin-1-yl]-methanone A solution of (2-fluoro-5-methanesulfonyl-phenyl)-[4-(5-trifluoromethyl-pyridin-2-yl)-piperazin-1-yl]-methanone (compound 2.3) (20 mg), 2-trifluoromethyl-2-propanol (0.053 mL), potassium carbonate or cesium carbonate (3 equivalents) in dimethylacetamide was heated at 150° C. for 30 min and then at 180° C. for 1 h in a microwave oven. After such time the reaction mixture was concentrated and purified by column chromatography ($SiO_2$) to yield the title compound as a light yellow solid (4.9 mg). MS (m/e): 540.3 (M+H$^+$, 100%).

EXAMPLE 2.4

Preparation of (2-Isopropoxy-5-methanesulfonyl-phenyl)-piperazin-1-yl-methanone trifluoro-acetic acid A solution of 2-isopropoxy-5-methanesulfonyl-benzoic acid (compound 1.2, 1.0 g), tert-butyl 1-piperazinecarboxylate (0.78 g), TBTU (1.4 g) and N-ethyldiisopropylamine (4 mL) was stirred at room temperature for 2 hours. After such time, the reaction mixture was concentrated in vacuo and purified by column chromatography ($SiO_2$) to give 4-(2-Isopropoxy-5-methanesulfonyl-benzoyl)-piperazine-1-carboxylic acid tert-butyl ester as a colorless foam (1.6 g). The latter was dissolved in dichloromethane (11 mL) and treated with trifluroacetic acid (4.2 mL) for 30 minutes. After such

| Expl. No. | Systematic Name | Starting materials | MW found (MH$^+$) |
|---|---|---|---|
| 102 | [2-(1-Ethyl-propoxy)-5-methanesulfonyl-phenyl]-[4-(4-trifluoromethyl-phenyl)-piperazin-1-yl]-methanone | (2-Iodo-5-methanesulfonyl-phenyl)-[4-(4-trifluoromethyl-phenyl)-piperazin-1-yl]-methanone (compound 1.9) and 3-Pentanol | 499.5 |
| 103 | [5-Methanesulfonyl-2-(3-methyl-oxetan-3-ylmethoxy)-phenyl]-[4-(4-trifluoromethyl-phenyl)-piperazin-1-yl]-methanone | (2-Iodo-5-methanesulfonyl-phenyl)-[4-(4-trifluoromethyl-phenyl)-piperazin-1-yl]-methanone (compound 1.9) and Methyloxethanemethanol | 513.4 |
| 104 | Rac-[2-(1-Cyclopropyl-ethoxy)-5-methanesulfonyl-phenyl]-[4-(4-trifluoromethyl-phenyl)-piperazin-1-yl]-methanone | (2-Iodo-5-methanesulfonyl-phenyl)-[4-(4-trifluoromethyl-phenyl)-piperazin-1-yl]-methanone (compound 1.9) and rac-1-cyclopropylethanol | 497.4 |

EXAMPLE 2.3

Preparation of (2-Fluoro-5-methanesulfonyl-phenyl)-[4-(5-trifluoromethyl-pyridin-2-yl)-piperazin-1-yl]-methanone Compound 2.3 was prepared in analogy to Example 5 using 2-fluoro-5-(methylsulfonyl)benzoic acid [247569-56-8] and 1-(5-trifluoromethyl-2-pyridyl)piperazine [132834-58-3]. MS (m/e): 432.4 (M+H$^+$, 100%).

time the reaction mixture was concentrated in vacuo to yield the title compound (1.6 g) as light yellow oil. MS (m/e): 327.1 (M+H$^+$, 100%).

EXAMPLE 2.5

Preparation of 4-Chloro-6-trifluoromethyl-pyrimidine

6-Trifluoromethyl-pyrimidin-4-ol ([1546-78-7], 5 g) was refluxed in phosphorus oxychloride (17 mL) for 2 hours. The reaction mixture was carefully concentrated in vacuo and the residue was distilled (Kugelrohr) under reduced pressure (bp=30-55° C. @ 10 mbar) to yield the title compound ([37552-81-1], 1.4 g). MS (EI): 182.0 (M).

EXAMPLE 106

Preparation of (2-Isopropoxy-5-methanesulfonyl-phenyl)-[4-(5-nitro-pyridin-2-yl)-piperazin-1-yl]-methanone A solution of (2-isopropoxy-5-methanesulfonyl-phenyl)-piperazin-1-yl-methanone trifluoro-acetic acid (compound 2.4, 80 mg) 2-chloro-5-nitro-pyridine (29 mg), potassium carbonate (50 mg) in 1-butanol (3 mL) was stirred at 120° C. for 20 hours. After such time the solution was concentrated in vacuo, and purified by column chromatography (SiO2) to yield the title compound as white foam (81 mg). MS (m/e): 449.1 (M+H$^+$, 100%).

EXAMPLE 107

Preparation of (2-Isopropoxy-5-methanesulfonyl-phenyl)-[4-(6-trifluoromethyl-pyrimidin-4-yl)-piperazin-1-yl]-methanone Example 107 was prepared in analogy to example 106 using 4-chloro-6-trifluoromethyl-pyrimidine [37552-81-1]. MS (m/e): 473.1 (M+H$^+$, 100%).

EXAMPLE 2.6

Preparation of 2-(4-fluorophenoxy)-5-nitrobenzoic acid 2-(4-Fluoro-phenoxy)-5-nitro-benzoic acid can be prepared by a similar method to that described in the literature (e.g. WO9938845) by reaction of 2-Chloro-5-nitro-benzoic acid ethyl ester [16588-17-3] with 4-Fluoro-phenol [371-35-7] yielding 2-(4-Fluoro-phenoxy)-5-nitro-benzoic acid ethyl ester. 2-(4-Fluoro-phenoxy)-5-nitro-benzoic acid ethyl ester can then be hydrolysed with sodium hydroxide for example to yield the title compound. MS (m/e): 276.1 (M+H$^+$, 100%).

EXAMPLE 2.7

Preparation of 2,3-Difluoro-4-piperazin-1-yl-benzonitrile-trifluoro-acetic acid (a) 4-(4-Cyano-2,3-difluoro-phenyl)-piperazine-1-carboxylic acid tert-butyl ester To a solution of N-Boc-Piperazine (0.65 g) in DMA (20 mL) was slowly added a solution of 2,3,4-trifluorobenzonitrile (0.49 g) in DMA (10 mL). The reaction mixture was stirred for 2 hours at 80° C. After such time the solvent was removed in vacuo and purified by column chromatography (SiO$_2$) to yield the title compound as white solid (0.76 g).

(b) 2,3-Difluoro-4-piperazin-1-yl-benzonitrile-trifluoro-acetic acid

To a solution of 4-(4-Cyano-2,3-difluoro-phenyl)-piperazine-1-carboxylic acid tert-butyl ester (0.72 g) in dichloromethane (5 mL) was added trifluoroacetic acid, and the reaction mixture was stirred at room temperature for 30 minutes. After such time the reaction mixture was concentrated in vacuo to yield the title compound (0.63 g). MS (m/e): 224.3 (M+H$^+$, 100%).

EXAMPLE 2.8

Preparation of 2,5-Difluoro-4-piperazin-1-yl-benzonitrile-trifluoro-acetic acid

Example 2.8 was prepared in analogy to Example 2.7 using 2,4,5-trifluorobenzonitrile. MS (m/e): 224.3 (M+H$^+$, 100%).

EXAMPLE 2.9

Preparation of 5-Methylsulfamoyl-2-trifluoromethoxy-benzoic acid (a) 5-Chlorosulfonyl-2-trifluoromethoxy-benzoic acid A solution of 2-trifluoromethoxy benzoic acid [1979-29-9] (1.0 g) was added in small batches to chlorosulfonic acid (3.2 mL) at 0° C. After completion of the addition, the reaction mixture was stirred at 70° C. for 4 hours then left at room temperature overnight and heated at 75° C. for another 3 hours. After such time the reaction was slowly poured onto ice, and the precipitate was then filtered, washed with water and dried to yield the title compound as a white solid (1.2 g). MS (m/e): 303.3 (M−H, 100%).

(b) 5-Methylsulfamoyl-2-trifluoromethoxy-benzoic acid

To a solution of 5-Chlorosulfonyl-2-trifluoromethoxy-benzoic acid (0.15 g) in dichloromethane (1.5 ml) was added a solution of methylamine in methanol (8M, 0.31 mL), and the reaction mixture was stirred for 2 minutes after precipitation was complete. The reaction mixture was then concentrated in vacuo and the residue was dissolved in 1N NaOH (2 mL) and extracted with diethylether. The aqueous phase was then acidified using 3 N hydrochloric acid solution (2 mL), and the solution was extracted with dichloromethane (2×10 mL). The combined organic phases were dried with sodium sulfate and concentrated in vacuo to yield the title compound as a white solid (0.12 g). MS (m/e): 298.0 (M−H, 100%).

EXAMPLE 2.10

Preparation of 5-Methanesulfonyl-2-(3,3,3-trifluoro-propoxy)-benzoic acid (a) 5-Methanesulfonyl-2-(3,3,3-trifluoro-propoxy)-benzoic acid methyl ester A solution of methyl 5-(methanesulfonyl)-salicylate [101371-44-2] (50 mg), triphenylphosphine (65 mg) 3,3,3-trifluoro-1-propanol and di-tert-butyl azodicarboxylate (55 mg) in THF (3 mL) was stirred at room temperature for 1 hour. The reaction mixture was then concentrated in vacuo and purified by column chromatography (SiO$_2$) to yield the title compound as a white solid (65 mg). MS (m/e): 327.5 (M+H$^+$, 100%).

(b) 5-Methanesulfonyl-2-(3,3,3-trifluoro-propoxy)-benzoic acid

To 5-methanesulfonyl-2-(3,3,3-trifluoro-propoxy)-benzoic acid methyl ester (620 mg) in ethanol at 60° C. was added 1N NaOH solution (3.8 mL), and the reaction mixture was stirred for 15 minutes. After such time, 3.8 ml of 1N HCl was slowly added to the reaction mixture, and the ethanol was evaporated in vacuo. The precipitate was then washed with water several times to give the title compound (497 mg). MS (m/e): 311.0, M−H$^+$, 100%).

EXAMPLE 2.11

Preparation of 5-Methanesulfonyl-2-(tetrahydro-pyran-4-yloxy)-benzoic acid

Compound 2.11 was prepared in analogy to compound 2.10 using tetrahydro-2H-pyran-4-ol. MS (m/e): 299.4 (M−H, 100%).

EXAMPLE 2.12

Preparation of 2-Cyclobutylmethoxy-5-methanesulfonyl-benzoic acid

Compound 2.12 was prepared in analogy to compound 2.10 using cyclobutyl methanol. MS (m/e): 299.4 (M−H, 100%).

EXAMPLE 2.13

Preparation of 3,5-Difluoro-4-piperazin-1-yl-benzonitrile trifluoro-acetic acid

Compound 2.13 was prepared in analogy to compound 2.7 using 3,4,5-trifluorobenzonitrile. MS (m/e): 224.1 (M+H$^+$, 100%).

EXAMPLE 2.14

Preparation of 2,6-Difluoro-4-piperazin-1-yl-benzonitrile trifluoro-acetic acid

Compound 2.14 was prepared in analogy to compound 2.7 using 2,4,6-trifluorobenzonitrile. MS (m/e): 224.1 (M+H$^+$, 100%).

EXAMPLE 2.15

Preparation of 5-Methanesulfonyl-2-trifluoromethoxy-benzoic acid (a) 5-Sulfino-2-trifluoromethoxy-benzoic acid 5-chlorosulfonyl-2-trifluoromethoxy-benzoic acid (1.0 g, compound 2.9.a) was added portionwise onto a solution of sodium sulfite (3.1 g) in 16 mL of water. The reaction mixture was kept under basic conditions by the addition of the proper amount of 20% NaOH and was stirred at room temperature for 45 minutes. After such time the reaction mixture was cooled down with an ice bath and was then acidified by the addition of 20% H$_2$SO$_4$ solution until reaching pH 2. The solution was then extracted several times with diethyl ether and ethyl acetate. The combined organic phases were dried (sodium sulfate) and concentrated in vacuo to yield the title compound as a white solid (0.88 g).

(b) 5-Methanesulfonyl-2-trifluoromethoxy-benzoic acid

To 5-Sulfino-2-trifluoromethoxy-benzoic acid (0.82 g) in DMF (5 mL) was added 1.3 g of potassium carbonate, and the reaction mixture was stirred for 5 minutes before methyl iodide (0.66 mL) was added. The reaction mixture was then stirred at room temperature for 60 hours. After such time the reaction mixture was concentrated in vacuo, and the residue was treated with 1N NaOH (10 mL) and THF (4 mL). The reaction mixture was stirred for a further 2 hours at room temperature. After such time the solution was acidified with concentrated HCl solution. THF was then removed in vacuo) and the precipitate was isolated by filtration and washed several times with water to yield the title compound. MS (m/e): 283.0 (M−H, 100%).

EXAMPLE 2.16

Preparation of 2,4-Difluoro-6-piperazin-1-yl-benzonitrile trifluoro-acetic acid

Compound 2.16 was prepared in analogy to compound 2.7 using 2,4,6-trifluorobenzonitrile of. MS (m/e): 224.1 (M+H$^+$, 100%).

EXAMPLE 2.17

Preparation of 2-(2-Fluoro-1-fluoromethyl-ethoxy)-5-methanesulfonyl-benzoic acid Compound 2.17 was prepared in analogy to compound 2.10 using 1,3-difluoro-2-propanol. MS (m/e): 293.1 (M−H, 100%).

EXAMPLE 2.18

Preparation of 5-Methanesulfonyl-2-(2,2,3,3,3-pentafluoro-propoxy)-benzoic acid (a) 5-Methanesulfonyl-2-(2,2,3,3,3-pentafluoro-propoxy)-benzoic acid methyl ester A solution of methyl 5-(methanesulfonyl)salicylate [101371-44-2] (0.50 g), trifluoro-methanesulfonic acid 2,2,3,3,3-pentafluoro-propyl ester (0.67 g) and potassium carbonate (0.60 g) in acetone was stirred at 60° C. for 5 hours. The reaction mixture was then concentrated in vacuo and purified by column chromatography (SiO$_2$) to yield the title compound as a white solid (0.44 g). MS (m/e): 363.1 (M+H$^+$, 100%).

(b) 5-Methanesulfonyl-2-(2,2,3,3,3-pentafluoro-propoxy)-benzoic acid

To 5-methanesulfonyl-2-(2,2,3,3,3-pentafluoro-propoxy)-benzoic acid methyl ester (414 mg) in THF (5 mL) was added a solution of lithium hydroxide monohydrate (72 mg) in water (5 mL), and the reaction mixture was stirred at room temperature for 1 hour. After such time 1.72 mL of 1N aqueous hydrochloric acid solution was added. The reaction mixture was then concentrated in vacuo, and the resulting precipitate was then washed several times with water to yield the title compound as a white solid (367 mg). MS (m/e): 347.1 (M−H, 100%).

EXAMPLE 2.19

Preparation of 2-tert-Butoxy-5-methanesulfonyl-benzoic acid (a) 2-tert-Butoxy-5-methanesulfonyl-benzoic acid methyl ester To a solution of methyl 5-(methanesulfonyl)-salicylate [101371-44-2] (0.50 g) in toluene (5 mL) was added N,N-dimethylformamide-di-tert-butylacetal, and the reaction mixture was stirred at 80° C. for 1 hour. After such time the reaction mixture was concentrated in vacuo and purified by column chromatography to yield the title compound as colourless oil (258 mg). MS (m/e): 304.4 (M+NH$_4^+$, 100%).

(b) 2-tert-Butoxy-5-methanesulfonyl-benzoic acid

To 2-tert-Butoxy-5-methanesulfonyl-benzoic acid methyl ester (1.58 g) in THF (25 mL) was added a solution lithium hydroxide monohydrate (0.35 g) in water (25 mL), and the reaction mixture was stirred at room temperature for 4 hours. After such time, the THF was removed in vacuo and to the remaining aqueous solution was added 8 mL of 1N HCl solution, leading to precipitation of the compound. The precipitate was filtered off and washed several times with water to yield the title compound (1.00 g) as a white solid. MS (m/e): 289.9 (M+NH$_4^+$).

EXAMPLE 2.20

Preparation of 1-(2,5-Difluoro-4-methanesulfonyl-phenyl)-piperazine trifluoro-acetic acid (a) 2,4,5-Trifluoro-benzenesulfinic acid 2,4,5-Trifluoro-benzenesulfonyl chloride ([220227-21-4], 2.5 g) was added portionwise onto a solution of sodium sulfite (10.3 g) in 50 mL of water. The reaction mixture was kept under basic conditions by the addition of the proper amount of 20% NaOH and was stirred at room temperature for 1 hour. Methanol was added to the reaction mixture, and the reaction mixture was stirred at room temperature for another hour. After such time, the reaction mixture was cooled down with an ice bath and was then acidified by the addition of 20% H$_2$SO$_4$ solution until reaching pH 2. The aqueous solution was then extracted several times with diethyl ether and ethyl acetate. The aqueous solution was further extracted with ethyl acetate using a Kutscher-Steudel apparatus (continuous extraction). The combined organic phases were dried (sodium sulfate) an concentrated in vacuo to yield the title compound as a white solid (2.1 g).

(b) 1,2,4-Trifluoro-5-methanesulfonyl-benzene

To 2,4,5-trifluoro-benzenesulfinic acid (2.0 g) in DMF (17 mL) was added 4.3 g of potassium carbonate, and the reaction mixture was stirred for 5 minutes before methyl iodide (2.2 mL) was added. The reaction mixture was then stirred at room temperature for 60 hours. After such time, water (30 mL) was poured onto the reaction mixture, and the reaction mixture was extracted with diethylether several times. The combined organic phases were dried with sodium sulfate, and the remaining mixture was distilled to yield the title compound as a light yellow oil (2.1 g).

(c) 1-(2,5-Difluoro-4-methanesulfonyl-phenyl)-piperazine trifluoro-acetic acid

The title compound was obtained in analogy to example 2.7 using 1,2,4-Trifluoro-5-methanesulfonyl-benzene. MS (m/e): 277.1 (M+H$^+$).

EXAMPLE 2.21

Preparation of 1-(3,5-Difluoro-4-methanesulfonyl-phenyl)-piperazine trifluoro-acetic acid Compound 2.21 was prepared in analogy to compound 2.20 using 2,4,6-trifluoro-benzenesulfonyl chloride [172326-59-9]. MS (m/e): 277.1 (M+H$^+$).

EXAMPLE 2.22

Preparation of 5-Methanesulfonyl-2-(2,2,3,3-tetrafluoro-propoxy)-benzoic acid

Compound 2.22 was prepared in analogy to compound 2.18 using 2,2,3,3-tetrafluoro-1-propyl triflate. MS (m/e): 329.1 (M−H).

EXAMPLE 2.23

Preparation of 1-(2,6-Difluoro-4-methanesulfonyl-phenyl)-piperazine trifluoro-acetic acid Compound 2.23 was prepared in analogy to compound 2.20 using 3,4,5-trifluoro-benzenesulfonyl chloride [351003-43-5]. MS (m/e): 277.1 (M+H$^+$).

EXAMPLE 2.24

Preparation of 4-Piperazin-1-yl-6-trifluoromethyl-pyrimidine trifluoro-acetic acid Compound 2.24 was prepared in analogy to compound 2.7 using 4-chloro-6-trifluoromethyl-pyrimidine [37552-81-1]. MS (m/e): 233.1 (M+H$^+$).

EXAMPLE 2.25

Preparation of 2-Piperazin-1-yl-5-trifluoromethyl-pyrimidine (a) 2-(4-Benzyl-piperazin-1-yl)-5-trifluoromethyl-pyrimidine To a solution of (3-Dimethylamino-2-trifluoromethyl-allylidene)-dimethyl-ammonium chloride ([176214-18-9], 0.60 g) in acetonitrile (10 mL) was added 4-Benzyl-piperazine-1-carboxamidine hydrochloride ([7773-69-5], 0.66 g) and triethylamine (0.87 mL), and the reaction mixture was stirred for 3 hours at room temperature. After such time, the reaction mixture was concentrated in vacuo and purified by column chromatography to yield the title compound as a light yellow solid (0.79 g). MS (m/e): 323.4 (M+H$^+$).

(b) 2-Piperazin-1-yl-5-trifluoromethyl-pyrimidine

To a solution of 2-(4-Benzyl-piperazin-1-yl)-5-trifluoromethyl-pyrimidine (0.63 g) in methanol was added Palladium-C (Degussa E101N; 5%), and the reaction mixture was heated at 60° C. under hydrogen atmosphere. The reaction mixture was then allowed to cool down to room temperature, the catalyst was filtered off, and solvent was removed in vacuo to yield the title compound as a colorless solid (0.41 g). MS (m/e): 233.1 (M+H$^+$).

In analogy to Example 5 compounds 108 to 280 of the following table were prepared from the acid derivatives and piperazine derivatives:

| Expl. No. | Systematic Name | Starting materials | MW found (MH$^+$) |
| --- | --- | --- | --- |
| 108 | [2-(4-Fluoro-phenoxy)-5-nitro-phenyl]-[4-(4-trifluoromethyl- | 1-(4-trifluoromethyl-phenyl)piperazine and 2-(4-fluorophenoxy)-5- | 490.5 |

-continued

| Expl. No. | Systematic Name | Starting materials | MW found (MH+) |
|---|---|---|---|
| | phenyl)-piperazin-1-yl]-methanone | nitrobenzoic acid (compound 2.6) | |
| 109 | 2,3-Difluoro-4-[4-(2-isopropoxy-5-methanesulfonyl-benzoyl)-piperazin-1-yl]-benzonitrile | 2,3-Difluoro-4-piperazin-1-yl-benzonitrile-trifluoro-acetic acid (compound 2.7) and 2-Isopropoxy-5-methanesulfonyl-benzoic acid (compound 1.2) | 464.3 |
| 110 | 2,5-Difluoro-4-[4-(2-isopropoxy-5-methanesulfonyl-benzoyl)-piperazin-1-yl]-benzonitrile | 2,5-Difluoro-4-piperazin-1-yl-benzonitrile-trifluoro-acetic acid (compound 2.8) and 2-Isopropoxy-5-methanesulfonyl-benzoic acid (compound 1.2) | 464.1 |
| 111 | 3-[4-(4-Cyano-3-fluoro-phenyl)-piperazine-1-carbonyl]-N-methyl-4-trifluoromethoxy-benzenesulfonamide | 2-Fluoro-4-piperazin-1-yl benzonitrile (WO 9808835) and 5-Methylsulfamoyl-2-trifluoromethoxy-benzoic acid (compound 2.9) | 487.1 |
| 112 | 3-Fluoro-4-{4-[5-methanesulfonyl-2-(3,3,3-trifluoro-propoxy)-benzoyl]-piperazin-1-yl}-benzonitrile | 3-Fluoro-4-piperazin-1-yl-benzonitrile (WO9625414) and 5-Methanesulfonyl-2-(3,3,3-trifluoro-propoxy)-benzoic acid (compound 2.10) | 500.3 |
| 113 | 4-{4-[5-Methanesulfonyl-2-(3,3,3-trifluoro-propoxy)-benzoyl]-piperazin-1-yl}-benzonitrile | 4-Piperazin-1-yl-benzonitrile (commercial) and 5-Methanesulfonyl-2-(3,3,3-trifluoro-propoxy)-benzoic acid (compound 2.10) | 482.3 |
| 114 | 2-Fluoro-4-{4-[5-methanesulfonyl-2-(3,3,3-trifluoro-propoxy)-benzoyl]-piperazin-1-yl}-benzonitrile | 2-Fluoro-4-piperazin-1-yl-benzonitrile (WO 9808835) and 5-Methanesulfonyl-2-(3,3,3-trifluoro-propoxy)-benzoic acid (compound 2.10) | 500.3 |
| 115 | [5-Methanesulfonyl-2-(3,3,3-trifluoro-propoxy)-phenyl]-[4-(4-trifluoromethyl-phenyl)-piperazin-1-yl]-methanone | 1-(4-Trifluoromethyl-phenyl)-piperazine (commercial) and 5-Methanesulfonyl-2-(3,3,3-trifluoro-propoxy)-benzoic acid (compound 2.10) | 525.2 |
| 116 | [4-(3-Fluoro-4-trifluoromethyl-phenyl)-piperazin-1-yl]-[5-methanesulfonyl-2-(3,3,3-trifluoro-propoxy)-phenyl]-methanone | 1-(3-Fluoro-4-trifluoromethyl-phenyl)-piperazine (compound 5.1) and 5-Methanesulfonyl-2-(3,3,3-trifluoro-propoxy)-benzoic acid (compound 2.10) | 543.3 |
| 117 | [4-(2-Fluoro-4-trifluoromethyl-phenyl)-piperazin-1-yl]-[5-methanesulfonyl-2-(3,3,3-trifluoro-propoxy)-phenyl]-methanone | 1-(2-Fluoro-4-trifluoromethyl-phenyl)-piperazine (compound 1.1) and 5-Methane-sulfonyl-2-(3,3,3-trifluoro-propoxy)-benzoic acid (compound 2.10) | 543.2 |
| 118 | 1-(3-Fluoro-4-{4-[5-methanesulfonyl-2-(3,3,3-trifluoro-propoxy)-benzoyl]-piperazin-1-yl}-phenyl)-ethanone | 1-(3-Fluoro-4-piperazin-1-yl-phenyl)-ethanone (WO9714690) and 5-Methanesulfonyl-2-(3,3,3-trifluoro-propoxy)-benzoic acid (compound 2.10) | 517.3 |
| 119 | [4-(2-Fluoro-4-methanesulfonyl-phenyl)-piperazin-1-yl]-[5-methanesulfonyl-2-(3,3,3-trifluoro-propoxy)-phenyl]-methanone | 1-(2-Fluoro-4-methanesulfonyl-phenyl)-piperazine (commercial) and 5-Methanesulfonyl-2-(3,3,3-trifluoro-propoxy)-benzoic acid (compound 2.10) | 553.2 |
| 120 | 4-{4-[5-Methanesulfonyl-2-(tetrahydro-pyran-4-yloxy)-benzoyl]-piperazin-1-yl}-benzonitrile | 4-Piperazin-1-yl-benzonitrile (commercial) and 5-Methanesulfonyl-2-(tetrahydro-pyran-4-yloxy)-benzoic acid (compound 2.11) | 470.0 |
| 121 | 2-Fluoro-4-{4-[5-methanesulfonyl-2-(tetrahydro-pyran-4- | 2-Fluoro-4-piperazin-1-yl-benzonitrile (WO 9808835) and 5-Methanesulfonyl-2- | 488.1 |

-continued

| Expl. No. | Systematic Name | Starting materials | MW found (MH+) |
|---|---|---|---|
| | yloxy)-benzoyl]-piperazin-1-yl}-benzonitrile | (tetrahydro-pyran-4-yloxy)-benzoic acid (compound 2.11) | |
| 122 | 3-Fluoro-4-{4-[5-methanesulfonyl-2-(tetrahydro-pyran-4-yloxy)-benzoyl]-piperazin-1-yl}-benzonitrile | 3-Fluoro-4-piperazin-1-yl-benzonitrile (WO9625414) and 5-Methanesulfonyl-2-(tetrahydro-pyran-4-yloxy)-benzoic acid (compound 2.11) | 488.0 |
| 123 | [5-Methanesulfonyl-2-(tetrahydro-pyran-4-yloxy)-phenyl]-[4-(4-trifluoromethyl-phenyl)-piperazin-1-yl]-methanone | 1-(4-Trifluoromethyl-phenyl)-piperazine (commercial) and 5-Methanesulfonyl-2-(tetrahydro-pyran-4-yloxy)-benzoic acid (compound 2.11) | 513.3 |
| 124 | [4-(3-Fluoro-4-trifluoromethyl-phenyl)-piperazin-1-yl]-[5-methanesulfonyl-2-(tetrahydro-pyran-4-yloxy)-phenyl]-methanone | 1-(3-Fluoro-4-trifluoromethyl-phenyl)-piperazine (compound 5.1) and 5-Methanesulfonyl-2-(tetrahydro-pyran-4-yloxy)-benzoic acid (compound 2.11) | 531.0 |
| 125 | [4-(2-Fluoro-4-trifluoromethyl-phenyl)-piperazin-1-yl]-[5-methanesulfonyl-2-(tetrahydro-pyran-4-yloxy)-phenyl]-methanone | 1-(2-Fluoro-4-trifluoromethyl-phenyl)-piperazine (compound 1.1) and 5-Methanesulfonyl-2-(tetrahydro-pyran-4-yloxy)-benzoic acid (compound 2.11) | 531.2 |
| 126 | 1-(3-Fluoro-4-{4-[5-methanesulfonyl-2-(tetrahydro-pyran-4-yloxy)-benzoyl]-piperazin-1-yl}-phenyl)-ethanone | 1-(3-Fluoro-4-piperazin-1-yl-phenyl)-ethanone (WO9714690) and 5-Methanesulfonyl-2-(tetrahydro-pyran-4-yloxy)-benzoic acid (compound 2.11) | 505.1 |
| 127 | [4-(2-Fluoro-4-methanesulfonyl-phenyl)-piperazin-1-yl]-[5-methanesulfonyl-2-(tetrahydro-pyran-4-yloxy)-phenyl]-methanone | 1-(2-Fluoro-4-methanesulfonyl-phenyl)-piperazine (commercial) and 5-Methanesulfonyl-2-(tetrahydro-pyran-4-yloxy)-benzoic acid (compound 2.11) | 541.3 |
| 128 | 2,3-Difluoro-4-[4-(2-isobutoxy-5-methanesulfonyl-benzoyl)-piperazin-1-yl]-benzonitrile | 2,3-Difluoro-4-piperazin-1-yl-benzonitrile-trifluoro-acetic acid (compound 2.7) and 2-Isobutoxy-5-methanesulfonyl-benzoic acid (compound 1.3) | 478.1 |
| 129 | 4-[4-(2-Cyclopropylmethoxy-5-methanesulfonyl-benzoyl)-piperazin-1-yl]-2,3-difluoro-benzonitrile | 2,3-Difluoro-4-piperazin-1-yl-benzonitrile-trifluoro-acetic acid (compound 2.7) and 2-Cyclopropylmethoxy-5-methanesulfonyl-benzoic acid (compound 1.4) | 476.3 |
| 130 | 2,3-Difluoro-4-{4-[5-methanesulfonyl-2-(tetrahydro-pyran-4-yloxy)-benzoyl]-piperazin-1-yl}-benzonitrile | 2,3-Difluoro-4-piperazin-1-yl-benzonitrile-trifluoro-acetic acid (compound 2.7) and 5-Methanesulfonyl-2-(tetrahydro-pyran-4-yloxy)-benzoic acid (compound 2.11) | 506.4 |
| 131 | 4-[4-(2-Cyclopentyloxy-5-methanesulfonyl-benzoyl)-piperazin-1-yl]-2,3-difluoro-benzonitrile | 2,3-Difluoro-4-piperazin-1-yl-benzonitrile-trifluoro-acetic acid (compound 2.7) and 2-Cyclopentyloxy-5-methanesulfonyl-benzoic acid (compound 1.6) | 490.5 |
| 132 | 2,5-Difluoro-4-[4-(2-isobutoxy-5-methanesulfonyl-benzoyl)-piperazin-1-yl]-benzonitrile | 2,5-Difluoro-4-piperazin-1-yl-benzonitrile-trifluoro-acetic acid (compound 2.8) and 2-Isobutoxy-5-methanesulfonyl-benzoic acid (compound 1.3) | 478.4 |
| 133 | 4-[4-(2-Cyclopropylmethoxy-5-methanesulfonyl-benzoyl)-piperazin-1-yl]- | 2,5-Difluoro-4-piperazin-1-yl-benzonitrile-trifluoro-acetic acid (compound 2.8) and 2-Cyclopropylmethoxy- | 476.3 |

-continued

| Expl. No. | Systematic Name | Starting materials | MW found (MH+) |
|---|---|---|---|
| | 2,5-difluoro-benzonitrile | 5-methanesulfonyl-benzoic acid (compound 1.4) | |
| 134 | 2,5-Difluoro-4-{4-[5-methanesulfonyl-2-(tetrahydro-pyran-4-yloxy)-benzoyl]-piperazin-1-yl}-benzonitrile | 2,5-Difluoro-4-piperazin-1-yl-benzonitrile-trifluoro-acetic acid (compound 2.8) and 5-Methanesulfonyl-2-(tetrahydro-pyran-4-yloxy)-benzoic acid (compound 2.11) | 506.4 |
| 135 | 4-[4-(2-Cyclopentyloxy-5-methanesulfonyl-benzoyl)-piperazin-1-yl]-2,5-difluoro-benzonitrile | 2,5-Difluoro-4-piperazin-1-yl-benzonitrile-trifluoro-acetic acid (compound 2.8) and 2-Cyclopentyloxy-5-methanesulfonyl-benzoic acid (compound 1.6) | 490.5 |
| 136 | 4-[4-(2-Cyclobutylmethoxy-5-methanesulfonyl-benzoyl)-piperazin-1-yl]-benzonitrile | 4-Piperazin-1-yl-benzonitrile (commercial) and 2-Cyclobutylmethoxy-5-methanesulfonyl-benzoic acid (compound 2.12) | 454.6 |
| 137 | 4-[4-(2-Cyclobutylmethoxy-5-methanesulfonyl-benzoyl)-piperazin-1-yl]-2-fluoro-benzonitrile | 2-Fluoro-4-piperazin-1-yl-benzonitrile (WO 9808835) and 2-Cyclobutylmethoxy-5-methanesulfonyl-benzoic acid (compound 2.12) | 472.3 |
| 138 | 4-[4-(2-Cyclobutylmethoxy-5-methanesulfonyl-benzoyl)-piperazin-1-yl]-3-fluoro-benzonitrile | 3-Fluoro-4-piperazin-1-yl-benzonitrile (WO9625414) and 2-Cyclobutylmethoxy-5-methanesulfonyl-benzoic acid (compound 2.12) | 472.3 |
| 139 | (2-Cyclobutylmethoxy-5-methanesulfonyl-phenyl)-[4-(4-trifluoromethyl-phenyl)-piperazin-1-yl]-methanone | 1-(4-Trifluoromethyl-phenyl)-piperazine (commercial) and 2-Cyclobutylmethoxy-5-methanesulfonyl-benzoic acid (compound 2.12) | 497.3 |
| 140 | (2-Cyclobutylmethoxy-5-methanesulfonyl-phenyl)-[4-(3-fluoro-4-trifluoromethyl-phenyl)-piperazin-1-yl]-methanone | 1-(3-Fluoro-4-trifluoromethyl-phenyl)-piperazine (compound 5.1) and 2-Cyclobutylmethoxy-5-methanesulfonyl-benzoic acid (compound 2.12) | 515.4 |
| 141 | (2-Cyclobutylmethoxy-5-methanesulfonyl-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and 2-Cyclobutylmethoxy-5-methanesulfonyl-benzoic acid (compound 2.12) | 515.4 |
| 142 | 1-{4-[4-(2-Cyclobutylmethoxy-5-methanesulfonyl-benzoyl)-piperazin-1-yl]-3-fluoro-phenyl}-ethanone | 1-(3-Fluoro-4-piperazin-1-yl-phenyl)-ethanone (WO9714690) and 2-Cyclobutylmethoxy-5-methanesulfonyl-benzoic acid (compound 2.12) | 489.5 |
| 143 | (2-Cyclobutylmethoxy-5-methanesulfonyl-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 2-Cyclobutylmethoxy-5-methanesulfonyl-benzoic acid (compound 2.12) | 525.3 |
| 144 | 2-[4-(2-Cyclobutylmethoxy-5-methanesulfonyl-benzoyl)-piperazin-1-yl]-5-trifluoromethyl-benzonitrile | 2-Piperazin-1-yl-5-trifluoromethyl-benzonitrile (compound 5.2) and 2-Cyclobutylmethoxy-5-methanesulfonyl-benzoic acid (compound 2.12) | 522.4 |
| 145 | 4-[4-(2-Cyclobutylmethoxy-5-methanesulfonyl-benzoyl)-piperazin-1-yl]-2,3-difluoro-benzonitrile | 2,3-Difluoro-4-piperazin-1-yl-benzonitrile-trifluoro-acetic acid (compound 2.7) and 2-Cyclobutylmethoxy-5-methanesulfonyl-benzoic acid (compound 2.12) | 490.5 |
| 146 | 4-[4-(2-Cyclobutylmethoxy-5-methanesulfonyl-benzoyl)-piperazin-1-yl]- | 2,5-Difluoro-4-piperazin-1-yl-benzonitrile-trifluoro-acetic acid (compound 2.8) and 2-Cyclobutylmethoxy- | 490.5 |

-continued

| Expl. No. | Systematic Name | Starting materials | MW found (MH+) |
|---|---|---|---|
|  | 2,5-difluoro-benzonitrile | 5-methanesulfonyl-benzoic acid (compound 2.12) |  |
| 147 | 4-[4-(2-Cyclobutylmethoxy-5-methanesulfonyl-benzoyl)-piperazin-1-yl]-3,5-difluoro-benzonitrile | 3,5-Difluoro-4-piperazin-1-yl-benzonitrile trifluoro acetic acid (compound 2.13) and 2-Cyclobutylmethoxy-5-methanesulfonyl-benzoic acid (compound 2.12) | 490.5 |
| 148 | 4-[4-(2-Cyclobutylmethoxy-5-methanesulfonyl-benzoyl)-piperazin-1-yl]-2,6-difluoro-benzonitrile | 2,6-Difluoro-4-piperazin-1-yl-benzonitrile trifluoro-acetic acid (compound 2.14) and 2-Cyclobutylmethoxy-5-methanesulfonyl-benzoic acid (compound 2.12) | 490.5 |
| 149 | 2,5-Difluoro-4-{4-[5-methanesulfonyl-2-(2,2,2-trifluoro-ethoxy)-benzoyl]-piperazin-1-yl}-benzonitrile | 2,5-Difluoro-4-piperazin-1-yl-benzonitrile-trifluoro-acetic acid (compound 2.8) and 5-Methanesulfonyl-2-(2,2,2-trifluoro-ethoxy)-benzoic acid (compound 1.5) | 504.0 |
| 150 | 2,3-Difluoro-4-{4-[5-methanesulfonyl-2-(2,2,2-trifluoro-ethoxy)-benzoyl]-piperazin-1-yl}-benzonitrile | 2,3-Difluoro-4-piperazin-1-yl-benzonitrile-trifluoro-acetic acid (compound 2.7) and 5-Methanesulfonyl-2-(2,2,2-trifluoro-ethoxy)-benzoic acid (compound 1.5) | 504.1 |
| 151 | 2,5-Difluoro-4-[4-(5-methanesulfonyl-2-trifluoromethoxy-benzoyl)-piperazin-1-yl]-benzonitrile | 2,5-Difluoro-4-piperazin-1-yl-benzonitrile-trifluoro-acetic acid (compound 2.8) and 5-Methanesulfonyl-2-trifluoromethoxy-benzoic acid (compound 2.15) | 490.0 |
| 152 | 4-[4-(5-Methanesulfonyl-2-trifluoromethoxy-benzoyl)-piperazin-1-yl]-benzonitrile | 4-Piperazin-1-yl-benzonitrile (commercial) and 5-Methanesulfonyl-2-trifluoromethoxy-benzoic acid (compound 2.15) | 454.3 |
| 153 | 2-Fluoro-4-[4-(5-methanesulfonyl-2-trifluoromethoxy-benzoyl)-piperazin-1-yl]-benzonitrile | 2-Fluoro-4-piperazin-1-yl-benzonitrile (WO 9808835) and 5-Methanesulfonyl-2-trifluoromethoxy-benzoic acid (compound 2.15) | 472.1 |
| 154 | 3-Fluoro-4-[4-(5-methanesulfonyl-2-trifluoromethoxy-benzoyl)-piperazin-1-yl]-benzonitrile | 3-Fluoro-4-piperazin-1-yl-benzonitrile (WO9625414) and 5-Methanesulfonyl-2-trifluoromethoxy-benzoic acid (compound 2.15) | 472.0 |
| 155 | (5-Methanesulfonyl-2-trifluoromethoxy-phenyl)-[4-(4-trifluoromethyl-phenyl)-piperazin-1-yl]-methanone | 1-(4-Trifluoromethyl-phenyl)-piperazine (commercial) and 5-Methanesulfonyl-2-trifluoromethoxy-benzoic acid (compound 2.15) | 514.2 (M + NH$_4^+$) |
| 156 | [4-(3-Fluoro-4-trifluoromethyl-phenyl)-piperazin-1-yl]-(5-methanesulfonyl-2-trifluoromethoxy-phenyl)-methanone | 1-(3-Fluoro-4-trifluoromethyl-phenyl)-piperazine (compound 5.1) and 5-Methanesulfonyl-2-trifluoromethoxy-benzoic acid (compound 2.15) | 532.2 (M + NH$_4^+$) |
| 157 | [4-(2-Fluoro-4-trifluoromethyl-phenyl)-piperazin-1-yl]-(5-methanesulfonyl-2-trifluoromethoxy phenyl)-methanone | 1-(2-Fluoro-4-trifluoromethyl-phenyl)-piperazine (compound 1.1) and 5-Methanesulfonyl-2-trifluoromethoxy-benzoic acid (compound 2.15) | 515.3 |
| 158 | 2,3-Difluoro-4-[4-(5-methanesulfonyl-2-trifluoromethoxy-benzoyl)-piperazin-1-yl]-benzonitrile | 2,3-Difluoro-4-piperazin-1-yl-benzonitrile-trifluoro-acetic acid (compound 2.7) and 5-Methanesulfonyl-2-trifluoromethoxy-benzoic acid (compound 2.15) | 507.4 (M + NH$_4^+$) |
| 159 | 3,5-Difluoro-4-[4-(5 methanesulfonyl-2-trifluoromethoxy-benzoyl)-piperazin-1-yl]- | 3,5-Difluoro-4-piperazin-1-yl-benzonitrile trifluoro-acetic acid (compound 2.13) and 5-Methanesulfonyl-2- | 507.3 (M + NH$^{4+}$) |

-continued

| Expl. No. | Systematic Name | Starting materials | MW found (MH+) |
|---|---|---|---|
|  | benzonitrile | trifluoromethoxy-benzoic acid (compound 2.15) |  |
| 160 | 2,6-Difluoro-4-[4-(5-methanesulfonyl-2-trifluoromethoxy-benzoyl)-piperazin-1-yl]-benzonitrile | 2,6-Difluoro-4-piperazin-1-yl-benzonitrile trifluoro-acetic acid (compound 2.14) and 5-Methanesulfonyl-2-trifluoromethoxy-benzoic acid (compound 2.15) | 507.4 (M + NH4+) |
| 161 | [4-(2-Fluoro-4-methanesulfonyl-phenyl)-piperazin-1-yl]-(5-methanesulfonyl-2-trifluoromethoxy-phenyl)-methanone | 1-(2-Fluoro-4-methanesulfonyl-phenyl)-piperazine (commercial) and 5-Methanesulfonyl-2-trifluoromethoxy-benzoic acid (compound 2.15) | 542.0 (M + NH4+) |
| 162 | 2-[4-(5-Methanesulfonyl-2-trifluoromethoxy-benzoyl)-piperazin-1-yl]-5-trifluoromethyl-benzonitrile | 2-Piperazin-1-yl-5-trifluoromethyl-benzonitrile (compound 5.2) and 5-Methanesulfonyl-2-trifluoromethoxy-benzoic acid (compound 2.15) | 539.2 (M + NH4+) |
| 163 | 3,5-Difluoro-4-[4-(2-isopropoxy-5-methanesulfonyl-benzoyl)-piperazin-1-yl]-benzonitrile | 3,5-Difluoro-4-piperazin-1-yl-benzonitrile trifluoro-acetic acid (compound 2.13) and 2-Isopropoxy-5-methanesulfonyl-benzoic acid (compound 1.2) | 464.1 |
| 164 | 3,5-Difluoro-4-[4-(2-isobutoxy-5-methanesulfonyl-benzoyl)-piperazin-1-yl]-benzonitrile | 3,5-Difluoro-4-piperazin-1-yl-benzonitrile trifluoro-acetic acid (compound 2.13) and 2-Isobutoxy-5-methanesulfonyl-benzoic acid (compound 1.3) | 478.0 |
| 165 | 4-[4-(2-Cyclopropylmethoxy-5-methanesulfonyl-benzoyl)-piperazin-1-yl]-3,5-difluoro-benzonitrile | 3,5-Difluoro-4-piperazin-1-yl-benzonitrile trifluoro-acetic acid (compound 2.13) and 2-Cyclopropylmethoxy-5-methanesulfonyl-benzoic acid (compound 1.4) | 476.1 |
| 166 | 3,5-Difluoro-4-{4-[5-methanesulfonyl-2-(2,2,2-trifluoro-ethoxy)-benzoyl]-piperazin-1-yl}-benzonitrile | 3,5-Difluoro-4-piperazin-1-yl-benzonitrile trifluoro-acetic acid (compound 2.13) and 5-Methanesulfonyl-2-(2,2,2-trifluoro-ethoxy)-benzoic acid (compound 1.5) | 504.1 |
| 167 | 4-[4-(2-Cyclopentyloxy-5-methanesulfonyl-benzoyl)-piperazin-1-yl]-3,5-difluoro-benzonitrile | 3,5-Difluoro-4-piperazin-1-yl-benzonitrile trifluoro-acetic acid (compound 2.13) and 2-Cyclopentyloxy-5-methanesulfonyl-benzoic acid (compound 1.6) | 490.3 |
| 168 | 2,6-Difluoro-4-[4-(2-isopropoxy-5-methanesulfonyl-benzoyl)-piperazin-1-yl]-benzonitrile | 2,6-Difluoro-4-piperazin-1-yl-benzonitrile trifluoro-acetic acid (compound 2.14) and 2-Isopropoxy-5-methanesulfonyl-benzoic acid (compound 1.2) | 481.1 (M + NH4+) |
| 169 | 2,6-Difluoro-4-[4-(2-isobutoxy-5-methanesulfonyl-benzoyl)-piperazin-1-yl]-benzonitrile | 2,6-Difluoro-4-piperazin-1-yl-benzonitrile trifluoro-acetic acid (compound 2.14) and 2-Isobutoxy-5-methanesulfonyl-benzoic acid (compound 1.3) | 495.0 (M + NH4+) |
| 170 | 4-[4-(2-Cyclopropylmethoxy-5-methanesulfonyl-benzoyl)-piperazin-1-yl]-2,6-difluoro-benzonitrile | 2,6-Difluoro-4-piperazin-1-yl-benzonitrile trifluoro-acetic acid (compound 2.14) and 2-Cyclopropylmethoxy-5-methanesulfonyl-benzoic acid (compound 1.4) | 493.0 (M + NH4+) |
| 171 | 2,6-Difluoro-4-{4-[5-methanesulfonyl-2-(2,2,2-trifluoro-ethoxy)-benzoyl]-piperazin-1-yl}-benzonitrile | 2,6-Difluoro-4-piperazin-1-yl-benzonitrile trifluoro-acetic acid (compound 2.14) and 5-Methanesulfonyl-2-(2,2,2-trifluoro-ethoxy)-benzoic acid (compound 1.5) | 521.3 (M + NH4+) |
| 172 | 4-[4-(2-Cyclopentyloxy-5-methanesulfonyl- | 2,6-Difluoro-4-piperazin-1-yl-benzonitrile trifluoro- | 507.3 (M + NH4+) |

-continued

| Expl. No. | Systematic Name | Starting materials | MW found (MH+) |
|---|---|---|---|
| | benzoyl)-piperazin-1-yl]-2,6-difluoro-benzonitrile | acetic acid (compound 2.14) and 2-Cyclopentyloxy-5-methanesulfonyl-benzoic acid (compound 1.6) | |
| 173 | 2,4-Difluoro-6-[4-(2-isopropoxy-5-methanesulfonyl-benzoyl)-piperazin-1-yl]-benzonitrile | 2,4-Difluoro-6-piperazin-1-yl-benzonitrile trifluoro-acetic acid (compound 2.16) and 2-Isopropoxy-5-methanesulfonyl-benzoic acid (compound 1.2) | 581.4 (M + NH$_4^+$) |
| 174 | 2-Fluoro-4-{4-[2-(2-fluoro-1-fluoromethyl-ethoxy)-5-methanesulfonyl-benzoyl]-piperazin-1-yl}-benzonitrile | 2-Fluoro-4-piperazin-1-yl-benzonitrile (WO 9808835) and 2-(2-Fluoro-1-fluoromethyl-ethoxy)-5-methanesulfonyl-benzoic acid (compound 2.17) | 482.3 |
| 175 | 3-Fluoro-4-{4-[2-(2-fluoro-1-fluoromethyl-ethoxy)-5-methanesulfonyl-benzoyl]-piperazin-1-yl}-benzonitrile | 3-Fluoro-4-piperazin-1-yl-benzonitrile (WO9625414) and 2-(2-Fluoro-1-fluoromethyl-ethoxy)-5-methanesulfonyl-benzoic acid (compound 2.17) | 482.4 |
| 176 | 2,3-Difluoro-4{4-[2-(2-fluoro-1-fluoromethyl-ethoxy)-5-methanesulfonyl-benzoyl]-piperazin-1-yl}-benzonitrile | 2,3-Difluoro-4-piperazin-1-yl-benzonitrile-trifluoro-acetic acid (compound 2.7) and 2-(2-Fluoro-1-fluoromethyl-ethoxy)-5-methanesulfonyl-benzoic acid (compound 2.17) | 500.3 |
| 177 | 2,5-Difluoro-4-{4-[2-(2-fluoro-1-fluoromethyl-ethoxy)-5-methanesulfonyl-benzoyl]-piperazin-1-yl}-benzonitrile | 2,5-Difluoro-4-piperazin-1-yl-benzonitrile-trifluoro-acetic acid (compound 2.8) and 2-(2-Fluoro-1-fluoromethyl-ethoxy)-5-methanesulfonyl-benzoic acid (compound 2.17) | 500.3 |
| 178 | 3-5-Difluoro-4-{4-[2-(2-fluoro-1-fluoromethyl-ethoxy)-5-methanesulfonyl-benzoyl]-piperazin-1-yl}-benzonitrile | 3,5-Difluoro-4-piperazin-1-yl-benzonitrile trifluoro-acetic acid (compound 2.13) and 2-(2-Fluoro-1-fluoromethyl-ethoxy)-5-methanesulfonyl-benzoic acid (compound 2.17) | 500.3 |
| 179 | 2,6-Difluoro-4-{4-[2-(2-fluoro-1-fluoromethyl-ethoxy)-5-methanesulfonyl-benzoyl]-piperazin-1-yl}-benzonitrile | 2,6-Difluoro-4-piperazin-1-yl-benzonitrile trifluoro-acetic acid (compound 2.14) and 2-(2-Fluoro-1-fluoromethyl-ethoxy)-5-methanesulfonyl-benzoic acid (compound 2.17) | 500.3 |
| 180 | 2-Fluoro-4-{4-[5-methanesulfonyl-2-(2,2,3,3,3-pentafluoro-propoxy)-benzoyl]-piperazin-1-yl}-benzonitrile | 2-Fluoro-4-piperazin-1-yl benzonitrile (WO 9808835) and 5-Methanesulfonyl-2-(2,2,3,3,3-pentafluoro-propoxy)-benzoic acid (compound 2.18) | 536.3 |
| 181 | 3-Fluoro-4-{4-[5-methanesulfonyl-2-(2,2,3,3,3-pentafluoro-propoxy)-benzoyl]-piperazin-1-yl}-benzonitrile | 3-Fluoro-4-piperazin-1-yl-benzonitrile (WO9625414) and 5-Methanesulfonyl-2-(2,2,3,3,3-pentafluoro-propoxy)-benzoic acid (compound 2.18) | 536.3 |
| 182 | [5-Methanesulfonyl-2-(2,2,3,3,3-pentafluoro-propoxy)-phenyl]-[4-(4-trifluoromethyl-phenyl)-piperazin-1-yl]-methanone | 1-(4-Trifluoromethyl-phenyl)-piperazine (commercial) and 5-Methanesulfonyl-2-(2,2,3,3,3-pentafluoro-propoxy)-benzoic acid (compound 2.18) | 561.3 |
| 183 | [4-(3-Fluoro-4-trifluoromethyl-phenyl)-piperazin-1-yl]-[5-methanesulfonyl-2-(2,2,3,3,3-pentafluoro-propoxy)-phenyl]-methanone | 1-(3-Fluoro-4-trifluoromethyl-phenyl)-piperazine (compound 5.1) and 5-Methanesulfonyl-2-(2,2,3,3,3-pentafluoro-propoxy)-benzoic acid (compound 2.18) | 579.0 |

-continued

| Expl. No. | Systematic Name | Starting materials | MW found (MH+) |
|---|---|---|---|
| 184 | 2,3-Difluoro-4-{4-[5-methanesulfonyl-2-(2,2,3,3,3-pentafluoro-propoxy)-benzoyl]-piperazin-1-yl}-benzonitrile | 2,3-Difluoro-4-piperazin-1-yl-benzonitrile-trifluoro-acetic acid (compound 2.7) and 5-Methanesulfonyl-2-(2,2,3,3,3-pentafluoro-propoxy)-benzoic acid (compound 2.18) | 554.0 |
| 185 | 2,5-Difluoro-4-{4-[5-methanesulfonyl-2-(2,2,3,3,3-pentafluoro-propoxy)-benzoyl]-piperazin-1-yl}-benzonitrile | 2,5-Difluoro-4-piperazin-1-yl-benzonitrile-trifluoro-acetic acid (compound 2.8) and 5-Methanesulfonyl-2-(2,2,3,3,3-pentafluoro-propoxy)-benzoic acid (compound 2.18) | 554.0 |
| 186 | 3,5-Difluoro-4-{4-[5-methanesulfonyl-2-(2,2,3,3,3-pentafluoro-propoxy)-benzoyl]-piperazin-1-yl}-benzonitrile | 3,5-Difluoro-4-piperazin-1-yl-benzonitrile trifluoro-acetic acid (compound 2.13) and 5-Methanesulfonyl-2-(2,2,3,3,3-pentafluoro-propoxy)-benzoic acid (compound 2.18) | 554.0 |
| 187 | 2,6-Difluoro-4-{4-[5-methanesulfonyl-2-(2,2,3,3,3-pentafluoro-propoxy)-benzoyl]-piperazin-1-yl}-benzonitrile | 2,6-Difluoro-4-piperazin-1-yl-benzonitrile trifluoro-acetic acid (compound 2.14) and 5-Methanesulfonyl-2-(2,2,3,3,3-pentafluoro-propoxy)-benzoic acid (compound 2.18) | 571.2 (M + NH$_4^+$) |
| 188 | [4-(2-Fluoro-4-methanesulfonyl-phenyl)-piperazin-1-yl]-[5-methanesulfonyl-2-(2,2,3,3,3-pentafluoro-propoxy)-phenyl]-methanone | 1-(2-Fluoro-4-methanesulfonyl-phenyl)-piperazine (commercial) and 5-Methanesulfonyl-2-(2,2,3,3,3-pentafluoro-propoxy)-benzoic acid (compound 2.18) | 589.3 |
| 189 | 4-{4-[2-(2-Fluoro-1-fluoromethyl-ethoxy)-5-methanesulfonyl-benzoyl]-piperazin-1-yl}-benzonitrile | 4-Piperazin-1-yl-benzonitrile (commercial) and 2-(2-Fluoro-1-fluoromethyl-ethoxy)-5-methanesulfonyl-benzoic acid (compound 2.17) | 464.1 |
| 190 | [2-(2-Fluoro-1-fluoromethyl-ethoxy)-5-methanesulfonyl-phenyl]-[4-(4-trifluoromethyl-phenyl)-piperazin-1-yl]-methanone | 1-(4-Trifluoromethyl-phenyl)-piperazine (commercial) and 2-(2-Fluoro-1-fluoromethyl-ethoxy)-5-methanesulfonyl-benzoic acid (compound 2.17) | 507.3 |
| 191 | [2-(2-Fluoro-1-fluoromethyl-ethoxy)-5-methanesulfonyl-phenyl]-[4-(3-fluoro-4-trifluoromethyl-phenyl)-piperazin-1-yl]-methanone | 1-(3-Fluoro-4-trifluoromethyl-phenyl)-piperazine (compound 5.1) and 2-(2-Fluoro-1-fluoromethyl-ethoxy)-5-methanesulfonyl-benzoic acid (compound 2.17) | 525.2 |
| 192 | [2-(2-Fluoro-1-fluoromethyl-ethoxy)-5-methanesulfonyl-phenyl]-[4-(2-fluoro-4-trifluoromethyl-phenyl)-piperazin-1-yl]-methanone | 1-(2-Fluoro-4-trifluoromethyl-phenyl)-piperazine (compound 1.1) and 2-(2-Fluoro-1-fluoromethyl-ethoxy)-5-methanesulfonyl-benzoic acid (compound 2.17) | 525.0 |
| 193 | [2-(2-Fluoro-1-fluoromethyl-ethoxy)-5-methanesulfonyl-phenyl]-[4-(2-fluoro-4-methanesulfonyl-phenyl)-piperazin-1-yl]-methanone | 1-(2-Fluoro-4-methanesulfonyl-phenyl)-piperazine (commercial) and 2-(2-Fluoro-1-fluoromethyl-ethoxy)-5-methanesulfonyl-benzoic acid (compound 2.17) | 535.3 |
| 194 | 2-{4-[2-(2-Fluoro-1-fluoromethyl-ethoxy)-5-methanesulfonyl-benzoyl]-piperazin-1-yl}-5-trifluoromethyl-benzonitrile | 2-Piperazin-1-yl-5-trifluoromethyl-benzonitrile (compound 5.2) and 2-(2-Fluoro-1-fluoromethyl-ethoxy)-5-methanesulfonyl-benzoic acid (compound 2.17) | 532.2 |

-continued

| Expl. No. | Systematic Name | Starting materials | MW found (MH+) |
|---|---|---|---|
| 195 | [4-(2,3-Difluoro-4-methanesulfonyl-phenyl)-piperazin-1-yl]-[2-(2-fluoro-1-fluoromethyl-ethoxy)-5-methanesulfonyl-phenyl]-methanone | 1-(2,3-Difluoro-4-methanesulfonyl-phenyl)-piperazine (compound 5.3) and 2-(2-Fluoro-1-fluoromethyl-ethoxy)-5-methanesulfonyl-benzoic acid (compound 2.17) | 553.2 |
| 196 | 4-[4-(2-tert-Butoxy-5-methanesulfonyl-benzoyl)-piperazin-1-yl]-2,3-difluoro-benzonitrile | 2,3-Difluoro-4-piperazin-1-yl-benzonitrile-trifluoro-acetic acid (compound 2.7) and 2-tert-Butoxy-5-methanesulfonyl-benzoic acid (compound 2.19) | 478.3 |
| 197 | [4-(2,5-Difluoro-4-methanesulfonyl-phenyl)-piperazin-1-yl]-(2-isopropoxy-5-methanesulfonyl-phenyl)-methanone | 1-(2,5-Difluoro-4-methanesulfonyl-phenyl)-piperazine trifluoro-acetic acid (compound 2.20) and 2-Isopropoxy-5-methanesulfonyl-benzoic acid (compound 1.2) | 534.3 (M + NH$_4^+$) |
| 198 | [4-(3,5-Difluoro-4-methanesulfonyl-phenyl)-piperazin-1-yl]-(2-isopropoxy-5-methanesulfonyl-phenyl)-methanone | 1-(3,5-Difluoro-4-methanesulfonyl-phenyl)-piperazine trifluoro-acetic acid (compound 2.21) and 2-Isopropoxy-5-methanesulfonyl-benzoic acid (compound 1.2) | 534.3 (M + NH$_4^+$) |
| 199 | 2-[4-(2-Isopropoxy-5-methanesulfonyl-benzoyl)-piperazin-1-yl]-benzonitrile | 2-Piperazin-1-yl-benzonitrile (commercial) and 2-Isopropoxy-5-methanesulfonyl-benzoic acid (compound 1.2) | 428.5 |
| 200 | [4-(2-Fluoro-phenyl)-piperazin-1-yl]-(2-isopropoxy-5-methanesulfonyl-phenyl)-methanone | 1-(2-Fluoro-phenyl)-piperazine (commercial) and 2-Isopropoxy-5-methanesulfonyl-benzoic acid (compound 1.2) | 421.3 |
| 201 | [4-(4-Chloro-phenyl)-piperazin-1-yl]-(2-isopropoxy-5-methanesulfonyl-phenyl)-methanone | 1-(4-Chloro-phenyl)-piperazine (commercial) and 2-Isopropoxy-5-methanesulfonyl-benzoic acid (compound 1.2) | 437.3 |
| 202 | 5-Chloro-2-[4-(2-isopropoxy-5-methanesulfonyl-benzoyl)-piperazin-1-yl]-benzonitrile | 5-Chloro-2-piperazin-1-yl-benzonitrile (WO9625414) and 2-Isopropoxy-5-methanesulfonyl-benzoic acid (compound 1.2) | 462.1 |
| 203 | [4-(4-Chloro-2-fluoro-phenyl)-piperazin-1-yl]-(2-isopropoxy-5-methanesulfonyl-phenyl)-methanone | 1-(4-Chloro-2-fluoro-phenyl)-piperazine hydrochloride (commercial) and 2-Isopropoxy-5-methanesulfonyl-benzoic acid (compound 1.2) | 455.4 |
| 204 | [4-(4-Chloro-3-trifluoromethyl-phenyl)-piperazin-1-yl]-(2-isopropoxy-5-methanesulfonyl-phenyl)-methanone | 1-(4-Chloro-3-trifluoromethyl-phenyl)-piperazine (commercial) and 2-Isopropoxy-5-methanesulfonyl-benzoic acid (compound 1.2) | 505.3 |
| 205 | [4-(3,4-Dichloro-phenyl)-piperazin-1-yl]-(2-isopropoxy-5-methanesulfonyl-phenyl)-methanone | 1-(3,4-Dichloro-phenyl)-piperazine (commercial) and 2-Isopropoxy-5-methanesulfonyl-benzoic acid (compound 1.2) | 471.0 |
| 206 | [4-(2-Fluoro-4-methyl-phenyl)-piperazin-1-yl]-(2-isopropoxy-5-methanesulfonyl-phenyl)-methanone | 1-(2-Fluoro-4-methyl-phenyl)-piperazine (compound 5.4) and 2-Isopropoxy-5-methanesulfonyl-benzoic acid (compound 1.2) | 435.3 |
| 207 | rac-2,3-Difluoro-4-{4-[5-methanesulfonyl-2-(2,2,2-trifluoro-1-methyl-ethoxy)-benzoyl]-piperazin-1-yl}-benzonitrile | 2,3-Difluoro-4-piperazin-1-yl-benzonitrile-trifluoro-acetic acid (compound 2.7) and rac-5-Methanesulfonyl-2-(2,2,2-trifluoro-1-methyl-ethoxy)-benzoic acid (compound 3.1) | 535.3 (M + NH$_4^+$) |

-continued

| Expl. No. | Systematic Name | Starting materials | MW found (MH+) |
|---|---|---|---|
| 208 | (2-Isopropoxy-5-methanesulfonyl-phenyl)-[4-(4-trifluoromethoxy-phenyl)-piperazin-1-yl]-methanone | 1-(4-Trifluoromethoxy-phenyl)-piperazine (WO03007954) and 2-Isopropoxy-5-methanesulfonyl-benzoic acid (compound 1.2) | 487.3 |
| 209 | 2-Fluoro-4-{4-[5-methanesulfonyl-2-(2,2,3,3-tetrafluoro-propoxy)-benzoyl]-piperazin-1-yl}-benzonitrile | 2-Fluoro-4-piperazin-1-yl-benzonitrile (WO 9808835) and 5-Methanesulfonyl-2-(2,2,3,3-tetrafluoro-propoxy)-benzoic acid (compound 2.22) | 535.3 (M + NH$_4^+$) |
| 210 | 3-Fluoro-4-{4-[5-methanesulfonyl-2-(2,2,3,3-tetrafluoro-propoxy)-benzoyl]-piperazin-1-yl}-benzonitrile | 3-Fluoro-4-piperazin-1-yl-benzonitrile (WO9625414) and 5-Methanesulfonyl-2-(2,2,3,3-tetrafluoro-propoxy)-benzoic acid (compound 2.22) | 535.5 (M + NH$_4^+$) |
| 211 | [5-Methanesulfonyl-2-(2,2,3,3-tetrafluoro-propoxy)-phenyl]-[4-(4-trifluoromethyl-phenyl)-piperazin-1-yl]-methanone | 1-(4-Trifluoromethyl-phenyl)-piperazine (commercial) and 5-Methanesulfonyl-2-(2,2,3,3-tetrafluoro-propoxy)-benzoic acid (compound 2.22) | 560.3 (M + NH$_4^+$) |
| 212 | [4-(2-Fluoro-4-trifluoromethyl-phenyl)-piperazin-1-yl]-[5-methanesulfonyl-2-(2,2,3,3-tetrafluoro-propoxy)-phenyl]-methanone | 1-(2-Fluoro-4-trifluoromethyl-phenyl)-piperazine (compound 1.1) and 5-Methanesulfonyl-2-(2,2,3,3-tetrafluoro-propoxy)-benzoic acid (compound 2.22) | 578.2 (M + NH$_4^+$) |
| 213 | 2,3-Difluoro-4-{4-[5-methanesulfonyl-2-(2,2,3,3-tetrafluoro-propoxy)-benzoyl]-piperazin-1-yl}-benzonitrile | 2,3-Difluoro-4-piperazin-1-yl-benzonitrile-trifluoro-acetic acid (compound 2.7) and 5-Methanesulfonyl-2-(2,2,3,3-tetrafluoro-propoxy)-benzoic acid (compound 2.22) | 553.2 (M + NH$_4^+$) |
| 214 | 2,5-Difluoro-4-{4-[5-methanesulfonyl-2-(2,2,3,3-tetrafluoro-propoxy)-benzoyl]-piperazin-1-yl}-benzonitrile | 2,5-Difluoro-4-piperazin-1-yl-benzonitrile-trifluoro-acetic acid (compound 2.8) and 5-Methanesulfonyl-2-(2,2,3,3-tetrafluoro-propoxy)-benzoic acid (compound 2.22) | 553.2 (M + NH$_4^+$) |
| 215 | 3,5-Difluoro-4-{4-[5-methanesulfonyl-2-(2,2,3,3-tetrafluoro-propoxy)-benzoyl]-piperazin-1-yl}-benzonitrile | 3,5-Difluoro-4-piperazin-1-yl-benzonitrile trifluoro-acetic acid (compound 2.13) and 5-Methanesulfonyl-2-(2,2,3,3-tetrafluoro-propoxy)-benzoic acid (compound 2.22) | 553.0 (M + NH$_4^+$) |
| 216 | 2,6-Difluoro-4-{4-[5-methanesulfonyl-2-(2,2,3,3-tetrafluoro-propoxy)-benzoyl]-piperazin-1-yl}-benzonitrile | 2,6-Difluoro-4-piperazin-1-yl-benzonitrile trifluoro-acetic acid (compound 2.14) and 5-Methanesulfonyl-2-(2,2,3,3-tetrafluoro-propoxy)-benzoic acid (compound 2.22) | 553.2 (M + NH$_4^+$) |
| 217 | [4-(2-Fluoro-4-methanesulfonyl-phenyl)-piperazin-1-yl]-[5-methanesulfonyl-2-(2,2,3,3-tetrafluoro-propoxy)-phenyl]-methanone | 1-(2-Fluoro-4-methanesulfonyl-phenyl)-piperazin (commercial) and 5-Methanesulfonyl-2-(2,2,3,3-tetrafluoro-propoxy)-benzoic acid (compound 2.22) | 588.3 (M + NH$_4^+$) |
| 218 | [4-(2,6-Difluoro-4-methanesulfonyl-phenyl)-piperazin-1-yl]-(2-isopropoxy-5-methanesulfonyl-phenyl)-methanone | 1-(2,6-Difluoro-4-methanesulfonyl-phenyl)-piperazine trifluoro-acetic acid (compound 2.23) and 2-Isopropoxy-5-methanesulfonyl-benzoic acid (compound 1.2) | 517.3 |
| 219 | 3-Chloro-4-[4-(2-isopropoxy-5-methanesulfonyl- | 3-Chloro-4-piperazin-1-yl-benzonitrile (WO 9625414) and 2-Isopropoxy-5- | 462.3 |

-continued

| Expl. No. | Systematic Name | Starting materials | MW found (MH$^+$) |
|---|---|---|---|
| | benzoyl)-piperazin-1-yl]-benzonitrile | methanesulfonyl-benzoic acid (compound 1.2) | |
| 220 | [4-(2-Chloro-4-nitro-phenyl)-piperazin-1-yl]-(2-isopropoxy-5-methanesulfonyl-phenyl)-methanone | 1-(2-Chloro-4-nitro-phenyl)-piperazine (EP 257864) and 2-Isopropoxy-5-methanesulfonyl-benzoic acid (compound 1.2) | 482.3 |
| 221 | 3-[4-(2-Isopropoxy-5-methanesulfonyl-benzoyl)-piperazin-1-yl]-benzonitrile | 3-Piperazin-1-yl-benzonitrile (WO02068399) and 2-Isopropoxy-5-methanesulfonyl-benzoic acid (compound 1.2) | 428.4 |
| 222 | [4-(3,5-Dichloro-pyridin-4-yl)-piperazin-1-yl]-(2-isopropoxy-5-methanesulfonyl-phenyl)-methanone | 1-(3,5-Dichloro-pyridin-4-yl)-piperazine (commercial) and 2-Isopropoxy-5-methanesulfonyl-benzoic acid (compound 1.2) | 474.0 |
| 223 | 5-Chloro-2-{4-[5-methanesulfonyl-2-(2,2,2-trifluoro-ethoxy)-benzoyl]-piperazin-1-yl}-benzonitrile | 5-Chloro-2-piperazin-1-yl-benzonitrile (WO9625414) and 5-Methanesulfonyl-2-(2,2,2-trifluoro-ethoxy)-benzoic acid (compound 1.5) | 502.1 |
| 224 | [4-(4-Chloro-2-fluoro-phenyl)-piperazin-1-yl]-[5-methanesulfonyl-2-(2,2,2-trifluoro-ethoxy)-phenyl]-methanone | 1-(4-Chloro-2-fluoro-phenyl)-piperazine hydrochloride (commercial) and 5-Methanesulfonyl-2-(2,2,2-trifluoro-ethoxy)-benzoic acid (compound 1.5) | 495.4 |
| 225 | [4-(4-Chloro-3-trifluoromethyl-phenyl)-piperazin-1-yl]-[5-methanesulfonyl-2-(2,2,2-trifluoro-ethoxy)-phenyl]-methanone | 1-(4-Chloro-3-trifluoromethyl-phenyl)-piperazine (commercial) and 5-Methanesulfonyl-2-(2,2,2-trifluoro-ethoxy)-benzoic acid (compound 1.5) | 545.3 |
| 226 | [4-(2,5-Difluoro-4-methanesulfonyl-phenyl)-piperazin-1-yl]-[5-methanesulfonyl-2-(2,2,2-trifluoro-ethoxy)-phenyl]-methanone | 1-(2,5-Difluoro-4-methanesulfonyl-phenyl)-piperazine trifluoro-acetic acid (compound 2.20) and 5-Methanesulfonyl-2-(2,2,2-trifluoro-ethoxy)-benzoic acid (compound 1.5) | 574.3 (M + NH$_4^+$) |
| 227 | [4-(2,6-Difluoro-4-methanesulfonyl-phenyl)-piperazin-1-yl]-[5-methanesulfonyl-2-(2,2,2-trifluoro-ethoxy)-phenyl]-methanone | 1-(2,6-Difluoro-4-methanesulfonyl-phenyl)-piperazine trifluoro-acetic acid (compound 2.23) and 5-Methanesulfonyl-2-(2,2,2-trifluoro-ethoxy)-benzoic acid (compound 1.5) | 557.4 |
| 228 | 5-Chloro-2-[4-(2-cyclopropylmethoxy-5-methanesulfonyl-benzoyl)-piperazin-1-yl]-benzonitrile | 5-Chloro-2-piperazin-1-yl-benzonitrile (WO9625414) and 2-Cyclopropylmethoxy-5-methanesulfonyl-benzoic acid (compound 1.4) | 474.1 |
| 229 | [4-(4-Chloro-2-fluoro-phenyl)-piperazin-1-yl]-(2-cyclopropylmethoxy-5-methanesulfonyl-phenyl)-methanone | 1-(4-Chloro-2-fluoro-phenyl)-piperazine hydrochloride (commercial) and 2-Cyclopropylmethoxy-5-methanesulfonyl-benzoic acid (compound 1.4) | 467.3 |
| 230 | (2-Cyclopropylmethoxy-5-methanesulfonyl-phenyl)-[4-(3,4-dichloro-phenyl)-piperazin-1-yl]-methanone | 1-(3,4-Dichloro-phenyl)-piperazine (commercial) and 2-Cyclopropylmethoxy-5-methanesulfonyl-benzoic acid (compound 1.4) | 483.3 |
| 231 | [4-(4-Chloro-3-trifluoromethyl-phenyl)-piperazin-1-yl]-(2-cyclopropylmethoxy-5-methanesulfonyl-phenyl)-methanone | 1-(4-Chloro-3-trifluoromethyl-phenyl)-piperazine (commercial) and 2-Cyclopropylmethoxy-5-methanesulfonyl-benzoic acid (compound 1.4) | 517.0 |
| 232 | (2-Cyclopropylmethoxy-5-methanesulfonyl-phenyl)-[4-(2,5-difluoro-4-methanesulfonyl-phenyl)-piperazin-1-yl]- | 1-(2,5-Difluoro-4-methanesulfonyl-phenyl)-piperazine trifluoro-acetic acid (compound 2.20) and 2-Cyclopropylmethoxy-5- | 546.3 (M + NH$_4^+$) |

-continued

| Expl. No. | Systematic Name | Starting materials | MW found (MH+) |
|---|---|---|---|
| | methanone | methanesulfonyl-benzoic acid (compound 1.4) | |
| 233 | (2-Cyclopropylmethoxy-5-methanesulfonyl-phenyl)-[4-(2,6-difluoro-4-methanesulfonyl-phenyl)-piperazin-1-yl]-methanone | 1-(2,6-Difluoro-4-methanesulfonyl-phenyl)-piperazine trifluoro-acetic acid (compound 2.23) and 2-Cyclopropylmethoxy-5-methanesulfonyl-benzoic acid (compound 1.4) | 546.3 (M + NH$_4^+$) |
| 234 | 4-[4-(2-tert-Butoxy-5-methanesulfonyl-benzoyl)-piperazin-1-yl]-2,5-difluoro-benzonitrile | 2,5-Difluoro-4-piperazin-1-yl-benzonitrile-trifluoro-acetic acid (compound 2.8) and 2-tert-Butoxy-5-methanesulfonyl-benzoic acid (compound 2.19) | 478.1 |
| 235 | 4-[4-(2-tert-Butoxy-5-methanesulfonyl-benzoyl)-piperazin-1-yl]-3,5-difluoro-benzonitrile | 3,5-Difluoro-4-piperazin-1-yl-benzonitrile trifluoro acetic acid (compound 2.13) and 2-tert-Butoxy-5-methanesulfonyl-benzoic acid (compound 2.19) | 478.1 |
| 236 | 4-[4-(2-tert-Butoxy-5-methanesulfonyl-benzoyl)-piperazin-1-yl]-2,6-difluoro-benzonitrile | 2,6-Difluoro-4-piperazin-1-yl-benzonitrile trifluoro-acetic acid (compound 2.14) and 2-tert-Butoxy-5-methanesulfonyl-benzoic acid (compound 2.19) | 478.1 |
| 237 | (2-tert-Butoxy-5-methanesulfonyl-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 2-tert-Butoxy-5-methanesulfonyl-benzoic acid (compound 2.19) | 530.2 (M + NH$_4^+$) |
| 238 | 2-[4-(2-tert-Butoxy-5-methanesulfonyl-benzoyl)-piperazin-1-yl]-5-trifluoromethyl-benzonitrile | 2-Piperazin-1-yl-5-trifluoromethyl-benzonitrile (compound 5.2) and 2-tert-Butoxy-5-methanesulfonyl-benzoic acid (compound 2.19) | 527.3 (M + NH$_4^+$) |
| 239 | (2-tert-Butoxy-5-methanesulfonyl-phenyl)-[4-(2,3-difluoro-4-methanesulfonyl-phenyl)-piperazin-1-yl]-methanone | 1-(2,3-Difluoro-4-methanesulfonyl-phenyl)-piperazine (compound 5.3) and 2-tert-Butoxy-5-methanesulfonyl-benzoic acid (compound 2.19) | 548.3 (M + NH$_4^+$) |
| 240 | (2-tert-Butoxy-5-methanesulfonyl-phenyl)-[4-(3-chloro-5-trifluoromethyl-pyridin-2-yl)-piperazin-1-yl]-methanone | 1-(3-Chloro-5-trifluoromethyl-pyridin-2-yl)-piperazine (commercial) and 2-tert-Butoxy-5-methanesulfonyl-benzoic acid (compound 2.19) | 520.3 |
| 241 | (2-tert-Butoxy-5-methanesulfonyl-phenyl)-[4-(5-chloro-pyridin-2-yl)-piperazin-1-yl]-methanone | 1-(5-Chloro-pyridin-2-yl)-piperazine (WO01062751) and 2-tert-Butoxy-5-methanesulfonyl-benzoic acid (compound 2.19) | 452.3 |
| 242 | (2-tert-Butoxy-5-methanesulfonyl-phenyl)-[4-(5-trifluoromethyl-pyridin-2-yl)-piperazin-1-yl]-methanone | 1-(5-Trifluoromethyl-pyridin-2-yl)-piperazine (commercial) and 2-tert-Butoxy-5-methanesulfonyl-benzoic acid (compound 2.19) | 486.4 |
| 243 | 4-[4-(2-tert-Butoxy-5-methanesulfonyl-benzoyl)-piperazin-1-yl]-2-fluoro-benzonitrile | 2-Fluoro-4-piperazin-1-yl-benzonitrile (WO 9808835) and 2-tert-Butoxy-5-methanesulfonyl-benzoic acid (compound 2.19) | 460.3 |
| 244 | 4-[4-(2-tert-Butoxy-5-methanesulfonyl-benzoyl)-piperazin-1-yl] 3-fluoro-benzonitrile | 3-Fluoro-4-piperazin-1-yl-benzonitrile (WO9625414) and 2-tert-Butoxy-5-methanesulfonyl-benzoic acid (compound 2.19) | 460.3 |
| 245 | (2-tert-Butoxy-5-methanesulfonyl-phenyl)-[4-(4- | 1-(4-Trifluoromethyl-phenyl)-piperazine (commercial) and 2-tert- | 485.5 |

| Expl. No. | Systematic Name | Starting materials | MW found (MH+) |
|---|---|---|---|
| | trifluoromethyl-phenyl)-piperazin-1-yl]-methanone | Butoxy-5-methanesulfonyl-benzoic acid (compound 2.19) | |
| 246 | (2-tert-Butoxy-5-methanesulfonyl-phenyl)-[4-(3-fluoro-4-trifluoromethyl-phenyl)-piperazin-1-yl]-methanone | 1-(3-Fluoro-4-trifluoromethyl-phenyl)-piperazine (compound 5.1) and 2-tert-Butoxy-5-methanesulfonyl-benzoic acid (compound 2.19) | 503.1 |
| 247 | (2-tert-Butoxy-5-methanesulfonyl-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and 2-tert-Butoxy-5-methanesulfonyl-benzoic acid (compound 2.19) | 503.3 |
| 248 | 6-[4-(2-tert-Butoxy-5-methanesulfonyl-benzoyl)-piperazin-1-yl]-nicotinonitrile | 6-Piperazin-1-yl-nicotinonitrile (commercial) and 2-tert-Butoxy-5-methanesulfonyl-benzoic acid (compound 2.19) | 443.4 |
| 249 | (2-tert-Butoxy-5-methanesulfonyl-phenyl)-[4-(2,5-difluoro-4-methanesulfonyl-phenyl)-piperazin-1-yl]-methanone | 1-(2,5-Difluoro-4-methanesulfonyl-phenyl)-piperazine trifluoro-acetic acid (compound 2.20) and 2-tert-Butoxy-5-methanesulfonyl-benzoic acid (compound 2.19) | 548.3 (M + NH$_4^+$) |
| 250 | (2-tert-Butoxy-5-methanesulfonyl-phenyl)-[4-(2,6-difluoro-4-methanesulfonyl-phenyl)-piperazin-1-yl]-methanone | 1-(2,6-Difluoro-4-methanesulfonyl-phenyl)-piperazine trifluoro-acetic acid (compound 2.23) and 2-tert-Butoxy-5-methanesulfonyl-benzoic acid (compound 2.19) | 548.3 (M + NH$_4^+$) |
| 251 | [4-(3,4-Dichloro-phenyl)-piperazin-1-yl]-[5-methanesulfonyl-2-(2,2,2-trifluoro-ethoxy)-phenyl]-methanone | 1-(3,4-Dichloro-phenyl)-piperazine (commercial) and 5-Methanesulfonyl-2-(2,2,2-trifluoro-ethoxy)-benzoic acid (compound 1.5) | 511.0 |
| 252 | 2-[4-(2-Isopropoxy-5-methanesulfonyl-benzoyl)-piperazin-1-yl]-nicotinonitrile | 2-Piperazin-1-yl-nicotinonitrile (commercial) and 2-Isopropoxy-5-methanesulfonyl-benzoic acid (compound 1.2) | 429.5 |
| 253 | (2-Isopropoxy-5-methanesulfonyl-phenyl)-[4-(4-trifluoromethyl-pyrimidin-2-yl)-piperazin-1-yl]-methanone | 2-Piperazin-1-yl-4-trifluoromethyl-pyrimidine (commercial) and 2-Isopropoxy-5-methanesulfonyl-benzoic acid (compound 1.2) | 473.0 |
| 254 | rac-[4-(2,5-Difluoro-4-methanesulfonyl-phenyl)-piperazin-1-yl]-[5-methanesulfonyl-2-(2,2,2-trifluoro-1-methyl-ethoxy)-phenyl]-methanone | 1-(2,5-Difluoro-4-methanesulfonyl-phenyl)-piperazine trifluoro-acetic acid (compound 2.20) and rac-5-Methanesulfonyl-2-(2,2,2-trifluoro-1-methyl-ethoxy)-benzoic acid (compound 3.1) | 571.0 |
| 255 | rac-[4-(2,6-Difluoro-4-methanesulfonyl-phenyl)-piperazin-1-yl]-[5-methanesulfonyl-2-(2,2,2-trifluoro-1-methyl-ethoxy)-phenyl]-methanone | 1-(2,6-Difluoro-4-methanesulfonyl-phenyl)-piperazine trifluoro-acetic acid (compound 2.23) and rac-5-Methanesulfonyl-2-(2,2,2-trifluoro-1-methyl-ethoxy)-benzoic acid (compound 3.1) | 571.2 |
| 256 | rac-5-Chloro-2-{4-[5-methanesulfonyl-2-(2,2,2-trifluoro-1-methyl-ethoxy)-benzoyl]-piperazin-1-yl}-benzonitrile | 5-Chloro-2-piperazin-1-yl-benzonitrile (WO9625414) and rac-5-Methanesulfonyl-2-(2,2,2-trifluoro-1-methyl-ethoxy)-benzoic acid (compound 3.1) | 516.2 |
| 257 | rac-[4-(4-Chloro-2-fluoro-phenyl)- | 1-(4-Chloro-2-fluoro-phenyl)-piperazine | 509.3 |

-continued

| Expl. No. | Systematic Name | Starting materials | MW found (MH+) |
|---|---|---|---|
| | piperazin-1-yl]-[5-methanesulfonyl-2-(2,2,2-trifluoro-1-methyl-ethoxy)-phenyl]-methanone | hydrochloride (commercial) and rac-5-Methanesulfonyl-2-(2,2,2-trifluoro-1-methyl-ethoxy)-benzoic acid (compound 3.1) | |
| 258 | rac-[4-(3,4-Dichloro-phenyl)-piperazin-1-yl]-[5-methanesulfonyl-2-(2,2,2-trifluoro-1-methyl-ethoxy)-phenyl]-methanone | 1-(3,4-Dichloro-phenyl)-piperazine (commercial) and rac-5-Methanesulfonyl-2-(2,2,2-trifluoro-1-methyl-ethoxy)-benzoic acid (compound 3.1) | 525.2 |
| 259 | rac-[4-(4-Chloro-3-trifluoromethyl-phenyl)-piperazin-1-yl]-[5-methanesulfonyl-2-(2,2,2-trifluoro-1-methyl-ethoxy)-phenyl]-methanone | 1-(4-Chloro-3-trifluoromethyl-phenyl)-piperazine (commercial) and rac-5-Methanesulfonyl-2-(2,2,2-trifluoro-1-methyl-ethoxy)-benzoic acid (compound 3.1) | 559.0 |
| 260 | rac-3,5-Difluoro-4-{4-[5-methanesulfonyl-2-(2,2,2-trifluoro-1-methyl-ethoxy)-benzoyl]-piperazin-1-yl}-benzonitrile | 3,5-Difluoro-4-piperazin-1-yl-benzonitrile trifluoro-acetic acid (compound 2.13) and rac-5-Methanesulfonyl-2-(2,2,2-trifluoro-1-methyl-ethoxy)-benzoic acid (compound 3.1) | 518.2 |
| 261 | rac-2,5-Difluoro-4-{4-[5-methanesulfonyl-2-(2,2,2-trifluoro-1-methyl-ethoxy)-benzoyl]-piperazin-1-yl-}-benzonitrile | 2,5-Difluoro-4-piperazin-1-yl-benzonitrile-trifluoro-acetic acid (compound 2.8) and rac-5-Methanesulfonyl-2-(2,2,2-trifluoro-1-methyl-ethoxy)-benzoic acid (compound 3.1) | 518.0 |
| 262 | rac-2,6-Difluoro-4-{4-[5-methanesulfonyl-2-(2,2,2-trifluoro-1-methyl-ethoxy)-benzoyl]-piperazin-1-yl}-benzonitrile | 2,6-Difluoro-4-piperazin-1-yl-benzonitrile trifluoro-acetic acid (compound 2.14) and rac-5-Methanesulfonyl-2-(2,2,2-trifluoro-1-methyl-ethoxy)-benzoic acid (compound 3.1) | 517.8 |
| 263 | (2-Cyclopropylmethoxy-5-methanesulfonyl-phenyl)-[4-(4-trifluoromethyl-pyrimidin-2-yl)-piperazin-1-yl]-methanone | 2-Piperazin-1-yl-4-trifluoromethyl-pyrimidine (commercial) and 2-Cyclopropylmethoxy-5-methanesulfonyl-benzoic acid (compound 1.4) | 485.1 |
| 264 | (2-Isopropoxy-5-methanesulfonyl-phenyl)-[4-(2-trifluoromethyl-pyrimidin-4-yl)-piperazin-1-yl]-methanone | 4-Piperazin-1-yl-2-trifluoromethyl-pyrimidine trifluoro-acetic acid (WO030249) and 2-Isopropoxy-5-methanesulfonyl-benzoic acid (compound 1.2) | 473.1 |
| 265 | (2-tert-Butoxy-5-methanesulfonyl-phenyl)-[4-(3-fluoro-5-trifluoromethyl-pyridin-2-yl)-piperazin-1-yl]-methanone | 1-(3-Fluoro-5-trifluoromethyl-pyridin-2-yl)-piperazine (compound 5.5) and 2-tert-Butoxy-5-methanesulfonyl-benzoic acid (compound 2.19) | 504.0 |
| 266 | (2-tert-Butoxy-5-methanesulfonyl-phenyl)-[4-(4-trifluoromethyl-pyrimidin-2-yl)-piperazin-1-yl]-methanone | 2-Piperazin-1-yl-4-trifluoromethyl-pyrimidine (commercial) and 2-tert-Butoxy-5-methanesulfonyl-benzoic acid (compound 2.19) | 487.1 |
| 267 | [5-Methanesulfonyl-2-(2,2,2-trifluoro-ethoxy)-phenyl]-[4-(4-trifluoromethyl-pyrimidin-2-yl)-piperazin-1-yl]-methanone | 2-Piperazin-1-yl-4-trifluoromethyl-pyrimidine (commercial) and 5-Methanesulfonyl-2-(2,2,2-trifluoro-ethoxy)-benzoic acid (compound 1.5) | 513.3 |
| 268 | rac-[5-Methanesulfonyl-2-(2,2,2-trifluoro-1-methyl-ethoxy)-phenyl]- | 2-Piperazin-1-yl-4-trifluoromethyl-pyrimidine (commercial) | 527.0 |

| Expl. No. | Systematic Name | Starting materials | MW found (MH⁺) |
|---|---|---|---|
| | [4-(4-trifluoromethyl-pyrimidin-2-yl)-piperazin-1-yl]-methanone | and rac-5-Methanesulfonyl-2-(2,2,2-trifluoro-1-methyl-ethoxy)-benzoic acid (compound 3.1) | |
| 269 | [4-(2,5-Difluoro-4-methanesulfonyl-phenyl)-piperazin-1-yl]-[5-methanesulfonyl-2-((S)-2,2,2-trifluoro-1-methyl-ethoxy)-phenyl]-methanone | 1-(2,5-Difluoro-4-methanesulfonyl-phenyl)-piperazine trifluoro-acetic acid and 5-Methanesulfonyl-2-((S)-2,2,2-trifluoro-1-methyl-ethoxy)-benzoic acid (compound 5.6) | 571.0 |
| 270 | [4-(2,5-Difluoro-4-methanesulfonyl-phenyl)-piperazin-1-yl]-[5-methanesulfonyl-2-((R)-2,2,2-trifluoro-1-methyl-ethoxy)-phenyl]-methanone | 1-(2,5-Difluoro-4-methanesulfonyl-phenyl)-piperazine trifluoro-acetic acid (compound 2.20) and 5-Methanesulfonyl-2-((R)-2,2,2-trifluoro-1-methyl-ethoxy)-benzoic acid (compound 5.7) | 571.0 |
| 271 | [4-(2,6-Difluoro-4-methanesulfonyl-phenyl)-piperazin-1-yl]-[5-methanesulfonyl-2-((S)-2,2,2-trifluoro-1-methyl-ethoxy)-phenyl]-methanone | 1-(2,6-Difluoro-4-methanesulfonyl-phenyl)-piperazine trifluoro-acetic acid (compound 2.23) and 5-Methanesulfonyl-2-((S)-2,2,2-trifluoro-1-methyl-ethoxy)-benzoic acid (compound 5.6) | 571.2 |
| 272 | [4-(2,6-Difluoro-4-methanesulfonyl-phenyl)-piperazin-1-yl]-[5-methanesulfonyl-2-((R)-2,2,2-trifluoro-1-methyl-ethoxy)-phenyl]-methanone | 1-(2,6-Difluoro-4-methanesulfonyl-phenyl)-piperazine trifluoro-acetic acid (compound 2.23) and 5-Methanesulfonyl-2-((R)-2,2,2-trifluoro-1-methyl-ethoxy)-benzoic acid (compound 5.7) | 571.2 |
| 273 | rac-[5-Methanesulfonyl-2-(2,2,2-trifluoro-1-methyl-ethoxy)-phenyl]-[4-(2-trifluoromethyl-pyrimidin-4-yl)-piperazin-1-yl]-methanone | 4-Piperazin-1-yl-2-trifluoromethyl-pyrimidine trifluoro-acetic acid (WO030249) and rac-5-Methanesulfonyl-2-(2,2,2-trifluoro-1-methyl-ethoxy)-benzoic acid (compound 3.1) | 527.0 |
| 274 | rac-[5-Methanesulfonyl-2-(2,2,2-trifluoro-1-methyl-ethoxy)-phenyl]-[4-(6-trifluoromethyl-pyrimidin-4-yl)-piperazin-1-yl]-methanone | 4-Piperazin-1-yl-6-trifluoromethyl-pyrimidine trifluoro-acetic acid (compound 2.24) and rac-5-Methanesulfonyl-2-(2,2,2-trifluoro-1-methyl-ethoxy)-benzoic acid (compound 3.1) | 527.2 |
| 275 | rac-[5-Methanesulfonyl-2-(2,2,2-trifluoro-1-methyl-ethoxy)-phenyl]-[4-(5-trifluoromethyl-pyrimidin-2-yl)-piperazin-1-yl]-methanone | 2-Piperazin-1-yl-5-trifluoromethyl-pyrimidine (compound 2.25) and rac-5-Methanesulfonyl-2-(2,2,2-trifluoro-1-methyl-ethoxy)-benzoic acid (compound 3.1) | 527.2 |
| 276 | (2-Isopropoxy-5-methanesulfonyl-phenyl)-[4-(5-trifluoromethyl-pyrimidin-2-yl)-piperazin-1-yl]-methanone | 2-Piperazin-1-yl-5-trifluoromethyl-pyrimidine (compound 2.25) and 2-Isopropoxy-5-methanesulfonyl-benzoic acid (compound 1.2) | 473.1 |
| 277 | (2-Cyclopropylmethoxy-5-methanesulfonyl-phenyl)-[4-(2-trifluoromethyl-pyrimidin-4-yl)-piperazin-1-yl]-methanone | 4-Piperazin-1-yl-2-trifluoromethyl-pyrimidine trifluoro-acetic acid (WO030249) and 2-Cyclopropylmethoxy-5-methanesulfonyl-benzoic acid (compound 1.4) | 485.1 |
| 278 | (2-Cyclopropylmethoxy-5-methanesulfonyl-phenyl)-[4-(6-trifluoromethyl-pyrimidin-4-yl)- | 4-Piperazin-1-yl-6-trifluoromethyl-pyrimidine trifluoro-acetic acid (compound 2.24) and 2-Cyclopropylmethoxy-5- | 485.5 |

-continued

| Expl. No. | Systematic Name | Starting materials | MW found (MH⁺) |
|---|---|---|---|
| | piperazin-1-yl]-methanone | methanesulfonyl-benzoic acid (compound 1.4) | |
| 279 | [5-Methanesulfonyl-2-(2,2,2-trifluoro-ethoxy)-phenyl]-[4-(2-trifluoromethyl-pyrimidin-4-yl)-piperazin-1-yl]-methanone | 4-Piperazin-1-yl-2-trifluoromethyl-pyrimidine trifluoro-acetic acid (WO030249) and 5-Methanesulfonyl-2-(2,2,2-trifluoro-ethoxy)-benzoic acid (compound 1.5) | 513.3 |
| 280 | [5-Methanesulfonyl-2-(2,2,2-trifluoro-ethoxy)-phenyl]-[4-(6-trifluoromethyl-pyrimidin-4-yl)-piperazin-1-yl]-methanone | 4-Piperazin-1-yl-6-trifluoromethyl-pyrimidine trifluoro-acetic acid (compound 2.24) and 5-Methanesulfonyl-2-(2,2,2-trifluoro-ethoxy)-benzoic acid (compound 1.5) | 513.3 |

In analogy to Example 1.2 (b) compounds 3.1 to 3.5 of the following table were prepared from 2-chloro-5-methane-sulfonyl-benzoic acid and the appropriate alcohol:

| Expl. No | Compound Name | Alcohol | MS (m/e) |
|---|---|---|---|
| 3.1 | rac-5-Methanesulfonyl-2-(2,2,2-trifluoro-1-methyl ethoxy)-benzoic acid (compound 3.1) | rac-1,1,1-Trifluoro-propan-2-ol | 311.3 (MH−) |
| 3.2 | 2-Cyclohexyloxy-5-methanesulfonyl-benzoic acid (compound 3.2) | Cyclohexanol | 297.3 (MH−) |
| 3.3 | 2-(2,2-Dimethyl-propoxy)-5-methanesulfonyl-benzoic acid (compound 3.3) | 2,2-Dimethyl-propan-1-ol | 285.1 (MH−) |
| 3.4 | 2-Cyclobutoxy-5-methanesulfonyl-benzoic acid (compound 3.4) | cyclobutanol | 269.3 (MH−) |
| 3.5 | rac-2-sec-Butoxy-5-methanesulfonyl-benzoic acid (compound 3.5) | Butan-2-ol | 271.4 (MH−) |

In analogy to Example 5 compounds 281 to 326 of the following table were prepared from the acid derivatives and piperazine derivatives.

| Expl. No. | Systematic Name | Starting materials | MW found (MH⁺) |
|---|---|---|---|
| 281 | 1-{4-[4-(2-Cyclohexyloxy-5-methanesulfonyl-benzoyl)-piperazin-1-yl]-3-fluoro-phenyl}-ethanone | 1-(3-Fluoro-4-piperazin-1-yl-phenyl)-ethanone (WO9714690) and 2-Cyclohexyloxy-5-methanesulfonyl-benzoic acid (compound 3.2) | 503.5 |
| 282 | 4-[4-(2-Cyclohexyloxy-5-methanesulfonyl-benzoyl)-piperazin-1-yl]-benzonitrile | 4-Piperazin-1-yl-benzonitrile (commercial) and 2-Cyclohexyloxy-5-methanesulfonyl-benzoic acid (compound 3.2) | 468.5 |
| 283 | 4-[4-(2-Cyclohexyloxy-5-methanesulfonyl-benzoyl)-piperazin-1-yl]-3-fluoro-benzonitrile | 3-Fluoro-4-piperazin-1-yl-benzonitrile (WO9625414) and 2-Cyclohexyloxy-5-methanesulfonyl-benzoic acid (compound 3.2) | 486.5 |
| 284 | 4-[4-(2-Cyclohexyloxy-5methanesulfonyl-benzoyl)-piperazin-1-yl]-2-fluoro-benzonitrile | 2-Fluoro-4-piperazin-1-yl-benzonitrile (WO 9808835) and 2-Cyclohexyloxy-5-methanesulfonyl-benzoic acid (compound 3.2) | 486.5 |
| 285 | (2-Cyclohexyloxy-5-methanesulfonyl-phenyl)-[4-(4-trifluoromethyl-phenyl)- | 1-(4-Trifluoromethyl-phenyl)-piperazine (commercial) and 2-Cyclohexyloxy-5- | 511.5 |

| Expl. No. | Systematic Name | Starting materials | MW found (MH+) |
|---|---|---|---|
|  | piperazin-1-yl]-methanone | methanesulfonyl-benzoic acid (compound 3.2) |  |
| 286 | (2-Cyclohexyloxy-5-methanesulfonyl-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and 2-Cyclohexyloxy-5-methanesulfonyl-benzoic acid (compound 3.2) | 529.5 |
| 287 | (2-Cyclohexyloxy-5-methanesulfonyl-phenyl)-[4-(3-fluoro-4-trifluoromethyl-phenyl)-piperazin-1-yl]-methanone | 1-(3-Fluoro-4-trifluoromethyl-phenyl)-piperazine (compound 5.1) and 2-Cyclohexyloxy-5-methanesulfonyl-benzoic acid (compound 3.2) | 529.3 |
| 288 | (2-Cyclohexyloxy-5-methanesulfonyl-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 2-Cyclohexyloxy-5-methanesulfonyl-benzoic acid (compound 3.2) | 539.5 |
| 289 | 1-(4-{4-[2-(2,2-Dimethyl-propoxy)-5-methanesulfonyl-benzoyl]-piperazin-1-yl}-3-fluoro-phenyl)-methanone | 1-(3-Fluoro-4-piperazin-1-yl-phenyl)-ethanone (WO9714690) and 2-(2,2-Dimethyl-propoxy)-5-methanesulfonyl-benzoic acid (compound 3.3) | 491.5 |
| 290 | 4-{4-[2-(2,2-Dimethyl-propoxy)-5-methanesulfonyl-benzoyl]-piperazin-1-yl}-benzonitrile | 4-Piperazin-1-yl-benzonitrile (commercial) and 2-(2,2-Dimethyl-propoxy)-5-methanesulfonyl-benzoic acid (compound 3.3) | 456.6 |
| 291 | 4-{4-[2-(2,2-Dimethyl-propoxy)-5-methanesulfonyl-benzoyl]-piperazin-1-yl}-3-fluoro-benzonitrile | 3-Fluoro-4-piperazin-1-yl-benzonitrile (WO9625414) and 2-(2,2-Dimethyl-propoxy)-5-methanesulfonyl-benzoic acid (compound 3.3) | 474.4 |
| 292 | 4-{4-[2-(2,2-Dimethyl-propoxy)-5-methanesulfonyl-benzoyl]-piperazin-1-yl}-2-fluoro-benzonitrile | 2-Fluoro-4-piperazin-1-yl-benzonitrile (WO 9808835) and 2-(2,2-Dimethyl-propoxy)-5-methanesulfonyl-benzoic acid (compound 3.3) | 474.5 |
| 293 | [2-(2,2-Dimethyl-propoxy)-5-methanesulfonyl-phenyl]-[4-(4-trifluoromethyl-phenyl)-piperazin-1-yl]-methanone | 1-(4-Trifluoromethyl-phenyl)-piperazine (commercial) and 2-(2,2-Dimethyl-propoxy)-5-methanesulfonyl-benzoic acid (compound 3.3) | 499.4 |
| 294 | [2-(2,2-Dimethyl-propoxy)-5-methanesulfonyl-phenyl]-[4-(2-fluoro-4-trifluoromethyl-phenyl)-piperazin-1-yl]-methanone | 1-(2-Fluoro-4-trifluoromethyl-phenyl)-piperazine (compound 1.1) and 2-(2,2-Dimethyl-propoxy)-5-methanesulfonyl-benzoic acid (compound 3.3) | 517.5 |
| 295 | [2-(2,2-Dimethyl-propoxy)-5-methane sulfonyl-phenyl]-[4-(3-fluoro-4-trifluoromethyl-phenyl)-piperazin-1-yl]-methanone | 1-(3-Fluoro-4-trifluoromethyl-phenyl)-piperazine (compound 5.1) and 2-(2,2-Dimethyl-propoxy)-5-methanesulfonyl-benzoic acid (compound 3.3) | 517.5 |
| 296 | [2-(2,2-Dimethyl-propoxy)-5-methanesulfonyl-phenyl]-[4-(2-fluoro-4-methanesulfonyl-phenyl)-piperazin-1-yl]-methanone | 1-(2-Fluoro-4-methanesulfonyl-phenyl)-piperazine (commercial) and 2-(2,2-Dimethyl-propoxy)-5-methanesulfonyl-benzoic acid (compound 3.3) | 527.3 |
| 297 | rac-1-(3-Fluoro-4-{4-[5-methanesulfonyl-2-(2,2,2-trifluoro-1-methyl-ethoxy)- | 1-(3-Fluoro-4-piperazin-1-yl-phenyl)-ethanone (WO9714690) and rac-5-Methanesulfonyl-2-(2,2,2- | 517.5 |

| Expl. No. | Systematic Name | Starting materials | MW found (MH+) |
|---|---|---|---|
| | benzoyl]-piperazin-1-yl}-phenyl)-ethanone | trifluoro-1-methyl-ethoxy)-benzoic acid (compound 3.1) | |
| 298 | rac-4-{4-[5-Methanesulfonyl-2-(2,2,2-trifluoro-1-methyl-ethoxy)-benzoyl]-piperazin-1-yl}-benzonitrile | 4-Piperazin-1-yl-benzonitrile (commercial) and rac-5-Methanesulfonyl-2-(2,2,2-trifluoro-1-methyl-ethoxy)-benzoic acid (compound 3.1) | 482.5 |
| 299 | rac-3-Fluoro-4-{4-[5-methanesulfonyl-2-(2,2,2-trifluoro-1-methyl-ethoxy)-benzoyl]-piperazin-1-yl}-benzonitrile | 3-Fluoro-4-piperazin-1-yl-benzonitrile (WO9625414) and rac-5-Methanesulfonyl-2-(2,2,2-trifluoro-1-methyl-ethoxy)-benzoic acid (compound 3.1) | 500.4 |
| 300 | rac-2-Fluoro-4-{4-[5-methanesulfonyl-2-(2,2,2-trifluoro-1-methyl-ethoxy)-benzoyl]-piperazin-1-yl}-benzonitrile | 2-Fluoro-4-piperazin-1-yl benzonitrile (WO 9808835) and rac-5-Methanesulfonyl-2-(2,2,2-trifluoro-1-methyl-ethoxy)-benzoic acid (compound 3.1) | 500.4 |
| 301 | rac-5-Methanesulfonyl-2-(2,2,2-trifluoro-1-methyl-ethoxy)-phenyl]-[4-(4-trifluoromethyl-phenyl)-piperazin-1-yl]-methanone | 1-(4-Trifluoromethyl-phenyl)-piperazine (commercial) and rac-5-Methanesulfonyl-2-(2,2,2-trifluoro-1-methyl-ethoxy)-benzoic acid (compound 3.1) | 525.3 |
| 302 | rac-[4-(2-Fluoro-4-trifluoromethyl-phenyl)-piperazin-1-yl]-[5-methanesulfonyl-2-(2,2,2-trifluoro-1-methyl-ethoxy)-phenyl]-methanone | 1-(2-Fluoro-4-trifluoromethyl-phenyl)-piperazine (compound 1.1) and rac-5-Methanesulfonyl-2-(2,2,2-trifluoro-1-methyl-ethoxy)-benzoic acid (compound 3.1) | 543.5 |
| 303 | rac-[4-(3-Fluoro-4-trifluoromethyl-phenyl)-piperazin-1-yl]-[5-methanesulfonyl-2-(2,2,2-trifluoro-1-methyl-ethoxy)-phenyl]-methanone | 1-(3-Fluoro-4-trifluoromethyl-phenyl)-piperazine (compound 5.1) and rac-5-Methanesulfonyl-2-(2,2,2-trifluoro-1-methyl-ethoxy)-benzoic acid (compound 3.1) | 543.5 |
| 304 | rac-[4-(2-Fluoro-4-methanesulfonyl-phenyl)-piperazin-1-yl]-[5-methanesulfonyl-2-(2,2,2-trifluoro-1-methyl-ethoxy)-phenyl]-methanone | 1-(2-Fluoro-4-methanesulfonyl-phenyl)-piperazine (commercial) and rac-5-Methanesulfonyl-2-(2,2,2-trifluoro-1-methyl-ethoxy)-benzoic acid (compound 3.1) | 553.0 |
| 305 | 4-{4-[5-Methanesulfonyl-2-(2-methoxy-ethoxy)-benzoyl]-piperazin-1-yl}-benzonitrile | 4-Piperazin-1-yl-benzonitrile (commercial) and 5-Methanesulfonyl-2-(2-methoxy-ethoxy)-benzoic acid (compound 1.10) | 444.3 |
| 306 | 3-Fluoro-4-{4-[5-methanesulfonyl-2-(2-methoxy-ethoxy)-benzoyl]-piperazin-1-yl}-benzonitrile | 3-Fluoro-4-piperazin-1-yl-benzonitrile (WO9625414) and 5-Methanesulfonyl-2-(2-methoxy-ethoxy)-benzoic acid (compound 1.10) | 462.5 |
| 307 | 2-Fluoro-4-{4-[5-methanesulfonyl-2-(2-methoxy-ethoxy)-benzoyl]-piperazin-1-yl}-benzonitrile | 2-Fluoro-4-piperazin-1-yl-benzonitrile (WO 9808835) and 5-Methanesulfonyl-2-(2-methoxy-ethoxy)-benzoic acid (compound 1.10) | 462.5 |
| 308 | [4-(2-Fluoro-4-trifluoromethyl-phenyl)-piperazin-1-yl]-[5-methanesulfonyl-2-(2-methoxy-ethoxy)-phenyl]-methanone | 1-(2-Fluoro-4-trifluoromethyl-phenyl)-piperazine (compound 1.1) and 5-Methanesulfonyl-2-(2-methoxy-ethoxy)-benzoic acid (compound 1.10) | 505.5 |
| 309 | [4-(3-Fluoro-4-trifluoromethyl-phenyl)-piperazin-1-yl]-[5-methanesulfonyl-2-(2-methoxy-ethoxy)-phenyl]-methanone | 1-(3-Fluoro-4-trifluoromethyl-phenyl)-piperazine (compound 5.1) and 5-Methanesulfonyl-2-(2-methoxy-ethoxy)-benzoic acid (compound 1.10) | 505.5 |
| 310 | [4-(2-Fluoro-4-methanesulfonyl- | 1-(2-Fluoro-4-methanesulfonyl-phenyl)- | 515.5 |

-continued

| Expl. No. | Systematic Name | Starting materials | MW found (MH+) |
|---|---|---|---|
| | phenyl)-piperazin-1-yl]-[5-methanesulfonyl-2-(2-methoxy-ethoxy)-phenyl]-methanone | piperazine (commercial) and 5-Methanesulfonyl-2-(2-methoxy-ethoxy)-benzoic acid (compound 1.10) | |
| 311 | 1-{4-[4-(2-Cyclobutoxy-5-methanesulfonyl-benzoyl)-piperazin-1-yl]-3-fluoro-phenyl}-ethanone | 1-(3-Fluoro-4-piperazin-1-yl-phenyl)-ethanone (WO9714690) and 2-Cyclobutoxy-5-methanesulfonyl-benzoic acid (compound 3.4) | 475.4 |
| 312 | 4-[4-(2-Cyclobutoxy-5-methanesulfonyl-benzoyl)-piperazin-1-yl]-benzonitrile | 4-Piperazin-1-yl-benzonitrile (commercial) and 2-Cyclobutoxy-5-methanesulfonyl-benzoic acid (compound 3.4) | 440.5 |
| 313 | 4-[4-(2-Cyclobutoxy-5-methanesulfonyl-benzoyl)-piperazin-1-yl]-3-fluoro-benzonitrile | 3-Fluoro-4-piperazin-1-yl-benzonitrile (WO9625414) and 2-Cyclobutoxy-5-methanesulfonyl-benzoic acid (compound 3.4) | 458.5 |
| 314 | 4-[4-(2-Cyclobutoxy-5-methanesulfonyl-benzoyl)-piperazin-1-yl]-2-fluoro-benzonitrile | 2-Fluoro-4-piperazin-1-yl-benzonitrile (WO 9808835) and 2-Cyclobutoxy-5-methanesulfonyl-benzoic acid (compound 3.4) | 458.5 |
| 315 | (2-Cyclobutoxy-5-methanesulfonyl-phenyl)-[4-(4-trifluoromethyl-phenyl)-piperazin-1-yl]-methanone | 1-(4-Trifluoromethyl-phenyl)-piperazine (commercial) and 2-Cyclobutoxy-5-methanesulfonyl-benzoic acid (compound 3.4) | 483.5 |
| 316 | (2-Cyclobutoxy-5-methanesulfonyl-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and 2-Cyclobutoxy-5-methanesulfonyl-benzoic acid (compound 3.4) | 501.5 |
| 317 | (2-Cyclobutoxy-5-methanesulfonyl-phenyl)-[4-(3-fluoro-4-trifluoromethyl-phenyl)-piperazin-1-yl]-methanone | 1-(3-Fluoro-4-trifluoromethyl-phenyl)-piperazine (compound 5.1) and 2-Cyclobutoxy-5-methanesulfonyl-benzoic acid (compound 3.4) | 501.5 |
| 318 | (2-Cyclobutoxy-5-methanesulfonyl-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 2-Cyclobutoxy-5-methanesulfonyl-benzoic acid (compound 3.4) | 511.5 |
| 319 | rac-1-{4-[4-(2-sec-Butoxy-5-methanesulfonyl-benzoyl)-piperazin-1-yl]-3-fluoro-phenyl}-ethanone | 1-(3-Fluoro-4-piperazin-1-yl-phenyl)-ethanone (WO9714690) and rac-2-sec-Butoxy-5-methanesulfonyl-benzoic acid (compound 3.5) | 477.4 |
| 320 | rac-4-[4-(2-sec-Butoxy-5-methanesulfonyl-benzoyl)-piperazin-1-yl]-benzonitrile | 4-Piperazin-1-yl-benzonitrile (commercial) and rac-2-sec-Butoxy-5-methanesulfonyl-benzoic acid (compound 3.5) | 442.5 |
| 321 | rac-4-[4-(2-sec-Butoxy-5-methanesulfonyl-benzoyl)-piperazin-1-yl]-3-fluoro-benzonitrile | 3-Fluoro-4-piperazin-1-yl-benzonitrile (WO9625414) and rac-2-sec-Butoxy-5-methanesulfonyl-benzoic acid (compound 3.5) | 460.5 |
| 322 | rac-4-[4-(2-sec-Butoxy-5-methanesulfonyl-benzoyl)-piperazin-1-yl]-2-fluoro-benzonitrile | 2-Fluoro-4-piperazin-1-yl-benzonitrile (WO 9808835) and rac-2-sec-Butoxy-5-methanesulfonyl-benzoic acid (compound 3.5) | 460.5 |
| 323 | rac-(2-sec-Butoxy-5-methanesulfonyl-phenyl)-[4-(4-trifluoromethyl-phenyl)-piperazin-1-yl]-methanone | 1-(4-Trifluoromethyl-phenyl)-piperazine (commercial) and rac-2-sec-Butoxy-5-methanesulfonyl-benzoic acid (compound 3.5) | 485.5 |

-continued

| Expl. No. | Systematic Name | Starting materials | MW found (MH+) |
|---|---|---|---|
| 324 | rac-(2-sec-Butoxy-5-methanesulfonyl-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and rac-2-sec-Butoxy-5-methanesulfonyl-benzoic acid (compound 3.5) | 503.3 |
| 325 | rac-(2-sec-Butoxy-5-methanesulfonyl-phenyl)-[4-(3-fluoro-4-trifluoromethyl-phenyl)-piperazin-1-yl]-methanone | 1-(3-Fluoro-4-trifluoromethyl-phenyl)-piperazine (compound 5.1) and rac-2-sec-Butoxy-5-methanesulfonyl-benzoic acid (compound 3.5) | 503.3 |
| 326 | rac-(2-sec-Butoxy-5-methanesulfonyl-phenyl)-[4-(2-fluoro-4-methanesulfonyl-phenyl)-piperazin-1-yl]-methanone | 1-(2-Fluoro-4-methanesulfonyl-phenyl)-piperazine (commercial) and rac-2-sec-Butoxy-5-methanesulfonyl-benzoic acid (compound 3.5) | 513.5 |

EXAMPLE 4.1

Preparation of
6-Ethoxy-2-fluoro-3-methanesulfonyl-benzoic acid (a) 3-Chlorosulfonyl-2,6-difluoro-benzoic acid 95 mmol of 2,6-difluorobenzoic acid in 19 ml of chorosulfonic acid was stirred for 2 h at 150°. The mixture was poured into 200 ml of ice and stirred for 20 min. The resulting slurry was filtered, washed with water and dried (20° overnight in the dessicator) to yield the title compound as a colorless solid. MS (m/e): 279.4 (MNa+, 81%)

(b) 2,6-Difluoro-3-sulfino-benzoic acid 41 mmol of 3-chlorosulfonyl-2,6-difluoro-benzoic acid was slowly added over 20 min. to a solution of 310 mmol sodium sulfite in 200 ml of water. The resulting mixture was stirred for one hour at room temperature, cooled to 0° C. and acidified with 20% aqueous sulfuric acid. The sulfinic acid was extracted with ethyl acetate, dried over MgSO$_4$ and concentrated to yield the title compound as a colorless solid. MS (m/e): 220.9 (M–H, 100%)

(c) 6-Ethoxy-2-fluoro-3-methanesulfonyl-benzoic acid

A mixture of 27 mmol 2,6-difluoro-3-sulfino-benzoic acid and 9 mmol Na$_2$CO$_3$ in 110 ml methanol was treated with 72 mmol of methyl iodide. The resulting mixture was stirred overnight at 60°, concentrated and the dark residue dissolved in 100 ml of ethanol. 100 ml of 2 molar aqueous NaOH was added, and the mixture was refluxed for 2 hours. Concentration to about 100 ml precipitated a yellowish solid which was filtered and triturated with diethyl ether to give the crude title compound, which was used without further purification.

EXAMPLE 4.2

Preparation of
1-(4-Trifluoromethanesulfonyl-phenyl)-piperazine

A mixture of 1 mmol 1-Bromo-4-trifluoromethanesulfonyl-benzene [Nodiff et al., J. Org. Chem. 25, 60 (1960)], 3 mmol of piperazine and 2 mmol of potassium carbonate in 5 ml of acetonitrile was refluxed for 2 hours. The resulting mixture was poured into water, extracted with ethyl acetate, dried, concentrated and purified by column chromatography (SiO$_2$; Et2O/cyclohexane) to yield the title compound as a colorless solid. MS (m/e): 295.2 (MH+, 100%)

EXAMPLE 4.3

Preparation of
1-(2,4-Bis-trifluoromethyl-phenyl)-piperazine
hydrochloride (a) 4-(2,4-Bis-trifluoromethyl-phenyl)-piperazine-1-carboxylic acid tert-butyl ester A mixture of 5 mmol 2,4-bis(trifluoromethyl)bromobenzene, 6 mmol N-BOC-piperazine, 8 mmol NaOtBu, 0.5 mmol rac-2,2'-bis(diphenylphosphino)-1,1'-binaphthyl and 1 mmol tris-(dibenzylideneacetone)dipalladium chloroform complex in 20 ml toluene was stirred at 80° C. for 3 hours. The mixture was then diluted with water, extracted with ethyl acetate, dried and purified by column chromatography (SiO$_2$; cyclohexane/ethyl acetate 9:1) to yield the title compound as a yellowish oil.

MS (m/e): 399.1 (MH+, 100%)

(b) 1-(2,4-Bis-trifluoromethyl-phenyl)-piperazine hydrochloride 3 mmol of 4-(2,4-Bis-trifluoromethyl-phenyl)-piperazine-1-carboxylic acid tert-butyl ester was stirred in 10 ml of 1,4-dioxane saturated with gaseous HCl. After 4 h at room temperature, the reaction mixture was evaporated to dryness to yield the title compound as a colorless solid. MS (m/e): 299.3 (MH+, 100%)

EXAMPLE 4.4

Preparation of 1-[4-(5-Methyl-[1,2,4]oxadiazol-3-yl)-phenyl]-piperazine hydrochloride (a) 4-[4-(5-Methyl-[1,2,4]oxadiazol-3-yl)-phenyl]-piperazine-1-carboxylic acid tert-butyl ester A well stirred mixture of 0.015 mmol of bis(tri-t-butylphosphine)palladium, 0.01 mmol of cetyltrimethylammonium bromide, 2 mmol of powdered potassium hydroxide, 2 mmol of 3-(4-bromo-phenyl)-5-methyl-[1,2,4]oxadiazole and 2.1 mmol of N-BOC-piperazine in 1 ml of toluene was heated under Ar to 90° C. for 17 hours. The resulting reaction mixture was diluted with water, extracted with ethyl acetate and the product purified by column chromatography (SiO₂; cyclohexane/ethyl acetate 7:3) to yield the title compound as a yellowish solid. MS (m/e): 345.3 (MH⁺, 100%)

(b) 1-[4-(5-Methyl-[1,2,4]oxadiazol-3-yl)-phenyl]-piperazine hydrochloride 1 mmol of 4-[4-(5-Methyl-[1,2,4]oxadiazol-3-yl)-phenyl]-piperazine-1-carboxylic acid tert-butyl ester was stirred in 3 ml of 1,4-dioxane saturated with gaseous HCl. After 2 h at room temperature, the reaction mixture was evaporated to dryness to yield the tide compound as a colorless solid. MS (m/e): 245.1 (MH⁺, 100%)

EXAMPLE 4.5

Preparation of 1-(4-Oxazol-2-yl-phenyl)-piperazine hydrochloride (a) 4-Bromo-N-(2,2-dimethoxy-ethyl)-benzamide A solution of 24 mmol aminoacetaldehyde dimethylacetal was dissolved in 30 ml of water and treated with 25 mmol of potassium hydrogencarbonate. A solution of 23 mmol of 4-bromobenzoyl chloride in 50 ml of acetone was slowly added under stirring over a period of 30 min. The acetone was evaporated and the aqueous phase was extracted 3 times with ethyl acetate to yield the crude title compound as a slightly brown solid.

MS (m/e): 287.1 (M–H, 43%)

(b) 2-(4-Bromo-phenyl)-oxazole

A solution of 21 mmol of phosphorous pentoxide in 20 ml of methylsulfonic acid was treated with 7 mmol of 4-Bromo-N-(2,2-dimethoxy-ethyl)-benzamide. The reaction mixture was heated for 5 hours at 130°, cooled to room temperature and poured into ice-water. The resulting solid was filtered off and dried to yield the crude title compound as a brownish solid. MS (m/e): 224.0 (MH⁺, 24%)

(c) 4-(4-Oxazol-2-yl-phenyl)-piperazine-1-carboxylic acid tert-butyl ester

Prepared in analogy to example 4.4 (a) from 2-(4-Bromo-phenyl)-oxazole and N-BOC -piperazine. MS (m/e): 330.3 (MH⁺, 100%)

(d) 1-(4-Oxazol-2-yl-phenyl)-piperazine hydrochloride

Prepared in analogy to example 4.4 (b) from 4-(4-Oxazol-2-yl-phenyl)-piperazine-1-carboxylic acid tert-butyl ester and hydrochloric acid in dioxane. MS (m/e): 230.1 (MH⁺, 100%)

EXAMPLE 4.6

Preparation of 1-[4-(5-Methyl-[1,3,4]oxadiazol-2-yl)-phenyl]-piperazine hydrochloride (a) 2-(4-Bromo-phenyl)-[1,3,4]oxadiazole 12.3 mmol of 4-bromo-benzoic acid hydrazide were dissolved in 26 ml of triethyl orthoformate. The reaction mixture was stirred overnight at 140°, evaporated and the residue crystallized from ethanol to give the title compound as a colorless solid. MS (m/e): 225.0 (MH⁺, 100%)

(b) 4-(4-[1,3,4]Oxadiazol-2-yl-phenyl)-piperazine-1-carboxylic acid tert-butyl ester Prepared in analogy to example 4.4 (a) from 2-(4-Bromo-phenyl)-[1,3,4]oxadiazole and N-BOC-piperazine.

MS (m/e): 342.2 (MH⁺, 100%)

(c) 1-[4-(5-Methyl-[1.3,4]oxadiazol-2-yl)-phenyl]-piperazine hydrochloride

Prepared in analogy to example 4.4 (b) from 4-(4-[1,3,4] Oxadiazol-2-yl-phenyl)-piperazine-1-carboxylic acid tert-butyl ester and hydrochloric acid in dioxane. MS (m/e): 245.3 (MH⁺, 100%)

EXAMPLE 4.7

Preparation of 1-[4-(2-Methyl-2H-tetrazol-5-yl)-phenyl]-piperazine hydrochloride (a) 5-(4-Bromo-phenyl)-2-methyl-2H-tetrazole A mixture of 3.5 mmol of 5-(4-bromo-phenyl)-2H-tetrazole, 0.2 mmol of tetrabutyl ammonium bromide, 4.4 mmol of methyl iodide, 6 ml of 1M aqueous sodium hydroxide and 6 ml of dichloromethane were stirred at room temperature for 24 hours. The reaction mixture was diluted with water and extracted with ethyl acetate. The organic phase was dried, evaporated and the product purified by column chromatography (SiO₂; cyclohexane/ethyl acetate 7:3). MS (m/e): 239.1 (MH⁺, 29%)

(b) 4-[4-(2-Methyl-2H-tetrazol-5-yl)-phenyl]-piperazine-1-carboxylic acid tert-butyl ester Prepared in analogy to example 4.4 (a) from 5-(4-Bromo-phenyl)-2-methyl-2H-tetrazole and N-BOC-piperazine. MS (m/e): 345.1 (MH⁺, 41%)

(c) 1-[4-(2-Methyl-2H-tetrazol-5-yl)-phenyl]-piperazine hydrochloride

Prepared in analogy to example 4.4 (b) from 4-[4-(2-Methyl-2H-tetrazol-5-yl)-phenyl]-piperazine-1-carboxylic acid tert-butyl ester and hydrochloric acid in dioxane. MS (m/e): 245.1 (MH⁺, 100%)

EXAMPLE 4.8

Preparation of 3,4,5,6-Tetrahydro-2H-[1,2']bipyrazinyl-5'-carboxylic acid methyl ester hydrochloride (a) 2,3,5,6-Tetrahydro-[1,2']bipyrazinyl-4,5'-dicarboxylic acid 4-tert-butyl ester 5'-methyl ester A mixture of 17 mmol methyl-5-chloropyrazine-2-carboxylate, 18 mmol of N-BOC-piperazine and 20 mmol of K₂CO₃ in 20 ml of acetonitrile was heated under reflux for 3 hours. The reaction mixture was concentrated, diluted with water and extracted with ethyl acetate. The title compound was recrystallized from ethyl acetate to yield a colorless solid. MS (m/e): 323.4 (MH⁺, 100%)

(b) 3,4,5,6-Tetrahydro-2H-[1,2']bipyrazinyl-5'-carboxylic acid methyl ester hydrochloride Prepared in analogy to example 4.4 (b) from 2,3,5,6-Tetrahydro-[1,2']bipyrazinyl-4,5'-dicarboxylic acid 4-tert-butyl ester 5'-methyl ester and 1,4-dioxane saturated with gaseous HCl. MS (m/e): 223.1 (MH⁺, 100%)

EXAMPLE 4.9

Preparation of 6'-Chloro-3,4,5,6-tetrahydro-2H-[1,2']bipyrazinyl trifluoroacetate (a) 6'-Chloro-2,3,5,6-tetrahydro-[1,2']bipyrazinyl-4-carboxylic acid tert-butyl ester A mixture of 10 mmol 2,6-dichloropyrazine and 21 mmol of N-BOC-piperazine in 15 ml acetonitrile was heated under reflux for 1.5 hours. The reaction mixture was concentrated and purified by chromatography (SiO₂; dichloromethane/methanol 95:5) to yield the title compound as a colorless solid. MS (m/e): 299.2 (MH⁺, 100%)

(b) 6'-Chloro-3,4,5,6-tetrahydro-2H-[1,2']bipyrazinyl trifluoroacetate

A solution of 2 mmol 6'-Chloro-2,3,5,6-tetrahydro-[1,2'] bipyrazinyl-4-carboxylic acid tert-butyl ester in 10 ml of dichloromethane was treated with 3 mmol of trifluoroacetic acid and stirred at room temperature for 17 hours. Concentration and crystallisation from diethylether yielded the title compound as a colorless solid. MS (m/e): 198.0 (M$^+$, 100%)

EXAMPLE 4.10

Preparation of 3,4,5,6-Tetrahydro-2H-[1,2']bipyrazinyl-5'-carboxylic acid amide hydrochloride (a) 5'-Carbamoyl-2,3,5,6-tetrahydro-[1,2']bipyrazinyl-4-carboxylic acid tert-butyl ester 3 mmol of 2,3,5,6-Tetrahydro-[1,2']bipyrazinyl-4,5'-dicarboxylic acid 4-tert-butyl ester 5'-methyl ester (example 1.13 (a)) was dissolved in a 7 molar solution of gaseous ammonia in methanol. The reaction vessel was tightly closed and heated overnight at 60° C. Cooling of the reaction mixtures led to crystallisation of the title compound. MS (m/e): 308.4 (MH$^+$, 100%)

(b) 3,4,5,6-Tetrahydro-2H-[1,2']bipyrazinyl-5'-carboxylic acid amide hydrochloride 0.25 mmol of 5'-Carbamoyl-2,3,5,6-tetrahydro-[1,2']bipyrazinyl-4-carboxylic acid tert-butyl ester was stirred for 1 hour in 1 ml of dioxane saturated with gaseous HCl. Concentration of the reaction mixture led to the title compound, as a colorless solid. MS (m/e): 208.3 (MH$^+$, 100%)

EXAMPLE 4.11

Preparation of Dimethyl-(4-piperazin-1-yl-[1,3,5]triazin-2-yl)-amine (a) 4-(4-Chloro-[1,3,5]triazin-2-yl)-piperazine-1-carboxylic acid tert-butyl ester A solution of 11 mmol of 2,4-dichlorotriazine (WO 02/083654) in 20 ml of acetonitrile was chilled and treated with 11 mmol of triethylamine and 11 mmol of N-BOC-piperazine. The reaction mixture was stirred for 2 hours at 0° C. then for 2 hours at room temperature. Addition of 100 ml brine and extraction with ethyl acetate yielded the crude product which was purified through trituration in ethyl acetate. MS (m/e): 300.3 (MH$^+$, 100%)

(b) 4-(4-Dimethylamino-[1,3,5]triazin-2-yl)-piperazine-1-carboxylic acid tert-butyl ester A solution of 2 mmol of 4-(4-Chloro-[1,3,5]triazin-2-yl)-piperazine-1-carboxylic acid tert-butyl ester in 15 ml of 2M dimethylamine in methanol was stirred at room temperature for 1 hour. Concentration and purification by chromatography (SiO$_2$; ethyl acetate/cyclohexane 1:1) yielded the title compound as a colorless solid. MS (m/e): 309.1 (MH$^+$, 100%)

(c) Dimethyl-(4-piperazin-1-yl-[1,3,5]triazin-2-yl)-amine

A solution of 1 mmol of 4-(4-Dimethylamino-[1,3,5]triazin-2-yl)-piperazine-1-carboxylic acid tert-butyl ester in 10 ml dichloromethane was chilled and treated with 14 mmol of trifluoroacetic acid. The reaction mixture was heated to 40° C. for 30 min. After cooling, 50 ml of 2M aqueous sodium hydroxide was added. The organic layer was separated, dried and concentrated to yield the title compound as a yellowish oil. MS (m/e): 267.0 (M+CH$_3$COO$^+$, 100%)

EXAMPLE 4.12

Preparation of 6'-Methoxy-3,4,5,6-tetrahydro-2H-[1,2']bipyrazinyl (a) 6'-Methoxy-2,3,5,6-tetrahydro-[1,2']bipyrazinyl-4-carboxylic acid tert-butyl ester 1 mmol of 6'-Chloro-2,3,5,6-tetrahydro-[1,2']bipyrazinyl-4-carboxylic acid tert-butyl ester [example 4.9 (a)] was dissolved in a solution of sodium methanolate (prepared by dissolving 1 mmol of sodium in 10 ml of methanol). The mixture was heated overnight to 70°, concentrated and the product purified by chromatography (SiO$_2$; dichloromethane/methanol 99:1) to yield the title compound as a colorless foam. MS (m/e): 295.3 (MH$^+$, 100%)

(b) 6'-Methoxy-3,4,5,6-tetrahydro-2H-[1,2']bipyrazinyl

Prepared in analogy to example 4.10 (c) from 6'-Methoxy-2,3,5,6-tetrahydro-[1,2']bipyrazinyl-4-carboxylic acid tert-butyl ester and trifluoroacetic acid. MS (m/e): 195.1 (MH$^+$, 80%)

EXAMPLE 4.13

Preparation of 2-Methoxy-4-piperazin-1-yl-[1,3,5]triazine (a) 4-(4-Methoxy-[1,3,5]triazin-2-yl)-piperazine-1-carboxylic acid tert-butyl ester 1 mmol of 4-(4-Chloro-[1,3,5]triazin-2-yl)-piperazine-1-carboxylic acid tert-butyl ester [example 4.11 a)] was dissolved in a solution of sodium methanolate (prepared by dissolving 1 mmol of sodium in 5 ml of methanol). The mixture was stirred at room temperature for 1 hour, concentrated and the title compound purified by recrystallisation from ethyl acetate/cyclohexane. MS (m/e): 296.3 (MH$^+$, 100%)

(b) 2-Methoxy-4-piperazin-1-yl-[1,3,5]triazine

Prepared in analogy to example 4.10 (c) from 4-(4-Methoxy-[1,3,5]triazin-2-yl)-piperazine-1-carboxylic acid tert-butyl ester and trifluoroacetic acid. MS (m/e): 196.4 (MH$^+$, 100%)

EXAMPLE 4.14

Preparation of 2-Dimethylcarbamoyloxy-5-methanesulfonyl-benzoic acid (a) 2-Hydroxy-5-methanesulfonyl-benzoic acid benzyl ester 5 mmol of N-(3-dimethylaminopropyl)-N'-ethyl-carbodiimid-hydrochloride was slowly added to a stirred suspension of 5 mmol 2-hydroxy-5-methanesulfonyl-benzoic acid, 5 mmol of benzyl alcohol and 0.5 mmol of 4-dimethylaminopyridine in 10 ml acetonitrile. The mixture was stirred overnight at room temperature, concentrated and treated with 10 ml of water. A few drops of diluted hydrochloric acid were added to acidify the solution. The resulting solid was filtered and then purified by chromatography (SiO$_2$; ethyl acetate/cyclohexane 3:7) to yield the title compound as a colorless solid. MS (m/e): 305.0 (M–H, 100%)

(b) 2-Dimethylcarbamoyloxy-5-methanesulfonyl-benzoic acid benzyl ester

A mixture of 1 mmol 2-hydroxy-5-methanesulfonyl-benzoic acid benzyl ester, 1.5 mmol of N-methylmorpholine and 0.2 mmol of 4-dimethylaminopyridine in 4 ml of dimethylformamide was treated with 1.3 mmol of N,N-dimethylcarbamoylchloride. The reaction mixture was stirred at 60° for 48 hours, concentrated in vacuo and the residue taken up in 5 ml of water. Acidification with diluted hydrochloric acid and extraction with ethyl acetate yielded a crude product which was purified by chromatography (SiO$_2$; ethyl acetate/cyclohexane 1.1). MS (m/e): 378.3 (MH$^+$, 100%)

(c) 2-Dimethylcarbamoyloxy-5-methanesulfonyl-benzoic acid 1 mmol of 2-dimethylcarbamoyloxy-5-methanesulfonyl-benzoic acid benzyl ester was dissolved in 5 ml of methanol. 25 mg of palladium 10% on charcoal was added and the reaction mixture hydrogenated at room temperature to yield the title compound as a slightly yellowish solid. MS (m/e): 288.0 (MH$^+$, 66%)

In analogy to Example 5 compounds 327 to 355 of the following table were prepared from the acid derivatives and piperazine derivatives:

| Expl. No. | Systematic Name | Starting materials | MW found (MH$^+$) |
|---|---|---|---|
| 327 | (6-Ethoxy-2-fluoro-3-methanesulfonyl-phenyl)-[4-(4-methanesulfonyl-phenyl)-piperazin-1-yl]-methanone | 1-(4-Methanesulfonyl-phenyl)-piperazine (commercial) and 6-Ethoxy-2-fluoro-3-methanesulfonyl-benzoic acid (compound 4.1) | 485.4 |
| 328 | (2-Isopropoxy-5-methanesulfonyl-phenyl)-[4-(4-trifluoromethanesulfonyl-phenyl)-piperazin-1-yl]-methanone | 1-(4-Trifluoromethanesulfonyl-phenyl)-piperazine (compound 4.2) and 2-Isopropoxy-5-methanesulfonyl-benzoic acid (compound 1.2) | 552.0 (M + NH$_4^+$) |
| 329 | (2-Cyclopentyloxy-5-methanesulfonyl-phenyl)-[4-(4-trifluoromethanesulfonyl-phenyl)-piperazin-1-yl]-methanone | 1-(4-Trifluoromethanesulfonyl-phenyl)-piperazine (compound 4.2) and 2-Cyclopentyloxy-5-methanesulfonyl-benzoic acid (compound 1.6) | 578.0 (M + NH$_4^+$) |
| 330 | (2-Isobutoxy-5-methanesulfonyl-phenyl)-[4-(4-trifluoromethanesulfonyl-phenyl)-piperazin-1-yl]-methanone | 1-(4-Trifluoromethanesulfonyl-phenyl)-piperazine (compound 4.2) and 2-Isobutoxy-5-methanesulfonyl-benzoic acid (compound 1.3) | 566.1 (M + NH$_4^+$) |
| 331 | [4-(2,4-Bis-trifluoromethyl-phenyl)-piperazin-1-yl]-(2-isopropoxy-5-methanesulfonyl-phenyl)-methanone | 1-(2,4-Bis-trifluoromethyl-phenyl)-piperazine hydrochloride (compound 4.3) and 2-Isopropoxy-5-methanesulfonyl-benzoic acid (compound 1.2) | 539.2 |
| 332 | [4-(2,4-Bis-trifluoromethyl-phenyl)-piperazin-1-yl]-(2-cyclopentyloxy-5-methanesulfonyl-phenyl)-methanone | 1-(2,4-Bis-trifluoromethyl-phenyl)-piperazine hydrochloride (compound 4.3) and 2-Cyclopentyloxy-5-methanesulfonyl-benzoic acid (compound 1.6) | 565.3 |
| 333 | [4-(2,4-Bis-trifluoromethyl-phenyl)-piperazin-1-yl]-(2-isobutoxy-5-methanesulfonyl-phenyl)-methanone | 1-(2,4-Bis-trifluoromethyl-phenyl)-piperazine hydrochloride (compound 4.3) and 2-Isobutoxy-5-methanesulfonyl-benzoic acid (compound 1.3) | 553.2 |
| 334 | (2-Isobutoxy-5-methanesulfonyl-phenyl)-{4-[4-(5-methyl-[1,2,4]oxadiazol-3-yl)-phenyl]-piperazin-1-yl}-methanone | 1-[4-(5-Methyl-[1,2,4]oxadiazol-3-yl)-phenyl]-piperazine hydrochloride (compound 4.4) and 2-Isobutoxy-5-methanesulfonyl-benzoic acid (compound 1.3) | 499.1 |
| 335 | (2-Cyclopentyloxy-5-methanesulfonyl-phenyl)-{4-[4-(5-methyl-[1,2,4]oxadiazol-3-yl)-phenyl]-piperazin-1-yl}-methanone | 1-[4-(5-Methyl-[1,2,4]oxadiazol-3-yl)-phenyl]-piperazine hydrochloride (compound 4.4) and 2-Cyclopentyloxy-5-methanesulfonyl-benzoic acid (compound 1.6) | 511.4 |
| 336 | (2-Isobutoxy-5-methanesulfonyl-phenyl)-[4-(4-oxazol-2-yl-phenyl)-piperazin-1-yl]-methanone | 1-(4-Oxazol-2-yl-phenyl)-piperazine; hydrochloride (compound 4.5) and 2-Isobutoxy-5-methanesulfonyl-benzoic acid (compound 1.3) | 484.4 |
| 337 | (2-Cyclopentyloxy-5-methanesulfonyl-phenyl)-[4-(4-oxazol- | 1-(4-Oxazol-2-yl-phenyl)-piperazine; hydrochloride (compound 4.5) and 2- | 496.4 |

-continued

| Expl. No. | Systematic Name | Starting materials | MW found (MH+) |
|---|---|---|---|
| | 2-yl-phenyl)-piperazin-1-yl]-methanone | Cyclopentyloxy-5-methanesulfonyl-benzoic acid (compound 1.6) | |
| 338 | (2-Isopropoxy-5-methanesulfonyl-phenyl)-{4-[4-(5-methyl-[1,3,4]oxadiazol-2-yl)-phenyl]-piperazin-1-yl}-methanone | 1-[4-(5-Methyl-[1,3,4]oxadiazol-2-yl)-phenyl]-piperazine hydrochloride (compound 4.6) and 2-Isopropoxy-5-methane sulfonyl-benzoic acid (compound 1.2) | 485.3 |
| 339 | (2-Isobutoxy-5-methanesulfonyl-phenyl)-{4-[4-(5-methyl-[1,3,4]oxadiazol-2-yl)-phenyl]-piperazin-1-yl}-methanone | 1-[4-(5-Methyl-[1,3,4]oxadiazol-2-yl)-phenyl]-piperazine hydrochloride (compound 4.6) and 2-Isobutoxy-5-methanesulfonyl-benzoic acid (compound 1.3) | 499.2 |
| 340 | (2-Cyclopentyloxy-5-methanesulfonyl-phenyl)-{4-[4-(5-methyl-[1,3,4]oxadiazol-2-yl)-phenyl]-piperazin-1-yl}-methanone | 1-[4-(5-Methyl-[1,3,4]oxadiazol-2-yl)-phenyl]-piperazine hydrochloride (compound 4.6) and 2-Cyclopentyloxy-5-methanesulfonyl-benzoic acid (compound 1.6) | 511.3 |
| 341 | (2-Isobutoxy-5-methanesulfonyl-phenyl)-{4-[4-(2-methyl-2H!-tetrazol-5-yl)-phenyl]-piperazin-1-yl}-methanone | 1-[4-(2-Methyl-2H-tetrazol-5-yl)-phenyl]-piperazine; hydrochloride (compound 4.7) and 2-Isobutoxy-5-methanesulfonyl-benzoic acid (compound 1.3) | 499.1 |
| 342 | 4-(2-Isopropoxy-5-methanesulfonyl-benzoyl)-3,4,5,6-tetrahydro-2H-[1,2']bipyrazinyl-5'-carboxylic acid methyl ester | 3,4,5,6-Tetrahydro-2H-[1,2']bipyrazinyl-5'-carboxylic acid methyl ester; hydrochloride (compound 4.8) and 2-Isopropoxy-5-methanesulfonyl-benzoic acid (compound 1.2) | 463.4 |
| 343 | 4-(2-Isobutoxy-5-methanesulfonyl-benzoyl)-3,4,5,6-tetrahydro-2H-[1,2']bipyrazinyl-5'-carboxylic acid methyl ester | 3,4,5,6-Tetrahydro-2H-[1,2']bipyrazinyl-5'-carboxylic acid methyl ester; hydrochloride (compound 4.8) and 2-Isobutoxy-5-methanesulfonyl-benzoic acid (compound 1.3) | 477.1 |
| 344 | (6'-Chloro-2,3,5,6-tetrahydro-[1,2']bipyrazinyl-4-yl)-(2-isopropoxy-5-methanesulfonyl-phenyl)-methanone | 6'-Chloro-3,4,5,6-tetrahydro-2H-[1,2']bipyrazinyl; trifluoro-acetic acid (compound 4.9) and 2-Isopropoxy-5-methanesulfonyl-benzoic acid (compound 1.2) | 439.1 |
| 345 | 4-(2-Isopropoxy-5-methanesulfonyl-benzoyl)-3,4,5,6-tetrahydro-2H-[1,2']bipyrazinyl-5'-carboxylic acid amide | 3,4,5,6-Tetrahydro-2H-[1,2']bipyrazinyl-5'-carboxylic acid amide; hydrochloride (compound 4.10) and 2-Isopropoxy-5-methanesulfonyl-benzoic acid (compound 1.2) | 448.3 |
| 346 | 4-(2-Isobutoxy-5-methanesulfonyl-benzoyl)-3,4,5,6-tetrahydro-2H-[1,2']bipyrazinyl-5'-carboxylic acid amide | 3,4,5,6-Tetrahydro-2H-[1,2']bipyrazinyl-5'-carboxylic acid amide; hydrochloride (compound 4.10) and 2-Isobutoxy-5-methanesulfonyl-benzoic acid (compound 1.3) | 462.3 |
| 347 | [4-(4-Dimethylamino-[1,3,5]triazin-2-yl)-piperazin-1-yl]-(2-isobutoxy-5-methanesulfonyl-phenyl)-methanone | Dimethyl-(4-piperazin-1-yl-[1,3,5]triazin-2-yl)-amine (compound 4.11) and 2-Isobutoxy-5-methanesulfonyl-benzoic acid (compound 1.3) | 463.3 |
| 348 | [4-(4-Dimethylamino-[1,3,5]triazin-2-yl)-piperazin-1-yl]-(2-isopropoxy-5-methanesulfonyl-phenyl)-methanone | Dimethyl-(4-piperazin-1-yl-[1,3,5]triazin-2-yl)-amine (compound 4.11) and 2-Isopropoxy-5-methane sulfonyl-benzoic acid (compound 1.2) | 449.3 |

-continued

| Expl. No. | Systematic Name | Starting materials | MW found (MH+) |
|---|---|---|---|
| 349 | (2-Isopropoxy-5-methanesulfonyl-phenyl)-(6'-methoxy-2,3,5,6-tetrahydro-[1,2']bipyrazinyl-4-yl)-methanone | 6'-Methoxy-3,4,5,6-tetrahydro-2H-[1,2']bipyrazinyl; trifluoro-acetic acid (compound 4.12) and 2-Isopropoxy-5-methanesulfonyl-benzoic acid (compound 1.2) | 435.2 |
| 350 | (2-Isopropoxy-5-methanesulfonyl-phenyl)-[4-(4-methoxy-[1,3,5]triazin-2-yl)-piperazin-1-yl]-methanone | 2-Methoxy-4-piperazin-1-yl-[1,3,5]triazine (compound 4.13) and 2-Isopropoxy-5-methanesulfonyl-benzoic acid (compound 1.2) | 436.4 |
| 351 | Dimethyl-carbamic acid 4-methanesulfonyl-2-[4-(4-trifluoromethyl-phenyl)-piperazine-1-carbonyl]-phenyl ester | 1-(4-Trifluoromethyl-phenyl)-piperazine (commercial) and 2-Dimethylcarbamoyloxy-5-methanesulfonyl-benzoic acid (compound 4.14) | 500.4 |
| 352 | Dimethyl-carbamic acid 2-[4-(2-fluoro-4-methanesulfonyl-phenyl)-piperazine-1-carbonyl]-4-methanesulfonyl-phenyl ester | 1-(2-Fluoro-4-methanesulfonyl-phenyl)-piperazine (commercial) and 2-Dimethylcarbamoyloxy-5-methanesulfonyl-benzoic acid (compound 4.14) | 528.3 |
| 353 | (2-Cyclopropylmethoxy-5-methanesulfonyl-phenyl)-(4-phenyl-piperazin-1-yl)-methanone | 1-Phenyl-piperazine (commercial) and 2-Cyclopropylmethoxy-5-methanesulfonyl-benzoic acid (compound 1.4) | 415.5 |
| 354 | (2-Cyclopropylmethoxy-5-methanesulfonyl-phenyl)-[4-(4-methoxy-phenyl)-piperazin-1-yl]-methanone | 1-(4-Methoxy-phenyl)-piperazine (commercial) and 2-Cyclopropylmethoxy-5-methanesulfonyl-benzoic acid (compound 1.4) | 445.3 |
| 355 | (2-Cyclopropylmethoxy-5-methanesulfonyl-phenyl)-[4-(4-hydroxy-phenyl)-piperazin-1-yl]-methanone | 4-Piperazin-1-yl-phenol (commercial) and 2-Cyclopropylmethoxy-5-methanesulfonyl-benzoic acid (compound 1.4) | 431.4 |

EXAMPLE 356

Preparation of 1-{3-Fluoro-4-[4-(2-isopropoxy-5-methanesulfonyl-benzoyl)-piperazin-1-yl]-phenyl}-ethanone oxime 0.12 mmol of 1-{3-Fluoro-4-[4-(2-isopropoxy-5-methanesulfonyl-benzoyl)-piperazin-1-yl]-phenyl}-ethanone was dissolved in 1 ml of a 1:1 mixture of ethanol and water. 0.8 mmol of hydroxylamine hydrochloride was added, followed by 8.4 mmol of sodium acetate. The resulting mixture was stirred overnight at room temperature, diluted with water, filtered, washed and dried to yield the title compound as a colorless solid.
MS (m/e): 478.2 (MH+, 100%)

EXAMPLE 357

Preparation of 1-{3-Fluoro-4-[4-(2-isopropoxy-5-methanesulfonyl-benzoyl)-piperazin-1-yl]-phenyl}-ethanone O-methyl-oxime 0.12 mmol of 1-{3-Fluoro-4-[4-(2-isopropoxy-5-methanesulfonyl-benzoyl)-piperazin-1-yl]-phenyl}-ethanone was dissolved in 1 ml of a 1:1 mixture of ethanol and water. 0.8 mmol of O-methyl-hydroxylamine hydrochloride was added, followed by 8.4 mmol of sodium acetate. The slurry was stirred overnight at room temperature, diluted with water, extracted with ethyl acetate, dried and concentrated. The resulting gum was triturated with diethyl ether/heptane to yield the title compound as a colorless solid. MS (m/e): 492.3 (MH+, 100%)

EXAMPLE 4.15

Preparation of (2,6-Difluoro-3-methanesulfonyl-phenyl)-[4-(2-fluoro-4-methanesulfonyl-phenyl)-piperazin-1-yl]-methanone (a) 3-Chlorosulfonyl-2,6-difluoro-benzoic acid
77 mmol of 2,6-difluorobenzoic acid were dissolved in 15.5 ml of chlorosulfonic acid and stirred for 2 h at 150° C. The reaction mixture was cooled to room temperature and poured into 100 ml of ice/water. The solid was filtered and dried to yield the title compound as a colorless solid. MS (m/e): 255.1 (M–H, 44%)

(b) 2,6-Difluoro-3-sulfino-benzoic acid
240 mmol of sodium sulfite were dissolved in 150 ml of water. 32 mmol of 3-Chlorosulfonyl-2,6-difluoro-benzoic acid was added under stirring over a period of about 20 min. After stirring for an additional hour at room temperature, the mixture was chilled and acidified with 20% aqueous sulfuric acid. The product was extracted with ethyl acetate to yield the title compound as a colorless solid. MS (m/e): 221.3 (M–H, 34%)

(c) 2,6-Difluoro-3-methanesulfonyl-benzoic acid

A suspension of 18 mmol sodium carbonate and 9 mmol 2,6-Difluoro-3-sulfino-benzoic acid in 30 ml of methanol was stirred at room temperature for 30 min, then heated to 60° C. 24 mmol of methyl iodide were added and the reaction mixture heated overnight at 60° C. The reaction mixture was diluted with water and extracted with ethyl acetate. The organic phase was discarded and the aqueous phase acidified by addition of concentrated hydrochloric acid. Extraction with ethyl acetate yielded the title compound as a slightly brownish solid. MS (m/e): 235.1 (M–H, 16%)

(d) (2,6-Difluoro-3-methanesulfonyl-phenyl)-[4-(2-fluoro-4-methanesulfonyl-phenyl)-piperazin-1-yl]-methanone This compound was prepared in analogy to example 5 from 1-(2-fluoro-4-methanesulfonyl-phenyl)-piperazine and 2,6-difluoro-3-methanesulfonyl-benzoic acid. MS (m/e): 477.0 (MH$^+$, 67%)

EXAMPLE 4.16

Preparation of 4-[4-(2,6-Difluoro-3-methanesulfonyl-benzoyl)-piperazin-1-yl]-benzonitrile Prepared in analogy to example 5 from 4-piperazin-1-yl-benzonitrile and 2,6-difluoro-3-methanesulfonyl-benzoic acid. MS (m/e): 406.3 (MH$^+$, 84%)

EXAMPLE 358

Preparation of (2-Cyclopentyloxy-6-ethoxy-3-methanesulfonyl-phenyl)-[4-(4-methanesulfonyl-phenyl)-piperazin-1-yl]-methanone 0.12 mmol of (6-Ethoxy-2-fluoro-3-methanesulfonyl-phenyl)-[4-(4-methanesulfonyl-phenyl)-piperazin-1-yl]-methanone (example 55) was added to a solution of sodium cyclopentanolate (prepared from 1 mmol sodium dissolved in 1 ml of cyclopentanol). The mixture was heated for 1 hour at 80° C., poured on ice/water and extracted with ethyl acetate. Chromatography (SiO$_2$; ethyl acetate) yielded the title compound as a slightly yellow solid. MS (m/e): 551.1 (MH$^+$, 29%)

EXAMPLE 359

Preparation of (2,6-diisopropoxy-3-methanesulfonyl-phenyl)-[4-(2-fluoro-4-methanesulfonyl-phenyl)-piperazin-1-yl]-methanone 0.27 mmol of 2,6-difluoro-3-methanesulfonyl-phenyl)-[4-(2-fluoro-4-methanesulfonyl-phenyl)-piperazin-1-yl]-methanone (example 4.15) was added to a solution of sodium isopropanolate (prepared by dissolving 3 mmol of sodium in 2 ml of isopropanol). The reaction mixture was heated under reflux for 5 hours, cooled, diluted with water and extracted with ethyl acetate, yielding the title compound as a slightly yellow solid. MS (m/e): 557.3 (MH$^+$, 66%)

EXAMPLE 360

Preparation of (2-Fluoro-6-isopropoxy-3-methanesulfonyl-phenyl)-[4-(2-fluoro-4-methanesulfonyl-phenyl)-piperazin-1-yl]-methanone 0.2 mmol of (2,6-difluoro-3-methanesulfonyl-phenyl)-[4-(2-fluoro-4-methanesulfonyl-phenyl)-piperazin-1-yl]-methanone were dissolved in a solution of sodium isopropanolate (prepared by dissolving 0.2 mmol of sodium in 1 ml of isopropanol). The reaction mixture was heated to 50° C. for 2 hours, then stirred at room temperature for 48 hours. The solution was diluted with water and extracted with ethyl acetate. The product was purified by chromatography (SiO$_2$, ethyl acetate/cyclohexane 9:1) to yield the title compound as a colorless solid. MS (m/e): 517.1 (MH$^+$, 100%)

EXAMPLE 361

Preparation of (6-Cyclopentyloxy-2-fluoro-3-methanesulfonyl-phenyl)-[4-(2-fluoro-4-methanesulfonyl-phenyl)-piperazin-1-yl]-methanone The compound was prepared in analogy to example 358 from (2,6-difluoro-3-methanesulfonyl-phenyl)-[4-(2-fluoro-4-methanesulfonyl-phenyl)-piperazin-1-yl]-methanone and sodium cyclopentanolate. MS (m/e): 560.5 (MNH$_4^+$, 43%)

EXAMPLE 362

Preparation of 4-[4-(2-Fluoro-6-isopropoxy-3-methanesulfonyl-benzoyl)-piperazin-1-yl]-benzonitrile The compound was prepared in analogy to example 359 from 4-[4-(2,6-difluoro-3-methanesulfonyl-benzoyl)-piperazin-1-yl]-benzonitrile and sodium isopropanolate. MS (m/e): 446.0 (MH$^+$, 49%)

EXAMPLE 5.1

Preparation of 1-(3-Fluoro-4-trifluoromethyl-phenyl)-piperazine (a) 4-(3-Fluoro-4-trifluoromethyl-phenyl)-piperazine-1-carboxylic acid tert-butyl ester A mixture of 4.9 mmol 4-chloro-2-fluorobenzotrifluoride, 5.9 mmol n-Boc-piperazine, 0.05 mmol palladium acetate, 6.9 mmol sodium-t-butoxide and 0.49 mmol 2-(di-t-butylphosphino)biphenyl in 10 ml toluene was heated for 16 h at 80° C. After cooling to RT, the mixture was diluted with ether; the suspension was filtered over decalite; and the filtrate evaporated. The residue was purified on silica eluting with a gradient of heptane/EtOAc to yield after evaporation the title compound.

(b) 1-(3-Fluoro-4-trifluoromethyl-phenyl)-piperazine

A mixture of 2.87 mmol 4-(3-Fluoro-4-trifluoromethyl-phenyl)-piperazine-1-carboxylic acid tert-butyl ester in 10 ml dichloromethane was treated with 14.4 mmol trifluoroacetic acid and refluxed for 3 h. The mixture was concentrated and treated with 10 ml water, NaOH and extracted with dichloromethane. The combined organic phases were dried with MgSO$_4$ and evaporated to yield the title compound 5.1. MS (m/e): 249.2 (MH$^+$, 100%)

EXAMPLE 5.2

Preparation of 2-Piperazin-1-yl-5-trifluoromethyl-benzonitrile

The compound was prepared in analogy to compound 5.1 from 2-Chloro-5-trifluoromethyl-benzonitrile (DE2550262). MS (m/e): 256.0 (MH$^+$, 100%)

EXAMPLE 5.3

Preparation of 1-(2,3-Difluoro-4-methanesulfonyl-phenyl)-piperazine

The compound was prepared in analogy to compound 2.20 from 2,3,4-Trifluoro-benzenesulfonyl chloride (commercial). MS (m/e): 277.2 (MH$^+$, 100%)

EXAMPLE 5.4

Preparation of 1-(2-Fluoro-4-methyl-phenyl)-piperazine

The compound was prepared in analogy to compound 1.1 from 4-bromo-3-fluorotoluene (commercial). MS (m/e): 195.3 (MH$^+$, 100%)

EXAMPLE 5.5

Preparation of 1-(3-Fluoro-5-trifluoromethyl-pyridin-2-yl)-piperazine

The compound was prepared in analogy to compound 2.7 from 2,3-Difluoro-5-trifluoromethyl-pyridine (EP0104715). MS (m/e): 250.2 (MH$^+$, 100%)

EXAMPLE 5.6

Preparation of 5-Methanesulfonyl-2-((S)-2,2,2-trifluoro-1-methyl-ethoxy)-benzoic acid (a) rac-5-Methanesulfonyl-2-(2,2,2-trifluoro-1-methyl-ethoxy)-benzoic acid methyl ester A mixture of 21.7 mmol 2-Hydroxy-5-methanesulfonyl-benzoic acid methyl ester [68029-77-6], 32.5 mmol trifluoro-methanesulfonic acid 2,2,2-trifluoro-1-methyl-ethyl ester [212556-43-9], 43.4 mmol potassium carbonate in 87 ml DMF was stirred at 80° C. for 48 hours. After cooling to RT, the mixture was concentrated in vacuo, taken in water and stirred for 1 hour. Filtration yielded the title compound.

(b) 5-Methanesulfonyl-2-((S)-2,2,2-trifluoro-1-methyl-ethoxy)-benzoic acid methyl ester The title compound was obtained by separation of rac-5-Methanesulfonyl-2-(2,2,2-trifluoro-1-methyl-ethoxy)-benzoic acid methyl ester by chiral HPLC (Chiralcel OD, 15% ethanol/Heptane, flow 35 ml, 220 nm, retention time: 86 min.).

(c) 5-Methanesulfonyl-2-((S)-2,2,2-trifluoro-1-methyl-ethoxy)-benzoic acid

The compound was prepared in analogy to compound 2.10(b) from 5-Methanesulfonyl-2-((S)-2,2,2-trifluoro-1-methyl-ethoxy)-benzoic acid methyl ester MS (m/e): 311.0 (M–H, 100%)

EXAMPLE 5.7

Preparation of 5-Methanesulfonyl-2-((R)-2,2,2-trifluoro-1-methyl-ethoxy)-benzoic acid (a) 5-Methanesulfonyl-2-((R)-2,2,2-trifluoro-1-methyl-ethoxy)-benzoic acid methyl ester The title compound was obtained by separation of rac-5-Methanesulfonyl-2-(2,2,2-trifluoro-1-methyl-ethoxy)-benzoic acid methyl ester by chiral HPLC (Chiralcel OD, 15% ethanol/Heptane, flow 35 ml, 220 nm, retention time: 74 min.).

(b) 5-Methanesulfonyl-2-((R)-2,2,2-trifluoro-1-methyl-ethoxy)-benzoic acid

The compound was prepared in analogy to compound 2.10(b) from 5-Methanesulfonyl-2-((R)-2,2,2-trifluoro-1-methyl-ethoxy)-benzoic acid methyl ester MS (m/e): 311.0 (M–H, 100%)

EXAMPLE 5.8

Preparation of 2-Chloro-4-piperazin-1-yl-benzonitrile

A mixture of 7.0 mmol 2-chloro-4-fluorobenzonitrile (commercial), 10.5 mmol piperazine in 4 ml N,N-dimethylacetamide was heated for 1 h at 85° C. After cooling to RT and evaporation in vacuo, the mixture was diluted with dichloromethane and purified on silica, eluting with a gradient of dichloromethane/MeOH to yield after evaporation the title compound. MS (m/e): 222.1 (MH$^+$, 100%)

EXAMPLE 5.9

Preparation of 1-(2-Fluoro-4-piperazin-1-yl-phenyl)-ethanone

The compound was prepared in analogy to compound 5.8 from 2,4-difluoroacetophenone (commercial). MS (m/e): 223.2 (M–H, 100%)

EXAMPLE 5.10

Preparation of 1-(3-Fluoro-4-methanesulfonyl-phenyl)-piperazine

The compound was prepared in analogy to compound 2.20 from 2,4-difluorobenzenesulfonylchloride (commercial). MS (m/e): 259.1 (MH$^+$, 100%)

EXAMPLE 5.11

Preparation of 1-(4-Fluoro-2-piperazin-1-yl-phenyl)-ethanone

The compound was prepared in analogy to compound 5.8 from 2,4-difluoroacetophenone (commercial). MS (m/e): 223.2 (M–H, 100%)

EXAMPLE 5.12

Preparation of 6-Isopropoxy-isophthalamic acid

The compound was prepared in analogy to compound 2.10 from 6-Hydroxy-isophthalamic acid methyl ester [89366-34-7]. MS (m/e): 222.1 (M–H, 100%)

EXAMPLE 5.13

Preparation of 5-Ethanesulfonyl-2-isopropoxy-benzoic acid (a) 5-Ethanesulfonyl-2-hydroxy-benzoic acid methyl ester The compound was prepared in analogy to compound 2.20(b) from 2-Hydroxy-5-sulfino-benzoic acid [19479-88-0] and ethyliodide (b) 5-Ethanesulfonyl-2-isopropoxy-benzoic acid The compound was prepared in analogy to compound 2.10 from 5-Ethanesulfonyl-2-hydroxy-benzoic acid methyl ester. MS (m/e): 271.1 (M–H, 100%)

EXAMPLE 5.14

Preparation of 1-(4-Difluoromethyl-2-fluoro-phenyl)-piperazine (a) 1-Chloro-4-difluoromethyl-2-fluoro-benzene 24.7 mmol 4-Chloro-3-fluorobenzaldehyde was dissolved in DAST (5.1 ml) under nitrogen. The mixture was stirred at room temperature for 3 hours, at 50° C. for 2 hours and then at room temperature for 65 hours. The solution was added dropwise to a saturated.bicarbonate solution (150 ml) under cooling. The aqueous layer was extracted 3 times with ethyl acetate. The combined extracts were dried over $Na_2SO_4$, filtered and the solvent was removed in vacuo. The residue was purified on silica eluting with heptane to yield after evaporation the title compound.

(b) 1-(4-Difluoromethyl-2-fluoro-phenyl)-piperazine

The compound was prepared in analogy to compound 1.1 from 1-Chloro-4-difluoromethyl-2-fluoro-benzene. MS (m/e): 231.2 (M+H$^+$, 100%)

EXAMPLE 5.15

Preparation of 1-(6-Trifluoromethyl-pyridin-3-yl)-piperazine

The compound was prepared in analogy to compound 1.1 from 5-Bromo-2-trifluoromethyl-pyridine [436799-32-5]. MS (m/e): 232.1 (M+H$^+$, 100%)

EXAMPLE 5.16

Preparation of 3-Fluoro-4-piperazin-1-yl-benzoic acid ethyl ester

The compound was prepared in analogy to compound 5.8 from Ethyl-3,4-difluorobenzoate (commercial). MS (m/e): 253.2 (M+H$^+$, 100%)

EXAMPLE 5.17

Preparation of 1-(2-Trifluoromethyl-pyridin-4-yl)-piperazine

The compound can be prepared from 4-Nitro-2-trifluoromethyl-pyridine 1-oxide [147149-97-1] in analogy to the procedure used for the preparation of 4-Bromo-2-methyl-6-trifluoromethyl-pyridine [615579-78-1] (WO03087056). MS (m/e): 227 (M+H$^+$, 100%)

EXAMPLE 5.18

Preparation of 1-(6-Methyl-pyridin-3-yl)-piperazine

The compound was prepared in analogy to compound 1.1 from 5-Bromo-2-methyl-pyridine (commercial). MS (m/e): 178.1 (M+H$^+$, 100%)

In analogy to Example 5 compounds 363 to 461 of the following table were prepared from the acid derivatives and piperazine derivatives:

| Expl. No. | Systematic Name | Starting materials | MW found (MH$^+$) |
| --- | --- | --- | --- |
| 363 | 2-[4-(2-Isopropoxy-5-methanesulfonyl-benzoyl)-piperazin-1-yl]-5-trifluoromethyl-benzonitrile | 2-Piperazin-1-yl-5-trifluoromethyl-benzonitrile (compound 5.2) and 2-Isopropoxy-5-methanesulfonyl-benzoic acid (compound 1.2) | 496.3 |
| 364 | 4-[4-(2-Isopropoxy-5-methanesulfonyl-benzoyl)-piperazin-1-yl]-2-trifluoromethyl-benzonitrile | 4-Piperazin-1-yl-2-trifluoromethyl-benzonitrile (WO0017163) and 2-Isopropoxy-5-methanesulfonyl-benzoic acid (compound 1.2) | 496.3 |
| 365 | 1-{4-[4-(2-Isopropoxy-5-methanesulfonyl-benzoyl)-piperazin-1-yl]-2-trifluoromethyl-phenyl}-ethanone | 1-(4-Piperazin-1-yl-2-trifluoromethyl-phenyl)-ethanone (WO0210277) and 2-Isopropoxy-5-methanesulfonyl-benzoic acid (compound 1.2) | 513.4 |
| 366 | 2-Chloro-4-[4-(2-isopropoxy-5-methanesulfonyl-benzoyl)-piperazin-1-yl]-benzonitrile | 2-Chloro-4-piperazin-1-yl-benzonitrile (compound 5.8) and 2-Isopropoxy-5-methanesulfonyl-benzoic acid (compound 1.2) | 462.3 |
| 367 | 1-{2-Fluoro-4-[4-(2-isopropoxy-5-methanesulfonyl-benzoyl)-piperazin-1-yl]-phenyl}-ethanone | 1-(2-Fluoro-4-piperazin-1-yl-phenyl)-ethanone (compound 5.9) and 2-Isopropoxy-5-methanesulfonyl-benzoic acid (compound 1.2) | 463.4 |
| 368 | [4-(3-Fluoro-4-methanesulfonyl-phenyl)-piperazin-1-yl]-(2-isopropoxy-5-methanesulfonyl-phenyl)-methanone | 1-(3-Fluoro-4-methanesulfonyl-phenyl)-piperazine (compound 5.10) and 2-Isopropoxy-5-methanesulfonyl-benzoic acid (compound 1.2) | 499.3 |
| 369 | 1-{4-[4-(2-Cyclopropyl methoxy-5-methanesulfonyl-benzoyl)-piperazin-1-yl]-2- | 1-(2-Fluoro-4-piperazin-1-yl-phenyl)-ethanone (compound 5.9) and 2-Cyclopropyl | 475.4 |

-continued

| Expl. No. | Systematic Name | Starting materials | MW found (MH+) |
|---|---|---|---|
| | fluoro-phenyl}-ethanone | methoxy-5-methanesulfonyl-benzoic acid (compound 1.4) | |
| 370 | (2-Cyclopropyl methoxy-5-methanesulfonyl-phenyl)-[4-(3-fluoro-4-methanesulfonyl-phenyl)-piperazin-1-yl]methanone- | 1-(3-Fluoro-4-methanesulfonyl-phenyl)-piperazine (compound 5.10) and 2-Cyclopropylmethoxy-5-methanesulfonyl-benzoic acid (compound 1.4) | 511.4 |
| 371 | [4-(3-Fluoro-4-methanesulfonyl-phenyl)-piperazin-1-yl]-(2-isobutoxy-5-methanesulfonyl-phenyl)-methanone | 1-(3-Fluoro-4-methanesulfonyl-phenyl)-piperazine (compound 5.10) and 2-Isobutoxy-5-methanesulfonyl-benzoic acid (compound 1.3) | 513.4 |
| 372 | 1-{2-Fluoro-4-[4-(2-isobutoxy-5-methanesulfonyl-benzoyl)-piperazin-1-yl]-phenyl}-ethanone | 1-(2-Fluoro-4-piperazin-1-yl-phenyl)-ethanone (compound 5.9) and 2-Isobutoxy-5-methanesulfonyl-benzoic acid (compound 1.3) | 477.3 |
| 373 | 2-[4-(2-Cyclopentyloxy-5-methanesulfonyl-benzoyl)-piperazin-1-yl]-5-trifluoromethyl-benzonitrile | 2-Piperazin-1-yl-5-trifluoromethyl-benzonitrile (compound 5.2) and 2-Cyclopentyloxy-5-methanesulfonyl-benzoic acid (compound 1.6) | 522.4 |
| 374 | 2-[4-(2-Cyclopropyl methoxy-5-methanesulfonyl-benzoyl)-piperazin-1-yl]-5-trifluoromethyl-benzonitrile | 2-Piperazin-1-yl-5-trifluoromethyl-benzonitrile (compound 5.2) and 2-Cyclopropylmethoxy-5-methanesulfonyl-benzoic acid (compound 1.4) | 508.6 |
| 375 | 2-[4-(2-Isobutoxy-5-methanesulfonyl-benzoyl)-piperazin-1-yl]-5-trifluoromethyl-benzonitrile | 2-Piperazin-1-yl-5-trifluoromethyl-benzonitrile (compound 5.2) and 2-Isobutoxy-5-methanesulfonyl-benzoic acid (compound 1.3) | 510.6 |
| 376 | 2-{4-[5-Methanesulfonyl-2-(2,2,2-trifluoro-ethoxy)-benzoyl]-piperazin-1-yl}-5-trifluoromethyl-benzonitrile | 2-Piperazin-1-yl-5-trifluoromethyl-benzonitrile (compound 5.2) and 5-Methanesulfonyl-2-(2,2,2-trifluoro-ethoxy)-benzoic acid (compound 1.5) | 536.5 |
| 377 | rac-[4-(3-Fluoro-4-methanesulfonyl-phenyl)-piperazin-1-yl]-[5-methanesulfonyl-2-(2,2,2-trifluoro-1-methyl-ethoxy)-phenyl]-methanone | 1-(3-Fluoro-4-methanesulfonyl-phenyl)-piperazine (compound 5.10) and rac-5-Methanesulfonyl-2-(2,2,2-trifluoro-1-methyl-ethoxy)-benzoic acid (compound 3.1) | 553.2 |
| 378 | rac-1-(2-Fluoro-4-{4-[5-methanesulfonyl-2-(2,2,2-trifluoro-1-methyl-ethoxy)-benzoyl]-piperazin-1-yl}-phenyl)-ethanone | 1-(2-Fluoro-4-piperazin-1-yl-phenyl)-ethanone (compound 5.9) and rac-5-Methanesulfonyl-2-(2,2,2-trifluoro-1-methyl-ethoxy)-benzoic acid (compound 3.1) | 517.4 |
| 379 | 1-{4-Fluoro-2-[4-(2-isopropoxy-5-methanesulfonyl-benzoyl)-piperazin-1-yl]-phenyl}-ethanone | 1-(4-Fluoro-2-piperazin-1 yl-phenyl)-ethanone (compound 5.11) and 2-Isopropoxy-5-methanesulfonyl-benzoic acid (compound 1.2) | 463.4 |
| 380 | 3-[4-(2-Fluoro-4-trifluoromethyl-phenyl)-piperazine-1-carbonyl]-4-isopropoxy-benzamide | 1-(2-Fluoro-4-trifluoromethyl-phenyl)-piperazine (compound 1.1) and 6-Isopropoxy-isophthalamic acid (compound 5.12) | 454.6 |
| 381 | 4-Isopropoxy-3-[4-(4-trifluoromethyl-phenyl)-piperazine-1-carbonyl]-benzamide | 1-(4-Trifluoromethyl-phenyl)-piperazine (commercial) and 6-Isopropoxy-isophthalamic acid (compound 5.12) | 436.4 |
| 382 | 3-[4-(3-Fluoro-4-trifluoromethyl-phenyl)-piperazine-1-carbonyl]-4-isopropoxy-benzamide | 1-(3-Fluoro-4-trifluoromethyl-phenyl)-piperazine (compound 5.1) and 6-Isopropoxy-isophthalamic acid (compound 5.12) | 454.6 |
| 383 | 3-[4-(2-Fluoro-4-methanesulfonyl-phenyl)-piperazine-1- | 1-(2-Fluoro-4-methanesulfonyl-phenyl)-piperazine (commercial) and 6- | 464.4 |

| Expl. No. | Systematic Name | Starting materials | MW found (MH+) |
|---|---|---|---|
| | carbonyl]-4-isopropoxy-benzamide | Isopropoxy-isophthalamic acid (compound 5.12) | |
| 384 | 3-[4-(2-Cyano-4-trifluoromethyl-phenyl)-piperazine-1-carbonyl]-4-isopropoxy-benzamide | 2-Piperazin-1-yl-5-trifluoromethyl-benzonitrile (compound 5.2) and 6-Isopropoxy-isophthalamic acid (compound 5.12) | 461.4 |
| 385 | 3-[4-(4-Cyano-phenyl)-piperazine-1-carbonyl]-4-isopropoxy-benzamide | 4-Piperazin-1-yl-benzonitrile (commercial) and 6-Isopropoxy-isophthalamic acid (compound 5.12) | 393.2 |
| 386 | 3-[4-(4-Cyano-2-fluoro-phenyl)-piperazine-1-carbonyl]-4-isopropoxy-benzamide | 3-Fluoro-4-piperazin-1-yl-benzonitrile (WO9625414) and 6-Isopropoxy-isophthalamic acid (compound 5.12) | 411.4 |
| 387 | 3-[4-(4-Cyano-3-fluoro-phenyl)-piperazine-1-carbonyl]-4-isopropoxy-benzamide | 2-Fluoro-4-piperazin-1-yl-benzonitrile (WO 9808835) and 6-Isopropoxy-isophthalamic acid (compound 5.12) | 411.4 |
| 388 | 3-[4-(4-Acetyl-2-fluoro-phenyl)-piperazine-1-carbonyl]-4-isopropoxy-benzamide | 1-(3-Fluoro-4-piperazin-1-yl-phenyl)-ethanone (WO9714690) and 6-Isopropoxy-isophthalamic acid (compound 5.12) | 428.6 |
| 389 | [4-(2,3-Difluoro-4-methanesulfonyl-phenyl)-piperazin-1-yl]-(2-isopropoxy-5-methanesulfonyl-phenyl)-methanone | 1-(2,3-Difluoro-4-methanesulfonyl-phenyl)-piperazine (compound 5.3) and 2-Isopropoxy-5-methanesulfonyl-benzoic acid (compound 1.2) | 517.4 |
| 390 | (5-Ethanesulfonyl-2-isopropoxy-phenyl)-[4-(4-trifluoromethyl-phenyl)-piperazin-1-yl]-methanone | 1-(4-Trifluoromethyl-phenyl)-piperazine (commercial) and 5-Ethanesulfonyl-2-isopropoxy-benzoic acid (compound 5.13) | 485.5 |
| 391 | (5-Ethanesulfonyl-2-isopropoxy-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 5-Ethanesulfonyl-2-isopropoxy-benzoic acid (compound 5.13) | 513.4 |
| 392 | 4-[4-(5-Ethanesulfonyl-2-isopropoxy-benzoyl)-piperazin-1-yl]-3-fluoro-benzonitrile | 3-Fluoro-4-piperazin-1-yl-benzonitrile (WO9625414) and 5-Ethanesulfonyl-2-isopropoxy-benzoic acid (compound 5.13) | 460.5 |
| 393 | (5-Ethanesulfonyl-2-isopropoxy-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and 5-Ethanesulfonyl-2-isopropoxy-benzoic acid (compound 5.13) | 503.3 |
| 394 | [4-(2,3-Difluoro-4-methanesulfonyl-phenyl)-piperazin-1-yl]-(5-ethanesulfonyl-2-isopropoxy-phenyl)-methanone | 1-(2,3-Difluoro-4-methanesulfonyl-phenyl)-piperazine (compound 5.3) and 5-Ethanesulfonyl-2-isopropoxy-benzoic acid (compound 5.13) | 531.3 |
| 395 | (2-Cyclopentyloxy-5-methanesulfonyl-phenyl)-[4-(2,3-difluoro-4-methanesulfonyl-phenyl)-piperazin-1-yl]-methanone | 1-(2,3-Difluoro-4-methanesulfonyl-phenyl)-piperazine (compound 5.3) and 2-Cyclopentyloxy-5-methanesulfonyl-benzoic acid (compound 1.6) | 542.1 |
| 396 | (2-Cyclopropylmethoxy-5-methanesulfonyl-phenyl)-[4-(2,3-difluoro-4-methanesulfonyl-phenyl)-piperazin-1-yl]-methanone | 1-(2,3-Difluoro-4-methanesulfonyl-phenyl)-piperazine (compound 5.3) and 2-Cyclopropylmethoxy-5-methanesulfonyl-benzoic acid (compound 1.4) | 529.3 |
| 397 | [4-(2,3-Difluoro-4-methanesulfonyl-phenyl)-piperazin-1-yl]-[5-methanesulfonyl-2-(2,2,2-trifluoro- | 1-(2,3-Difluoro-4-methanesulfonyl-phenyl)-piperazine (compound 5.3) and 5-Methanesulfonyl-2-(2,2,2-trifluoro-ethoxy)- | 557.2 |

-continued

| Expl. No. | Systematic Name | Starting materials | MW found (MH+) |
|---|---|---|---|
| | ethoxy)-phenyl]-methanone | benzoic acid (compound 1.5) | |
| 398 | rac-[4-(2,3-Difluoro-4-methanesulfonyl-phenyl)-piperazin-1-yl]-[5-methanesulfonyl-2-(2,2,2-trifluoro-1-methyl-ethoxy)-phenyl]-methanone | 1-(2,3-Difluoro-4-methanesulfonyl-phenyl)-piperazine (compound 5.3) and rac-5-Methanesulfonyl-2-(2,2,2-trifluoro-1-methyl-ethoxy)-benzoic acid (compound 3.1) | 571.3 |
| 399 | [4-(2,3-Difluoro-4-methanesulfonyl-phenyl)-piperazin-1-yl]-(5-methanesulfonyl-2-trifluoromethoxy-phenyl)-methanone | 1-(2,3-Difluoro-4-methanesulfonyl-phenyl)-piperazine (compound 5.3) and 5-Methanesulfonyl-2-trifluoromethoxy-benzoic acid (compound 2.15) | 543.2 |
| 400 | [4-(4-Difluoromethyl-2-fluoro-phenyl)-piperazin-1-yl]-(2-isopropoxy-5-methanesulfonyl-phenyl)-methanone | 1-(4-Difluoromethyl-2-fluoro-phenyl)-piperazine (compound 5.14) and 2-Isopropoxy-5-methanesulfonyl-benzoic acid (compound 1.2) | 471.1 |
| 401 | [4-(3-Chloro-5-trifluoromethyl-pyridin-2-yl)-piperazin-1-yl]-[5-methanesulfonyl-2-(2,2,2-trifluoro-ethoxy)-phenyl]-methanone | 1-(3-Chloro-5-trifluoromethyl-pyridin-2-yl)-piperazine (commercial) and 5-Methanesulfonyl-2-(2,2,2-trifluoro-ethoxy)-benzoic acid (compound 1.5) | 546.3 |
| 402 | [5-Methanesulfonyl-2-(2,2,2-trifluoro-ethoxy)-phenyl]-[4-(5-trifluoromethyl-pyridin-2-yl)-piperazin-1-yl]-methanone | 1-(5-Trifluoromethyl-pyridin-2-yl)-piperazine (commercial) and 5-Methanesulfonyl-2-(2,2,2-trifluoro-ethoxy)-benzoic acid (compound 1.5) | 512.4 |
| 403 | 6-{4-[5-Methanesulfonyl-2-(2,2,2-trifluoro-ethoxy)-benzoyl]-piperazin-1-yl}-nicotinonitrile | 6-Piperazin-1-yl-nicotinonitrile (commercial) and 5-Methanesulfonyl-2-(2,2,2-trifluoro-ethoxy)-benzoic acid (compound 1.5) | 469.3 |
| 404 | 6-[4-(2-Cyclopropylmethoxy-5-methanesulfonyl-benzoyl)-piperazin-1-yl]-nicotinonitrile | 6-Piperazin-1-yl-nicotinonitrile (commercial) and 2-Cyclopropylmethoxy-5-methanesulfonyl-benzoic acid (compound 1.4) | 441.4 |
| 405 | (2-Cyclopropylmethoxy-5-methanesulfonyl-phenyl)-[4-(5-trifluoromethyl-pyridin-2-yl)-piperazin-1-yl]-methanone | 1-(5-Trifluoromethyl-pyridin-2-yl)-piperazine (commercial) and 2-Cyclopropylmethoxy-5-methanesulfonyl-benzoic acid (compound 1.4) | 484.5 |
| 406 | [4-(3-Chloro-5-trifluoromethyl-pyridin-2-yl)-piperazin-1-yl]-(2-cyclopropylmethoxy-5-methanesulfonyl-phenyl)-methanone | 1-(3-Chloro-5-trifluoromethyl-pyridin-2-yl)-piperazine (commercial) and 2-Cyclopropylmethoxy-5-methanesulfonyl-benzoic acid (compound 1.4) | 518.3 |
| 407 | rac-[4-(3-Chloro-5-trifluoromethyl-pyridin-2-yl)-piperazin-1-yl]-[5-methanesulfonyl-2-(2,2,2-trifluoro-1-methyl-ethoxy)-phenyl]-methanone | 1-(3-Chloro-5-trifluoromethyl-pyridin-2-yl)-piperazine (commercial) and rac-5-Methanesulfonyl-2-(2,2,2-trifluoro-1-methyl-ethoxy)-benzoic acid (compound 3.1) | 560.3 |
| 408 | rac-[5-Methanesulfonyl-2-(2,2,2-trifluoro-1-methyl-ethoxy)-phenyl]-[4-(5-trifluoromethyl-pyridin-2-yl)-piperazin-1-yl]-methanone | 1-(5-Trifluoromethyl-pyridin-2-yl)-piperazine (commercial) and rac-5-Methanesulfonyl-2-(2,2,2-trifluoro-1-methyl-ethoxy)-benzoic acid (compound 3.1) | 526.2 |
| 409 | rac-6-{4-[5-Methanesulfonyl-2-(2,2,2-trifluoro-1-methyl-ethoxy)-benzoyl]-piperazin-1-yl}-nicotinonitrile | 6-Piperazin-1-yl-nicotinonitrile (commercial) and rac-5-Methanesulfonyl-2-(2,2,2-trifluoro-1-methyl-ethoxy)-benzoic acid (compound 3.1) | 483.4 |

-continued

| Expl. No. | Systematic Name | Starting materials | MW found (MH+) |
|---|---|---|---|
| 410 | [4-(6-Chloro-5-trifluoromethyl-pyridin-2-yl)-piperazin-1-yl]-(2-cyclopropyl methoxy-5-methanesulfonyl-phenyl)-methanone | 1-(6-Chloro-5-trifluoromethyl-pyridin-2-yl)-piperazine (WO03097636) and 2-Cyclopropylmethoxy-5-methanesulfonyl-benzoic acid (compound 1.4) | 518.3 |
| 411 | 6-[4-(2-Cyclopentyloxy-5-methanesulfonyl-benzoyl)-piperazin-1-yl]-nicotinonitrile | 6-Piperazin-1-yl-nicotinonitrile (commercial) and 2-Cyclopentyloxy-5-methanesulfonyl-benzoic acid (compound 1.6) | 455.5 |
| 412 | (2-Cyclopentyloxy-5-methanesulfonyl-phenyl)-[4-(5-trifluoromethyl pyridin-2-yl)-piperazin-1-yl]-methanone | 1-(5-Trifluoromethyl-pyridin-2-yl)-piperazine (commercial) and 2-Cyclopentyloxy-5-methanesulfonyl-benzoic acid (compound 1.6) | 498.3 |
| 413 | [4-(3-Chloro-5-trifluoromethyl-pyridin-2-yl)-piperazin-1-yl]-(2-cyclopentyloxy-5-methanesulfonyl-phenyl)-methanone | 1-(3-Chloro-5-trifluoromethyl-pyridin-2-yl)-piperazine (commercial) and 2-Cyclopentyloxy-5-methanesulfonyl-benzoic acid (compound 1.6) | 532.3 |
| 414 | [4-(6-Chloro-5-trifluoromethyl-pyridin-2-yl)-piperazin-1-yl]-(2-isopropoxy-5-methanesulfonyl-phenyl)-methanone | 1-(6-Chloro-5-trifluoromethyl-pyridin-2-yl)-piperazine (WO03097636) and 2-Isopropoxy-5-methanesulfonyl-benzoic acid (compound 1.2) | 506.3 |
| 415 | (2-Isopropoxy-5-methanesulfonyl-phenyl)-[4-(5-trifluoromethyl-pyridin-2-yl)-piperazin-1-yl]-methanone | 1-(5-Trifluoromethyl-pyridin-2-yl)-piperazine (commercial) and 2-Isopropoxy-5-methanesulfonyl-benzoic acid (compound 1.2) | 472.2 |
| 416 | 6-[4-(2-Isopropoxy-5-methanesulfonyl-benzoyl)-piperazin-1-yl]-nicotinonitrile | 6-Piperazin-1-yl-nicotinonitrile (commercial) and 2-Isopropoxy-5-methanesulfonyl-benzoic acid (compound 1.2) | 429.5 |
| 417 | [4-(3-Chloro-5-trifluoromethyl-pyridin-2-yl)-piperazin-1-yl]-(2-isopropoxy-5-methanesulfonyl-phenyl)-methanone | 1-(3-Chloro-5-trifluoromethyl-pyridin-2-yl)-piperazine (commercial) and 2-Isopropoxy-5-methanesulfonyl-benzoic acid (compound 1.2) | 506.3 |
| 418 | rac-[4-(5-Chloro-pyridin-2-yl)-piperazin-1-yl]-[5-methanesulfonyl-2-(2,2,2-trifluoro-1-methyl-ethoxy)-phenyl]-methanone | 1-(5-Chloro-pyridin-2-yl)-piperazine (WO01062751) and rac-5-Methanesulfonyl-2-(2,2,2-trifluoro-1-methyl-ethoxy)-benzoic acid (compound 3.1) | 492.3 |
| 419 | [4-(5-Chloro-pyridin-2-yl)-piperazin-1-yl]-(2-cyclopentyloxy-5-methanesulfonyl-phenyl)-methanone | 1-(5-Chloro-pyridin-2-yl)-piperazine (WO01062751) and 2-Cyclopentyloxy-5-methanesulfonyl-benzoic acid (compound 1.6) | 464.3 |
| 420 | [4-(5-Chloro-pyridin-2-yl)-piperazin-1-yl]-(2-cyclopropylmethoxy-5-methanesulfonyl-phenyl)-methanone | 1-(5-Chloro-pyridin-2-yl)-piperazine (WO01062751) and 2-Cyclopropylmethoxy-5-methanesulfonyl-benzoic acid (compound 1.4) | 450.4 |
| 421 | [4-(5-Chloro-pyridin-2-yl)-piperazin-1-yl]-[5-methanesulfonyl-2-(2,2,2-trifluoro-ethoxy)-phenyl]-methanone | 1-(5-Chloro-pyridin-2-yl)-piperazine (WO01062751) and 5-Methanesulfonyl-2-(2,2,2-trifluoro-ethoxy)-benzoic acid (compound 1.5) | 478.2 |
| 422 | [4-(5-Chloro-pyridin-2-yl)-piperazin-1-yl]-(2-isopropoxy-5-methanesulfonyl-phenyl)-methanone | 1-(5-Chloro-pyridin-2-yl)-piperazine (WO01062751) and 2-Isopropoxy-5-methanesulfonyl-benzoic acid (compound 1.2) | 438.3 |
| 423 | Rac-[4-(6-Chloro-pyridazin-3-yl)-piperazin-1-yl]-[5- | 3-Chloro-6-piperazin-1-yl-pyridazine (WO02030405) and rac-5-Methanesulfonyl-2- | 493.3 |

-continued

| Expl. No. | Systematic Name | Starting materials | MW found (MH+) |
|---|---|---|---|
| | methanesulfonyl-2-(2,2,2-trifluoro-1-methyl-ethoxy)-phenyl]-methanone | (2,2,2-trifluoro-1-methyl-ethoxy)-benzoic acid (compound 3.1) | |
| 424 | [4-(6-Chloro-pyridazin-3-yl)-piperazin-1-yl]-(2-cyclopentyloxy-5-methanesulfonyl-phenyl)-methanone | 3-Chloro-6-piperazin-1-yl-pyridazine (WO02030405) and 2-Cyclopentyloxy-5-methanesulfonyl-benzoic acid (compound 1.6) | 465.4 |
| 425 | (2-Isopropoxy-5-methanesulfonyl-phenyl)-[4-(6-trifluoromethyl-pyridin-3-yl)-piperazin-1-yl]-methanone | 1-(6-Trifluoromethyl-pyridin-3-yl)-piperazine (compound 5.15) and 2-Isopropoxy-5-methanesulfonyl-benzoic acid (compound 1.2) | 472.2 |
| 426 | [5-Methanesulfonyl-2-(2,2,2-trifluoro-ethoxy)-phenyl]-[4-(6-trifluoromethyl-pyridin-3-yl)-piperazin-1-yl]-methanone | 1-(6-Trifluoromethyl-pyridin-3-yl)-piperazine (compound 5.15) and 5-Methanesulfonyl-2-(2,2,2-trifluoro-ethoxy)-benzoic acid (compound 1.5) | 512.4 |
| 427 | rac-[5-Methanesulfonyl-2-(2,2,2-trifluoro-1-methyl-ethoxy)-phenyl]-[4-(6-trifluoromethyl-pyridin-3-yl)-piperazin-1-yl]-methanone | 1-(6-Trifluoromethyl-pyridin-3-yl)-piperazine (compound 5.15) and rac-5-Methanesulfonyl-2-(2,2,2-trifluoro-1-methyl-ethoxy)-benzoic acid (compound 3.1) | 526.2 |
| 428 | 3-Fluoro-4-[4-(2-isopropoxy-5-methanesulfonyl-benzoyl)-piperazin-1-yl]-benzoic acid ethyl ester | 3-Fluoro-4-piperazin-1-yl-benzoic acid ethyl ester (compound 5.16) and 2-Isopropoxy-5-methanesulfonyl-benzoic acid (compound 1.2) | 493.4 |
| 429 | [4-(5-Bromo-pyridin-2-yl)-piperazin-1-yl]-(2-isopropoxy-5-methanesulfonyl-phenyl)-methanone | 1-(5-Bromo-pyridin-2-yl)-piperazine (WO9534555) and 2-Isopropoxy-5-methanesulfonyl-benzoic acid (compound 1.2) | 482.4 |
| 430 | (2-Cyclopentyloxy-5-methanesulfonyl-phenyl)-[4-(6-trifluoromethyl-pyridin-3-yl)-piperazin-1-yl]-methanone | 1-(6-Trifluoromethyl-pyridin-3-yl)-piperazine (compound 5.15) and 2-Cyclopentyloxy-5-methanesulfonyl-benzoic acid (compound 1.6) | 498.3 |
| 431 | (2-Cyclopropyl methoxy-5-methanesulfonyl-phenyl)-[4-(6-trifluoromethyl-pyridin-3-yl)-piperazin-1-yl]-methanone | 1-(6-Trifluoromethyl-pyridin-3-yl)-piperazine (compound 5.15) and 2-Cyclopropyl methoxy-5-methanesulfonyl-benzoic acid (compound 1.4) | 484.5 |
| 432 | [4-(5-Bromo-pyridin-2-yl)-piperazin-1-yl]-[5-methanesulfonyl-2-(2,2,2-trifluoro-ethoxy)-phenyl]-methanone | 1-(5-Bromo-pyridin-2-yl)-piperazine (WO 9534555) and 5-Methanesulfonyl-2-(2,2,2-trifluoro-ethoxy)-benzoic acid (compound 1.5) | 522.2 |
| 433 | [5-Methanesulfonyl-2-(2,2,2-trifluoro-ethoxy)-phenyl]-[4-(2-trifluoromethyl-pyridin-4-yl)-piperazin-1-yl]-methanone | 1-(2-Trifluoromethyl-pyridin-4-yl)-piperazine (compound 5.17) and 5-Methanesulfonyl-2-(2,2,2-trifluoro-ethoxy)-benzoic acid (compound 1.5) | 512.4 |
| 434 | (2-Isopropoxy-5-methanesulfonyl-phenyl)-[4-(2-trifluoromethyl-pyridin-4-yl)-piperazin-1-yl]-methanone | 1-(2-Trifluoromethyl-pyridin-4-yl)-piperazine (compound 5.17) and 2-Isopropoxy-5-methanesulfonyl-benzoic acid (compound 1.2) | 472.2 |
| 435 | rac-[4-(5-Bromo-pyridin-2-yl)-piperazin-1-yl]-[5-methanesulfonyl-2-(2,2,2-trifluoro-1-methyl-ethoxy)-phenyl]-methanone | 1-(5-Bromo-pyridin-2-yl)-piperazine (WO 9534555) and rac-5-Methanesulfonyl-2-(2,2,2-trifluoro-1-methyl-ethoxy)-benzoic acid (compound 3.1) | 536.3 |

-continued

| Expl. No. | Systematic Name | Starting materials | MW found (MH+) |
|---|---|---|---|
| 436 | [4-(3-Fluoro-5-trifluoromethyl-pyridin-2-yl)-piperazin-1-yl]-[5-methanesulfonyl-2-(2,2,2-trifluoro-ethoxy)-phenyl]-methanone | 1-(3-Fluoro-5-trifluoromethyl-pyridin-2-yl)-piperazine (compound 5.5) and 5-Methanesulfonyl-2-(2,2,2-trifluoro-ethoxy)-benzoic acid (compound 1.5) | 530.3 |
| 437 | [4-(3-Fluoro-5-trifluoromethyl-pyridin-2-yl)-piperazin-1-yl]-(2-isopropoxy-5-methanesulfonyl-phenyl)-methanone | 1-(3-Fluoro-5-trifluoromethyl-pyridin-2-yl)-piperazine (compound 5.5) and 2-Isopropoxy-5-methanesulfonyl-benzoic acid (compound 1.2) | 490.4 |
| 438 | rac-[4-(3-Fluoro-5-trifluoromethyl-pyridin-2-yl)-piperazin-1-yl]-[5-methanesulfonyl-2-(2,2,2-trifluoro-1-methyl-ethoxy)-phenyl]-methanone | 1-(3-Fluoro-5-trifluoromethyl-pyridin-2-yl)-piperazine (compound 5.5) and rac-5-Methanesulfonyl-2-(2,2,2-trifluoro-1-methyl-ethoxy)-benzoic acid (compound 3.1) | 544.3 |
| 439 | (2-Cyclopentyloxy-5-methanesulfonyl-phenyl)-[4-(3-fluoro-5-trifluoromethyl-pyridin-2-yl)-piperazin-1-yl]-methanone | 1-(3-Fluoro-5-trifluoromethyl-pyridin-2-yl)-piperazine (compound 5.5) and 2-Cyclopentyloxy-5-methanesulfonyl-benzoic acid (compound 1.6) | 516.4 |
| 440 | (2-Cyclopropylmethoxy-5-methanesulfonyl-phenyl)-[4-(3-fluoro-5-trifluoromethyl-pyridin-2-yl)-piperazin-1-yl]-methanone | 1-(3-Fluoro-5-trifluoromethyl-pyridin-2-yl)-piperazine (compound 5.5) and 2-Cyclopropylmethoxy-5-methanesulfonyl-benzoic acid (compound 1.4) | 502.3 |
| 441 | rac-[5-Methanesulfonyl-2-(2,2,2-trifluoro-1-methyl-ethoxy)-phenyl]-[4-(2-trifluoromethyl-pyridin-4-yl)-piperazin-1-yl]-methanone | 1-(2-Trifluoromethyl-pyridin-4-yl)-piperazine (compound 5.17) and rac-5-Methanesulfonyl-2-(2,2,2-trifluoro-1-methyl-ethoxy)-benzoic acid (compound 3.1) | 526.2 |
| 442 | [5-Methanesulfonyl-2-(2,2,2-trifluoro-ethoxy)-phenyl]-[4-(6-methyl-pyridin-3-yl)-piperazin-1-yl]-methanone | 1-(6-Methyl-pyridin-3-yl)-piperazine (compound 5.18) and 5-Methanesulfonyl-2-(2,2,2-trifluoro-ethoxy)-benzoic acid (compound 1.5) | 458.4 |
| 443 | (2-Isopropoxy-5-methanesulfonyl-phenyl)-[4-(6-methyl-pyridin-3-yl)-piperazin-1-yl]-methanone | 1-(6-Methyl-pyridin-3-yl)-piperazine (compound 5.18) and 2-Isopropoxy-5-methanesulfonyl-benzoic acid (compound 1.2) | 418.3 |
| 444 | (2-Cyclopentyloxy-5-methanesulfonyl-phenyl)-[4-(6-methyl-pyridin-3-yl)-piperazin-1-yl]-methanone | 1-(6-Methyl-pyridin-3-yl)-piperazine (compound 5.18) and 2-Cyclopentyloxy-5-methanesulfonyl-benzoic acid (compound 1.6) | 444.4 |
| 445 | (2-Cyclopropyl methoxy-5-methanesulfonyl-phenyl)-[4-(6-methyl-pyridin-3-yl)-piperazin-1-yl]-methanone | 1-(6-Methyl-pyridin-3-yl)-piperazine (compound 5.18) and 2-Cyclopropylmethoxy-5-methanesulfonyl-benzoic acid (compound 1.4) | 430.5 |
| 446 | [5-Methanesulfonyl-2-(2,2,2-trifluoro-ethoxy)-phenyl]-[4-(5-methyl-pyridin-2-yl)-piperazin-1-yl]-methanone | 1-(5-Methyl-pyridin-2-yl)-piperazine (WO03032996) and 5-Methanesulfonyl-2-(2,2,2-trifluoro-ethoxy)-benzoic acid (compound 1.5) | 458.0 |
| 447 | (2-Isopropoxy-5-methanesulfonyl-phenyl)-[4-(5-methyl-pyridin-2-yl)-piperazin-1-yl]-methanone | 1-(5-Methyl-pyridin-2-yl)-piperazine (WO03032996) and 2-Isopropoxy-5-methanesulfonyl-benzoic acid (compound 1.2) | 418.3 |
| 448 | (2-Cyclopropylmethoxy-5-methanesulfonyl-phenyl)-[4-(5-methyl-pyridin-2-yl)-piperazin-1-yl]-methanone | 1-(5-Methyl-pyridin-2-yl)-piperazine (WO03032996) and 2-Cyclopropylmethoxy-5-methanesulfonyl-benzoic acid (compound 1.4) | 430.5 |

-continued

| Expl. No. | Systematic Name | Starting materials | MW found (MH+) |
|---|---|---|---|
| 449 | rac-[5-Methanesulfonyl-2-(2,2,2-trifluoro-1-methyl-ethoxy)-phenyl]-[4-(5-methyl-pyridin-2-yl)-piperazin-1-yl]-methanone | 1-(5-Methyl-pyridin-2-yl)-piperazine (WO03032996) and rac-5-Methanesulfonyl-2-(2,2,2-trifluoro-1-methyl-ethoxy)-benzoic acid (compound 3.1) | 472.3 |
| 450 | rac-[5-Methanesulfonyl-2-(2,2,2-trifluoro-1-methyl-ethoxy)-phenyl]-[4-(6-methyl-pyridin-3-yl)-piperazin-1-yl]-methanone | 1-(6-Methyl-pyridin-3-yl)-piperazine (compound 5.18) and rac-5-Methanesulfonyl-2-(2,2,2-trifluoro-1-methyl-ethoxy)-benzoic acid (compound 3.1) | 472.2 |
| 451 | [5-Methanesulfonyl-2-(2,2,2-trifluoro-ethoxy)-phenyl]-[4-(4-trifluoromethyl-pyridin-2-yl)-piperazin-1-yl]-methanone | 1-(4-Trifluoromethyl-pyridin-2-yl)-piperazine (WO02002529) and 5-Methanesulfonyl-2-(2,2,2-trifluoro-ethoxy)-benzoic acid (compound 1.5) | 512.4 |
| 452 | (2-Isopropoxy-5-methanesulfonyl-phenyl)-[4-(4-trifluoromethyl-pyridin-2-yl)-piperazin-1-yl]-methanone | 1-(4-Trifluoromethyl-pyridin-2-yl)-piperazine (WO02002529) and 2-Isopropoxy-5-methanesulfonyl-benzoic acid (compound 1.2) | 472.3 |
| 453 | (2-tert-Butoxy-5-methanesulfonyl-phenyl)-[4-(4-trifluoromethyl-pyridin-2-yl)-piperazin-1-yl]-methanone | 1-(4-Trifluoromethyl-pyridin-2-yl)-piperazine (WO02002529) and 2-tert-Butoxy-5-methanesulfonyl-benzoic acid (compound 2.19) | 486.2 |
| 454 | [4-(2-Fluoro-4-methanesulfonyl-phenyl)-piperazin-1-yl]-[5-methanesulfonyl-2-((S)-2,2,2-trifluoro-1-methyl-ethoxy)-phenyl]-methanone | 1-(2-Fluoro-4-methanesulfonyl-phenyl)-piperazine (commercial) and 5-Methanesulfonyl-2-((S)-2,2,2-trifluoro-1-methyl-ethoxy)-benzoic acid (compound 5.6) | 570.4 (M + NH4+) |
| 455 | rac-[5-Methanesulfonyl-2-(2,2,2-trifluoro-1-methyl-ethoxy)-phenyl]-[4-(4-trifluoromethyl-pyridin-2-yl)-piperazin-1-yl]-methanone | 1-(4-Trifluoromethyl-pyridin-2-yl)-piperazine (WO02002529) and rac-5-Methanesulfonyl-2-(2,2,2-trifluoro-1-methyl-ethoxy)-benzoic acid (compound 3.1) | 526.0 |
| 456 | [4-(2-Fluoro-4-methanesulfonyl-phenyl)-piperazin-1-yl]-[5-methanesulfonyl-2-((R)-2,2,2-trifluoro-1-methyl-ethoxy)-phenyl]-methanone | 1-(2-Fluoro-4-methanesulfonyl-phenyl)-piperazine (commercial) and 5-Methanesulfonyl-2-((R)-2,2,2-trifluoro-1-methyl-ethoxy)-benzoic acid (compound 5.7) | 570.4 (M + NH4+) |
| 457 | (2-Cyclopentyloxy-5-methanesulfonyl-phenyl)-[4-(4-trifluoromethyl-pyridin-2-yl)-piperazin-1-yl]-methanone | 1-(4-Trifluoromethyl-pyridin-2-yl)-piperazine (WO02002529) and 2-Cyclopentyloxy-5-methanesulfonyl-benzoic acid (compound 1.6) | 498.2 |
| 458 | (2-Isopropoxy-5-methanesulfonyl-phenyl)-[4-(6-trifluoromethyl-pyridin-2-yl)-piperazin-1-yl]-methanone | 1-(6-Trifluoromethyl-pyridin-2-yl)-piperazine (EP 462638) and 2-Isopropoxy-5-methanesulfonyl-benzoic acid (compound 1.2) | 472.1 |
| 459 | rac-[5-Methanesulfonyl-2-(2,2,2-trifluoro-1-methyl-ethoxy)-phenyl]-[4-(6-trifluoromethyl-pyridin-2-yl)-piperazin-1-yl]-methanone | 1-(6-Trifluoromethyl-pyridin-2-yl)-piperazine (EP 462638) and rac-5-Methanesulfonyl-2-(2,2,2-trifluoro-1-methyl-ethoxy)-benzoic acid (compound 3.1) | 526.0 |
| 460 | [5-Methanesulfonyl-2-(2,2,2-trifluoro-ethoxy)-phenyl]-[4-(6-trifluoromethyl-pyridin-2-yl)-piperazin-1-yl]-methanone | 1-(6-Trifluoromethyl-pyridin-2-yl)-piperazine (EP 462638) and 5-Methanesulfonyl-2-(2,2,2-trifluoro-ethoxy)-benzoic acid (compound 1.5) | 512.2 |

-continued

| Expl. No. | Systematic Name | Starting materials | MW found (MH+) |
|---|---|---|---|
| 461 | 3-Fluoro-4-[4-(2-isopropoxy-5-methanesulfonyl-benzoyl)-piperazin-1-yl]-benzaldehyde | 1-(4-Difluoromethyl-2-fluoro-phenyl)-piperazine (compound 5.14) and 2-Isopropoxy-5-methanesulfonyl-benzoic acid (compound 1.2) | 449.1 |

EXAMPLE 462

Preparation of rac-{4-[2-Fluoro-4-(1-hydroxy-ethyl)-phenyl]-piperazin-1-yl}-(2-isopropoxy-5-methanesulfonyl-phenyl)-methanone 0.086 mmol of 1-{3-Fluoro-4-[4-(2-isopropoxy-5-methanesulfonyl-benzoyl)-piperazin-1-yl]-phenyl}-ethanone was dissolved in 1 ml ethanol and 0.26 mmol sodium borohydride was added The mixture was refluxed for 40 min., cooled to room temperature, quenched with water, acidified with HCl 1N and extracted with ethyl acetate. The combined extracts were dried over $Na_2SO_4$, filtered and the solvent was removed in vacuo. The residue was purified on silica eluting with heptane/ethylacetate to yield after evaporation the title compound. MS (m/e): 465.4 (M+H+, 100%)

EXAMPLE 463

Preparation of {4-[2-Fluoro-4-(1-hydroxy-1-methyl-ethyl)-phenyl]-piperazin-1-yl}-(2-isopropoxy-5-methanesulfonyl-phenyl)-methanone To a solution of 0.173 mmol 1-{3-Fluoro-4-[4-(2-isopropoxy-5-methanesulfonyl-benzoyl)-piperazin-1-yl]-phenyl}-ethanone in tetrahydrofuran (2 ml) was added dropwise 0.190 mmol 1.6M Methyllithium solution in ether at −75° C. The mixture was stirred for 2 hours and then allowed to warm to 0° C. The mixture was quenched with a 20% $NH_4Cl$ solution and extracted 3 times with ethyl acetate. The combined extracts were dried over $Na_2SO_4$, filtered and the solvent was removed in vacuo. The residue was purified on silica, eluting with dichloromethane/MeOH to yield after evaporation the title compound.

MS (m/e): 479.5 (M+H+, 100%)

The examples 464-471 have been prepared by separation of the racemic material by chiral HPLC:

| Expl. No. | Systematic Name | Starting materials | Separation Conditions | MW found (MH+) |
|---|---|---|---|---|
| 464 | [5-Methanesulfonyl-2-((S or R)-2,2,2-trifluoro-1-methyl-ethoxy)-phenyl]-[4-(5-trifluoromethyl-pyridin-2-yl)-piperazin-1-yl]-methanone | rac-[5-Methanesulfonyl-2-(2,2,2-trifluoro-1-methyl-ethoxy)-phenyl]-[4-(5-trifluoromethyl-pyridin-2-yl)-piperazin-1-yl]-methanone (example 408) | Chiralpak AD, 20% Isopropanol/Heptane, flow 35 ml, 254 nm, 170 min. | 525.8 (M) |
| 465 | [5-Methanesulfonyl-2-((R or S)-2,2,2-trifluoro-1-methyl-ethoxy)-phenyl]-[4-(5-trifluoromethyl-pyridin-2-yl)-piperazin-1-yl]-methanone | rac-[5-Methanesulfonyl-2-(2,2,2-trifluoro-1-methyl-ethoxy)-phenyl]-[4-(5-trifluoromethyl-pyridin-2-yl)-piperazin-1-yl]-methanone (example 408) | Chiralpak AD, 20% Isopropanol/Heptane, flow 35 ml, 254 nm, 245 min. | 525.3 (M) |
| 466 | [4-(2-Fluoro-4-trifluoromethyl-phenyl)-piperazin-1-yl]-[5-methanesulfonyl-2-((S or R)-2,2,2-trifluoro-1-methyl-ethoxy)-phenyl]-methanone | rac-[4-(2-Fluoro-4-trifluoromethyl-phenyl)-piperazin-1-yl]-[5-methanesulfonyl-2-(2,2,2-trifluoro-1-methyl-ethoxy)-phenyl]-methanone (example 302) | Chiralpak AD, 25% Isopropanol/Heptane, flow 35 ml 220 nm, 141 min. | 543.2 |
| 467 | [4-(2-Fluoro-4-trifluoromethyl-phenyl)-piperazin-1-yl]-[5-methanesulfonyl-2-((R or S)-2,2,2-trifluoro-1-methyl-ethoxy)-phenyl]-methanone | rac-[4-(2-Fluoro-4-trifluoromethyl-phenyl)-piperazin-1-yl]-[5-methanesulfonyl-2-(2,2,2-trifluoro-1-methyl-ethoxy)-phenyl]-methanone (example 302) | Chiralpak AD, 25% Isopropanol/Heptane, flow 35 ml, 220 nm, 199 min. | 543.2 |

-continued

| Expl. No. | Systematic Name | Starting materials | Separation Conditions | MW found (MH+) |
|---|---|---|---|---|
| 468 | [5-Methanesulfonyl-2-((S or R)-2,2,2-trifluoro-1-methyl-ethoxy)-phenyl]-[4-(4-trifluoromethyl-phenyl)-piperazin-1-yl]-methanone | rac-5-Methanesulfonyl-2-(2,2,2-trifluoro-1-methyl-ethoxy)-phenyl]-[4-(4-trifluoromethyl-phenyl)-piperazin-1-yl]-methanone (example 301) | Chiralpak AD, 25% Isopropanol/Heptane, flow 35 ml, 220 nm, 197 min. | 525.2 |
| 469 | [5-Methanesulfonyl-2-((R or S)-2,2,2-trifluoro-1-methyl-ethoxy)-phenyl]-[4-(4-trifluoromethyl-phenyl)-piperazin-1-yl]-methanone | rac-5-Methanesulfonyl-2-(2,2,2-trifluoro-1-methyl-ethoxy)-phenyl]-[4-(4-trifluoromethyl-phenyl)-piperazin-1-yl]-methanone (example 301) | Chiralpak AD, 25% Isopropanol/Heptane, flow 35 ml, 220 nm, 280 min. | 525.2 |
| 470 | [4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone | rac-[4-(3-Fluoro-5-trifluoromethyl-pyridin-2-yl)-piperazin-1-yl]-[5-methanesulfonyl-2-(2,2,2-trifluoro-1-methyl-ethoxy)-phenyl]-methanone (example 438) | Chiralpak AD, 20% Isopropanol/Heptane, flow 35 ml, 254 nm, 110 min. | 544.3 |
| 471 | [4-(3-Fluoro-5-trifluoromethyl-pyridin-2-yl)-piperazin-1-yl]-[5-methanesulfonyl-2-((R)-2,2,2-trifluoro-1-methyl-ethoxy)phenyl]-methanone | rac-[4-(3-Fluoro-5-trifluoromethyl-pyridin-2-yl)-piperazin-1-yl]-[5-methanesulfonyl-2-(2,2,2-trifluoro-1-methyl-ethoxy)-phenyl]-methanone (example 438) | Chiralpak AD, 20% Isopropanol/Heptane, flow 35 ml, 254 nm, 145 min. | 544.0 |

EXAMPLE 6.1

Preparation of 2-isobutoxy-5-methylsulfamoyl-benzoic acid (a) 5-Chlorosulfonyl-2-hydroxy-benzoic acid To 3.26 mol chlorosulfonic acid at 0° C. was added 652 mmol salicylic acid in small portions, and the mixture was then allowed to stir at RT for 1 h, then at 50° C. for 1 h, and finally at 70° C. for 1 h. The mixture was then added dropwise to 1000 ml ice-water with stirring and stirring continued for an additional 30 min. The ensuing white crystals were collected by filtration, washed three times with water, and then dried in vacuo at 45° C. for 16 h to yield the title compound. MS (m/e): 236.8 ([{$^{37}$Cl}M–H]$^-$, 33%), 235.0 ([{$^{37}$Cl}M–H]$^-$, 100%)

(b) 2-Hydroxy-5-methylsulfamoyl-benzoic acid

To 63 mmol 5-chlorosulfonyl-2-hydroxy-benzoic acid in 120 ml dichloromethane at RT was added dropwise 317 mmol methylamine (8 M solution in ethanol), and the mixture was allowed to stir at RT for 1 h. The mixture was then concentrated in vacuo. The residue was suspended in 1 M aq NaOH solution and extracted twice with ether. The aqueous phase was acidified with 5 M aq HCl, saturated with NaCl, and extracted 3 times with THF. The combined THF extracts were washed twice with saturated aqueous NaCl solution and dried with Na$_2$SO$_4$. Evaporation in vacuo yielded the title compound. MS (m/e): 249.0 (M+NH$_4$$^+$, 100%), 231.9 (M+H$^+$, 63%)

(c) 2-Hydroxy-5-methylsulfamoyl-benzoic acid methyl ester

To 77 mmol 2-hydroxy-5-methylsulfamoyl-benzoic acid in 300 ml THF was added 85 mmol CDI, and the mixture heated at 70° C. for 1 h. 770 mmol methanol was then added, and the mixture was heated at 70° C. for 16 h. The mixture was then cooled to room temperature and concentrated in vacuo. The residue was chromatographed on silica gel (eluant: ethyl acetate/heptane/dichloromethane 45:45:10) to afford the title compound. MS (m/e): 244.1 ([M–H]$^-$, 100%)

(d) 2-Isobutoxy-5-methylsulfamoyl-benzoic acid methyl ester

To 2.9 mmol 2-hydroxy-5-methylsulfamoyl-benzoic acid methyl ester, 3.1 mmol 2-methyl-1-propanol and 3.3 mmol triphenylphosphine in 10 ml THF was added 3.1 mmol di-tert-butyl azodicarboxylate, and the mixture was stirred at RT for 2 h. The mixture was then concentrated in vacuo. The residue was chromatographed on silica gel (eluant: ethyl acetate/heptane 2:3) to afford the title compound. MS (m/e): 300.2 ([M–H]$^-$, 100%)

(e) 2-Isobutoxy-5-methylsulfamoyl-benzoic acid

To 3.3 mmol 2-isobutoxy-5-methylsulfamoyl-benzoic acid methyl ester in 10 ml THF was added 20 mmol 2 M aq NaOH, and the mixture was heated at 50° C. for 2 h. The mixture was then cooled to RT and extracted twice with ether. The aqueous phase was acidified with 10% aq citric acid and extracted 3 times with ethyl acetate. The combined organic phases were dried with Na$_2$SO$_4$. Evaporation in vacuo followed by trituration in ether afforded the title compound. MS (m/e): 286.2 ([M–H]$^-$, 100%)

In analogy to Example 6.1(d) and (e), compounds 6.2 to 6.10 of the following table were prepared from 2-hydroxy- 5-methylsulfamoyl-benzoic acid methyl ester and the appropriate alcohol, followed by hydrolysis with aqueous sodium hydroxide:

| Expl. No | Systematic Name | alcohol | MS (M/e) |
|---|---|---|---|
| 6.2 | 2-(2,2-Dimethyl-propoxy)-5-methylsulfamoyl-benzoic acid | 2,2-Dimethyl-1-propanol | 300.2 (M − H) |
| 6.3 | 2-Isopropoxy-5-methylsulfamoyl-benzoic acid | 2-Propanol | 272.2 (M − H) |
| 6.4 | 2-Cyclopentyloxy-5-methylsulfamoyl-benzoic acid | Cyclopentanol | 298.2 (M − H) |
| 6.5 | 2-Cyclobutoxy-5-methylsulfamoyl-benzoic acid | Cyclobutanol | 284.1 (M − H) |
| 6.6 | 2-Cyclopropylmethoxy-5-methylsulfamoyl-benzoic acid | Cyclopropyl-methanol | 284.1 (M − H) |
| 6.7 | 2-Cyclobutylmethoxy-5-methylsulfamoyl-benzoic acid | Cyclobutyl-methanol | 298.2 (M − H) |
| 6.8 | 5-Methylsulfamoyl-2-(tetrahydro-pyran-4-yloxy)-benzoic acid | Tetrahydro-2H-pyran-4-ol | 314.1 (M − H) |
| 6.9 | 2-(2-Methoxy-ethoxy)-5-methylsulfamoyl-benzoic acid | 2-Methoxy-ethanol | 288.1 (M − H) |
| 6.10 | 5-Methylsulfamoyl-2-(3,3,3-trifluoro-propoxy)-benzoic acid | 3,3,3-Trifluoro-1-propanol | 326.2 (M − H) |

EXAMPLE 6.11

Preparation of 5-methylsulfamoyl-2-(2,2,2-trifluoro-ethoxy)-benzoic acid (a) 5-Methylsulfamoyl-2-(2,2,2-trifluoro-ethoxy)-benzoic acid methyl ester To 3.3 mmol 2-hydroxy-5-methylsulfamoyl-benzoic acid methyl ester and 3.3 mmol potassium carbonate in 50 ml acetone was added dropwise 4.9 mmol 2,2,2-trifluoro-ethyl trifluoromethanesulfonate, and the mixture was heated at 60° C. for 16 h. The mixture was then concentrated in vacuo. The residue was suspended in dichloromethane and filtered. The filtrate was concentrated in vacuo, and the residue was chromatographed on silica gel (eluant: ethyl acetate/heptane 3:7) to afford the tide compound. MS (m/e): 328.0 (M+H+, 100%)

(b) 5-Methylsulfamoyl-2-(2,2,2-trifluoro-ethoxy)-benzoic acid

To 2.3 mmol 5-methylsulfamoyl-2-(2,2,2-trifluoro-ethoxy)-benzoic acid methyl ester in 10 ml THF was added 20 mmol 2 M aq NaOH, and the mixture was heated at 50° C. for 2 h. The mixture was then cooled to RT and extracted twice with ether. The aqueous phase was acidified with 10% aq citric acid and extracted 3 times with ethyl acetate. The combined organic phases were dried with $Na_2SO_4$. Evaporation in vacuo followed by trituration in ether afforded the tide compound. MS (m/e): 312.0 ([M−H]−, 100%)

EXAMPLE 6.19

Preparation of rac-5-methylsulfamoyl-2-(2,2,2-trifluoro-1-methyl-ethoxy)-benzoic acid (a) rac-5-Methylsulfamoyl-2-(2,2,2-trifluoro-1-methyl-ethoxy)-benzoic acid methyl ester To 4.1 mmol 2-hydroxy-5-methylsulfamoyl-benzoic acid methyl ester and 4.1 mmol potassium carbonate in 5 ml DMF was added dropwise 6.1 mmol trifluoro-methanesulfonic acid 2,2,2-trifluoro-1-methyl-ethyl ester, and the mixture was heated at 90° C. for 16 h. The mixture was then cooled to RT, poured onto water and extracted 3 times with ethyl acetate. The combined organic phases were dried with $Na_2SO_4$. Evaporation in vacuo followed by chromatography on silica gel (eluant: dichloromethane) afforded the title compound.

MS (m/e): 359.2 (M+$NH_4^+$, 80%), 342.0 (M+H+, 100%)

(b) rac-5-Methylsulfamoyl-2-(2,2,2-trifluoro-1-methyl-ethoxy)-benzoic acid

To 1.6 mmol 5-methylsulfamoyl-2-(2,2,2-trifluoro-1-methyl-ethoxy)-benzoic acid methyl ester in 10 ml THF was added 20 mmol 2 M aq NaOH, and the mixture was heated at 50° C. for 2 h. The mixture was then cooled to RT and extracted twice with ether. The aqueous phase was acidified with 10% aq citric acid and extracted twice with ethyl acetate. The combined organic phases were dried with $Na_2SO_4$. Evaporation in vacuo followed by trituration in ether and hexane afforded the title compound. MS (m/e): 326.2 ([M−H]−, 100%)

EXAMPLE 6.14

Preparation of 5-cyclopropanesulfonyl-2-isopropoxy-benzoic acid (a) 2-Hydroxy-5-sulfino-benzoic acid To 317 mmol sodium sulfite in 200 ml water at RT was added dropwise over 30 min a solution of 42.3 mmol 5-chlorosulfonyl-2-hydroxy-benzoic acid in 80 ml dioxane and stirring continued for a further 30 min. 5 M aq NaOH was then added dropwise until the reaction mixture was pH 14, and the mixture was then allowed to stir at RT for a further 2 h. The mixture was then cooled to 0° C. and concentrated $H_2SO_4$ added until the reaction mixture was pH 1. Ethyl acetate was added, and the phases were separated. The organic phase was dried with $Na_2SO_4$. Evaporation in vacuo yielded the title compound.

MS (m/e): 201.0 ([M−H]−, 100%)

(b) 5-(3-Chloro-propane-1-sulfonyl)-2-hydroxy-benzoic acid

To 16.7 mmol 2-hydroxy-5-sulfino-benzoic acid and 41.7 mmol triethylamine in 40 ml DMF was added 18.3 mmol 1-chloro-3-iodopropane, and the mixture heated at 40° C. for 1 h. The mixture was then cooled to room temperature and concentrated in vacuo. The residue was chromatographed on silica gel (eluant: dichloromethane/methanol/acetic acid gradient) to afford the title compound. MS (m/e): 279.1 ([$^{37}$Cl]M−H]−, 33%), 277.0 ([$^{35}$Cl]M−H]−, 100%)

(c) 5-Cyclopropanesulfonyl-2-hydroxy-benzoic acid

To 8.0 mmol 5-(3-chloro-propane-1-sulfonyl)-2-hydroxy-benzoic acid in 30 ml THF at −78° C. was added dropwise over 30 min 23.9 mmol of a 0.9 M solution of potassium bis(trimethylsilyl)amide in toluene. The reaction mixture was then allowed to warm to RT and stirring continued for a further 30 min at RT. The mixture was then diluted with THF/ethyl acetate (1:1) and washed sequentially with 1 M aq HCl and saturated aqueous NaCl solution, dried with $Na_2SO_4$, and concentrated in vacuo. The residue was triturated in ether/pentane to afford the title compound. MS (m/e): 241.2 ([M−H]−, 100%)

(d) 5-Cyclopropanesulfonyl-2-hydroxy-benzoic acid methyl ester

To 7.2 mmol 5-cyclopropanesulfonyl-2-hydroxy-benzoic acid in 20 ml dichloroethane containing a few drops of DMF was added dropwise 8.7 mmol oxalyl chloride. After stirring for 90 min at RT, the reaction mixture was cooled to 0° C. and then 144 mmol methanol was added, followed by 72 mmol pyridine, and stirring continued at RT for 1 h. The mixture was then washed with 1 M aq HCl, dried with Na$_2$SO$_4$, and concentrated in vacuo. The residue was chromatographed on silica gel (eluant: ethyl acetate/heptane gradient) to afford the title compound. MS (m/e): 255.2 ([M−H]$^-$, 100%)

(e) 5-Cyclopropanesulfonyl-2-isopropoxy-benzoic acid

To 0.6 mmol 5-cyclopropanesulfonyl-2-hydroxy-benzoic acid methyl ester, 3.7 mmol 2-propanol and 0.9 mmol diphenyl-2-pyridylphosphine in 8 ml THF was added 0.9 mmol di-tert-butyl azodicarboxylate, and the mixture was stirred at RT for 3 h. 4 mmol 5 M aq NaOH solution was then added, and the mixture heated at 60° C. for 1 h. The mixture was then concentrated in vacuo. The residue was resuspended in ethyl acetate and washed twice with 1 M aq NaOH solution. The combined aqueous phases were then acidified to pH 1 by addition of 25% aq HCl and extracted three times with ethyl acetate. The combined organic extracts were then dried with Na$_2$SO$_4$, and concentrated in vacuo to afford the tide compound. MS (m/e): 282.9 ([M−H]$^-$, 100%)

In analogy to Example 6.14 (e), compounds 6.15 to 6.18 of the following table were prepared from 5-cyclopropanesulfonyl-2-hydroxy-benzoic acid methyl ester and the appropriate alcohol, followed by hydrolysis with aqueous sodium hydroxide:

| Expl. No | Systematic Name | alcohol | MS (m/e) |
|---|---|---|---|
| 6.15 | 5-Cyclopropanesulfonyl-2-isobutoxy-benzoic acid | 2-Methyl-1-propanol | 297.1 (M − H) |
| 6.16 | 2-Cyclopentyloxy-5-cyclopropanesulfonyl-benzoic acid | Cyclopentanol | 309.1 (M − H) |
| 6.17 | 5-Cyclopropanesulfonyl-2-cyclopropylmethoxy-benzoic acid | Cyclopropyl-methanol | 295.2 (M − H) |
| 6.18 | 2-Cyclobutoxy-5-cyclopropanesulfonyl-benzoic acid | Cyclobutanol | 295.2 (M − H) |

EXAMPLE 6.12

Preparation of 1-(4-ethanesulfonyl-2-fluoro-phenyl)-piperazine (a) 3,4-Difluoro-benzenesulfinic acid To 2.47 mol sodium sulfite in 1120 ml water at RT was added dropwise over 20 min a solution of 329 mmol 3,4-difluoro-benzenesulfonyl chloride in 560 ml dioxane and stirring continued for a further 30 min. 1 M aq NaOH was then added dropwise until the reaction mixture was pH 14, and the mixture was then allowed to stir at RT for a further 16 h. The mixture was then cooled to 0° C. and concentrated H$_2$SO$_4$ added until the reaction mixture was pH 1. The mixture was extracted three times with ethyl acetate, and the combined organic phases washed with saturated aq NaCl solution and then dried with Na$_2$SO$_4$. Evaporation in vacuo yielded the title compound. MS (m/e): 177.1 ([M−H]$^-$, 100%)

(b) 4-Ethanesulfonyl-1,2-difluoro-benzene

To 3.0 mmol 3,4-difluoro-benzenesulfinic acid and 3.0 mmol triethylamine in 10 ml DMF was added 7.5 mmol iodoethane and the mixture heated at 90° C. for 9 h. The reaction mixture was then poured onto water and extracted three times with ethyl acetate. The combined organic phases were then washed twice with saturated aq. NaCl solution, dried over Na$_2$SO$_4$, and concentrated in vacuo. The residue was chromatographed on silica gel (eluant: ethyl acetate/heptane 1:7) to afford the title compound. MS (m/e): 206.9 (M+H$^+$, 100%)

(c) 1-(4-Ethanesulfonyl-2-fluoro-phenyl)-piperazine

To 2.0 mmol 4-ethanesulfonyl-1,2-difluoro-benzene in 5 ml N,N-dimethylacetamide was added 5.6 mmol piperazine and the mixture was heated at 80° C. for 45 min. The mixture was then concentrated in vacuo to afford the title compound. MS (m/e): 273.0 (M+H$^+$, 100%)

In analogy to Example 6.12 (b) and (c), compounds 6.13, and 6.21 to 6.23 of the following table were prepared from 3,4-difluoro-benzenesulfinic acid and the indicated alkyl halides, followed by reaction with piperazine:

| Expl. No. | Systematic Name | alkyl halide | MW found (M + H$^+$) |
|---|---|---|---|
| 6.13 | 1-[4-(Butane-1-sulfonyl)-2-fluoro-phenyl]-piperazine | Iodobutane | 301.1 |
| 6.21 | 1-[2-Fluoro-4-(propane-2-sulfonyl)-phenyl]-piperazine | 2-Iodopropane | 287.0 |
| 6.22 | 1-(4-Cyclopropylmethanesulfonyl-2-fluoro-phenyl)-piperazine | Bromomethyl-cylopropane and NaI | 299.2 |
| 6.23 | 1-[2-Fluoro-4-(2-methoxy-ethanesulfonyl)-phenyl]-piperazine | 1-Iodo-2-methoxy-ethane | 303.1 |

EXAMPLE 6.20

Preparation of 1-(4-Cyclopropanesulfonyl-2-fluoro-phenyl)-piperazine (a) 4-(3-Chloro-propane-1-sulfonyl)-1,2-difluoro-benzene To 28.3 mmol 3,4-difluoro-benzenesulfinic acid and 36.8 mmol triethylamine in 100 ml DMF was added 70.7 mmol 1-chloro-3-iodopropane and the mixture stirred at RT for 1 h. The reaction mixture was then poured onto water and extracted three times with ethyl acetate. The combined organic phases were then washed with saturated aq. NaCl solution, dried over Na$_2$SO$_4$, and concentrated in vacuo. The residue was chromatographed on silica gel (eluant: ethyl acetate/heptane gradient) to afford the title compound.

MS (m/e): 257.2 ({$^{37}$Cl}M+H$^+$, 33%), 255.1({$^{35}$Cl}M+H$^+$, 100%), (b) 4-Cyclopropanesulfonyl-1,2-difluoro-benzene To 11.8 mmol 4-(3-chloro-propane-1-sulfonyl)-1,2-difluoro-benzene in 400 ml THF at −78° C. was added dropwise over 30 min 14.2 mmol of a 0.9 M solution of potassium bis(trimethylsilyl)amide in THF. The reaction mixture was then allowed to warm to RT and stirring continued for a further 30 min at RT. The mixture was then quenched by addition of 1 M aq HCl and extracted three times with ethyl acetate. The combined organic phases were dried with Na$_2$SO$_4$, and concentrated in vacuo. The residue was chromatographed on silica gel (eluant: ethyl acetate/heptane 1:5) to afford the title compound. MS (m/e): 219.2 (M+H$^+$, 100%)

(c) 1-(4-Cyclopropanesulfonyl-2-fluoro-phenyl)-piperazine

To 0.2 mmol 4-cyclopropanesulfonyl-1,2-difluoro-benzene in 5 ml N,N-dimethylacetamide was added 0.5 mmol piperazine and the mixture was heated at 80° C. for 90 min.

The mixture was then concentrated in vacuo to afford the title compound. MS (m/e): 285.0 (M+H+, 100%)

EXAMPLE 6.24

Preparation of 1-(4-cyclobutanesulfonyl-2-fluoro-phenyl)-piperazine hydrochloride (a) 4-Cyclobutanesulfonyl-1,2-difluoro-benzene To 5.6 mmol 3,4-difluoro-benzenesulfinic acid and 6.2 mmol triethylamine in 10 ml DMF were added 8.4 mmol bromocyclobutane and 0.2 mmol sodium iodide and the mixture heated at 100° C. for 48 h. The reaction mixture was then poured onto water and extracted three times with ethyl acetate. The combined organic phases were then washed with saturated aq. NaCl solution, dried over $Na_2SO_4$, and concentrated in vacuo. The residue was chromatographed on silica gel (eluant: ethyl acetate/heptane gradient) to afford the title compound. MS (m/e): 233.1 (M+H+, 100%)

(b) 1-(4-Cyclobutanesulfonyl-2-fluoro-phenyl)-piperazine hydrochloride

To 2.8 mmol 4-cyclobutanesulfonyl-1,2-difluoro-benzene in 20 ml N,N-dimethylacetamide was added 8.3 mmol piperazine, and the mixture was heated at 80° C. for 45 min. The mixture was then concentrated in vacuo, and the residue was chromatographed on silica gel (eluant: ethyl acetate/methanol gradient). The product-containing fractions were combined and concentrated in vacuo. The residue was resuspended in 100 ml dioxane, and 6.0 mmol HCl (as a 4 M solution in dioxane) was added. After stirring for 10 min, the ensuing white crystals were collected by filtration, washing twice with ether, to afford the title compound.

MS (m/e): 299.1 (M+H+, 100%)

In analogy to Example 6.24 (a) and (b), compound 6.25 of the following table was prepared from the 3,4-difluoro-benzenesulfinic acid, bromocyclobutane and sodium iodide, followed by reaction with piperazine and subsequent treatment with HCl in dioxane:

| Expl. No | Systematic Name | Starting Materials | MW found (M + H+) |
|---|---|---|---|
| 6.25 | 1-(4-Cyclopentanesulfonyl-2-fluoro-phenyl)-piperazine hydrochloride) | difluoro-benzenesulfinic acid and bromocyclopentane | 313.3 |

EXAMPLE 6.26

Preparation of 1-[2-fluoro-4-(3,3,3-trifluoro-propane-1-sulfonyl)-phenyl]-piperazine (a) 1,2-Difluoro-4-(3,3,3-trifluoro-propylsulfanyl)-benzene To 3.4 mmol 3,4-difluoro-thiophenol and 5.1 mmol 1-iodo-3,3,3-trifluoropropane in 5 ml acetone was added 3.7 mmol potassium carbonate, and the mixture heated at 140° C. for 3 h under microwave irradiation. The reaction mixture was then poured onto water and extracted three times with ethyl acetate. The combined organic phases were then washed with saturated aq. NaCl solution, dried over $Na_2SO_4$, and concentrated in vacuo to afford the title compound. MS (m/e): 243.1 (M+H+, 100%)

(b) 1,2-Difluoro-4-(3,3,3-trifluoro-propane-1-sulfonyl)-benzene

To 3.0 mmol 1,2-difluoro-4-(3,3,3-trifluoro-propylsulfanyl)-benzene in 5 ml dichloromethane was added 8.3 mmol m-chloroperbenzoic acid, and the mixture heated at 50° C. for 48 h. The reaction mixture was then cooled to room temperature and diluted with dichloromethane and washed three times with saturated aq NaHCO3 solution. The organic phase was then washed with saturated aq. NaCl solution, dried over $Na_2SO_4$, and concentrated in vacuo. The residue was chromatographed on silica gel (eluant: ethyl acetate/heptane gradient) to afford the title compound. MS (m/e): 275.1 (M+H+, 100%)

(c) 1-[2-Fluoro-4-(3,3,3-trifluoro-propane-1-sulfonyl)-phenyl]-piperazine

To 0.5 mmol 1,2-difluoro-4-(3,3,3-trifluoro-propane-1-sulfonyl)-benzene in 5 ml N,N-dimethylacetamide was added 1.5 mmol piperazine, and the mixture was heated at 80° C. for 90 min. The mixture was then concentrated in vacuo, and the residue was chromatographed on silica gel (eluant: methanol/dichloromethane gradient) to afford the title compound. MS (m/e): 341.2 (M+H+, 100%)

In analogy to Example 6.26 (a) to (c), compounds 6.27 and 6.28 of the following table were prepared from 3,4-difluoro-thiophenol and the indicated alkylating agent, followed by oxidation with m-chloroperbenzoic acid and reaction with piperazine:

| Expl No | Systematic name | Alkylating agent | MW found (M + H+) |
|---|---|---|---|
| 6.27 | 1-[2-Fluoro-4-(tetrahydro-pyran-4-sulfonyl)-phenyl]-piperazine | Toluene-4-sulfonic acid tetrahydro-pyran-4-yl ester | 329.1 |
| 6.28 | 1-(4-Cyclohexanesulfonyl-2-fluoro-phenyl)-piperazine | Iodocyclohexane | 327.3 |

EXAMPLE 6.29

Preparation of 1-[2,3-difluoro-4-(propane-2-sulfonyl)-phenyl]-piperazine hydrochloride (a) 1,2,3-Trifluoro-4-(propane-2-sulfonyl)-benzene To 20.4 mmol 2,3,4-trifluoro-benzenesulfinic acid (prepared in analogy to example 2.20(a) from 2,3,4-trifluoro-benzenesulfonyl chloride) and 61.2 mmol triethylamine in 20 ml DMF was added 40.8 mmol 2-iodopropane, and the mixture stirred at room temperature for 16 h. The reaction mixture was then poured onto water and extracted three times with ethyl acetate. The combined organic phases were then washed twice with saturated aq. NaCl solution, dried over $Na_2SO_4$, and concentrated in vacuo. The residue was chromatographed on silica gel (eluant: ethyl acetate/heptane 1:4) to afford the title compound.

MS (m/e): 239.1 (M+H+, 100%)

(b) 4-[2,3-Difluoro-4-(propane-2-sulfonyl)-phenyl]-piperazine-1-carboxylic acid tert-butyl ester To 7.6 mmol 1,2,3-trifluoro-4-(propane-2-sulfonyl)-benzene in 20 ml N,N-dimethylacetamide was added 15.9 mmol tert-butyl-1-piperazine carboxylate, and the mixture was heated at 90° C. for 1 h. The mixture was then cooled to room temperature and concentrated in vacuo. The residue was chromatographed on silica gel (eluant: ethyl acetate/heptane 1:2) to afford the title compound.

MS (m/e): 405.2 (M+H+, 100%)

(c) 1-[2,3-Difluoro-4-(propane-2-sulfonyl)-phenyl]-piperazine hydrochloride

To 7.5 mmol 4-[2,3-difluoro-4-(propane-2-sulfonyl)-phenyl]-piperazine-1-carboxylic acid tert-butyl ester in 100 ml dioxane was added 30.2 mmol HCl (as a 4 M solution in dioxane), and the mixture was heated at 80° C. for 1 h. The mixture was then cooled to room temperature, and the ensuing white crystals were collected by filtration, washing twice with ether, to afford the title compound.

MS (m/e): 305.2 (M+H$^+$, 100%)

In analogy to Example 6.29 (a) to (c), compounds 6.30, 6.32 and 6.33 of the following table were prepared from the indicated sulfinic acids and alkyl halides, followed by reaction with tert-butyl-1-piperazine carboxylate and hydrolysis with HCl in dioxane:

| Expl. No | Systematic Name | starting materials | MW found (M + H) |
| --- | --- | --- | --- |
| 6.30 | 1-(4-Ethanesulfonyl-2,3-difluoro-phenyl)-piperazine hydrochloride | 2,3,4-trifluoro-benzenesulfinic acid and iodoethane | 291.2 |
| 6.32 | 1-[2,5-Difluoro-4-(propane-2-sulfonyl)-phenyl]-piperazine hydrochloride | 2,4,5-Trifluoro-benzenesulfinic acid and 2-iodopropane | 305.1 |
| 6.33 | 1-(4-Ethanesulfonyl-2,5-difluoro-phenyl)-piperazine hydrochloride | 2,4,5-Trifluoro-benzenesulfinic acid and iodoethane | 291.1 |

EXAMPLE 6.31

Preparation of 1-(4-cyclopropanesulfonyl-2,3-difluoro-phenyl)-piperazine hydrochloride (a) 1-(3-Chloro-propane-1-sulfonyl)-2,3,4-trifluoro-benzene To 30.6 mmol 2,3,4-trifluoro-benzenesulfinic acid (acid (prepared in analogy to example 2.20(a) from 2,3,4-trifluoro-benzenesulfonyl chloride) and 91.8 mmol triethylamine in 20 ml DMF was added 61.2 mmol 1-chloro-3-iodopropane, and the mixture stirred at room temperature for 1 h. The reaction mixture was then poured onto water and extracted three times with ethyl acetate. The combined organic phases were then washed twice with saturated aq. NaCl solution, dried over Na$_2$SO$_4$, and concentrated in vacuo. The residue was chromatographed on silica gel (eluant: ethyl acetate/heptane 1:4) to afford the title compound. MS (m/e): 275.2 ({$^{37}$Cl}M+H$^+$, 33%), 273.1 ({$^{35}$Cl}M+H$^+$, 100%), (b) 1-Cyclopropanesulfonyl-2,3,4-trifluoro-benzene To 5.9 mmol 1-(3-chloro-propane-1-sulfonyl)-2,3,4-trifluoro-benzene in 200 ml THF at −78° C. was added dropwise over 30 min 7.0 mmol of a 0.9 M solution of potassium bis(trimethylsilyl)amide in THF. The reaction mixture was then allowed to warm to RT, and stirring continued for a further 30 min at RT. The mixture was then quenched by addition of 1 M aq HCl and extracted three times with ethyl acetate. The combined organic phases were dried with Na$_2$SO$_4$, and concentrated in vacuo. The residue was chromatographed on silica gel (eluant: ethyl acetate/heptane 1:4) to afford the title compound. MS (m/e): 237.2 (M+H$^+$, 100%)

(c) 4-(4-Cyclopropanesulfonyl-2,3-difluoro-phenyl)-piperazine-1-carboxylic acid tert-butyl ester To 4.2 mmol 1-cyclopropanesulfonyl-2,3,4-trifluoro-benzene in 20 ml N,N-dimethylacetamide was added 8.9 mmol tert-butyl-1-piperazine carboxylate, and the mixture was heated at 90° C. for 1 h. The mixture was then cooled to room temperature and concentrated in vacuo. The residue was chromatographed on silica gel (eluant: dichloromethane/ethyl acetate gradient) to afford the title compound. MS (m/e): 403.3 (M+H$^+$, 100%)

(d) 1-(4-Cyclopropanesulfonyl-2,3-difluoro-phenyl)-piperazine hydrochloride

To 3.7 mmol 4-(4-Cyclopropanesulfonyl-2,3-difluoro-phenyl)-piperazine-1-carboxylic acid tert-butyl ester in 100 ml dioxane was added 14.9 mmol HCl (as a 4 M solution in dioxane), and the mixture was heated at 80° C. for 1 h. The mixture was then cooled to room temperature, and the ensuing white crystals were collected by filtration, washing twice with ether, to afford the title compound. MS (m/e): 303.2 (M+H$^+$, 100%)

In analogy to Example 6.31 (a) to (d), compound 6.34 of the following table was prepared from the indicated sulfinic acid and alkyl halide, followed by treatment with potassium bis(trimethylsilyl)amide, reaction with tert-butyl-1-piperazine carboxylate and deprotection with HCl in dioxane:

| Expl. No | Systematic Name | starting materials | MW found (M + H) |
| --- | --- | --- | --- |
| 6.34 | 1-(4-Cyclopropanesulfonyl-2,5-difluoro-phenyl)-piperazine hydrochloride | 2,4,5-Trifluoro-benzenesulfinic acid and 2-iodopropane | 303.1 |

EXAMPLE 6.35

Preparation of rac-2-Methyl-1-(4-trifluoromethyl-phenyl)-piperazine hydrochloride (a) rac-3-Methyl-4-(4-trifluoromethyl-phenyl)-piperazine-1-carboxylic acid tert-butyl ester To 1-bromo-4-trifluoromethyl-benzene (1 g), rac-3-Methyl-piperazine-1-carboxylic acid tert-butyl ester (1 g), in toluene (10 mL) was added sodium tert-butylate (0.6 g), 2-(dicyclohexylphosphino)biphenyl (31 mg), and tris(dibenzylideneacetone)Pd-CHCl$_3$ (23 mg). The reaction mixture was then stirred at 80° C. overnight. Ethyl acetate was then added to the reaction mixture. Solids were filtered off. The filtrate was then concentrated in vacuo, and the residue was purified by column chromatography to yield 0.46 g of the title compound. MS (m/e): 345.2 (M+H$^+$, 100%)

(b) rac-2-Methyl-1-(4-trifluoromethyl-phenyl)-piperazine hydrochloride

To 0.58 mmol rac-3-methyl-4-(4-trifluoromethyl-phenyl)-piperazine-1-carboxylic acid tert-butyl ester in 3 ml dioxane was added 8.7 mmol HCl (as a 4 M solution in dioxane), and the mixture was heated at 90° C. for 3 h. The mixture was then cooled 0° C. and diluted with 10 ml ether. The ensuing white crystals were collected by filtration, washing with ether, and dried in vacuo to afford the title compound.

MS (m/e): 245.1 (M+H$^+$, 100%)

EXAMPLE 6.36

Preparation of 5-Acetyl-2-isopropoxy-benzoic acid (a) 5-Acetyl-2-isopropoxy-benzoic acid methyl ester To 25.8 mmol methyl-5-acetyl-2-hydroxybenzoate, 28.3 mmol 2-propanol and 29.6 mmol triphenylphosphine in 100 ml THF was added 28.3 mmol di-tert-butyl azodicarboxylate, and the mixture was stirred at RT for 90 min. The mixture was then concentrated in vacuo to afford the title compound. MS (m/e): 237.1 (M+H$^+$, 100%)

(b) 5-Acetyl-2-isopropoxy-benzoic acid

To 25.8 mmol 5-acetyl-2-isopropoxy-benzoic acid methyl ester in 100 ml THF was 400 mmol 2 M aq NaOH, and the mixture was heated at 80° C. for 2 h. The mixture en cooled to RT and extracted twice with ether. The aqueous phase was acidified with q hydrochloric acid and extracted 3 times with ethyl acetate. The combined organic were dried with Na$_2$SO$_4$. Evaporation in vacuo followed by trituration in ether ed the title compound. MS (m/e): 221.2 ([M−H]$^−$, 100%)

In analogy to Example 5 compounds 472 to 619 of the following table were ed from the acid derivatives and piperazine derivatives:

| Expl. No. | Systematic Name | Starting materials | MW found (MH$^+$) |
|---|---|---|---|
| 472 | 3-[4-(4-Cyano-2-fluoro-phenyl)-piperazine-1-carbonyl]-4-ethoxy-benzenesulfonamide | 3-Fluoro-4-piperazin-1-yl-benzonitrile (WO9625414) and 2-Ethoxy-5-sulfamoyl-benzoic acid (JP53050139) | 433.2 |
| 473 | 3-[4-(4-Cyano-3-fluoro-phenyl)-piperazine-1-carbonyl]-4-ethoxy-benzenesulfonamide | 2-Fluoro-4-piperazin-1-yl-benzonitrile (WO 9808835) and 2-Ethoxy-5-sulfamoyl-benzoic acid (JP53050139) | 431.3 (M − H) |
| 474 | 3-[4-(4-Cyano-phenyl)-piperazine-1-carbonyl]-4-ethoxy-benzenesulfonamide | 4-Piperazin-1-yl-benzonitrile (commercial) and 2-Ethoxy-5-sulfamoyl-benzoic acid (JP53050139) | 413.3 (M − H) |
| 475 | 3-[4-(4-Cyano-3-fluoro-phenyl)-piperazine-1-carbonyl]-4-isobutoxy-N-methyl-benzenesulfonamide | 2-Fluoro-4-piperazin-1-yl-benzonitrile (WO 9808835) and 2-Isobutoxy-5-methylsulfamoyl-benzoic acid (compound 6.1) | 475.1 |
| 476 | 3-[4-(4-Cyano-3-fluoro-phenyl)-piperazine-1-carbonyl]-4-(2,2-dimethyl-propoxy)-N-methyl-benzenesulfonamide | 2-Fluoro-4-piperazin-1-yl-benzonitrile (WO 9808835) and 2-(2,2-Dimethyl-propoxy)-5-methylsulfamoyl-benzoic acid (compound 6.2) | 489.3 |
| 477 | 3-[4-(4-Cyano-3-fluoro-phenyl)-piperazine-1-carbonyl]-4-isopropoxy-N-methyl-benzenesulfonamide | 2-Fluoro-4-piperazin-1-yl-benzonitrile (WO 9808835) and 2-Isopropoxy-5-methylsulfamoyl-benzoic acid (compound 6.3) | 461.2 |
| 478 | 3-[4-(4-Cyano-3-fluoro-phenyl)-piperazine-1-carbonyl]-4-cyclopentyloxy-N-methyl-benzenesulfonamide | 2-Fluoro-4-piperazin-1-yl-benzonitrile (WO 9808835) and 2-Cyclopentyloxy-5-methylsulfamoyl-benzoic acid (compound 6.4) | 487.3 |
| 479 | 3-[4-(4-Cyano-3-fluoro-phenyl)-piperazine-1-carbonyl]-4-cyclobutoxy-N-methyl-benzenesulfonamide | 2-Fluoro-4-piperazin-1-yl-benzonitrile (WO 9808835) and 2-Cyclobutoxy-5-methylsulfamoyl-benzoic acid (compound 6.5) | 473.1 |
| 480 | 3-[4-(4-Cyano-3-fluoro-phenyl)-piperazine-1-carbonyl]-4-cyclopropylmethoxy-N-methyl-benzenesulfonamide | 2-Fluoro-4-piperazin-1-yl-benzonitrile (WO 9808835) and 2-Cyclopropylmethoxy-5-methylsulfamoyl-benzoic acid (compound 6.6) | 473.2 |
| 481 | 3-[4-(4-Cyano-3-fluoro-phenyl)-piperazine-1-carbonyl]-4-cyclobutylmethoxy-N-methyl-benzenesulfonamide | 2-Fluoro-4-piperazin-1-yl-benzonitrile (WO 9808835) and 2-Cyclobutylmethoxy-5-methylsulfamoyl-benzoic acid (compound 6.7) | 487.3 |
| 482 | 3-[4-(4-Cyano-3-fluoro-phenyl)-piperazine-1-carbonyl]-N-methyl-4-(tetrahydro-pyran-4-yloxy)-benzenesulfonamide | 2-Fluoro-4-piperazin-1-yl-benzonitrile (WO 9808835) and 5-Methylsulfamoyl-2-(tetrahydro-pyran-4-yloxy)-benzoic acid (compound 6.8) | 503.2 |
| 483 | 3-[4-(4-Cyano-3-fluoro-phenyl)-piperazine-1-carbonyl]-4-(2-methoxy-ethoxy)-N-methyl-benzenesulfonamide | 2-Fluoro-4-piperazin-1-yl-benzonitrile (WO 9808835) and 2-(2-Methoxy-ethoxy)-5-methylsulfamoyl-benzoic acid (compound 6.9) | 477.3 |
| 484 | 3-[4-(4-Cyano-3-fluoro-phenyl)-piperazine-1- | 2-Fluoro-4-piperazin-1-yl-benzonitrile (WO 9808835) and 5- | 515.2 |

| Expl. No. | Systematic Name | Starting materials | MW found (MH+) |
|---|---|---|---|
| | carbonyl]-N-methyl-4-(3,3,3-trifluoro-propoxy)-benzenesulfonamide | Methylsulfamoyl-2-(3,3,3-trifluoro-propoxy)-benzoic acid (compound 6.10) | |
| 485 | 3-[4-(4-Cyano-phenyl)-piperazine-1-carbonyl]-4-(2-methoxy-ethoxy)-N-methyl-benzenesulfonamide | 4-Piperazin-1-yl-benzonitrile (commercial) and 2-(2-Methoxy-ethoxy)-5-methylsulfamoyl-benzoic acid (compound 6.9) | 459.1 |
| 486 | 3-[4-(4-Cyano-phenyl)-piperazine-1-carbonyl]-N-methyl-4-(3,3,3-trifluoro-propoxy)-benzenesulfonamide | 4-Piperazin-1-yl-benzonitrile (commercial) and 5-Methylsulfamoyl-2-(3,3,3-trifluoro-propoxy)-benzoic acid (compound 6.10) | 497.0 |
| 487 | 3-[4-(4-Cyano-phenyl)-piperazine-1-carbonyl]-N-methyl-4-(tetrahydro-pyran-4-yloxy)-benzenesulfonamide | 4-Piperazin-1-yl-benzonitrile (commercial) and 5-Methylsulfamoyl-2-(tetrahydro-pyran-4-yloxy)-benzoic acid (compound 6.8) | 485.2 |
| 488 | 3-[4-(4-Cyano-phenyl)-piperazine-1-carbonyl]-4-isobutoxy-N-methyl-benzenesulfonamide | 4-Piperazin-1-yl-benzonitrile (commercial) and 2-Isobutoxy-5-methylsulfamoyl-benzoic acid (compound 6.1) | 457.3 |
| 489 | 3-[4-(4-Cyano-phenyl)-piperazine-1-carbonyl]-4-(2,2-dimethyl-propoxy)-N-methyl-benzenesulfonamide | 4-Piperazin-1-yl-benzonitrile (commercial) and 2-(2,2-Dimethyl-propoxy)-5-methylsulfamoyl-benzoic acid (compound 6.2) | 471.1 |
| 490 | 3-[4-(4-Cyano-phenyl)-piperazine-1-carbonyl]-4-isopropoxy-N-methyl-benzenesulfonamide | 4-Piperazin-1-yl-benzonitrile (commercial) and 2-Isopropoxy-5-methylsulfamoyl-benzoic acid (compound 6.3) | 443.2 |
| 491 | 3-[4-(4-Cyano-phenyl)-piperazine-1-carbonyl]-4-cyclopentyloxy-N-methyl-benzenesulfonamide | 4-Piperazin-1-yl-benzonitrile (commercial) and 2-Cyclopentyloxy-5-methylsulfamoyl-benzoic acid (compound 6.4) | 469.2 |
| 492 | 3-[4-(4-Cyano-phenyl)-piperazine-1-carbonyl]-4-cyclobutoxy-N-methyl-benzenesulfonamide | 4-Piperazin-1-yl-benzonitrile (commercial) and 2-Cyclobutoxy-5-methylsulfamoyl-benzoic acid (compound 6.5) | 455.3 |
| 493 | 3-[4-(4-Cyano-phenyl)-piperazine-1-carbonyl]-4-cyclopropylmethoxy-N-methyl-benzenesulfonamide | 4-Piperazin-1-yl-benzonitrile (commercial) and 2-Cyclopropylmethoxy-5-methylsulfamoyl-benzoic acid (compound 6.6) | 455.3 |
| 494 | 3-[4-(4-Cyano-phenyl)-piperazine-1-carbonyl]-4-cyclobutylmethoxy-N-methyl-benzenesulfonamide | 4-Piperazin-1-yl-benzonitrile (commercial) and 2-Cyclobutylmethoxy-5-methylsulfamoyl-benzoic acid (compound 6.7) | 469.2 |
| 495 | 3-[4-(2-Fluoro-4-methanesulfonyl-phenyl)-piperazine-1-carbonyl]-4-isobutoxy-N-methyl-benzenesulfonamide | 1-(2-Fluoro-4-methanesulfonyl-phenyl)-piperazine (commercial) and 2-Isobutoxy-5-methylsulfamoyl-benzoic acid (compound 6.1) | 528.0 |
| 496 | 4-(2,2-Dimethyl-propoxy)-3-[4-(2-fluoro-4-methanesulfonyl-phenyl)-piperazine-1-carbonyl]-N-methyl-benzenesulfonamide | 1-(2-Fluoro-4-methanesulfonyl-phenyl)-piperazine (commercial) and 2-(2,2-Dimethyl-propoxy)-5-methylsulfamoyl-benzoic acid (compound 6.2) | 559.2 (M + NH4+) |
| 497 | 3-[4-(2-Fluoro-4-methanesulfonyl-phenyl)-piperazine-1-carbonyl]-4-isopropoxy-N-methyl-benzenesulfonamide | 1-(2-Fluoro-4-methanesulfonyl-phenyl)-piperazine (commercial) and 2-Isopropoxy-5-methylsulfamoyl-benzoic acid (compound 6.3) | 514.1 |
| 498 | 4-Cyclopentyloxy-3-[4-(2-fluoro-4-methanesulfonyl-phenyl)-piperazine-1-carbonyl]-N-methyl-benzenesulfonamide | 1-(2-Fluoro-4-methanesulfonyl-phenyl)-piperazine (commercial) and 2-Cyclopentyloxy-5-methylsulfamoyl-benzoic acid (compound 6.4) | 557.0 (M + NH4+) |
| 499 | 4-Cyclobutoxy-3-[4-(2-fluoro-4- | 1-(2-Fluoro-4-methanesulfonyl-phenyl)-piperazine (commercial) | 526.0 |

| Expl. No. | Systematic Name | Starting materials | MW found (MH+) |
|---|---|---|---|
|  | methanesulfonyl-phenyl)-piperazine-1-carbonyl]-N-methyl-benzenesulfonamide | and 2-Cyclobutoxy-5-methylsulfamoyl-benzoic acid (compound 6.5) |  |
| 500 | 4-Cyclopropylmethoxy-3-[4-(2-fluoro-4-methanesulfonyl-phenyl)-piperazine-1-carbonyl]-N-methyl-benzenesulfonamide | 1-(2-Fluoro-4-methanesulfonyl-phenyl)-piperazine (commercial) and 2-Cyclopropylmethoxy-5-methylsulfamoyl-benzoic acid (compound 6.6) | 526.0 |
| 501 | 4-Cyclobutylmethoxy-3-[4-(2-fluoro-4-methanesulfonyl-phenyl)-piperazine-1-carbonyl]-N-methyl-benzenesulfonamide | 1-(2-Fluoro-4-methanesulfonyl-phenyl)-piperazine (commercial) and 2-Cyclobutylmethoxy-5-methylsulfamoyl-benzoic acid (compound 6.7) | 557.0 (M + NH4+) |
| 502 | 3-[4-(2-Fluoro-4-methanesulfonyl-phenyl)-piperazine-1-carbonyl]-4-(2-methoxy-ethoxy)-N-methyl-benzenesulfonamide | 1-(2-Fluoro-4-methanesulfonyl-phenyl)-piperazine (commercial) and 2-(2-Methoxy-ethoxy)-5-methylsulfamoyl-benzoic acid (compound 6.9) | 530.1 |
| 503 | 3-[4-(2-Fluoro-4-methanesulfonyl-phenyl)-piperazine-1-carbonyl]-N-methyl-4-(3,3,3-trifluoro-propoxy)-benzenesulfonamide | 1-(2-Fluoro-4-methanesulfonyl-phenyl)-piperazine (commercial) and 5-Methylsulfamoyl-2-(3,3,3-trifluoro-propoxy)-benzoic acid (compound 6.10) | 585.0 (M + NH4+) |
| 504 | 3-[4-(4-Cyano-2-fluoro-phenyl)-piperazine-1-carbonyl]-4-isobutoxy-N-methyl-benzenesulfonamide | 3-Fluoro-4-piperazin-1-yl-benzonitrile (WO9625414) and 2-Isobutoxy-5-methylsulfamoyl-benzoic acid (compound 6.1) | 475.0 |
| 505 | 3-[4-(4-Cyano-2-fluoro-phenyl)-piperazine-1-carbonyl]-4-(2,2-dimethyl-propoxy)-N-methyl-benzenesulfonamide | 3-Fluoro-4-piperazin-1-yl-benzonitrile (WO9625414) and 2-(2,2-Dimethyl-propoxy)-5-methylsulfamoyl-benzoic acid (compound 6.2) | 489.0 |
| 506 | 3-[4-(4-Cyano-2-fluoro-phenyl)-piperazine-1-carbonyl]-4-isopropoxy-N-methyl-benzenesulfonamide | 3-Fluoro-4-piperazin-1-yl-benzonitrile (WO9625414) and 2-Isopropoxy-5-methylsulfamoyl-benzoic acid (compound 6.3) | 478.0 (M + NH4+) |
| 507 | 3-[4-(4-Cyano-2-fluoro-phenyl)-piperazine-1-carbonyl]-4-cyclopentyloxy-N-methyl-benzenesulfonamide | 3-Fluoro-4-piperazin-1-yl-benzonitrile (WO9625414) and 2-Cyclopentyloxy-5-methylsulfamoyl-benzoic acid (compound 6.4) | 487.1 |
| 508 | 3-[4-(4-Cyano-2-fluoro-phenyl)-piperazine-1-carbonyl]-4-cyclobutoxy-N-methyl-benzenesulfonamide | 3-Fluoro-4-piperazin-1-yl-benzonitrile (WO9625414) and Cyclobutoxy-5-methylsulfamoyl-benzoic acid (compound 6.5) | 472.8 |
| 509 | 3-[4-(4-Cyano-2-fluoro-phenyl)-piperazine-1-carbonyl]-4-cyclopropylmethoxy-N-methyl-benzenesulfonamide | 3-Fluoro-4-piperazin-1-yl-benzonitrile (WO9625414) and 2-Cyclopropylmethoxy-5-methylsulfamoyl-benzoic acid (compound 6.6) | 472.8 |
| 510 | 3-[4-(4-Cyano-2-fluoro-phenyl)-piperazine-1-carbonyl]-4-cyclobutylmethoxy-N-methyl-benzenesulfonamide | 3-Fluoro-4-piperazin-1-yl-benzonitrile (WO9625414) and 2-Cyclobutylmethoxy-5-methylsulfamoyl-benzoic acid (compound 6.7) | 487.1 |
| 511 | 3-[4-(4-Cyano-2-fluoro-phenyl)-piperazine-1-carbonyl]-N-methyl-4-(tetrahydro-pyran-4-yloxy)-benzenesulfonamide | 3-Fluoro-4-piperazin-1-yl-benzonitrile (WO9625414) and 5-Methylsulfamoyl-2-(tetrahydro-pyran-4-yloxy)-benzoic acid (compound 6.8) | 503.0 |
| 512 | 3-[4-(4-Cyano-2-fluoro-phenyl)-piperazine-1-carbonyl]-4-(2-methoxy-ethoxy)-N-methyl-benzenesulfonamide | 3-Fluoro-4-piperazin-1-yl-benzonitrile (WO9625414) and 2-(2-Methoxy-ethoxy)-5-methylsulfamoyl-benzoic acid (compound 6.9) | 477.1 |
| 513 | 3-[4-(4-Cyano-2-fluoro-phenyl)-piperazine-1-carbonyl]-N-methyl-4- | 3-Fluoro-4-piperazin-1-yl-benzonitrile (WO9625414) and 5-Methylsulfamoyl-2-(3,3,3-trifluoro- | 515.1 |

-continued

| Expl. No. | Systematic Name | Starting materials | MW found (MH+) |
|---|---|---|---|
|  | (3,3,3-trifluoro-propoxy)-benzenesulfonamide | propoxy)-benzoic acid (compound 6.10) |  |
| 514 | 3-[4-(4-Acetyl-2-fluoro-phenyl)-piperazine-1-carbonyl]-4-isobutoxy-N-methyl-benzenesulfonamide | 1-(3-Fluoro-4-piperazin-1-yl-phenyl)-ethanone (WO9714690) and 2-Isobutoxy-5-methylsulfamoyl-benzoic acid (compound 6.1) | 492.1 |
| 515 | 3-[4-(4-Acetyl-2-fluoro-phenyl)-piperazine-1-carbonyl]-4-(2,2-dimethyl-propoxy)-N-methyl-benzenesulfonamide | 1-(3-Fluoro-4-piperazin-1-yl-phenyl)-ethanone (WO9714690) and 2-(2,2-Dimethyl-propoxy)-5-methylsulfamoyl-benzoic acid (compound 6.2) | 506.3 |
| 516 | 3-[4-(4-Acetyl-2-fluoro-phenyl)-piperazine-1-carbonyl]-4-isopropoxy-N-methyl-benzenesulfonamide | 1-(3-Fluoro-4-piperazin-1-yl-phenyl)-ethanone (WO9714690) and 2-Isopropoxy-5-methylsulfamoyl-benzoic acid (compound 6.3) | 478.2 |
| 517 | 3-[4-(4-Acetyl-2-fluoro-phenyl)-piperazine-1-carbonyl]-4-cyclopentyloxy-N-methyl-benzenesulfonamide | 1-(3-Fluoro-4-piperazin-1-yl-phenyl)-ethanone (WO9714690) and 2-Cyclopentyloxy-5-methylsulfamoyl-benzoic acid (compound 6.4) | 504.2 |
| 518 | 3-[4-(4-Acetyl-2-fluoro-phenyl)-piperazine-1-carbonyl]-4-cyclobutoxy-N-methyl-benzenesulfonamide | 1-(3-Fluoro-4-piperazin-1-yl-phenyl)-ethanone (WO9714690) and 2-Cyclobutoxy-5-methylsulfamoyl-benzoic acid (compound 6.5) | 590.6 |
| 519 | 3-[4-(4-Acetyl-2-fluoro-phenyl)-piperazine-1-carbonyl]-4-cyclopropylmethoxy-N-methyl-benzenesulfonamide | 1-(3-Fluoro-4-piperazin-1-yl-phenyl)-ethanone (WO9714690) and 2-Cyclopropylmethoxy-5-methylsulfamoyl-benzoic acid (compound 6.6) | 490.2 |
| 520 | 3-[4-(4-Acetyl-2-fluoro-phenyl)-piperazine-1-carbonyl]-4-cyclobutylmethoxy-N-methyl-benzenesulfonamide | 1-(3-Fluoro-4-piperazin-1-yl-phenyl)-ethanone (WO9714690) and 2-Cyclobutylmethoxy-5-methylsulfamoyl-benzoic acid (compound 6.7) | 504.2 |
| 521 | 3-[4-(4-Acetyl-2-fluoro-phenyl)-piperazine-1-carbonyl]-N-methyl-4-(tetrahydro-pyran-4-yloxy)-benzenesulfonamide | 1-(3-Fluoro-4-piperazin-1-yl-phenyl)-ethanone (WO9714690) and 5-Methylsulfamoyl-2-(tetrahydro-pyran-4-yloxy)-benzoic acid (compound 6.8) | 520.3 |
| 522 | 3-[4-(4-Acetyl-2-fluoro-phenyl)-piperazine-1-carbonyl]-4-(2-methoxy-ethoxy)-N-methyl-benzenesulfonamide | 1-(3-Fluoro-4-piperazin-1-yl-phenyl)-ethanone (WO9714690) and 2-(2-Methoxy-ethoxy)-5-methylsulfamoyl-benzoic acid (compound 6.9) | 494.2 |
| 523 | 3-[4-(4-Acetyl-2-fluoro-phenyl)-piperazine-1-carbonyl]-N-methyl-4-(3,3,3-trifluoro-propoxy)-benzenesulfonamide | 1-(3-Fluoro-4-piperazin-1-yl-phenyl)-ethanone (WO9714690) and 5-Methylsulfamoyl-2-(3,3,3-trifluoro-propoxy)-benzoic acid (compound 6.10) | 532.2 |
| 524 | 4-Isobutoxy-N-methyl-3-[4-(4-trifluoromethyl-phenyl)-piperazine-1-carbonyl]-benzenesulfonamide | 1-(4-Trifluoromethyl-phenyl)-piperazine (commercial) and 2-Isobutoxy-5-methylsulfamoyl-benzoic acid (compound 6.1) | 500.2 |
| 525 | 4-(2,2-Dimethyl-propoxy)-N-methyl-3-[4-(4-trifluoromethyl-phenyl)-piperazine-1-carbonyl]-benzenesulfonamide | 1-(4-Trifluoromethyl-phenyl)-piperazine (commercial) and 2-(2,2-Dimethyl-propoxy)-5-methylsulfamoyl-benzoic acid (compound 6.2) | 514.2 |
| 526 | 4-Isopropoxy-N-methyl-3-[4-(4-trifluoromethyl-phenyl)-piperazine-1-carbonyl]-benzenesulfonamide | 1-(4-Trifluoromethyl-phenyl)-piperazine (commercial) and 2-Isopropoxy-5-methylsulfamoyl-benzoic acid (compound 6.3) | 486.2 |
| 527 | 4-Cyclopentyloxy-N-methyl-3-[4-(4-trifluoromethyl-phenyl)-piperazine-1-carbonyl]-benzenesulfonamide | 1-(4-Trifluoromethyl-phenyl)-piperazine (commercial) and 2-Cyclopentyloxy-5-methylsulfamoyl-benzoic acid (compound 6.4) | 512.3 |
| 528 | 4-Cyclobutoxy-N-methyl-3-[4-(4-trifluoromethyl-phenyl)-piperazine-1-carbonyl]-benzenesulfonamide | 1-(4-Trifluoromethyl-phenyl)-piperazine (commercial) and 2-Cyclobutoxy-5-methylsulfamoyl-benzoic acid (compound 6.5) | 498.2 |
| 529 | 4-Cyclopropylmethoxy-N-methyl-3-[4-(4-trifluoromethyl-phenyl)- | 1-(4-Trifluoromethyl-phenyl)-piperazine (commercial) and 2-Cyclopropylmethoxy-5- | 498.2 |

-continued

| Expl. No. | Systematic Name | Starting materials | MW found (MH+) |
|---|---|---|---|
| | piperazine-1-carbonyl]-benzenesulfonamide | methylsulfamoyl-benzoic acid (compound 6.6) | |
| 530 | 4-Cyclobutylmethoxy-N-methyl-3-[4-(4-trifluoromethyl-phenyl)-piperazine-1-carbonyl]-benzenesulfonamide | 1-(4-Trifluoromethyl-phenyl)-piperazine (commercial) and 2-Cyclobutylmethoxy-5-methylsulfamoyl-benzoic acid (compound 6.7) | 512.3 |
| 531 | N-Methyl-3-[4-(4-trifluoromethyl-phenyl)-piperazine-1-carbonyl]-4-(3,3,3-trifluoro-propoxy)-benzenesulfonamide | 1-(4-Trifluoromethyl-phenyl)-piperazine (commercial) and 5-Methylsulfamoyl-2-(3,3,3-trifluoro-propoxy)-benzoic acid (compound 6.10) | 540.2 |
| 532 | 3-[4-(4-Cyano-3-fluoro-phenyl)-piperazine-1-carbonyl]-N-methyl-4-(2,2,2-trifluoro-ethoxy)-benzenesulfonamide | 2-Fluoro-4-piperazin-1-yl-benzonitrile (WO 9808835) and 5-Methylsulfamoyl-2-(2,2,2-trifluoro-ethoxy)-benzoic acid (compound 6.11) | 501.1 |
| 533 | 3-[4-(4-Cyano-phenyl)-piperazine-1-carbonyl]-N-methyl-4-(2,2,2-trifluoro-ethoxy)-benzenesulfonamide | 4-Piperazin-1-yl-benzonitrile (commercial) and 5-Methylsulfamoyl-2-(2,2,2-trifluoro-ethoxy)-benzoic acid (compound 6.11) | 483.3 |
| 534 | 3-[4-(4-Cyano-2-fluoro-phenyl)-piperazine-1-carbonyl]-N-methyl-4-(2,2,2-trifluoro-ethoxy)-benzenesulfonamide | 3-Fluoro-4-piperazin-1-yl-benzonitrile (WO9625414) and 5-Methylsulfamoyl-2-(2,2,2-trifluoro-ethoxy)-benzoic acid (compound 6.11) | 501.1 |
| 535 | 3-[4-(4-Acetyl-2-fluoro-phenyl)-piperazine-1-carbonyl]-N-methyl-4-(2,2,2-trifluoro-ethoxy)-benzenesulfonamide | 1-(3-Fluoro-4-piperazin-1-yl-phenyl)-ethanone (WO9714690) and 5-Methylsulfamoyl-2-(2,2,2-trifluoro-ethoxy)-benzoic acid (compound 6.11) | 518.2 |
| 536 | 3-[4-(2-Fluoro-4-methanesulfonyl-phenyl)-piperazine-1-carbonyl]-N-methyl-4-(2,2,2-trifluoro-ethoxy)-benzenesulfonamide | 1-(2-Fluoro-4-methanesulfonyl-phenyl)-piperazine (commercial) and 5-Methylsulfamoyl-2-(2,2,2-trifluoro-ethoxy)-benzoic acid (compound 6.11) | 554.1 |
| 537 | N-Methyl-4-(2,2,2-trifluoro-ethoxy)-3-[4-(4-trifluoromethyl-phenyl)-piperazine-1-carbonyl]-benzene sulfonamide | 1-(4-Trifluoromethyl-phenyl)-piperazine (commercial) and 5-Methylsulfamoyl-2-(2,2,2-trifluoro-ethoxy)-benzoic acid (compound 6.11) | 526.0 |
| 538 | [4-(4-Ethanesulfonyl-2-fluoro-phenyl)-piperazin-1-yl]-(2-isopropoxy-5-methanesulfonyl-phenyl)-methanone | 1-(4-Ethanesulfonyl-2-fluoro-phenyl)-piperazine (compound 6.12) and 2-Isopropoxy-5-methanesulfonyl-benzoic acid (compound 1.2) | 513.3 |
| 539 | {4-[4-(Butane-1-sulfonyl)-2-fluoro-phenyl]-piperazin-1-yl}-(2-isopropoxy-5-methanesulfonyl-phenyl)-methanone | 1-[4-(Butane-1-sulfonyl)-2-fluoro-phenyl]-piperazine (compound 6.13) and 2-Isopropoxy-5-methanesulfonyl-benzoic acid (compound 1.2) | 541.0 |
| 540 | 4-[4-(5-Cyclopropanesulfonyl-2-isopropoxy-benzoyl)-piperazin-1-yl]-3-fluoro-benzonitrile | 3-Fluoro-4-piperazin-1-yl-benzonitrile (WO9625414) and 5-Cyclopropanesulfonyl-2-isopropoxy-benzoic acid (compound 6.14) | 472.3 |
| 541 | (5-Cyclopropane sulfonyl-2-isopropoxy-phenyl)-[4-(2-fluoro-4-trifluoro methyl-phenyl)-piperazin-1-yl]-methanone | 1-(2-Fluoro-4-trifluoromethyl-phenyl)-piperazine (compound 1.1) and 5-Cyclopropanesulfonyl-2-isopropoxy-benzoic acid (compound 6.14) | 515.4 |
| 542 | (5-Cyclopropanesulfonyl-2-isobutoxy-phenyl)-[4-(2-fluoro-4-methane sulfonyl-phenyl)-piperazin-1-yl]-methanone | 1-(2-Fluoro-4-methanesulfonyl-phenyl)-piperazine (commercial) and 5-Cyclopropanesulfonyl-2-isobutoxy-benzoic acid (compound 6.15) | 539.5 |
| 543 | 4-[4-(5-Cyclopropanesulfonyl-2-isobutoxy-benzoyl)-piperazin-1-yl]-3-fluoro-benzonitrile | 3-Fluoro-4-piperazin-1-yl-benzonitrile (WO9625414) and 5-Cyclopropanesulfonyl-2-isobutoxy-benzoic acid (compound 6.15) | 486.5 |

-continued

| Expl. No. | Systematic Name | Starting materials | MW found (MH+) |
|---|---|---|---|
| 544 | (5-Cyclopropanesulfonyl-2-isobutoxy-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and 5-Cyclopropanesulfonyl-2-isobutoxy-benzoic acid (compound 6.15) | 529.4 |
| 545 | (2-Cyclopentyloxy-5-cyclopropanesulfonyl-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 2-Cyclopentyloxy-5-cyclopropanesulfonyl-benzoic acid (compound 6.16) | 551.3 |
| 546 | 4-[4-(2-Cyclopentyloxy-5-cyclopropanesulfonyl-benzoyl)-piperazin-1-yl]-3-fluoro-benzonitrile | 3-Fluoro-4-piperazin-1-yl-benzonitrile (WO9625414) and 2-Cyclopentyloxy-5-cyclopropane sulfonyl-benzoic acid (compound 6.16) | 498.3 |
| 547 | (2-Cyclopentyloxy-5-cyclopropanesulfonyl-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and 2-Cyclopentyloxy-5-cyclopropanesulfonyl-benzoic acid (compound 6.16) | 541.3 |
| 548 | (5-Cyclopropanesulfonyl-2-cyclopropylmethoxy-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 5-Cyclopropanesulfonyl-2-cyclopropylmethoxy-benzoic acid (compound 6.17) | 537.4 |
| 549 | 4-[4-(5-Cyclopropanesulfonyl-2-cyclopropylmethoxy-benzoyl)-piperazin-1-yl]-3-fluoro-benzonitrile | 3-Fluoro-4-piperazin-1-yl-benzonitrile (WO9625414) and 5-Cyclopropanesulfonyl-2-cyclopropylmethoxy-benzoic acid (compound 6.17) | 484.5 |
| 550 | (5-Cyclopropanesulfonyl-2-cyclopropylmethoxy-phenyl)-[4-(2-fluoro-4-trifluoromethyl-phenyl)-piperazin-1-yl]-methanone | 1-(2-Fluoro-4-trifluoromethyl-phenyl)-piperazine (compound 1.1) and 5-Cyclopropanesulfonyl-2-cyclopropylmethoxy-benzoic acid (compound 6.17) | 527.3 |
| 551 | (2-Cyclobutoxy-5-cyclopropanesulfonyl-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 2-Cyclobutoxy-5-cyclopropanesulfonyl-benzoic acid (compound 6.18) | 537.4 |
| 552 | (5-Cyclopropanesulfonyl-2-isopropoxy-phenyl)-[4-(2-fluoro-4-methanesulfonyl-phenyl)-piperazin-1-yl]-methanone | 1-(2-Fluoro-4-methanesulfonyl-phenyl)-piperazine (commercial) and 5-Cyclopropanesulfonyl-2-isopropoxy-benzoic acid (compound 6.14) | 525.3 |
| 553 | rac-3-[4-(2-Fluoro-4-methanesulfonyl-phenyl)-piperazine-1-carbonyl]-N-methyl-4-(2,2,2-trifluoro-1-methyl-ethoxy)-benzenesulfonamide | 1-(2-Fluoro-4-methanesulfonyl-phenyl)-piperazine (commercial) and rac-5-Methylsulfamoyl-2-(2,2,2-trifluoro-1-methyl-ethoxy)-benzoic acid (compound 6.19) | 585.1 (M + NH4+) |
| 554 | rac-N-Methyl-4-(2,2,2-trifluoro-1-methyl-ethoxy)-3-[4-(4-trifluoromethyl-phenyl)-piperazine-1-carbonyl]-benzenesulfonamide | 1-(4-Trifluoromethyl-phenyl)-piperazine (commercial) and rac-5-Methylsulfamoyl-2-(2,2,2-trifluoro-1-methyl-ethoxy)-benzoic acid (compound 6.19) | 557.2 (M + NH4+) |
| 555 | rac-3-[4-(4-Cyano-2-fluoro-phenyl)-piperazine-1-carbonyl]-N-methyl-4-(2,2,2-trifluoro-1-methyl-ethoxy)-benzene sulfonamide | 3-Fluoro-4-piperazin-1-yl-benzonitrile (WO9625414) and rac-5-Methylsulfamoyl-2-(2,2,2-trifluoro-1-methyl-ethoxy)-benzoic acid (compound 6.19) | 532.3 (M + NH4+) |
| 556 | [4-(4-Cyclopropane sulfonyl-2-fluoro-phenyl)-piperazin-1-yl]-(2-isopropoxy-5-methanesulfonyl-phenyl)-methanone | 1-(4-Cyclopropanesulfonyl-2-fluoro-phenyl)-piperazine (compound 6.20) and 2-Isopropoxy-5-methanesulfonyl-benzoic acid (compound 1.2) | 542.2 (M + NH4+) |
| 557 | rac-3-[4-(4-Cyano-2,5-difluoro-phenyl)- | 2,5-Difluoro-4-piperazin-1-yl-benzonitrile-trifluoro-acetic acid | 550.1 (M + NH4+) |

-continued

| Expl. No. | Systematic Name | Starting materials | MW found (MH+) |
|---|---|---|---|
| | piperazine-1-carbonyl]-N-methyl-4-(2,2,2-trifluoro-1-methyl-ethoxy)-benzene sulfonamide | (compound 2.8) and rac-5-Methylsulfamoyl-2-(2,2,2-trifluoro-1-methyl-ethoxy)-benzoic acid (compound 6.19) | |
| 558 | rac-3-[4-(4-Cyano-2,3-difluoro-phenyl)-piperazine-1-carbonyl]-N-methyl-4-(2,2,2-trifluoro-1-methyl-ethoxy)-benzene sulfonamide | 2,3-Difluoro-4-piperazin-1-yl-benzonitrile-trifluoro-acetic acid (compound 2.7) and rac-5-Methylsulfamoyl-2-(2,2,2-trifluoro-1-methyl-ethoxy)-benzoic acid (compound 6.19) | 550.1 (M + NH4+) |
| 559 | {4-[2-Fluoro-4-(propane-2-sulfonyl)-phenyl]-piperazin-1-yl}-(2-isopropoxy-5-methanesulfonyl-phenyl)-methanone | 1-[2-Fluoro-4-(propane-2-sulfonyl)-phenyl]-piperazine (compound 6.21) and 2-Isopropoxy-5-methanesulfonyl-benzoic acid (compound 1.2) | 544.3 (M + NH4+) |
| 560 | [4-(4-Cyclopropylmethanesulfonyl-2-fluoro-phenyl)-piperazin-1-yl]-(2-isopropoxy-5-methanesulfonyl-phenyl)-methanone | 1-(4-Cyclopropylmethanesulfonyl-2-fluoro-phenyl)-piperazine (compound 6.22) and 2-Isopropoxy-5-methanesulfonyl-benzoic acid (compound 1.2) | 556.2 (M + NH4+) |
| 561 | {4-[2-Fluoro-4-(2-methoxy-ethanesulfonyl)-phenyl]-piperazin-1-yl}-(2-isopropoxy-5-methanesulfonyl-phenyl)-methanone | 1-[2-Fluoro-4-(2-methoxy-ethanesulfonyl)-phenyl]-piperazine (compound 6.23) and 2-Isopropoxy-5-methanesulfonyl-benzoic acid (compound 1.2) | 560.3 (M + NH4+) |
| 562 | (2-Cyclopropylmethoxy-5-methanesulfonyl-phenyl)-[4-(4-ethanesulfonyl-2-fluoro-phenyl)-piperazin-1-yl]-methanone | 1-(4-Ethanesulfonyl-2-fluoro-phenyl)-piperazine (compound 6.12) and 2-Cyclopropylmethoxy-5-methanesulfonyl-benzoic acid (compound 1.4) | 542.2 (M + NH4+) |
| 563 | (2-Cyclopentyloxy-5-methanesulfonyl-phenyl)-[4-(4-ethanesulfonyl-2-fluoro-phenyl)-piperazin-1-yl]-methanone | 1-(4-Ethanesulfonyl-2-fluoro-phenyl)-piperazine (compound 6.12) and 2-Cyclopentyloxy-5-methanesulfonyl-benzoic acid (compound 1.6) | 556.1 (M + NH4+) |
| 564 | (2-Cyclohexyloxy-5-methanesulfonyl-phenyl)-[4-(4-ethanesulfonyl-2-fluoro-phenyl)-piperazin-1-yl]-methanone | 1-(4-Ethanesulfonyl-2-fluoro-phenyl)-piperazine (compound 6.12) and 2-Cyclohexyloxy-5-methanesulfonyl-benzoic acid (compound 3.2) | 570.2 (M + NH4+) |
| 565 | [2-(2,2-Dimethyl-propoxy)-5-methanesulfonyl-phenyl]-[4-(4-ethanesulfonyl-2-fluoro-phenyl)-piperazin-1-yl]-methanone | 1-(4-Ethanesulfonyl-2-fluoro-phenyl)-piperazine (compound 6.12) and 2-(2,2-Dimethyl-propoxy)-5-methanesulfonyl-benzoic acid (compound 3.3) | 558.2 (M + NH4+) |
| 566 | [4-(4-Ethanesulfonyl-2-fluoro-phenyl)-piperazin-1-yl]-(2-isobutoxy-5-methanesulfonyl-phenyl)-methanone | 1-(4-Ethanesulfonyl-2-fluoro-phenyl)-piperazine (compound 6.12) and 2-Isobutoxy-5-methanesulfonyl-benzoic acid (compound 1.3) | 544.2 (M + NH4+) |
| 567 | (2-Cyclobutoxy-5-methanesulfonyl-phenyl)-[4-(4-ethanesulfonyl-2-fluoro-phenyl)-piperazin-1-yl]-methanone | 1-(4-Ethanesulfonyl-2-fluoro-phenyl)-piperazine (compound 6.12) and 2-Cyclobutoxy-5-methanesulfonyl-benzoic acid (compound 3.4) | 542.3 (M + NH4+) |
| 568 | rac-(2-sec-Butoxy-5-methanesulfonyl-phenyl)-[4-(4-ethanesulfonyl-2-fluoro-phenyl)-piperazin-1-yl]-methanone | 1-(4-Ethanesulfonyl-2-fluoro-phenyl)-piperazine (compound 6.12) and rac-2-sec-Butoxy-5-methanesulfonyl-benzoic acid (compound 3.5) | 544.2 (M + NH4+) |
| 569 | (2-Cyclobutylmethoxy-5-methanesulfonyl-phenyl)-[4-(4-ethanesulfonyl-2-fluoro- | 1-(4-Ethanesulfonyl-2-fluoro-phenyl)-piperazine (compound 6.12) and 2-Cyclobutylmethoxy-5-methanesulfonyl-benzoic acid | 556.1 (M + NH4+) |

-continued

| Expl. No. | Systematic Name | Starting materials | MW found (MH+) |
|---|---|---|---|
| | phenyl)-piperazin-1-yl]-methanone | (compound 2.12) | |
| 570 | [4-(4-Cyclobutanesulfonyl-2-fluoro-phenyl)-piperazin-1-yl]-(2-isopropoxy-5-methanesulfonyl-phenyl)-methanone | 1-(4-Cyclobutanesulfonyl-2-fluoro-phenyl)-piperazine hydrochloride (compound 6.24) and 2-Isopropoxy-5-methanesulfonyl-benzoic acid (compound 1.2) | 556.1 (M + NH4+) |
| 571 | [4-(4-Cyclopentanesulfonyl-2-fluoro-phenyl)-piperazin-1-yl]-(2-isopropoxy-5-methanesulfonyl-phenyl)-methanone | 1-(4-Cyclopentanesulfonyl-2-fluoro-phenyl)-piperazine hydrochloride (compound 6.25) and 2-Isopropoxy-5-methanesulfonyl-benzoic acid (compound 1.2) | 570.3 (M + NH4+) |
| 572 | [4-(4-Cyclopropane sulfonyl-2-fluoro-phenyl)-piperazin-1-yl]-(2-cyclopropylmethoxy-5-methanesulfonyl-phenyl)-methanone | 1-(4-Cyclopropanesulfonyl-2-fluoro-phenyl)-piperazine (compound 6.20) and 2-Cyclopropylmethoxy-5-methanesulfonyl-benzoic acid (compound 1.4) | 537.2 |
| 573 | (2-Cyclopentyloxy-5-methanesulfonyl-phenyl)-[4-(4-cyclopropanesulfonyl-2-fluoro-phenyl)-piperazin-1-yl]-methanone | 1-(4-Cyclopropanesulfonyl-2-fluoro-phenyl)-piperazine (compound 6.20) and 2-Cyclopentyloxy-5-methanesulfonyl-benzoic acid (compound 1.6) | 568.0 (M + NH4+) |
| 574 | (2-Cyclohexyloxy-5-methanesulfonyl-phenyl)-[4-(4-cyclopropanesulfonyl-2-fluoro-phenyl)-piperazin-1-yl]-methanone | 1-(4-Cyclopropanesulfonyl-2-fluoro-phenyl)-piperazine (compound 6.20) and 2-Cyclohexyloxy-5-methanesulfonyl-benzoic acid (compound 3.2) | 582.1 (M + NH4+) |
| 575 | [4-(4-Cyclopropanesulfonyl-2-fluoro-phenyl)-piperazin-1-yl]-[2-(2,2-dimethyl-propoxy)-5-methanesulfonyl-phenyl]-methanone | 1-(4-Cyclopropanesulfonyl-2-fluoro-phenyl)-piperazine (compound 6.20) and 2-(2,2-Dimethyl-propoxy)-5-methanesulfonyl-benzoic acid (compound 3.3) | 570.2 (M + NH4+) |
| 576 | (2-Cyclobutoxy-5-methanesulfonyl-phenyl)-[4-(4-cyclopropanesulfonyl-2-fluoro-phenyl)-piperazin-1-yl]-methanone | 1-(4-Cyclopropanesulfonyl-2-fluoro-phenyl)-piperazine (compound 6.20) and 2-Cyclobutoxy-5-methane sulfonyl-benzoic acid (compound 3.4) | 536.9 |
| 577 | {4-[2-Fluoro-4-(3,3,3-trifluoro-propane-1-sulfonyl)-phenyl]-piperazin-1-yl}-(2-isopropoxy-5-methanesulfonyl-phenyl)-methanone | 1-[2-Fluoro-4-(3,3,3-trifluoro-propane-1-sulfonyl)-phenyl]-piperazine (compound 6.26) and 2-Isopropoxy-5-methanesulfonyl-benzoic acid (compound 1.2) | 581.0 |
| 578 | [4-(4-Cyclopropane sulfonyl-2-fluoro-phenyl)-piperazin-1-yl]-(2-isobutoxy-5-methanesulfonyl-phenyl)-methanone | 1-(4-Cyclopropanesulfonyl-2-fluoro-phenyl)-piperazine (compound 6.20) and 2-Isobutoxy-5-methanesulfonyl-benzoic acid (compound 1.3) | 556.1 (M + NH4+) |
| 579 | {4-[2-Fluoro-4-(tetrahydro-pyran-4-sulfonyl)-phenyl]-piperazin-1-yl}-(2-isopropoxy-5-methanesulfonyl-phenyl)-methanone | 1-[2-Fluoro-4-(tetrahydro-pyran-4-sulfonyl)-phenyl]-piperazine (compound 6.27) and 2-Isopropoxy-5-methanesulfonyl-benzoic acid (compound 1.2) | 586.2 (M + NH4+) |
| 580 | (2-tert-Butoxy-5-methanesulfonyl-phenyl)-{4-[2-fluoro-4-(propane-2-sulfonyl)-phenyl]-piperazin-1-yl-}-methanone | 1-[2-Fluoro-4-(propane-2-sulfonyl)-phenyl]-piperazine (compound 6.21) and 2-tert-Butoxy-5-methane sulfonyl-benzoic acid (compound 2.19) | 558.2 (M + NH4+) |
| 581 | (2-tert-Butoxy-5-methanesulfonyl-phenyl)-[4-(4-ethanesulfonyl-2-fluoro-phenyl)-piperazin-1-yl]-methanone | 1-(4-Ethanesulfonyl-2-fluoro-phenyl)-piperazine (compound 6.12) and 2-tert-Butoxy-5-methane sulfonyl-benzoic acid (compound 2.19) | 544.2 (M + NH4+) |

-continued

| Expl. No. | Systematic Name | Starting materials | MW found (MH+) |
|---|---|---|---|
| 582 | (2-tert-Butoxy-5-methanesulfonyl-phenyl)-[4-(4-cyclopropanesulfonyl-2-fluoro-phenyl)-piperazin-1-yl]-methanone | 1-(4-Cyclopropanesulfonyl-2-fluoro-phenyl)-piperazine (compound 6.20) and 2-tert-Butoxy-5-methane sulfonyl-benzoic acid (compound 2.19) | 556.1 (M + NH4+) |
| 583 | {4-[2-Fluoro-4-(propane-2-sulfonyl)-phenyl]-piperazin-1-yl}-[5-methanesulfonyl-2-(2,2,2-trifluoro-ethoxy)-phenyl]-methanone | 1-[2-Fluoro-4-(propane-2-sulfonyl)-phenyl]-piperazine (compound 6.21) and 5-Methanesulfonyl-2-(2,2,2-trifluoro-ethoxy)-benzoic acid (compound 1.5) | 584.1 (M + NH4+) |
| 584 | [4-(4-Ethanesulfonyl-2-fluoro-phenyl)-piperazin-1-yl]-[5-methanesulfonyl-2-(2,2,2-trifluoro-ethoxy)-phenyl]-methanone | 1-(4-Ethanesulfonyl-2-fluoro-phenyl)-piperazine (compound 6.12) and 5-Methanesulfonyl-2-(2,2,2-trifluoro-ethoxy)-benzoic acid (compound 1.5) | 570.3 (M + NH4+) |
| 585 | [4-(4-Cyclopropanesulfonyl-2-fluoro-phenyl)-piperazin-1-yl]-[5-methanesulfonyl-2-(2,2,2-trifluoro-ethoxy)-phenyl]-methanone | 1-(4-Cyclopropanesulfonyl-2-fluoro-phenyl)-piperazine (compound 6.20) and 5-Methanesulfonyl-2-(2,2,2-trifluoro-ethoxy)-benzoic acid (compound 1.5) | 582.1 (M + NH4+) |
| 586 | rac{4-[2-Fluoro-4-(propane-2-sulfonyl)-phenyl]-piperazin-1-yl}-[5-methanesulfonyl-2-(2,2,2-trifluoro-1-methyl-ethoxy)-phenyl]-methanone | 1-[2-Fluoro-4-(propane-2-sulfonyl)-phenyl]-piperazine (compound 6.21) and rac-5-Methanesulfonyl-2-(2,2,2-trifluoro-1-methyl-ethoxy)-benzoic acid (compound 3.1) | 598.2 (M + NH4+) |
| 587 | rac-[4-(4-Ethanesulfonyl-2-fluoro-phenyl)-piperazin-1-yl]-[5-methanesulfonyl-2-(2,2,2-trifluoro-1-methyl-ethoxy)-phenyl]-methanone | 1-(4-Ethanesulfonyl-2-fluoro-phenyl)-piperazine (compound 6.12) and rac-5-Methanesulfonyl-2-(2,2,2-trifluoro-1-methyl-ethoxy)-benzoic acid (compound 3.1) | 584.1 (M + NH4+) |
| 588 | rac-[4-(4-Cyclopropanesulfonyl-2-fluoro-phenyl)-piperazin-1-yl]-[5-methanesulfonyl-2-(2,2,2-trifluoro-1-methyl-ethoxy)-phenyl]-methanone | 1-(4-Cyclopropanesulfonyl-2-fluoro-phenyl)-piperazine (compound 6.20) and rac-5-Methanesulfonyl-2-(2,2,2-trifluoro-1-methyl-ethoxy)-benzoic acid (compound 3.1) | 596.2 (M + NH4+) |
| 589 | [4-(4-Cyclohexanesulfonyl-2-fluoro-phenyl)-piperazin-1-yl]-(2-isopropoxy-5-methanesulfonyl-phenyl)-methanone | 1-(4-Cyclohexanesulfonyl-2-fluoro-phenyl)-piperazine (compound 6.28) and 2-Isopropoxy-5-methanesulfonyl-benzoic acid (compound 1.2) | 584.3 (M + NH4+) |
| 590 | {4-[2,3-Difluoro-4-(propane-2-sulfonyl)-phenyl]-piperazin-1-yl}-(2-isopropoxy-5-methanesulfonyl-phenyl)-methanone | 1-[2,3-Difluoro-4-(propane-2-sulfonyl)-phenyl]-piperazine hydrochloride (compound 6.29) and 2-Isopropoxy-5-methanesulfonyl-benzoic acid (compound 1.2) | 545.2 |
| 591 | [4-(4-Ethanesulfonyl-2,3-difluoro-phenyl)-piperazin-1-yl]-(2-isopropoxy-5-methanesulfonyl-phenyl)-methanone | 1-(4-Ethanesulfonyl-2,3-difluoro-phenyl)-piperazine hydrochloride (compound 6.30) and 2-Isopropoxy-5-methanesulfonyl-benzoic acid (compound 1.2) | 531.1 |
| 592 | [4-(4-Cyclopropanesulfonyl-2,3-difluoro-phenyl)-piperazin-1-yl]-(2-isopropoxy-5-methanesulfonyl-phenyl)-methanone | 1-(4-Cyclopropanesulfonyl-2,3-difluoro-phenyl)-piperazine hydrochloride (compound 6.31) and 2-Isopropoxy-5-methanesulfonyl-benzoic acid (compound 1.2) | 543.3 |
| 593 | {4-[2,5-Difluoro-4-(propane-2-sulfonyl)-phenyl]-piperazin-1-yl}-(2-isopropoxy-5-methanesulfonyl-phenyl)-methanone | 1-[2,5-Difluoro-4-(propane-2-sulfonyl)-phenyl]-piperazine hydrochloride (compound 6.32) and 2-Isopropoxy-5-methanesulfonyl-benzoic acid (compound 1.2) | 545.2 |
| 594 | [4-(4-Ethanesulfonyl-2,5-difluoro-phenyl)-piperazin-1-yl]-(2-isopropoxy-5- | 1-(4-Ethanesulfonyl-2,5-difluoro-phenyl)-piperazine hydrochloride (compound 6.33) and 2-Isopropoxy-5-methanesulfonyl-benzoic acid | 531.1 |

-continued

| Expl. No. | Systematic Name | Starting materials | MW found (MH⁺) |
|---|---|---|---|
| | methanesulfonyl-phenyl)-methanone | (compound 1.2) | |
| 595 | [4-(4-Cyclopropanesulfonyl-2,5-difluoro-phenyl)-piperazin-1-yl]-(2-isopropoxy-5-methanesulfonyl-phenyl)-methanone | 1-(4-Cyclopropanesulfonyl-2,5-difluoro-phenyl)-piperazine hydrochloride (compound 6.34) and 2-Isopropoxy-5-methanesulfonyl-benzoic acid (compound 1.2) | 543.3 |
| 596 | (2-tert-Butoxy-5-methanesulfonyl-phenyl)-[4-(4-cyclobutanesulfonyl-2-fluoro-phenyl)-piperazin-1-yl]-methanone | 1-(4-Cyclobutanesulfonyl-2-fluoro-phenyl)-piperazine hydrochloride (compound 6.24) and 2-tert-Butoxy-5-methanesulfonyl-benzoic acid (compound 2.19) | 553.6 |
| 597 | (2-tert-Butoxy-5-methanesulfonyl-phenyl)-{4-[2,3-difluoro-4-(propane-2-sulfonyl)-phenyl]-piperazin-1-yl}-methanone | 1-[2,3-Difluoro-4-(propane-2-sulfonyl)-phenyl]-piperazine hydrochloride (compound 6.29) and 2-tert-Butoxy-5-methanesulfonyl-benzoic acid (compound 2.19) | 503.1 (M-tBu + H) |
| 598 | (2-tert-Butoxy-5-methanesulfonyl-phenyl)-[4-(4-ethanesulfonyl-2,3-difluoro-phenyl)-piperazin-1-yl]-methanone | 1-(4-Ethanesulfonyl-2,3-difluoro-phenyl)-piperazine hydrochloride (compound 6.30) and 2-tert-Butoxy-5-methanesulfonyl-benzoic acid (compound 2.19) | 489.2 (M-tBu + H) |
| 599 | (2-tert-Butoxy-5-methanesulfonyl-phenyl)-[4-(4-cyclopropanesulfonyl-2,3-difluoro-phenyl)-piperazin-1-yl]-methanone | 1-(4-Cyclopropanesulfonyl-2,3-difluoro-phenyl)-piperazine hydrochloride (compound 6.31) and 2-tert-Butoxy-5-methanesulfonyl-benzoic acid (compound 2.19) | 501.1 (M-tBu + H) |
| 600 | (2-tert-Butoxy-5-methanesulfonyl-phenyl)-{4-[2,5-difluoro-4-(propane-2-sulfonyl)-phenyl]-piperazin-1-yl}-methanone | 1-[2,5-Difluoro-4-(propane-2-sulfonyl)-phenyl]-piperazine hydrochloride (compound 6.32) and 2-tert-Butoxy-5-methanesulfonyl-benzoic acid (compound 2.19) | 503.2 (M-tBu + H) |
| 601 | (2-tert-Butoxy-5-methanesulfonyl-phenyl)-[4-(4-ethanesulfonyl-2,5-difluoro-phenyl)-piperazin-1-yl]-methanone | 1-(4-Ethanesulfonyl-2,5-difluoro-phenyl)-piperazine hydrochloride (compound 6.33) and 2-tert-Butoxy-5-methanesulfonyl-benzoic acid (compound 2.19) | 489.1 (M-tBu + H) |
| 602 | (2-tert-Butoxy-5-methanesulfonyl-phenyl)-[4-(4-cyclopropanesulfonyl-2,5-difluoro-phenyl)-piperazin-1-yl]-methanone | 1-(4-Cyclopropanesulfonyl-2,5-difluoro-phenyl)-piperazine hydrochloride (compound 6.34) and 2-tert-Butoxy-5-methanesulfonyl-benzoic acid (compound 2.19) | 501.3 (M-tBu + H) |
| 603 | [4-(4-Cyclobutanesulfonyl-2-fluoro-phenyl)-piperazin-1-yl]-[5-methanesulfonyl-2-(2,2,2-trifluoro-ethoxy)-phenyl]-methanone | 1-(4-Cyclobutanesulfonyl-2-fluoro-phenyl)-piperazine hydrochloride (compound 6.24) and 5-Methanesulfonyl-2-(2,2,2-trifluoro-ethoxy)-benzoic acid (compound 1.5) | 579.1 |
| 604 | {4-[2,3-Difluoro-4-(propane-2-sulfonyl)-phenyl]-piperazin-1-yl}-[5-methanesulfonyl-2-(2,2,2-trifluoro-ethoxy)-phenyl]-methanone | 1-[2,3-Difluoro-4-(propane-2-sulfonyl)-phenyl]-piperazine hydrochloride (compound 6.29) and 5-Methanesulfonyl-2-(2,2,2-trifluoro-ethoxy)-benzoic acid (compound 1.5) | 602.2 (M + NH4+) |
| 605 | [4-(4-Ethanesulfonyl-2,3-difluoro-phenyl)-piperazin-1-yl]-[5-methanesulfonyl-2-(2,2,2-trifluoro-ethoxy)-phenyl]-methanone | 1-(4-Ethanesulfonyl-2,3-difluoro-phenyl)-piperazine hydrochloride (compound 6.30) and 5-Methanesulfonyl-2-(2,2,2-trifluoro-ethoxy)-benzoic acid (compound 1.5) | 571.2 |
| 606 | [4-(4-Cyclopropanesulfonyl-2,3-difluoro-phenyl)-piperazin-1-yl]-[5-methanesulfonyl-2-(2,2,2-trifluoro-ethoxy)-phenyl]-methanone | 1-(4-Cyclopropanesulfonyl-2,3-difluoro-phenyl)-piperazine hydrochloride (compound 6.31) and 5-Methanesulfonyl-2-(2,2,2-trifluoro-ethoxy)-benzoic acid (compound 1.5) | 600.2 (M + NH4+) |
| 607 | {4-[2,5-Difluoro-4-(propane-2-sulfonyl)- | 1-[2,5-Difluoro-4-(propane-2-sulfonyl)-phenyl]-piperazine | 602.3 (M + NH4+) |

-continued

| Expl. No. | Systematic Name | Starting materials | MW found (MH+) |
|---|---|---|---|
| | phenyl]-piperazin-1-yl}-[5-methanesulfonyl-2-(2,2,2-trifluoro-ethoxy)-phenyl]-methanone | hydrochloride (compound 6.32) and 5-Methanesulfonyl-2-(2,2,2-trifluoro-ethoxy)-benzoic acid (compound 1.5) | |
| 608 | [4-(4-Ethanesulfonyl-2,5-difluoro-phenyl)-piperazin-1-yl]-[5-methanesulfonyl-2-(2,2,2-trifluoro-ethoxy)-phenyl]-methanone | 1-(4-Ethanesulfonyl-2,5-difluoro-phenyl)-piperazine hydrochloride (compound 6.33) and 5-Methanesulfonyl-2-(2,2,2-trifluoro-ethoxy)-benzoic acid (compound 1.5) | 588.3 (M + NH4+) |
| 609 | [4-(4-Cyclopropanesulfonyl-2,5-difluoro-phenyl)-piperazin-1-yl]-[5-methanesulfonyl-2-(2,2,2-trifluoro-ethoxy)-phenyl]-methanone | 1-(4-Cyclopropanesulfonyl-2,5-difluoro-phenyl)-piperazine hydrochloride (compound 6.34) and 5-Methanesulfonyl-2-(2,2,2-trifluoro-ethoxy)-benzoic acid (compound 1.5) | 600.2 (M + NH4+) |
| 610 | rac-[4-(4-Cyclobutanesulfonyl-2-fluoro-phenyl)-piperazin-1-yl]-[5-methanesulfonyl-2-(2,2,2-trifluoro-1-methyl-ethoxy)-phenyl]-methanone | 1-(4-Cyclobutanesulfonyl-2-fluoro-phenyl)-piperazine hydrochloride (compound 6.24) and rac-5-Methanesulfonyl-2-(2,2,2-trifluoro-1-methyl-ethoxy)-benzoic acid (compound 3.1) | 593.2 |
| 611 | rac-{4-[2,3-Difluoro-4-(propane-2-sulfonyl)-phenyl]-piperazin-1-yl}-[5-methanesulfonyl-2-(2,2,2-trifluoro-1-methyl-ethoxy)-phenyl]-methanone | 1-[2,3-Difluoro-4-(propane-2-sulfonyl)-phenyl]-piperazine hydrochloride (compound 6.29) and rac-5-Methanesulfonyl-2-(2,2,2-trifluoro-1-methyl-ethoxy)-benzoic acid (compound 3.1) | 599.2 |
| 612 | rac-[4-(4-Ethanesulfonyl-2,3-difluoro-phenyl)-piperazin-1-yl]-[5-methanesulfonyl-2-(2,2,2-trifluoro-1-methyl-ethoxy)-phenyl]-methanone | 1-(4-Ethanesulfonyl-2,3-difluoro-phenyl)-piperazine hydrochloride (compound 6.30) and rac-5-Methanesulfonyl-2-(2,2,2-trifluoro-1-methyl-ethoxy)-benzoic acid (compound 3.1) | 602.2 (M + NH4+) |
| 613 | rac-[4-(4-Cyclopropanesulfonyl-2,3-difluoro-phenyl)-piperazin-1-yl]-[5-methanesulfonyl-2-(2,2,2-trifluoro-1-methyl-ethoxy)-phenyl]-methanone | 1-(4-Cyclopropanesulfonyl-2,3-difluoro-phenyl)-piperazine hydrochloride (compound 6.31) and rac-5-Methanesulfonyl-2-(2,2,2-trifluoro-1-methyl-ethoxy)-benzoic acid (compound 3.1) | 614.3(M + NH4+) |
| 614 | rac-4-[2,5-Difluoro-4-(propane-2-sulfonyl)-phenyl]-piperazin-1-yl}-[5-methanesulfonyl-2-(2,2,2-trifluoro-1-methyl-ethoxy)-phenyl]-methanone | 1-[2,5-Difluoro-4-(propane-2-sulfonyl)-phenyl]-piperazine hydrochloride (compound 6.32) and rac-5-Methanesulfonyl-2-(2,2,2-trifluoro-1-methyl-ethoxy)-benzoic acid (compound 3.1) | 616.2 (M + NH4+) |
| 615 | rac-[4-(4-Ethanesulfonyl-2,5-difluoro-phenyl)-piperazin-1-yl]-[5-methanesulfonyl-2-(2,2,2-trifluoro-1-methyl-ethoxy)-phenyl]-methanone | 1-(4-Ethanesulfonyl-2,5-difluoro-phenyl)-piperazine hydrochloride (compound 6.33) and rac-5-Methanesulfonyl-2-(2,2,2-trifluoro-1-methyl-ethoxy)-benzoic acid (compound 3.1) | 602.3 (M + NH4+) |
| 616 | rac-[4-(4-Cyclopropanesulfonyl-2,5-difluoro-phenyl)-piperazin-1-yl]-[5-methanesulfonyl-2-(2,2,2-trifluoro-1-methyl-ethoxy)-phenyl]-methanone | 1-(4-Cyclopropanesulfonyl-2,5-difluoro-phenyl)-piperazine hydrochloride (compound 6.34) and rac-5-Methanesulfonyl-2-(2,2,2-trifluoro-1-methyl-ethoxy)-benzoic acid (compound 3.1) | 614.3 (M + NH4+) |
| 617 | [4-(4-Hydroxy-phenyl)-piperazin-1-yl]-(2-isopropoxy-5-methanesulfonyl-phenyl)-methanone | 4-Piperazin-1-yl-phenol (commercial) and 2-Isopropoxy-5-methanesulfonyl-benzoic acid (compound 1.2) | 419.1 |
| 618 | rac-(2-Isopropoxy-5-methanesulfonyl- | rac-2-Methyl-1-(4-trifluoromethyl-phenyl)-piperazine hydrochloride | 485.2 |

-continued

| Expl. No. | Systematic Name | Starting materials | MW found (MH+) |
|---|---|---|---|
| 619 | phenyl)-[3-methyl-4-(4-trifluoromethyl-phenyl)-piperazin-1-yl]-methanone<br>1-{4-Isopropoxy-3-[4-(4-trifluoromethyl-phenyl)-piperazine-1-carbonyl]-phenyl}-ethanone | (compound 6.35) and 2-Isopropoxy-5-methanesulfonyl-benzoic acid (compound 1.2)<br>1-(4-Trifluoromethyl-phenyl)-piperazine (commercial) and 5-Acetyl-2-isopropoxy-benzoic acid (compound 6.36) | 435.2 |

EXAMPLE 6.37

Preparation of 4-isopropoxy-3-[4-(4-trifluoromethyl-phenyl)-piperazine-1-carbonyl]-benzoic acid (a) 4-Isopropoxy-3-[4-(4-trifluoromethyl-phenyl)-piperazine-1-carbonyl]-benzonitrile To a solution of 3.6 mmol 5-cyano-2-isopropoxy-benzoic acid (compound 1.13) in 20 ml THF were added 4.0 mmol TBTU, 21.6 mmol N-ethyldiisopropylamine and 4.0 mmol 1-(4-trifluoromethyl-phenyl)-piperazine (commercial). The reaction was then stirred at RT for 16 h, concentrated in vacuo, and purified by chromatography on silica gel (eluant: ethyl acetate/heptane 1:1) to afford the title compound. MS (m/e): 418.3 (M+H+, 100%)

(b) 4-Isopropoxy-3-[4-(4-trifluoromethyl-phenyl)-piperazine-1-carbonyl]-benzoic acid To 3.2 mmol 4-isopropoxy-3-[4-(4-trifluoromethyl-phenyl)-piperazine-1-carbonyl]-benzonitrile in 15 ml ethanol was added 30 mmol 2 M aq NaOH and the mixture was heated at 85° C. for 16 h. The mixture was then cooled to RT, diluted with water and acidified to pH 1 with conc HCl, and then extracted three times with ethyl acetate. The combined organic phases were dried with $Na_2SO_4$, concentrated in vacuo, and the residue purified by chromatography on silica gel (eluant: methanol/dichloromethane 5:95) to afford the title compound. MS (m/e): 435.3 ([M−H]−, 100%)

EXAMPLE 620

Preparation of 4-isopropoxy-3-[4-(4-trifluoromethyl-phenyl)-piperazine-1-carbonyl]-benzoic acid methyl ester To 0.3 mmol 4-isopropoxy-3-[4-(4-trifluoromethyl-phenyl)-piperazine-1-carbonyl]-benzoic acid in 2 ml DMF was added 0.4 mmol CDI, and the mixture heated at 50° C. for 30 min. 5.2 mmol methanol was then added, and the mixture was stirred at RT for 16 h. The mixture was then cooled to room temperature, concentrated in vacuo, and the residue chromatographed on silica gel (eluant: ethyl acetate/heptane 1:4) to afford the title compound. MS (m/e): 451.2 (M+H+, 100%)

EXAMPLE 621

Preparation of 4-isopropoxy-N-methyl-3-[4-(4-trifluoromethyl-phenyl)-piperazine-1-carbonyl]-benzamide To 0.3 mmol 4-isopropoxy-3-[4-(4-trifluoromethyl-phenyl)-piperazine-1-carbonyl]-benzoic acid in 2 ml DMF was added 0.4 mmol CDI, and the mixture heated at 50° C. for 30 min. 5.2 mmol methylamine (41% aq solution) was then added, and the mixture was stirred at RT for 16 h. The mixture was then cooled to room temperature, concentrated in vacuo, and the residue chromatographed on silica gel (eluant: ethyl acetate) to afford the title compound. MS (m/e): 450.1 (M+H+, 100%)

EXAMPLE 6.38

Preparation of 3-[4-(4-Cyano-3-fluoro-phenyl)-piperazine-1-carbonyl]-4-hydroxy-benzenesulfonamide (a) 2-Hydroxy-5-sulfamoyl-benzoic acid Ammonia gas was bubbled through a solution of 107 mmol 5-chlorosulfonyl-2-hydroxy-benzoic acid in 250 ml acetone at 0° C. for 2 h. Argon gas was then bubbled through the reaction mixture for 1 h to purge excess ammonia. The mixture was then diluted with water, the pH adjusted to pH 14 by addition of 5 M aq NaOH solution, and the mixture was then extracted with ether/ethyl acetate (1:1). The aqueous phase was acidified with concentrated HCl, saturated with NaCl, and extracted twice with THF. The combined THF extracts were dried with $Na_2SO_4$. Evaporation of the solvent in vacuo followed by drying of the residue by heating at 60° C. overnight in vacuo yielded the title compound.

MS (m/e): 216.1 ([M−H]−, 100%)

(b) 2-Hydroxy-5-sulfamoyl-benzoic acid methyl ester

To 62 mmol 2-hydroxy-5-sulfamoyl-benzoic acid in 80 ml THF was added 80 mmol CDI and the mixture heated at 50° C. for 1 h. 616 mmol methanol was then added, and the mixture was heated at 50° C. for 16 h. The mixture was then cooled to room temperature, concentrated in vacuo, and the residue chromatographed on silica gel (eluant: dichloromethane/methanol 20:1). The product containing fractions were concentrated in vacuo and the residue suspended in ethyl acetate and washed with aq NaHCO3 solution. The organic phase was dried with $Na_2SO_4$ and concentrated in vacuo to afford the title compound. MS (m/e): 230.2 ([M−H]−, 100%)

(c) 2-(4-Methoxy-benzyloxy)-5-sulfamoyl-benzoic acid methyl ester

To 4.8 mmol 2-hydroxy-5-sulfamoyl-benzoic acid methyl ester, 5.2 mmol 4-methoxybenzyl alcohol and 5.2 mmol triphenylphosphine in 8 ml THF was added 5.2 mmol di-tert-butyl azodicarboxylate, and the mixture was stirred at RT for 2 h. The mixture was then concentrated in vacuo. The residue was chromatographed on silica gel (eluant: ethyl acetate/heptane gradient) to afford the title compound. MS (m/e): 350.2 ([M−H]−, 100%)

(d) 2-(4-Methoxy-benzyloxy)-5-sulfamoyl-benzoic acid

To 2.5 mmol 2-(4-methoxy-benzyloxy)-5-sulfamoyl-benzoic acid methyl ester in 6 ml THF was added 5 mmol 2 M aq NaOH, and the mixture was heated at 60° C. for 30 min. The mixture was then cooled to RT and extracted twice with ethyl acetate. The aqueous phase was acidified to pH 1 with 5 M aq HCl and extracted with ethyl acetate. The combined organic phases were washed with saturated aq NaCl and dried with $Na_2SO_4$. Evaporation in vacuo afforded the title compound. MS (m/e): 336.1 ([M–H]⁻, 100%)

(e) (3-[4-(4-Cyano-3-fluoro-phenyl)-piperazine-1-carbonyl]-4-(4-methoxy-benzyloxy)-benzenesulfonamide To a solution of 3.5 mmol 2-(4-methoxy-benzyloxy)-5-sulfamoyl-benzoic acid in 4 ml dimethylformamide and 12 ml THF were added 5.3 mmol TBTU, 17.5 mmol N-ethyl-diisopropylamine and 3.5 mmol 3-fluoro-4-piperazin-1-yl-benzonitrile (WO9625414). The reaction was then stirred at RT for 1 h, concentrated in vacuo, and purified by chromatography on silica gel (eluant: ethyl acetate/heptane gradient) to afford the title compound. MS (m/e): 525.1 (M+H⁺)

(f) (3-[4-(4-Cyano-3-fluoro-phenyl)-piperazine-1-carbonyl]-4-hydroxy-benzenesulfonamide Hydrogen gas was bubbled through a solution of 1.0 mmol (3-[4-(4-Cyano-3-fluoro-phenyl)-piperazine-1-carbonyl]-4-(4-methoxy-benzyloxy)-benzenesulfonamide in 40 ml THF containing 50 mg 10% palladioum on charcoal and a few drops of acetic acid for 6 h at RT. The reaction mixture was then purged with argon, filtered through celite, and the filtrate was concentrated in vacuo. The residue was purified by chromatography on silica gel (eluant: methanol/dichloromethane gradient) to afford the title compound. MS (m/e): 403.1 ([M–H]⁻, 100%)

In analogy to Example 6.38(e) and (f), compounds 6.39 and 6.40 of the following table were prepared from 2-(4-methoxy-benzyloxy)-5-sulfamoyl-benzoic acid and the appropriate piperazine, followed by hydrogenolysis with catalytic palladium on charcoal:

| Expl. No | name | piperazine | MS (m/e) |
|---|---|---|---|
| 6.39 | 3-[4-(4-Cyano-2-fluoro-phenyl)-piperazine-1-carbonyl]-4-hydroxy-benzenesulfonamide | 3-Fluoro-4-piperazin-1-yl-benzonitrile (WO9625414) | 403.1 (M – H) |
| 6.40 | 3-[4-(2-Fluoro-4-methanesulfonyl-phenyl)-piperazine-1-carbonyl]-4-hydroxy-benzenesulfonamide | 1-(2-Fluoro-4-methanesulfonyl-phenyl)-piperazine (commercial) | 456.2 (M – H) |

EXAMPLE 622

Preparation of 3-[4-(4-cyano-3-fluoro-phenyl)-piperazine-1-carbonyl]-4-isobutoxy-benzenesulfonamide To 0.1 mmol (3-[4-(4-cyano-3-fluoro-phenyl)-piperazine-1-carbonyl]-4-hydroxy benzenesulfonamide (compound 6.38), 0.5 mmol 2-methyl-1-propanol and 0.3 mmol diphenyl-2-pyridylphosphine in 4 ml THF was added 0.3 mmol di-tert-butyl azodicarboxylate, and the mixture was stirred at 60° C. for 4 h. The mixture was then diluted with ethyl acetate and washed twice with 5 M aq HCl and then with saturated aq NaCl solution. The organic phase was then dried with $Na_2SO_4$, and concentrated in vacuo. The residue was triturated in ether to afford the title compound. MS (m/e): 459.2 ([M–H]⁻, 100%)

In analogy to Example 622, compounds 623 to 632 of the following table were prepared from compounds 6.38 to 6.40 and the appropriate alcohol:

| Expl. No | name | Starting materials | MW found (MH⁺) |
|---|---|---|---|
| 623 | 3-[4-(4-Cyano-3-fluoro-phenyl)-piperazine-1-carbonyl]-4-cyclopentyloxy-benzenesulfonamide | 3-[4-(4-Cyano-3-fluoro-phenyl)-piperazine-1-carbonyl]-4-hydroxy-benzenesulfonamide (compound 6.38) and cyclopentanol | 471.3 (M – H) |
| 624 | 3-[4-(4-Cyano-2-fluoro-phenyl)-piperazine-1-carbonyl]-4-isopropoxy-benzenesulfonamide | 3-[4-(4-Cyano-2-fluoro-phenyl)-piperazine-1-carbonyl]-4-hydroxy-benzenesulfonamide (compound 6.39) and 2-propanol | 445.2 (M – H) |
| 625 | 3-[4-(4-Cyano-2-fluoro-phenyl)-piperazine-1-carbonyl]-4-isobutoxy-benzenesulfonamide | 3-[4-(4-Cyano-2-fluoro-phenyl)-piperazine-1-carbonyl]-4-hydroxy-benzenesulfonamide (compound 6.39) and 2-methyl-1-propanol | 459.2 (M – H) |
| 626 | 3-[4-(4-Cyano-2-fluoro-phenyl)-piperazine-1-carbonyl]-4-cyclopentyloxy-benzenesulfonamide | 3-[4-(4-Cyano-2-fluoro-phenyl)-piperazine-1-carbonyl]-4-hydroxy-benzenesulfonamide (compound 6.39) and cyclopentanol | 471.3 (M – H) |
| 627 | 3-[4-(2-Fluoro-4-methanesulfonyl-phenyl)-piperazine-1-carbonyl]-4-isobutoxy-benzenesulfonamide | 3-[4-(2-Fluoro-4-methanesulfonyl-phenyl)-piperazine-1-carbonyl]-4-hydroxy-benzenesulfonamide (compound 6.40) and 2-methyl-1-propanol | 512.3 (M – H) |
| 628 | 4-Cyclopentyloxy-3-[4-(2-fluoro-4-methanesulfonyl-phenyl)-piperazine-1-carbonyl]-benzenesulfonamide | 3-[4-(2-Fluoro-4-methanesulfonyl-phenyl)-piperazine-1-carbonyl]-4-hydroxy-benzenesulfonamide (compound 6.40) and cyclopentanol | 524.5 (M – H) |
| 629 | 3-[4-(4-Cyano-3-fluoro-phenyl)-piperazine-1-carbonyl]-4-isopropoxy-benzenesulfonamide | 3-[4-(4-Cyano-3-fluoro-phenyl)-piperazine-1-carbonyl]-4-hydroxy-benzenesulfonamide (compound 6.38) and 2-propanol | 445.1 (M – H) |
| 630 | 3-[4-(4-Cyano-3-fluoro-phenyl)-piperazine-1-carbonyl]-4-cyclobutylmethoxy-benzenesulfonamide | 3-[4-(4-Cyano-3-fluoro-phenyl)-piperazine-1-carbonyl]-4-hydroxy-benzenesulfonamide (compound 6.38) and cyclobutanemethanol | 471.3 (M – H) |
| 631 | 3-[4-(2-Fluoro-4-methanesulfonyl-phenyl)-piperazine-1-carbonyl]-4-isopropoxy-benzenesulfonamide | 3-[4-(2-Fluoro-4-methanesulfonyl-phenyl)-piperazine-1-carbonyl]-4-hydroxy-benzenesulfonamide (compound 6.40) and 2-propanol | 498.4 (M – H) |
| 632 | 4-Cyclobutylmethoxy-3-[4-(2-fluoro-4-methanesulfonyl-phenyl)-piperazine-1-carbonyl]-benzenesulfonamide | 3-[4-(2-Fluoro-4-methanesulfonyl-phenyl)-piperazine-1-carbonyl]-4-hydroxy-benzenesulfonamide (compound 6.40) and cyclobutanemethanol | 524.5 (M – H) |

EXAMPLE 7.1

Preparation of 3-Piperazin-1-yl-5-trifluoromethyl-pyridazine (a)-3-Chloro-5-trifluoromethyl-pyridazine
5-Trifluoromethyl-pyridazin-3-ol [244268-34-6 (1 g) was added to a stirred solution of phosphoryloxychloride, and the reaction mixture was stirred at 80° C. for 1 hour. After such time, the reaction mixture was allowed to cool to room temperature, poured onto ice and after 5 minutes was extracted twice from the aqueous solution with dichloromethane. The combined organic phases were dried with sodium sulfate and concentrated in vacuo. The residue was distilled in a Kugelrohr apparatus (bp=80-100° C. @ 12 mBar) to yield the title compound (0.26 g). MS (m/e): 182.0

(b) 4-(5-Trifluoromethyl-pyridazin-3-yl)-piperazine-1-carboxylic acid tert-butyl ester 3-Chloro-5-trifluoromethyl-pyridazine (200 mg) was added to piperazine-1-carboxylic acid tert-butyl ester (231 mg) in dimethylacetamide (3 mL), and the reaction mixture was stirred at 100° C. for 3 hours. After such time, the reaction mixture was allowed to cool down to room temperature and diluted with ethyl acetate. The solid was filtered off and washed with ethyl acetate. The filtrate was then concentrated in vacuo and then purified by column chromatography ($SiO_2$, Heptane/EtOAc) to yield the title compound as a white solid (364 mg). MS (m/e): 333.4 ($M+H^+$, 100%)

(c) 3-Piperazin-1-yl-5-trifluoromethyl-pyridazine 4-(5-Trifluoromethyl-pyridazin-3-yl)-piperazine-1-carboxylic acid tert-butyl ester (45 mg) was dissolved in dichloromethane (0.5 mL), and trifluoroacetic acid was added (0.5 mL). The reaction mixture was stirred for 30 minutes before being concentrated in vacuo to afford the crude title compound which was used directly in the next step without further purification or analysis.

EXAMPLE 7.2

Preparation of 5-Methanesulfonyl-2-(2,2,2-trifluoro-1,1-dimethyl-ethoxy)-benzoic acid To 2-Fluoro-5-methanesulfonyl-benzoic acid (247569-56-8) (600 mg) in dimethylacetamide (10 mL) was added cesium carbonate at 170° C. 2-trifluoromethyl-propanol (0.94 mL) was first added to the reaction mixture followed by additionally 0.47 mL every 24 hours. After a total of 72 hours, the reaction mixture was acidified by addition of formic acid, concentrated in vacuo and purified by preparative HPLC to yield the title compound as a light brown solid (897 mg). MS (m/e): 325.3. (M−H, 100%)

EXAMPLE 7.3

Preparation of 5-Methanesulfonyl-2-piperazin-1-yl-pyrimidine (a) 3-Dimethylamino-2-methanesulfonyl-allylidene-dimethyl-ammonium; chloride To sulfonyl-acetic acid (1.5 g) in dimethylformamide was slowly added phosphorus oxychloride over 5 minutes, and the reaction was then stirred at 70° C. for 1 hour and then at room temperature overnight. The reaction mixture was then directly poured over a short column chromatography ($SiO_2$, 100 g), eluting successively with 500 mL of EtOAc, THF, EtOAc/EtOH (50/50), EtOH and finally MeOH to yield the title compound (1.58 g). MS (m/e): 204.9 ($M^+$).

(b) 5-Methanesulfonyl-2-piperazin-1-yl-pyrimidine

The title compound was prepared in analogy to Example 2.25 using 3-Dimethylamino-2-methanesulfonyl-allylidene-dimethyl-ammonium; chloride as starting material. MS (m/e): 243.1 ($M+H^+$, 100%).

EXAMPLE 7.4

Preparation of 1-(5-Methanesulfonyl-pyridin-2-yl)-piperazine trifluoro-acetic acid The title compound was prepared in analogy to Example 7.1 (b-c) from 2-bromo-5-(methanesulfonyl) pyridine and piperazine-1-carboxylic acid tert-butyl ester. MS (m/e): 242.1 ($M+H^+$, 100%)

In analogy to Example 5, compounds 633 to 644 of the following table were prepared from the acid derivatives and piperazine derivatives:

| Expl. No. | Systematic Name | Starting materials | MW found ($MH^+$) |
|---|---|---|---|
| 633 | rac-[5-Methanesulfonyl-2-(2,2,2-trifluoro-1-methyl-ethoxy)-phenyl]-[4-(5-trifluoromethyl-pyridazin-3-yl)-piperazin-1-yl]-methanone | 3-Piperazin-1-yl-5-trifluoromethyl-pyridazine (compound 7.1) and rac-5-Methanesulfonyl-2-(2,2,2-trifluoro-1-methyl-ethoxy)-benzoic acid (compound 3.1) | 527.0 |
| 634 | [5-Methanesulfonyl-2-(2,2,2-trifluoro-1,1-dimethyl-ethoxy)-phenyl]-[4-(5-trifluoromethyl-pyrimidin-2-yl)-piperazin-1-yl]-methanone | 2-Piperazin-1-yl-5-trifluoromethyl-pyrimidine (compound 2.25) and 5-Methanesulfonyl-2-(2,2,2-trifluoro-1,1-dimethyl-ethoxy)-benzoic acid (compound 7.2) | 541.0 |
| 635 | [5-Methanesulfonyl-2-((S)-2,2,2-trifluoro-1-methyl-ethoxy)-phenyl]-[4-(5-trifluoromethyl-pyrimidin-2-yl)-piperazin-1-yl]-methanone | 2-Piperazin-1-yl-5-trifluoromethyl-pyrimidine (compound 2.25) and 5-Methanesulfonyl-2-((S)-2,2,2-trifluoro-1-methyl-ethoxy)-benzoic acid (compound 5.6) | 527.2 |
| 636 | [5-Methanesulfonyl-2-((R)-2,2,2-trifluoro-1-methyl-ethoxy)-phenyl]-[4-(5-trifluoromethyl-pyrimidin-2-yl)-piperazin-1-yl]-methanone | 2-Piperazin-1-yl-5-trifluoromethyl-pyrimidine (compound 2.25) and 5-Methanesulfonyl-2-((R)-2,2,2-trifluoro-1-methyl-ethoxy)-benzoic acid (compound 5.7) | 527.2 |
| 637 | [4-(3-Fluoro-5-trifluoromethyl-pyridin-2-yl)-piperazin-1-yl]-[5-methanesulfonyl-2-(2,2,2-trifluoro-1,1-dimethyl-ethoxy)-phenyl]-methanone | 1-(3-Fluoro-5-trifluoromethyl-pyridin-2-yl)-piperazine (compound 5.5) and 5-Methanesulfonyl-2-(2,2,2-trifluoro-1,1-dimethyl-ethoxy)-benzoic acid (compound 7.2) | 558.2 |
| 638 | [5-Methanesulfonyl-2-(2,2,2-trifluoro-ethoxy)-phenyl]-[4-(5-trifluoromethyl-pyrimidin-2-yl)-piperazin-1-yl]-methanone | 2-Piperazin-1-yl-5-trifluoromethyl-pyrimidine (compound 2.25) and 5-Methanesulfonyl-2-(2,2,2-trifluoro-ethoxy)-benzoic acid (compound 1.5) | 513.3 |
| 639 | (2-Cyclopropylmethoxy-5-methanesulfonyl-phenyl)-[4-(5-trifluoromethyl-pyrimidin-2-yl)-piperazin-1-yl]-methanone | 2-Piperazin-1-yl-5-trifluoromethyl-pyrimidine (compound 2.25) and 2-Cyclopropylmethoxy-5-methanesulfonyl-benzoic acid (compound 1.4) | 485.4 |
| 640 | [4-(2,5-Difluoro-4-methanesulfonyl-phenyl)-piperazin-1-yl]-[5- | 1-(2,5-Difluoro-4-methanesulfonyl-phenyl)-piperazine trifluoro- | 585.3 |

-continued

| Expl. No. | Systematic Name | Starting materials | MW found (MH⁺) |
|---|---|---|---|
| | methanesulfonyl-2-(2,2,2-trifluoro-1,1-dimethyl-ethoxy)-phenyl]-methanone | acetic acid (compound 2.20) and 5-Methanesulfonyl-2-(2,2,2-trifluoro-1,1-dimethyl-ethoxy)-benzoic acid (compound 7.2) | |
| 641 | [4-(2,3-Difluoro-4-methanesulfonyl-phenyl)-piperazin-1-yl]-[5-methanesulfonyl-2-(2,2,2-trifluoro-1,1-dimethyl-ethoxy)-phenyl]-methanone | 1-(2,3-Difluoro-4-methanesulfonyl-phenyl)-piperazine (compound 5.3) and 5-Methanesulfonyl-2-(2,2,2-trifluoro-1,1-dimethyl-ethoxy)-benzoic acid (compound 7.2) | 585.3 |
| 642 | [4-(2,6-Difluoro-4-methanesulfonyl-phenyl)-piperazin-1-yl]-[5-methanesulfonyl-2-(2,2,2-trifluoro-1,1-dimethyl-ethoxy)-phenyl]-methanone | 1-(2,6-Difluoro-4-methanesulfonyl-phenyl)-piperazine trifluoro-acetic acid (compound 2.23) and 5-Methanesulfonyl-2-(2,2,2-trifluoro-1,1-dimethyl-ethoxy)-benzoic acid (compound 7.2) | 585.2 |
| 643 | rac-[4-(5-Methane sulfonyl-pyrimidin-2-yl)-piperazin-1-yl]-[5-methanesulfonyl-2-(2,2,2-trifluoro-1-methyl-ethoxy)-phenyl]-methanone | 5-Methanesulfonyl-2-piperazin-1-yl-pyrimidine (compound 7.3) and rac-5-Methanesulfonyl-2-(2,2,2-trifluoro-1-methyl-ethoxy)-benzoic acid (compound 3.1) | 537.3 |
| 644 | rac-[4-(5-Methanesulfonyl-pyridin-2-yl)-piperazin-1-yl]-[5-methanesulfonyl-2-(2,2,2-trifluoro-1-methyl-ethoxy)-phenyl]-methanone | 1-(5-Methanesulfonyl-pyridin-2-yl)-piperazine trifluoro-acetic acid (compound 7.4) and rac-5-Methanesulfonyl-2-(2,2,2-trifluoro-1-methyl-ethoxy)-benzoic acid (compound 3.1) | 536.3 |

EXAMPLE 645

Preparation of (2-Allyloxy-5-nitro-phenyl)-[4-(4-trifluoromethyl-phenyl)-piperazin-1-yl]-methanone The title compound was prepared in analogy to example 62 from (2-Hydroxy-5-nitro-phenyl)-[4-(4-trifluoromethyl-phenyl)-piperazin-1-yl]-methanone (compound 2.1) and cyclopropyl bromide. MS (m/e): 436.5 (MH⁺, 100%)

EXAMPLE 7.5

Preparation of 2-Benzyloxy-5-methanesulfonyl-benzoic acid

The title compound was prepared in analogy to example 2.10 from methyl 5-(methanesulfonyl)salicylate and benzylalcohol. MS (m/e): 305.3 (M−H, 100%)

EXAMPLE 646

Preparation of (2-Benzyloxy-5-methanesulfonyl-phenyl)-[4-(3-fluoro-5-trifluoromethyl-pyridin-2-yl)-piperazin-1-yl]-methanone The title compound was prepared in analogy to example 5 from 1-(3-Fluoro-5-trifluoromethyl-pyridin-2-yl)-piperazine (compound 5.5) and 2-Benzyloxy-5-methanesulfonyl-benzoic acid (compound 7.5). MS (m/e): 538.4 (MH⁺, 100%)

EXAMPLE 647

Preparation of (2-Benzyloxy-5-methanesulfonyl-phenyl)-[4-(2-fluoro-4-methanesulfonyl-phenyl)-piperazin-1-yl]-methanone The title compound was prepared in analogy to example 5 from 1-(2-Fluoro-4-methanesulfonyl-phenyl)-piperazine (commercial) and 2-Benzyloxy-5-methanesulfonyl-benzoic acid (compound 7.5). MS (m/e): 547.4 (MH⁺, 100%)

EXAMPLE 648

Preparation of [4-(2-Fluoro-4-methanesulfonyl-phenyl)-piperazin-1-yl]-(2-hydroxy-5-methanesulfonyl-phenyl)-methanone A mixture of 0.915 mmol (2-benzyloxy-5-methanesulfonyl-phenyl)-[4-(2-fluoro-4-methanesulfonyl-phenyl)-piperazin-1-yl]-methanone, 0.05 mmol palladium on charcoal (10%) in 12.5 ml methanol was hydrogenated at atmospheric pressure at room temperature for 2 hours. After addition of chloroform, the mixture was filtered, and the solvent was evaporated to provide the title compound. MS (m/e): 474.3 (M+NH4⁺, 100%)

EXAMPLE 7.6

Preparation of 5-Piperazin-1-yl-2-trifluoromethyl-pyrimidine (a) 5-Chloro-2-trifluoromethyl-pyrimidine To a solution of 38 mmol trifluoroacetamidine in 70 ml acetonitrile was added 37.92 mmol ((Z)-2-Chloro-3-dimethylamino-allylidene)-dimethyl-ammonium hexafluoro phosphate (CAS: 291756-76-8) followed by 45.5 mmol triethylamine. The yellow solution was stirred at room temperature for 5 hours, then poured onto water and extracted 3 times with ether. The combined extracts were dried over sodium sulfate, filtered and distilled at 760 mm Hg to provide the title compound. MS (m/e): 182.2 (M⁺, 100%)

(b) 4-(2-Trifluoromethyl-pyrimidin-5-yl)-piperazine-1-carboxylic acid tert-butyl ester 0.26 mmol 5-Chloro-2-trifluoromethyl-pyrimidine was added to 0.26 mmol piperazine-1-carboxylic acid tert-butyl ester in 1.5 ml dimethylacetamide, and the reaction mixture was stirred at 150° C. for 10 min. in a microwave oven. After such time, the reaction mixture was concentrated and the residue was then purified by column chromatography (SiO₂, Heptane/EtOAc) to yield the title compound. MS (m/e): 333.2 (M+H⁺, 100%)

(c) 5-Piperazin-1-yl-2-trifluoromethyl-pyrimidine

The title compound was prepared in analogy to Example 7.1 (c) from 4-(2-trifluoromethyl-pyrimidin-5-yl)-piperazine-1-carboxylic acid tert-butyl ester MS (m/e): 233.0 (M+H⁺, 100%)

EXAMPLE 7.7

Preparation of 5'-Trifluoromethyl-3,4,5,6-tetrahydro-2H-[1,2']bipyrazinyl (a) 2-Bromo-5-trifluoromethyl-pyrazine To a suspension of 0.423 mmol copper (II) bromide in THF (1 ml) was added dropwise 0.51 mmol tert-butylnitrite at 0° C. within 2 minutes. 0.37 mmol 5-Trifluoromethyl-pyrazin-2-ylamine (CAS: 69816-38-2; WO9518097) in solution in THF (0.5 ml) was added dropwise within 5 minutes at 0° C. The mixture was stirred at 0° C. for 1 hour, at room temperature for 21 hours and quenched with water. The aqueous phase was extracted with ether. The combined extracts were dried over sodium sulfate and filtered and concentrated at atmospheric pressure. The residue was then purified by column chromatography ($SiO_2$, ether) to yield the title compound.

(b) 5'-Trifluoromethyl-3,4,5,6-tetrahydro-2H-[1,2']bipyrazinyl

The title compound was prepared in analogy to Example 7.6 (b-c) from 2-Bromo-5-trifluoromethyl-pyrazine MS (m/e): 233.0 (M+H$^+$, 100%)

EXAMPLE 7.8

Preparation of 3-Piperazin-1-yl-6-trifluoromethyl-pyridazine

The title compound was prepared in analogy to Example 7.6 (b-c) from 3-Chloro-6-trifluoromethyl-pyridazine (CAS: 258506-68-2). MS (m/e): 233.0 (M+H$^+$, 100%)

In analogy to Example 5, compounds 649 to 660 of the following table were prepared from the acid derivatives and piperazine derivatives:

| Expl. No. | Systematic Name | Starting materials | MW found (MH$^+$) |
|---|---|---|---|
| 649 | [5-Methanesulfonyl-2-((S)-2,2,2-trifluoro-1-methyl-ethoxy)-phenyl]-[4-(2-trifluoromethyl-pyrimidin-5-yl)-piperazin-1-yl]-methanone | 5-Piperazin-1-yl-2-trifluoromethyl-pyrimidine (compound 7.6) and 5-Methanesulfonyl-2-((S)-2,2,2-trifluoro-1-methyl-ethoxy)-benzoic acid (compound 5.6) | 527.2 |
| 650 | [5-Methanesulfonyl-2-((R)-2,2,2-trifluoro-1-methyl-ethoxy)-phenyl]-[4-(2-trifluoromethyl-pyrimidin-5-yl)-piperazin-1-yl]-methanone | 5-Piperazin-1-yl-2-trifluoromethyl-pyrimidine (compound 7.6) and 5-Methanesulfonyl-2-((R)-2,2,2-trifluoro-1-methyl-ethoxy)-benzoic acid (compound 5.7) | 527.0 |
| 651 | (2-Isopropoxy-5-methanesulfonyl-phenyl)-[4-(2-trifluoromethyl-pyrimidin-5-yl)-piperazin-1-yl]-methanone | 5-Piperazin-1-yl-2-trifluoromethyl-pyrimidine (compound 7.6) and 2-Isopropoxy-5-methane sulfonyl-benzoic acid (compound 1.2) | 473.0 |
| 652 | [5-Methanesulfonyl-2-((S)-2,2,2-trifluoro-1-methyl-ethoxy)-phenyl]-(5'-trifluoromethyl-2,3,5,6-tetrahydro-[1,2']bipyrazinyl-4-yl)-methanone | 5'-Trifluoromethyl-3,4,5,6-tetrahydro-2H-[1,2']bipyrazinyl (compound 7.7) and 5-Methanesulfonyl-2-((S)-2,2,2-trifluoro-1-methyl-ethoxy)-benzoic acid (compound 5.6) | 527.2 |
| 653 | [5-Methanesulfonyl-2-((R)-2,2,2-trifluoro-1-methyl-ethoxy)-phenyl]-(5'-trifluoromethyl-2,3,5,6-tetrahydro-[1,2']bipyrazinyl-4-yl)-methanone | 5'-Trifluoromethyl-3,4,5,6-tetrahydro-2H-[1,2']bipyrazinyl (compound 7.7) and 5-Methanesulfonyl-2-((R)-2,2,2-trifluoro-1-methyl-ethoxy)-benzoic acid (compound 5.7) | 527.2 |
| 654 | (2-Isopropoxy-5-methanesulfonyl-phenyl)-(5'-trifluoromethyl-2,3,5,6-tetrahydro-[1,2']bipyrazinyl-4-yl)-methanone | 5'-Trifluoromethyl-3,4,5,6-tetrahydro-2H-[1,2']bipyrazinyl (compound 7.7) and 2-Isopropoxy-5-methanesulfonyl-benzoic acid (compound 1.2) | 473.4 |
| 655 | [5-Methanesulfonyl-2-((S)-2,2,2-trifluoro-1-methyl-ethoxy)-phenyl]-[4-(6-trifluoromethyl-pyridazin-3-yl)-piperazin-1-yl]-methanone | 3-Piperazin-1-yl-6-trifluoromethyl-pyridazine (compound 7.8) and 5-Methanesulfonyl-2-((S)-2,2,2-trifluoro-1-methyl-ethoxy)-benzoic acid (compound 5.6) | 527.3 |
| 656 | (2-Isopropoxy-5-methanesulfonyl-phenyl)-[4-(6-trifluoromethyl-pyridazin-3-yl)-piperazin-1-yl]-methanone | 3-Piperazin-1-yl-6-trifluoromethyl-pyridazine (compound 7.8) and 2-Isopropoxy-5-methane sulfonyl-benzoic acid (compound 1.2) | 473.3 |
| 657 | [5-Methanesulfonyl-2-((R)-2,2,2-trifluoro-1-methyl-ethoxy)-phenyl]-[4-(6-trifluoromethyl-pyridazin-3-yl)-piperazin-1-yl]-methanone | 3-Piperazin-1-yl-6-trifluoromethyl-pyridazine (compound 7.8) and 5-Methanesulfonyl-2-((R)-2,2,2-trifluoro-1-methyl-ethoxy)-benzoic acid (compound 5.7) | 527.3 |
| 658 | [5-Methanesulfonyl-2-(2,2,2-trifluoro-1,1-dimethyl-ethoxy)-phenyl]-[4-(2-trifluoromethyl-pyrimidin-5-yl)-piperazin-1-yl]-methanone | 5-Piperazin-1-yl-2-trifluoromethyl-pyrimidine (compound 7.6) and 5-Methanesulfonyl-2-(2,2,2-trifluoro-1,1-dimethyl-ethoxy)-benzoic acid (compound 7.2) | 541.3 |
| 659 | [5-Methanesulfonyl-2-(2,2,2-trifluoro-1,1-dimethyl-ethoxy)-phenyl]-[4-(6-trifluoromethyl-pyridazin-3-yl)-piperazin-1-yl]-methanone | 3-Piperazin-1-yl-6-trifluoromethyl-pyridazine (compound 7.8) and 5-Methanesulfonyl-2-(2,2,2-trifluoro-1,1-dimethyl-ethoxy)-benzoic acid (compound 7.2) | 541.3 |
| 660 | [5-Methanesulfonyl-2-(2,2,2-trifluoro-1,1-dimethyl-ethoxy)-phenyl]-(5'-trifluoromethyl-2,3,5,6-tetrahydro-[1,2']bipyrazinyl-4-yl)-methanone | 5'-Trifluoromethyl-3,4,5,6-tetrahydro-2H-[1,2']bipyrazinyl (compound 7.7) and 5-Methanesulfonyl-2-(2,2,2-trifluoro-1,1-dimethyl-ethoxy)-benzoic acid (compound 7.2) | 541.3 |

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM Complete Medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake Buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07)cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-culture plates. On day 2, the medium was aspirated, and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 μM non-radioactive glycine. The plates were incubated with gentle shaking, and the reaction was stopped by aspiration of the mixture and washing (three times) with ice-cold UB. The cells were lysed with scintillation liquid, shaken 3 hours and the radioactivity in the cells counted using a scintillation counter.

The prepared compounds show an $IC_{50}$ (μM) at GlyT-1 in the range of 0.006-5.0.

The preferred compounds show an $IC_{50}$ (μM) at GlyT-1 in the range of 0.006-0.05, as shown in the table below.

| Example No. | $IC_{50}$ (μM) |
|---|---|
| 1 | 0.039 |
| 5 | 0.012 |
| 15 | 0.015 |
| 28 | 0.012 |
| 54 | 0.05 |
| 62 | 0.017 |
| 63 | 0.028 |
| 64 | 0.025 |
| 66 | 0.032 |
| 68 | 0.008 |
| 70 | 0.008 |
| 71 | 0.008 |
| 72 | 0.026 |
| 74 | 0.016 |
| 78 | 0.012 |
| 80 | 0.029 |
| 84 | 0.04 |
| 88 | 0.007 |
| 92 | 0.05 |
| 95 | 0.035 |
| 100 | 0.02 |
| 104 | 0.046 |
| 105 | 0.039 |
| 109 | 0.021 |
| 111 | 0.035 |
| 112 | 0.024 |
| 116 | 0.019 |
| 117 | 0.044 |
| 118 | 0.024 |
| 128 | 0.02 |
| 131 | 0.03 |
| 132 | 0.038 |
| 135 | 0.041 |
| 136 | 0.027 |
| 137 | 0.027 |
| 138 | 0.017 |
| 139 | 0.024 |
| 142 | 0.034 |
| 144 | 0.045 |
| 145 | 0.015 |
| 146 | 0.019 |
| 147 | 0.031 |
| 148 | 0.036 |
| 164 | 0.019 |
| 165 | 0.47 |
| 167 | 0.016 |
| 169 | 0.012 |
| 170 | 0.031 |
| 172 | 0.019 |
| 180 | 0.036 |
| 182 | 0.03 |
| 184 | 0.022 |
| 186 | 0.048 |
| 194 | 0.047 |
| 196 | 0.041 |
| 202 | 0.024 |
| 207 | 0.023 |
| 209 | 0.041 |
| 210 | 0.039 |
| 211 | 0.043 |
| 212 | 0.029 |
| 213 | 0.021 |
| 215 | 0.049 |
| 228 | 0.047 |
| 234 | 0.043 |
| 244 | 0.042 |
| 247 | 0.03 |
| 249 | 0.032 |
| 250 | 0.061 |
| 251 | 0.032 |
| 256 | 0.032 |
| 258 | 0.086 |
| 260 | 0.043 |
| 261 | 0.043 |
| 262 | 0.042 |
| 281 | 0.021 |
| 282 | 0.027 |
| 283 | 0.008 |
| 284 | 0.01 |
| 285 | 0.042 |
| 287 | 0.033 |
| 288 | 0.025 |
| 289 | 0.018 |
| 290 | 0.017 |
| 291 | 0.013 |
| 292 | 0.021 |
| 293 | 0.034 |
| 294 | 0.037 |
| 295 | 0.016 |
| 296 | 0.043 |
| 298 | 0.021 |
| 299 | 0.044 |
| 300 | 0.016 |
| 301 | 0.03 |
| 302 | 0.013 |
| 303 | 0.006 |
| 311 | 0.045 |
| 313 | 0.018 |
| 317 | 0.041 |
| 319 | 0.031 |
| 321 | 0.018 |
| 322 | 0.028 |
| 324 | 0.039 |
| 325 | 0.033 |
| 328 | 0.032 |
| 329 | 0.016 |
| 330 | 0.018 |

-continued

| Example No. | IC$_{50}$ (μM) |
|---|---|
| 363 | 0.008 |
| 367 | 0.036 |
| 369 | 0.032 |
| 371 | 0.041 |
| 372 | 0.006 |
| 373 | 0.035 |
| 375 | 0.035 |
| 393 | 0.032 |
| 400 | 0.023 |
| 407 | 0.027 |
| 408 | 0.037 |
| 411 | 0.045 |
| 412 | 0.033 |
| 413 | 0.03 |
| 417 | 0.046 |
| 430 | 0.037 |
| 435 | 0.029 |
| 437 | 0.026 |
| 438 | 0.047 |
| 439 | 0.021 |
| 459 | 0.04 |
| 461 | 0.046 |
| 464 | 0.02 |
| 465 | 0.04 |
| 466 | 0.026 |
| 468 | 0.02 |
| 469 | 0.02 |
| 470 | 0.03 |
| 475 | 0.04 |
| 481 | 0.03 |
| 488 | 0.039 |
| 491 | 0.037 |
| 494 | 0.03 |
| 504 | 0.025 |
| 505 | 0.024 |
| 506 | 0.046 |
| 507 | 0.031 |
| 408 | 0.026 |
| 509 | 0.03 |
| 510 | 0.015 |
| 514 | 0.045 |
| 515 | 0.04 |
| 517 | 0.035 |
| 518 | 0.033 |
| 519 | 0.035 |
| 524 | 0.012 |
| 525 | 0.021 |
| 526 | 0.009 |
| 527 | 0.006 |
| 528 | 0.015 |
| 529 | 0.013 |
| 530 | 0.0057 |
| 531 | 0.028 |
| 534 | 0.049 |
| 537 | 0.03 |
| 546 | 0.035 |
| 554 | 0.019 |
| 557 | 0.042 |
| 558 | 0.029 |
| 561 | 0.038 |
| 562 | 0.044 |
| 563 | 0.043 |
| 564 | 0.041 |
| 566 | 0.03 |
| 568 | 0.044 |
| 570 | 0.046 |
| 571 | 0.05 |
| 573 | 0.037 |
| 574 | 0.034 |
| 576 | 0.039 |
| 578 | 0.041 |
| 589 | 0.032 |
| 595 | 0.049 |
| 637 | 0.047 |

The present invention also provides pharmaceutical compositions containing compounds of formula I or pharmaceutically acceptable salts of the compounds of formula I and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutical acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Thus, pharmaceutical compositions containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

Thus, the invention also provides a method of inhibiting glycine uptake comprising administering to an individual a glycine inhibiting amount of one or more compounds of formula I. The invention further provides a method of inhibiting glycine uptake which comprises administering to an individual a glycine inhibiting amount of one of the following compounds 1-[5-(aminosulfonyl)-2-methoxybenzoyl]-4-(3-chlorophenyl)-piperazine, 1-[5-(aminosulfonyl)-2-methoxybenzoyl]-4-(4-fluorophenyl)-piperazine, 1-[5-(aminosulfonyl)-2-methoxybenzoyl]-4-[3-(trifluoromethyl)phenyl]-piperazine, 4-(3-amino-4-nitrophenyl)-1-[4-(dimethylamino)-2-methoxy-5-nitrobenzoyl]-2-methyl-piperazine, 1-[4-(dimethylamino)-2-methoxy-5-nitrobenzoyl]-2-methyl-4-(4-nitrophenyl)-piperazine, 4-[4-(dimethylamino)-2-methoxy-5-nitrobenzoyl]-2-methyl-1-(4-nitrophenyl)-piperazine, 1-(2-chloro-4-nitrophenyl)-4-[4-(dimethylamino)-2-methoxy-5-nitrobenzoyl]-piperazine, 1-[4-(dimethylamino)-2-methoxy-5-nitrobenzoyl]-4-(2,4-dinitrophenyl)-2-methyl-piperazine, 1-(4-chloro-2-nitrophenyl)-4-[4-(dimethylamino)-2-methoxy-5-nitrobenzoyl]-piperazine or 4-[4-(dimethylamino)-2-methoxy-5-nitrobenzoyl]-1-(2,4-dinitrophenyl)-2-methyl-piperazine.

The invention provides a method of treating an illness selected from the group consisting of psychoses, pain, disfunction in memory and learning, schizophrenia, dementia, attention deficit disorders, and Alzheimer's disease, which method comprises administering to an individual an effective amount of one or more compounds of formula I. The invention further provides a method of treating an illness selected from the group consisting of psychoses, pain, disfunction in memory and learning, schizophrenia, dementia, attention deficit disorders, and Alzheimer's disease, which method comprises administering to an individual an effective amount of one or more compounds of the following compounds 1-[5-(aminosulfonyl)-2-methoxybenzoyl]-4-(3-chlorophenyl)-piperazine, 1-[5-(aminosulfonyl)-2-methoxybenzoyl]-4-(4-fluorophenyl)-piperazine, 1-[5-(aminosulfonyl)-2-methoxybenzoyl]-4-[3-(trifluoromethyl)phenyl]-piperazine, 4-(3-amino-4-nitrophenyl)-1-[4-(dimethylamino)-2-methoxy-5-nitrobenzoyl]-2-methyl-piperazine, 1-[4-(dimethylamino)-2-methoxy-5-nitrobenzoyl]-2-methyl-4-(4-nitrophenyl)-piperazine.

4-[4-(dimethylamino)-2-methoxy-5-nitrobenzoyl]-2-methyl-1-(4-nitrophenyl)-piperazine, 1-(2-chloro-4-nitrophenyl)-4-[4-(dimethylamino)-2-methoxy-5-nitrobenzoyl]-piperazine, 1-[4-(dimethylamino)-2-methoxy-5-nitrobenzoyl]-4-(2,4-dinitrophenyl)-2-methyl-piperazine, 1-(4-chloro-2-nitrophenyl)-4-[4-(dimethylamino)-2-methoxy-5-nitrobenzoyl]-piperazine or 4-[4-(dimethylamino)-2-methoxy-5-nitrobenzoyl]-1-(2,4-dinitrophenyl)-2-methyl-piperazine.

In particular, the method provides a method of treating schizophrenia, which method comprises administering to an individual an effective amount of one or more compounds of formula I. The invention further provides a method of treating schizophrenia, which method comprises administering to an individual an effective amount of one or more compounds of the following compounds 1-[5-(aminosulfonyl)-2-methoxybenzoyl]-4-(3-chlorophenyl)-piperazine, 1-[5-(aminosulfonyl)-2-methoxybenzoyl]-4-(4-fluorophenyl)-piperazine, 1-[5-(aminosulfonyl)-2-methoxybenzoyl]-4-[3-(trifluoromethyl)phenyl]-piperazine, 4-(3-amino-4-nitrophenyl)-1-[4-(dimethylamino)-2-methoxy-5-nitrobenzoyl]-2-methyl-piperazine, 1-[4-(dimethylamino)-2-methoxy-5-nitrobenzoyl]-2-methyl-4-(4-nitrophenyl)-piperazine, 4-[4-(dimethylamino)-2-methoxy-5-nitrobenzoyl]-2-methyl-1-(4-nitrophenyl)-piperazine, 1-(2-chloro-4-nitrophenyl)-4-[4-(dimethylamino)-2-methoxy-5-nitrobenzoyl]-piperazine, 1-[4-(dimethylamino)-2-methoxy-5-nitrobenzoyl]-4-(2,4-dinitrophenyl)-2-methyl-piperazine, 1-(4-chloro-2-nitrophenyl)-4-[4-(dimethylamino)-2-methoxy-5-nitrobenzoyl]-piperazine or 4-[4-(dimethylamino)-2-methoxy-5-nitrobenzoyl]-1-(2,4-dinitrophenyl)-2-methyl-piperazine.

In particular, the method provides a method of treating Alzheimer's disease, which method comprises administering to an individual an effective amount of one or more compounds of formula I. The invention further provides a method of treating Alzhemier's disease, which method comprises administering to an individual an effective amount of one or more compounds of the following compounds 1-[5-(aminosulfonyl)-2-methoxybenzoyl]-4-(3-chlorophenyl)-piperazine, 1-[5-(aminosulfonyl)-2-methoxybenzoyl]-4-(4-fluorophenyl)-piperazine, 1-[5-(aminosulfonyl)-2-methoxybenzoyl]-4-[3-(trifluoromethyl)phenyl]-piperazine, 4-(3-amino-4-nitrophenyl)-1-[4-(dimethylamino)-2-methoxy-5-nitrobenzoyl]-2-methyl-piperazine, 1-[4-(dimethylamino)-2-methoxy-5-nitrobenzoyl]-2-methyl-4-(4-nitrophenyl)-piperazine, 4-[4-(dimethylamino)-2-methoxy-5-nitrobenzoyl]-2-methyl-1-(4-nitrophenyl)-piperazine, 1-(2-chloro-4-nitrophenyl)-4-[4-(dimethylamino)-2-methoxy-5-nitrobenzoyl]-piperazine, 1-[4-(dimethylamino)-2-methoxy-5-nitrobenzoyl]-4-(2,4-dinitrophenyl)-2-methyl-piperazine, 1-(4-chloro-2-nitrophenyl)-4-[4-(dimethylamino)-2-methoxy-5-nitrobenzoyl]-piperazine or 4-[4-(dimethylamino)-2-methoxy-5-nitrobenzoyl]-1-(2,4-dinitrophenyl)-2-methyl-piperazine.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions or suspensions. The pharmaceutical compositions also can be administered rectally, for example, in the form of suppositories or parenterally, for example, in the form of injectable solutions.

The dosage at which a compound of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:

1. A compound of formula

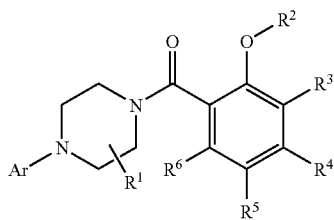

I wherein

Ar is unsubstituted or substituted aryl or 6-membered heteroaryl containing one, two or three nitrogen atoms, wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkyl substituted by hydroxy, $(CH_2)_n$—$(C_1-C_6)$-alkoxy, $(C_1-C_6)$-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by $(C_1-C_6)$-alkyl;

$R^1$ is hydrogen or $(C_1-C_6)$-alkyl;

$R^2$ is hydrogen, $(C_1-C_6)$-alkyl, $(C_2-C_6)$-alkenyl, $(C_1-C_6)$-alkyl substituted by halogen, $(C_1-C_6)$-alkyl substituted by hydroxy, $(CH_2)_n$—$(C_3-C_7)$-cycloalkyl optionally substituted by $(C_1-C_6)$-alkoxy or by halogen, $CH(CH_3)$—$(C_3-C_7)$-cycloalkyl, $(CH_2)_{n+1}$—$C(O)$—$R^9$, $(CH_2)_{n+1}$—CN, bicyclo[2.2.1]heptyl, $(CH_2)_{n+1}$—O—$(C_1-C_6)$-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy;

$R^3$, $R^4$ and $R^6$ are each independently hydrogen, hydroxy, halogen, $(C_1-C_6)$-alkyl, $(C_1-C_6)$-alkoxy or O—$(C_3-C_6)$-cycloalkyl;

$R^5$ is $NO_2$, CN, $C(O)R^9$ or $SO_2R^{10}$;

$R^7$ and $R^8$ are each independently hydrogen or $(C_1-C_6)$-alkyl;

$R^9$ is hydrogen, $(C_1-C_6)$-alkyl, $(C_1-C_6)$-alkoxy or $NR^7R^8$;

$R^{10}$ is $(C_1-C_6)$-alkyl optionally substituted by halogen, $(CH_2)_n$—$(C_3-C_6)$-cycloalkyl, $(CH_2)_n$—$(C_3-C_6)$-alkoxy, $(CH_2)_n$-heterocycloalkyl or $NR^7R^8$;

n is 0, 1, or 2;

or a pharmaceutically acceptable acid addition salt thereof.

2. A compound of formula

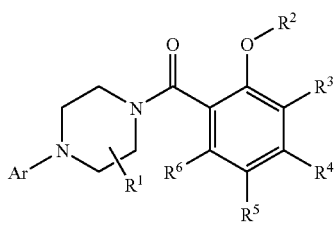

I-1 wherein

Ar is substituted aryl or unsubstituted or substituted 6-membered heteroaryl containing one, two or three nitrogen atoms, and wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkoxy, $(C_1-C_6)$-alkoxy substituted by halogen, $NR^7R^8$, $C(O)R^9$ and $SO_2R^{10}$;

$R^1$ is hydrogen or $(C_1-C_6)$-alkyl;

$R^2$ is $(C_1-C_6)$-alkyl, $(C_1-C_6)$-alkyl substituted by halogen, $(C_3-C_6)$-cycloalkyl, heterocycloalkyl, $(C_1-C_6)$-alkyl-$(C_3-C_6)$-cycloalkyl, $(C_1-C_6)$-alkyl-heterocycloalkyl, $(C_1-C_6)$-alkyl-C(O)—$R^9$, $(C_1-C_6)$-alkyl-CN, $(C_2-C_6)$-alkyl-O—$R^{13}$, $(C_2-C_6)$-alkyl-$NR^7R^8$, aryl, 6-membered heteroaryl containing one, two or three nitrogen atoms, $(C_1-C_6)$-alkyl-aryl or $(C_1-C_6)$-alkyl-5 or -6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy;

$R^3$, $R^4$ and $R^6$ are each independently hydrogen, hydroxy, halogen, CN, $(C_1-C_6)$-alkyl, $(C_1-C_6)$-alkoxy or $NR^7R^8$;

$R^5$ is $NO_2$, CN, $C(O)R^9$, $SO_2R^{10}$ or $NR^{11}R^{12}$;

$R^7$ and $R^8$ are each independently hydrogen or $(C_1-C_6)$-alkyl;

$R^9$ is hydroxy, $(C_1-C_6)$-alkyl, $(C_3-C_6)$-cycloalkyl, $(C_1-C_6)$-alkoxy or $NR^7R^8$;

$R^{10}$ is $(C_1-C_6)$-alkyl, $(C_3-C_6)$-cycloalkyl or $NR^7R^8$;

$R^{11}$ and $R^{12}$ are each independently hydrogen, C(O)—$(C_1-C_6)$-alkyl, or $SO_2$—$(C_1-C_6)$-alkyl, or form together with the N-atom to which they are attached a 5-membered heteroaryl group, optionally substituted by halogen, $(C_1-C_6)$-alkyl, $(C_1-C_6)$-alkyl substituted by halogen or $(C_3-C_6)$-cycloalkyl;

$R^{13}$ is hydroxy, $(C_1-C_6)$-alkyl or $(C_3-C_6)$-cycloalkyl;

or a pharmaceutically acceptable acid addition salt thereof.

3. A compound of formula I according to claim 1, wherein Ar is a substituted 6-membered heteroaryl group containing one, two or three nitrogen atoms, $R^2$ is $(C_1$-$C_6)$-alkyl or $CH_2)_n$—$(C_3$-$C_7)$-cycloalkyl, and $R^5$ is $SO_2CH_3$.

4. A compound of formula I according to claim 3, wherein the compound is selected from the group consisting of

[4-(3-chloro-5-trifluoromethyl-pyridin-2-yl)-piperazin-1-yl]-(2-cyclopropylmethoxy-5-methanesulfonyl-phenyl)-methanone, 6-[4-(2-cyclopentyloxy-5-methanesulfonyl-benzoyl)-piperazin-1-yl]-nicotinonitrile, (2-cyclopentyloxy-5-methanesulfonyl-phenyl)-[4-(5-trifluoromethyl-pyridin-2-yl)-piperazin-1-yl]-methanone,

[4-(3-chloro-5-trifluoromethyl-pyridin-2-yl)-piperazin-1-yl]-(2-cyclopentyloxy-5-methanesulfonyl-phenyl)-methanone, (2-cyclopentyloxy-5-methanesulfonyl-phenyl)-[4-(6-trifluoromethyl-pyridin-3-yl)-piperazin-1-yl]-methanone,

[4-(3-fluoro-5-trifluoromethyl-pyridin-2-yl)-piperazin-1-yl]-(2-isopropoxy-5-methanesulfonyl-phenyl)-methanone and (2-cyclopentyloxy-5-methanesulfonyl-phenyl)-[4-(3-fluoro-5-trifluoromethyl-pyridin-2-yl)-piperazin-1-yl]-methanone.

5. A compound of formula I according to claim 1, wherein Ar is a substituted 6-membered heteroaryl group containing one, two or three nitrogen atoms, $R^2$ is $(C_1$-$C_6)$-alkyl substituted by halogen and $R^5$ is $SO_2CH_3$.

6. A compound of formula I according to claim 5, wherein the compound is selected from the group consisting of rac-[4-(3-chloro-5-trifluoromethyl-pyridin-2-yl)-piperazin-1-yl]-[5-methanesulfonyl-2-(2,2,2-trifluoro-1-methyl-ethoxy)-phenyl]-methanone, rac-[5-methanesulfonyl-2-(2,2,2-trifluoro-1-methyl-ethoxy)-phenyl]-[4-(5-trifluoromethyl-pyridin-2-yl)-piperazin-1-yl]-methanone, rac-[4-(5-bromo-pyridin-2-yl)-piperazin-1-yl]-[5-methanesulfonyl-2-(2,2,2-trifluoro-1-methyl-ethoxy)-phenyl]-methanone, rac-[4-(3-fluoro-5-trifluoromethyl-pyridin-2-yl)-piperazin-1-yl]-[5-methanesulfonyl-2-(2,2,2-trifluoro-1-methyl-ethoxy)-phenyl]-methanone, rac-[5-methanesulfonyl-2-(2,2,2-trifluoro-1-methyl-ethoxy)-phenyl]-[4-(6-trifluoromethyl-pyridin-2-yl)-piperazin-1-yl]-methanone,

[5-methanesulfonyl-2-((S or R)-2,2,2-trifluoro-1-methyl-ethoxy)-phenyl]-[4-(5-trifluoromethyl-pyridin-2-yl)-piperazin-1-yl]-methanone,

[5-methanesulfonyl-2-((R or S)-2,2,2-trifluoro-1-methyl-ethoxy)-phenyl]-[4-(5-trifluoromethyl-pyridin-2-yl)-piperazin-1-yl]-methanone,

[4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone and

[4-(3-fluoro-5-trifluoromethyl-pyridin-2-yl)-piperazin-1-yl]-[5-methanesulfonyl-2-(2,2,2-trifluoro-1,1-dimethyl-ethoxy)-phenyl]-methanone.

7. A process for preparing a compound of formula

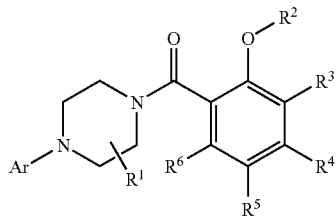

I wherein

Ar is unsubstituted or substituted aryl or 6-membered heteroaryl containing one, two or three nitrogen atoms, wherein the substituted aryl and the substituted heteroaryl groups are substituted by one or more substituents selected from the group consisting of hydroxy, halogen, $NO_2$, CN, $(C_1$-$C_6)$-alkyl, $(C_1$-$C_6)$-alkyl substituted by halogen, $(C_1$-$C_6)$-alkyl substituted by hydroxy, $(CH_2)_n$—$(C_1$-$C_6)$-alkoxy, $(C_1$-$C_6)$-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by $(C_1$-$C_6)$-alkyl;

$R^1$ is hydrogen or $(C_1$-$C_6)$-alkyl;

$R^2$ is hydrogen, $(C_1$-$C_6)$-alkyl, $(C_2$-$C_6)$-alkenyl, $(C_1$-$C_6)$-alkyl substituted by halogen, $(C_1$-$C_6)$-alkyl substituted by hydroxy, $(CH_2)_n$—$(C_3$-$C_7)$-cycloalkyl optionally substituted by $(C_1$-$C_6)$-alkoxy or by halogen, $CH(CH_3)$—$(C_3$-$C_7)$-cycloalkyl, $(CH_2)_{n+1}$—$C(O)$—$R^9$, $(CH_2)_{n+1}$—$CN$, bicyclo [2.2.1]heptyl, $(CH_2)_{n+1}$—$O$—$(C_1$-$C_6)$-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1$-$C_6)$-alkyl and $(C_1$-$C_6)$-alkoxy;

$R^3$, $R^4$ and $R^6$ are each independently hydrogen, hydroxy, halogen, $(C_1$-$C_6)$-alkyl, $(C_1$-$C_6)$-alkoxy or O—$(C_3$-$C_6)$-cycloalkyl;

$R^5$ is $NO_2$, CN, $C(O)R^9$ or $SO_2R^{10}$;

$R^7$ and $R^8$ are each independently hydrogen or $(C_1$-$C_6)$-alkyl;

$R^9$ is hydrogen, $(C_1$-$C_6)$-alkyl, $(C_1$-$C_6)$-alkoxy or $NR^7R^8$;

$R^{10}$ is $(C_1$-$C_6)$-alkyl optionally substituted by halogen, $(CH_2)_n$—$(C_3$-$C_6)$-cycloalkyl, $(CH_2)_n$—$(C_3$-$C_6)$-alkoxy, $(CH_2)_n$-heterocycloalkyl or $NR^7R^8$;

n is 0, 1, or 2;

or a pharmaceutically acceptable acid addition salt thereof, which process comprises reacting a compound of formula

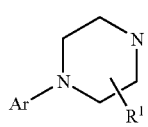

II with a compound of formula

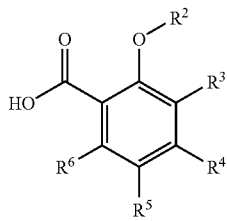

in the presence of an activating agent to produce a compound of formula

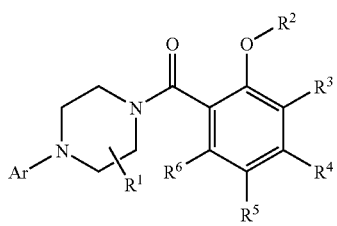

wherein the substituents are as defined above.

8. A process according to claim 7, wherein the activating agent is TBTU (2-(1H-benzotriazole-1-yl)-1,1,3,3-tetramethyluroniumtetrafluoro borate).

9. A process for preparing a compound of formula

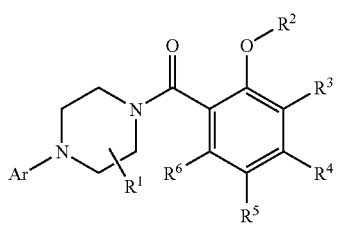

wherein
Ar is unsubstituted or substituted aryl or 6-membered heteroaryl containing one, two or three nitrogen atoms, wherein the substituted heteroaryl groups are substituted by one or more substituents selected from the group consisting of hydroxy, halogen, $NO_2$, CN, $(C_1\text{-}C_6)$-alkyl, $(C_1\text{-}C_6)$-alkyl substituted by halogen, $(C_1\text{-}C_6)$-alkyl substituted by hydroxy, $(CH_2)_n$—$(C_1\text{-}C_6)$-alkoxy, $(C_1\text{-}C_6)$-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by $(C_1\text{-}C_6)$-alkyl;
$R^1$ is hydrogen or $(C_1\text{-}C_6)$-alkyl;
$R^2$ is hydrogen, $(C_1\text{-}C_6)$-alkyl, $(C_2\text{-}C_6)$-alkenyl, $(C_1\text{-}C_6)$-alkyl substituted by halogen, $(C_1\text{-}C_6)$-alkyl substituted by hydroxy, $(CH_2)_n$—$(C_3\text{-}C_7)$-cycloalkyl optionally substituted by $(C_1\text{-}C_6)$-alkoxy or by halogen, $CH(CH_3)$—$(C_3\text{-}C_7)$-cycloalkyl, $(CH_2)_{n+1}$—$C(O)$—$R^9$, $(CH_2)_{n+1}$—CN, bicyclo [2.2.1]heptyl, $(CH_2)_{n+1}$—O—$(C_1\text{-}C_6)$-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1\text{-}C_6)$-alkyl and $(C_1\text{-}C_6)$-alkoxy;
$R^3$, $R^4$ and $R^6$ are each independently hydrogen, hydroxy, halogen, $(C_1\text{-}C_6)$-alkyl, $(C_1\text{-}C_6)$-alkoxy or O—$(C_3\text{-}C_6)$-cycloalkyl;
$R^5$ is $NO_2$, CN, $C(O)R^9$ or $SO_2R^{10}$;
$R^7$ and $R^8$ are each independently hydrogen or $(C_1\text{-}C_6)$-alkyl;
$R^9$ is hydrogen, $(C_1\text{-}C_6)$-alkyl, $(C_1\text{-}C_6)$-alkoxy or $NR^7R^8$;
$R^{10}$ is $(C_1\text{-}C_6)$-alkyl optionally substituted by halogen, $(CH_2)_n$—$(C_3\text{-}C_6)$-cycloalkyl, $(CH_2)_n$—$(C_3\text{-}C_6)$-alkoxy, $(CH_2)_n$-heterocycloalkyl or $NR^7R^8$;
n is 0, 1, or 2;
or a pharmaceutically acceptable acid addition salt thereof,
which process comprises reacting a compound of formula

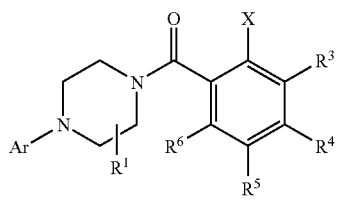

with a compound of formula $R^2OH$ optionally in the presence of a catalyst and a base to produce a compound of formula

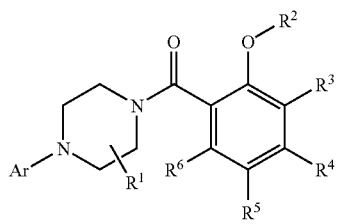

wherein X is halogen and the other substituents are as defined above.

10. The process according to claim 9 wherein the catalyst is Cu(I)I and the base is potassium carbonate, cesium carbonate or sodium.

11. A process for preparing a compound of formula

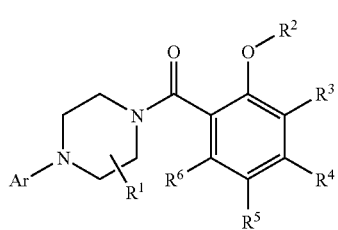

wherein
Ar is unsubstituted or substituted aryl or 6-membered heteroaryl containing one, two or three nitrogen atoms, wherein the substituted heteroaryl groups are substituted by one or more substituents selected from the group consisting of hydroxy, halogen, $NO_2$, CN, ($C_1$-$C_6$)-alkyl, ($C_1$-$C_6$)-alkyl substituted by halogen, ($C_1$-$C_6$)-alkyl substituted by hydroxy, $(CH_2)_n$—($C_1$-$C_6$)-alkoxy, ($C_1$-$C_6$)-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by ($C_1$-$C_6$)-alkyl;

$R^1$ is hydrogen or ($C_1$-$C_6$)-alkyl;

$R^2$ is hydrogen, ($C_1$-$C_6$)-alkyl, ($C_2$-$C_6$)-alkenyl, ($C_1$-$C_6$)-alkyl substituted by halogen, ($C_1$-$C_6$)-alkyl substituted by hydroxy, $(CH_2)_n$—($C_3$-$C_7$)-cycloalkyl optionally substituted by ($C_1$-$C_6$)-alkoxy or by halogen, $CH(CH_3)$—($C_3$-$C_7$)-cycloalkyl, $(CH_2)_{n+1}$—$C(O)$—$R^9$, $(CH_2)_{n+1}$—CN, bicyclo[2.2.1]heptyl, $(CH_2)_{n+1}$—O—($C_1$-$C_6$)-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, ($C_1$-$C_6$)-alkyl and ($C_1$-$C_6$)-alkoxy;

$R^3$, $R^4$ and $R^6$ are each independently hydrogen, hydroxy, halogen, ($C_1$-$C_6$)-alkyl, ($C_1$-$C_6$)-alkoxy or O—($C_3$-$C_6$)-cycloalkyl;

$R^5$ is $NO_2$, CN, $C(O)R^9$ or $SO_2R^{10}$;

$R^7$ and $R^8$ are each independently hydrogen or ($C_1$-$C_6$)-alkyl;

$R^9$ is hydrogen, ($C_1$-$C_6$)-alkyl, ($C_1$-$C_6$)-alkoxy or $NR^7R^8$;

$R^{10}$ is ($C_1$-$C_6$)-alkyl optionally substituted by halogen, $(CH_2)_n$—($C_3$-$C_6$)-cycloalkyl, $(CH_2)_n$—($C_3$-$C_6$)-alkoxy, $(CH_2)_n$-heterocycloalkyl or $NR^7R^8$;

n is 0, 1, or 2;

or a pharmaceutically acceptable acid addition salt thereof, which process comprises reacting a compound of formula

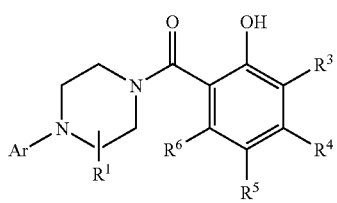

VI with a compound of formula $R^2X$ in the presence of a base and optionally in the presence of microwaves to produce a compound of formula

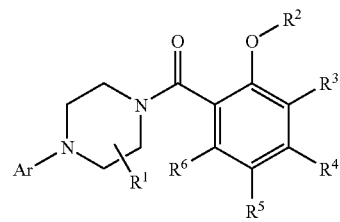

I wherein X is halogen, mesylate or triflate and the other substituents are as defined above.

12. A process for preparing a compound of formula

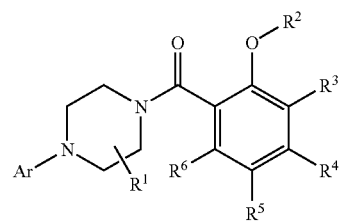

I wherein
Ar is unsubstituted or substituted aryl or 6-membered heteroaryl containing one, two or three nitrogen atoms, wherein the substituted heteroaryl groups are substituted by one or more substituents selected from the group consisting of hydroxy, halogen, $NO_2$, CN, ($C_1$-$C_6$)-alkyl, ($C_1$-$C_6$)-alkyl substituted by halogen, ($C_1$-$C_6$)-alkyl substituted by hydroxy, $(CH_2)_n$—($C_1$-$C_6$)-alkoxy, ($C_1$-$C_6$)-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by ($C_1$-$C_6$)-alkyl;

$R^1$ is hydrogen or ($C_1$-$C_6$)-alkyl;

$R^2$ is hydrogen, ($C_1$-$C_6$)-alkyl, ($C_2$-$C_6$)-alkenyl, ($C_1$-$C_6$)-alkyl substituted by halogen, ($C_1$-$C_6$)-alkyl substituted by hydroxy, $(CH_2)_n$—($C_3$-$C_7$)-cycloalkyl optionally substituted by ($C_1$-$C_6$)-alkoxy or by halogen, $CH(CH_3)$—($C_3$-$C_7$)-cycloalkyl, $(CH_2)_{n+1}$—$C(O)$—$R^9$, $(CH_2)_{n+1}$—CN, bicyclo[2.2.1]heptyl, $(CH_2)_{n+1}$—O—($C_1$-$C_6$)-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, ($C_1$-$C_6$)-alkyl and ($C_1$-$C_6$)-alkoxy;

$R^3$, $R^4$ and $R^6$ are each independently hydrogen, hydroxy, halogen, ($C_1$-$C_6$)-alkyl, ($C_1$-$C_6$)-alkoxy or O—($C_3$-$C_6$)-cycloalkyl;

$R^5$ is $NO_2$, CN, $C(O)R^9$ or $SO_2R^{10}$;

$R^7$ and $R^8$ are each independently hydrogen or ($C_1$-$C_6$)-alkyl;

$R^9$ is hydrogen, ($C_1$-$C_6$)-alkyl, ($C_1$-$C_6$)-alkoxy or $NR^7R^8$;

$R^{10}$ is ($C_1$-$C_6$)-alkyl optionally substituted by halogen, $(CH_2)_n$—($C_3$-$C_6$)-cycloalkyl, $(CH_2)_n$—($C_3$-$C_6$)-alkoxy, $(CH_2)_n$-heterocycloalkyl or $NR^7R^8$;

n is 0, 1, or 2;
or a pharmaceutically acceptable acid addition salt thereof,
which process comprises reacting a compound of formula

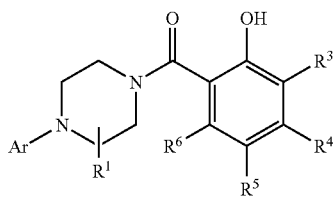

with a compound of formula

R²OH under Mitsunobu conditions in the presence of a phosphine to produce a compound of formula

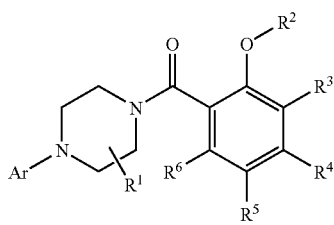

wherein the substituents are as defined above.

13. A process for preparing a compound of formula

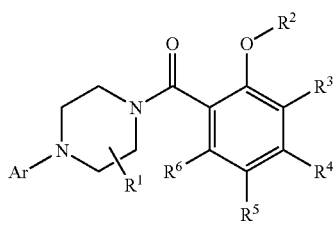

wherein
Ar is unsubstituted or substituted aryl or 6-membered heteroaryl containing one, two or three nitrogen atoms, wherein the substituted aryl and the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkyl substituted by hydroxy, $(CH_2)_n$—$(C_1-C_6)$-alkoxy, $(C_1-C_6)$-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by $(C_1-C_6)$-alkyl;
$R^1$ is hydrogen or $(C_1-C_6)$-alkyl;
$R^2$ is hydrogen, $(C_1-C_6)$-alkyl, $(C_2-C_6)$-alkenyl, $(C_1-C_6)$-alkyl substituted by halogen, $(C_1-C_6)$-alkyl substituted by hydroxy, $(CH_2)_n$—$(C_3-C_7)$-cycloalkyl optionally substituted by $(C_1-C_6)$-alkoxy or by halogen, $CH(CH_3)$—$(C_3-C_7)$-cycloalkyl, $(CH_2)_{n+1}$—$C(O)$—$R^9$, $(CH_2)_{n+1}$—CN, bicyclo[2.2.1]heptyl, $(CH_2)_{n+1}$—O—$(C_1-C_6)$-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy;
$R^3$, $R^4$ and $R^6$ are each independently hydrogen, hydroxy, halogen, $(C_1-C_6)$-alkyl, $(C_1-C_6)$-alkoxy or O—$(C_3-C_6)$-cycloalkyl;
$R^5$ is $NO_2$, CN, $C(O)R^9$ or $SO_2R^{10}$,
$R^7$ and $R^8$ are each independently hydrogen or $(C_1-C_6)$-alkyl;
$R^9$ is hydrogen, $(C_1-C_6)$-alkyl, $(C_1-C_6)$-alkoxy or $NR^7R^8$;
$R^{10}$ is $(C_1-C_6)$-alkyl optionally substituted by halogen, $(CH_2)_n$—$(C_3-C_6)$-cycloalkyl, $(CH_2)_n$—$(C_3-C_6)$-alkoxy, $(CH_2)_n$-heterocycloalkyl or $NR^7R^8$;
n is 0, 1, or 2;
or a pharmaceutically acceptable acid addition salt thereof,
which process comprises reacting a compound of formula

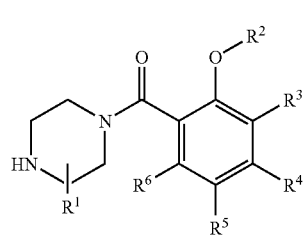

with a compound of formula

ArX to produce a compound of formula

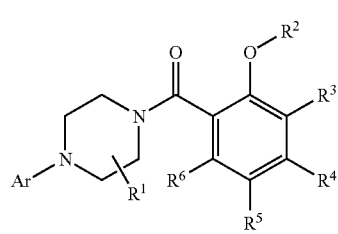

wherein X is halogen and the other substituents are as defined above.

14. A composition comprising one or more compounds of formula

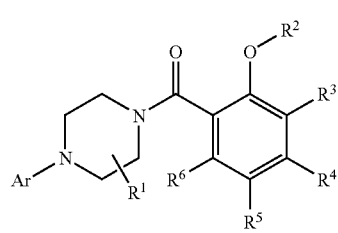

wherein

Ar is unsubstituted or substituted 6-membered heteroaryl containing one, two or three nitrogen atoms, wherein the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkyl substituted by hydroxy, $(CH_2)_n$—$(C_1-C_6)$-alkoxy, $(C_1-C_6)$-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by $(C_1-C_6)$-alkyl;

$R^1$ is hydrogen or $(C_1-C_6)$-alkyl;

$R^2$ is hydrogen, $(C_1-C_6)$-alkyl, $(C_2-C_6)$-alkenyl, $(C_1-C_6)$-alkyl substituted by halogen, $(C, C_6)$-alkyl substituted by hydroxy, $(CH_2)_n$—$(C_3-C_7)$-cycloalkyl optionally substituted by $(C_1-C_6)$-alkoxy or by halogen, $CH(CH_3$—$(C_3-C_7)$-cycloalkyl, $(CH_2)_{n+}$—$C(O)$—$R^9$, $(CH_2)_{n+1}$—CN, bicyclo[2.2.1]heptyl, $(CH_2)_{n+1}$—O—$(C_1-C_6)$-alkyl, $(CH_2)_n$-heterocycloalkyl, $(CH_2)_n$-aryl or $(CH_2)_n$-5 or 6-membered heteroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1-C_6)$-alkyl and $(C_1-C_6)$-alkoxy;

$R^3$, $R^4$ and $R^6$ are each independently hydrogen, hydroxy, halogen, $(C_1-C_6)$-alkyl, $(C_1-C_6)$-allcoxy or O—$(C_3-C_6)$-cycloalkyl;

R5 is $NO_2$, CN, $C(O)R^9$ or $S_2R^{10}$;

$R^7$ and $R^8$ are each independently hydrogen or $(C_1-C_6)$-alkyl;

$R^9$ is hydrogen, $(C_1-C_6)$-alkyl, $(C_1-C_6)$-allcoxy or $NR^7R^8$;

$R_{10}$ is $(C_1-C_6)$-alkyl optionally substituted by halogen, $(CH_2)_n$—$(C_3-C_6)$-cycloalkyl $(CH_2)_n$—$(C_3-C_6)$-alkoxy, $(CH_2)_n$-heterocycloalkyl or $NR^7R^8$;

n is 0, 1 , or 2;

or a pharmaceutically acceptable acid addition salt thereof, and a pharmaceutically acceptable excipient.

15. A method of treating schizophrenia which comprises administering to an individual an effective amount of one or more compounds of formula

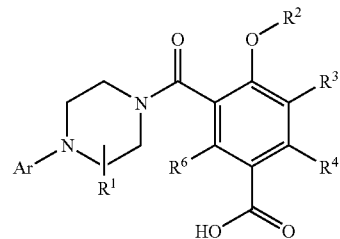

Ia wherein

Ar is unsubstituted or substituted 6-membered heteroaryl containing one, two or three nitrogen atoms, wherein the substituted heteroaryl groups are substituted by one or more substituents selected from the group consisting of hydroxy, halogen, $NO_2$, CN, $(C_1-C_6)$-alkyl, $(C_1-C_6)$-alkyl substituted by halogen, $(C_1-C_6)$-alkyl substituted by hydroxy, $(CH_2)_n$—$(C_1-C_6)$-alkoxy, $(C_1-C_6)$-alkoxy substituted by halogen, $NR^7R^8$, $C(O)R^9$, $SO_2R^{10}$, and —$C(CH_3)$=$NOR^7$, or are substituted by a 5-membered aromatic heterocycle containing 1-4 heteroatoms selected from N and O, which is optionally substituted by $(C_1-C_6)$-alkyl;

$R^1$ is hydrogen or $(C_1-C_6)$-alkyl;

$R^2$ is hydrogen, $(C_1-C_6)$-alkyl, $(C_2-C_6)$-alkenyl, $(C_1-C_6)$-alkyl substituted by halogen, $(C_1-C_6)$-alkyl substituted by hydroxy, $(CH_2)_n$—$(C_3-C_7)$-cycloalkyl optionally substituted by $(C_1-C_6)$-alkoxy or by halogen, $CH(CH_3)$—$(C_3-C_7)$-cycloalkyl, $(CH_2)_{n+}$—$C(O)$—$R^9$, $(CH_2)_{n+1}$—CN, bicyclo[2.2.1]heptyl, $(CH_2)_{n+1}$—O—$(C_1-C_6)$-alkyl, $(CH_2)_n$-heterocycloalkyl, $(CH_2)_n$-aryl or $(CH_2)_n$-5 or 6-membered hetaroaryl containing one, two or three heteroatoms selected from the group consisting of oxygen, sulphur or nitrogen wherein aryl, heterocycloalkyl and heteroaryl are unsubstituted or substituted by one or more substituents selected from the group consisting of hydroxy, halogen, $(C_1-C_6)$-alkyl and $(C_1-C_1)$-alkoxy;

$R^3$, $R^4$ and $R^6$ are each independently hydrogen, hydroxy, halogen, $(C_1-C_6)$-alkyl, $(C_1-C_6)$-alkoxy or O—$(C_3-C_6)$-cycloalkyl;

$R^5$ is $NO_2$, CN, $C(O)R^9$ or $SO_2R^{10}$;

$R^7$ and $R^8$ are each independently hydrogen or $(C_1-C_6)$-alkyl;

$R^9$ is hydrogen, $(C_1-C_6)$-alkyl, $(C_1-C_6)$-alkoxy or $NR^7R^8$;

$R^{10}$ is $(C_1-C_6)$-alkyl optionally substituted by halogen, $(CH_2)_n$—$(C_3-C_6)$-cycloalkyl, $(CH_2)_n$—$(C_3-C_6)$-alkoxy, $(CH_2)_n$-heterocycloalkyl or $NR^7R^8$;

n is 0, 1, or 2;

or a pharmaceutically acceptable acid addition salt thereof.

* * * * *

UNITED STATES PATENT AND TRADEMARK OFFICE
CERTIFICATE OF CORRECTION

PATENT NO.         : 7,319,099 B2
APPLICATION NO. : 10/911359
DATED                 : January 15, 2008
INVENTOR(S)       : Jolidon et al.

It is certified that error appears in the above-identified patent and that said Letters Patent is hereby corrected as shown below:

IN THE CLAIMS:

- Claim 1, Column 171, line 37: "Ar is unsubstituted or substituted aryl or 6-membered" should read -- Ar is unsubstituted or substituted 6-membered --.

- Claim 1, Column 171, lines 39-40: "wherein the substituted aryl and the substituted heteroaryl groups" should read -- wherein the substituted heteroaryl groups --.

- Claim 2, Column 172, lines 26-27: "Ar is substituted aryl or unsubstituted or substituted 6-membered heteroaryl" should read -- Ar is unsubstituted or substituted 6-membered heteroaryl --.

- Claim 2, Column 172, lines 28-29: "wherein the substituted aryl and the substituted heteroaryl groups" should read -- wherein the substituted heteroaryl groups --.

- Claim 7, Column 174, lines 15-16: "Ar is unsubstituted or substituted aryl or 6-membered heteroaryl" should read -- Ar is unsubstituted or substituted 6-membered heteroaryl --.

- Claim 7, Column 174, lines 17-18: "wherein the substituted aryl and the substituted heteroaryl groups" should read -- wherein the substituted heteroaryl groups --.

UNITED STATES PATENT AND TRADEMARK OFFICE
CERTIFICATE OF CORRECTION

PATENT NO. : 7,319,099 B2
APPLICATION NO. : 10/911359
DATED : January 15, 2008
INVENTOR(S) : Jolidon et al.

It is certified that error appears in the above-identified patent and that said Letters Patent is hereby corrected as shown below:

- Claim 9, Column 175, lines 46-47: "Ar is unsubstituted or substituted aryl or 6-membered heteroaryl" should read -- Ar is unsubstituted or substituted 6-membered heteroaryl --.

- Claim 11, Column 177, lines 2-3: "Ar is unsubstituted or substituted aryl or 6-membered heteroaryl" should read -- Ar is unsubstituted or substituted 6-membered heteroaryl --.

- Claim 12, Column 178, lines 31-32: "Ar is unsubstituted or substituted aryl or 6-membered heteroaryl" should read -- Ar is unsubstituted or substituted 6-membered heteroaryl --.

- Claim 13, Column 179, lines 47-48: "Ar is unsubstituted or substituted aryl or 6-membered heteroaryl" should read -- Ar is unsubstituted or substituted 6- --.

- Claim 13, Column 179, lines 49-50: "wherein the substituted aryl and the substituted heteroaryl groups" should read -- wherein the substituted heteroaryl groups --.

- Claim 14, Column 181, line 27: "heteroatorns" should read -- heteroatoms --.

- Claim 14, Column 181, line 39: "R5 is $NO_2$," should read -- $R^5$ is $NO_2$, --.

- Claim 14, Column 181, line 44: "$R_{10}$ is $(C_1-C_6)$-alkyl" should read -- $R^{10}$ is $(C_1-C_6)$-alkyl --.

- Claim 14, Column 181, line 48: "n is 0, 1, or2;" should read -- n is 0, 1, or 2; --.

UNITED STATES PATENT AND TRADEMARK OFFICE
CERTIFICATE OF CORRECTION

PATENT NO. : 7,319,099 B2
APPLICATION NO. : 10/911359
DATED : January 15, 2008
INVENTOR(S) : Jolidon et al.

Page 3 of 3

It is certified that error appears in the above-identified patent and that said Letters Patent is hereby corrected as shown below:

- Claim 15, Column 182, lines 1-13: Formula Ia

"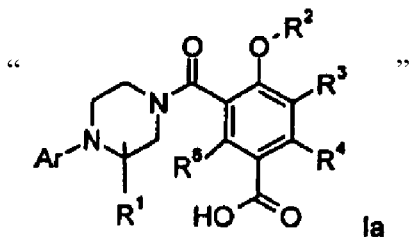"

should be deleted and replaced with formula I

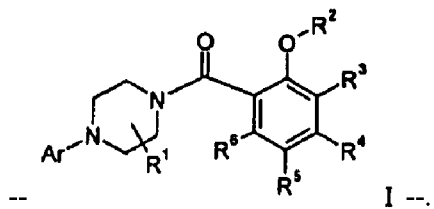
-- I --.

Signed and Sealed this

Fifth Day of August, 2008

JON W. DUDAS
*Director of the United States Patent and Trademark Office*